US012734249B2

(12) United States Patent
Stanton et al.

(10) Patent No.: US 12,734,249 B2
(45) **Date of Patent: *Sep. 15, 2026**

(54) LIPIDS AND COMPOSITIONS THEREOF

(71) Applicant: Generation Bio Co., Cambridge, MA (US)

(72) Inventors: Matthew G. Stanton, Cambridge, MA (US); Birte Nolting, Cambridge, MA (US); Andrew Milstead, Cambridge, MA (US)

(73) Assignee: Generation Bio Co., Cambridge, MA (US)

( * ) Notice: Subject to any disclaimer, the term of this patent is extended or adjusted under 35 U.S.C. 154(b) by 290 days.

This patent is subject to a terminal disclaimer.

(21) Appl. No.: 18/287,751

(22) PCT Filed: Apr. 20, 2022

(86) PCT No.: PCT/US2022/025455

§ 371 (c)(1),
(2) Date: Oct. 20, 2023

(87) PCT Pub. No.: WO2022/226008

PCT Pub. Date: Oct. 27, 2022

(65) Prior Publication Data

US 2024/0226325 A1 Jul. 11, 2024

Related U.S. Application Data

(60) Provisional application No. 63/217,869, filed on Jul. 2, 2021, provisional application No. 63/176,943, filed on Apr. 20, 2021.

(51) Int. Cl.

| | |
|---|---|
| ***A61K 48/00*** | (2006.01) |
| ***A61K 9/51*** | (2006.01) |
| ***A61K 31/7105*** | (2006.01) |
| ***A61K 31/711*** | (2006.01) |
| ***A61K 47/24*** | (2006.01) |
| ***A61K 47/28*** | (2006.01) |
| ***C07C 229/12*** | (2006.01) |

(52) U.S. Cl.

CPC ........ *A61K 48/0033* (2013.01); *A61K 9/5123* (2013.01); *A61K 31/7105* (2013.01); *A61K 31/711* (2013.01); *A61K 47/24* (2013.01); *A61K 47/28* (2013.01); *C07C 229/12* (2013.01)

(58) Field of Classification Search

CPC .............. A61K 48/0033; A61K 9/5123; A61K 31/7105; A61K 31/711; A61K 471/24; A61K 471/28; C07C 229/12

See application file for complete search history.

(56) References Cited

U.S. PATENT DOCUMENTS

| | | | | |
|---|---|---|---|---|
| 9,402,816 | B2 * | 8/2016 | Colletti | A61K 47/60 |
| 12,263,228 | B2 * | 4/2025 | Stanton | A61K 9/5123 |
| 2016/0009637 | A1 | 1/2016 | Manoharan et al. | |
| 2016/0317458 | A1 | 11/2016 | Brito et al. | |
| 2018/0169016 | A1 | 6/2018 | DeRosa et al. | |
| 2021/0023008 | A1 | 1/2021 | Nakai et al. | |
| 2021/0369862 | A1 | 12/2021 | De Smedt et al. | |
| 2024/0285796 | A1 | 8/2024 | Stanton et al. | |
| 2024/0293574 | A1 | 9/2024 | Stanton et al. | |

(Continued)

FOREIGN PATENT DOCUMENTS

| | | | |
|---|---|---|---|
| RU | 2658007 | C2 | 6/2018 |
| WO | 2015/095346 | A1 | 6/2015 |
| WO | 2018/220553 | A1 | 12/2018 |

(Continued)

OTHER PUBLICATIONS

Witzigmann et al., Lipid nanoparticle technology for therapeutic gene regulation in the liver. Adv Drug Deliv Rev. 2020;159:344-363.

International Search Report and Written Opinion for Application No. PCT/US2022/025455, dated Oct. 14, 2022, 12 pages.

Ball et al., Lipid Nanoparticle Formulations for Enhanced Co-delivery of siRNA and mRNA. Nano Lett. Jun. 13, 2018;18(6):3814-3822.

Gauthier et al., Lectin recognition and hepatocyte endocytosis of GalNAc-decorated nanostructured lipid carriers. J Drug Target. Jan. 2021;29(1):99-107.

(Continued)

*Primary Examiner* — Shirley V Gembeh

(74) *Attorney, Agent, or Firm* — McCarter & English, LLP; Marcie B. Clarke; Yelena Margolin

(57) ABSTRACT

Provided herein are lipids having the Formula I or Formula la, and pharmaceutically acceptable salts thereof, wherein R', $R^1$, $R^2$, $R^3$, $R^4$, $R^5$, $R^{6a}$, $R^{6b}$, $X^1$, $X^2$, and n are as defined herein for Formula I and Formula la, respectively. Also provided herein are lipid nanoparticle (LNP) compositions comprising lipid having the Formula I or la and a capsid-free, non-viral vector (e.g., ceDNA). In one aspect of any of the aspects or embodiments herein, these LNPs can be used to deliver a capsid-free, non-viral DNA vector to a target site of interest (e.g., cell, tissue, organ, and the like).

I or Ia

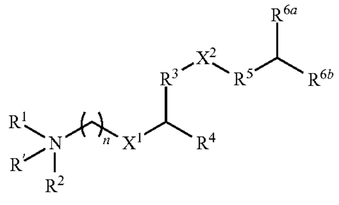

51 Claims, 6 Drawing Sheets

Specification includes a Sequence Listing.

(56) References Cited

U.S. PATENT DOCUMENTS

2025/0249123 A1 8/2025 Stanton et al.

FOREIGN PATENT DOCUMENTS

| | | | |
|---|---|---|---|
| WO | 2019/235635 | A1 | 12/2019 |
| WO | 2022/016089 | A2 | 1/2022 |
| WO | 2022/226008 | A2 | 10/2022 |
| WO | 2023/287861 | A2 | 1/2023 |

OTHER PUBLICATIONS

Martini et al., A New Era for Rare Genetic Diseases: Messenger RNA Therapy. Hum Gene Ther. Oct. 2019;30 (10):1180-1189.

Bastin et al., Salt Selection and Optimisation Procecures for Pharmaceutical New Chemical Entities. Organic Process Research & Development. 2000;4:427-435.

Belikov, Pharmaceutical Chemistry, Fourth Edition. MEDpress—inform. pp. 27-29, (2007).

Boonme et al., Influence of lipids on the properties of solid lipid nanoparticles from microemulsion technique. European Journal of Lipid Science and Technology. Jul. 2013;115(7):820-824.

Gavrilov, Pharmaceutical Technology. GEOTAR—Media. p. 20, (2010).

Hajj et al., Branched-Tail Lipid Nanoparticles Potently Deliver mRNA In Vivo due to Enhanced Ionization at Endosomal pH. Small. Feb. 2019;15(6):e1805097, 7 pages.

Sun et al., Structure and Function of Cationic and Ionizable Lipids for Nucleic Acid Delivery. Pharm Res. Jan. 2023;40 (1):27-46.

Russian Office Action for Application No. 2023129760, dated Dec. 12, 2025, 24 pages.

* cited by examiner

SEQUENCE LISTING

<160> NUMBER OF SEQ ID NOS: 1

<210> SEQ ID NO 1
<211> LENGTH: 16
<212> TYPE: DNA
<213> ORGANISM: Adeno-associated virus

<400> SEQUENCE: 1
gcgcgctcgc tcgctc 16

LIPIDS AND COMPOSITIONS THEREOF

CROSS REFERENCE TO RELATED APPLICATIONS

This application is a 35 U.S.C. § 371 national stage filing of International Application No. PCT/US2022/025455, filed on Apr. 20, 2022 which claims priority to U.S. Provisional Application No. 63/176,943, filed on Apr. 20, 2021, and U.S. Provisional Application No. 63/217,869, filed on Jul. 2, 2021. The entire contents of each of the aforementioned applications are incorporated herein by reference.

SEQUENCE LISTING

The instant application contains a Sequence Listing which has been filed electronically in ASCII format and is hereby incorporated by reference in its entirety. Said SSCII copy, created on Oct. 20, 2023 is named 131698-08320_SL.txt and is 470 bytes in size.

BACKGROUND

Gene therapy aims to improve clinical outcomes for patients suffering from either genetic disorders or acquired diseases caused by an aberrant gene expression profile. Various types of gene therapy that deliver therapeutic nucleic acids into a patient's cells as a drug to treat disease have been developed to date.

Delivery and expression of a corrective gene in the patient's target cells can be carried out via numerous methods, including the use of engineered viral gene delivery vectors, and potentially plasmids, minigenes, oligonucleotides, minicircles, or variety of closed-ended DNAs. Among the many virus-derived vectors available (e.g., recombinant retrovirus, recombinant lentivirus, recombinant adenovirus, and the like), recombinant adeno-associated virus (rAAV) is gaining acceptance as a versatile, as well as relatively reliable, vector in gene therapy. However, viral vectors, such as adeno-associated vectors, can be highly immunogenic and elicit humoral and cell-mediated immunity that can compromise efficacy, particularly with respect to re-administration.

Non-viral gene delivery circumvents certain disadvantages associated with viral transduction, particularly those due to the humoral and cellular immune responses to the viral structural proteins that form the vector particle, and any de novo virus gene expression. Among the advantages of the non-viral delivery technology is the use of lipid nanoparticles (LNPs) as a carrier. LNPs provide a unique opportunity that allows one to design cationic lipids as a LNP component which can circumvent the humoral and cellular immune responses posing significant toxicity associated with viral gene therapy.

Cationic lipids are roughly composed of a cationic amine moiety, a hydrophobic domain typically having one or two aliphatic hydrocarbon chains (i.e., the hydrophobic tail(s), which may be saturated or unsaturated), and a linker or biodegradable group connecting the cationic amine moiety and the hydrophobic domain. The cationic amine moiety and a polyanion nucleic acid interact electrostatically to form a positively charged liposome or lipid membrane structure. Thus, uptake into cells is promoted and nucleic acids are delivered into cells.

Some cationic lipids (e.g., DODAP and DOTAP) have two or more structurally identical hydrophobic tails in the hydrophobic domain. Some other cationic lipids have two or more hydrophobic tails that are structurally different from each other. Asymmetrical cationic lipids known in the art, such as CLinDMA, are asymmetrical typically in that either: (i) the hydrophobic tails differ structurally by incorporating different chemical moieties and functional groups (e.g., CLinDMA incorporating cholesterol in one of the hydrophobic tails); or (ii) the hydrophobic tails differ in length. Symmetrical cationic lipids are usually favored because they pose less synthesis challenges.

Some widely used cationic lipids such as CLinDMA, DLinDMA (DODAP), and DOTAP have been employed for ribonucleic acid (siRNA or mRNA) delivery but suffer from sub-optimal delivery efficiency along with toxicity at higher doses. In view of the shortcomings of the current cationic lipids, there is a need in the field to provide lipid scaffolds that not only demonstrate enhanced efficacy along with reduced toxicity, but with improved pharmacokinetics and intracellular kinetics such as cellular uptake and nucleic acid release from the lipid carrier.

SUMMARY

The cationic lipids provided in the present disclosure comprise one hydrophobic tail containing a biodegradable group, and a hydrophobic tail that does not contain a biodegradable group. Some of the exemplary lipids provided in this disclosure comprise a hydrophobic tail that bifurcates at the terminal ends to form two branched aliphatic hydrocarbon chains, and a hydrophobic tail that does not bifurcate. The inventors have found that the cationic lipids of the present disclosure can be synthesized at satisfactory yield and purity. The inventors have also found that the cationic lipids of the present disclosure, when formulated as lipid nanoparticles (LNP) for carrying a therapeutic nucleic acid, exhibit sustained excellent and stable in vivo expression level of the transgene insert within the nucleic acid and are well-tolerated in vivo. Many of the exemplary cationic lipids of the present disclosure, when formulated as LNPs carrying a therapeutic nucleic acid, were found to exhibit in vivo expression and in vivo tolerability that are superior to their reference lipid counterpart described above. Moreover, without wishing to be bound by theory, the inventors believe that a delicate interplay between the length (i.e., number of carbon atoms) of terminal branched aliphatic hydrocarbon chains in the bifurcated hydrophobic tails and the length of non-bifurcated hydrophobic tail is important towards, inter alia, achieving excellent encapsulation efficiencies of an LNP composition.

Accordingly, in one aspect, provided herein are lipids represented by Formula I or Ia:

I or Ia

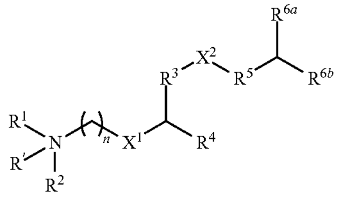

as well as pharmaceutically acceptable salts thereof, wherein R', $R^1$, $R^2$, $R^3$, $R^4$, $R^5$, $R^{6a}$, $R^{6b}$, $X^1$, $X^2$, and n are as defined herein for each of Formula I or Ia, respectively.

Also provided are pharmaceutical compositions comprising a lipid described herein, or a pharmaceutically acceptable salt thereof, and a pharmaceutically acceptable carrier.

Another aspect of the present disclosure relates to a composition comprising a lipid nanoparticle (LNP) comprising a lipid described herein, or a pharmaceutically acceptable salt thereof, and a nucleic acid. In one embodiment of any of the aspects or embodiments herein, the nucleic acid is encapsulated in the LNP. In a particular embodiment, the nucleic acid is a closed-ended DNA (ceDNA).

A further aspect of the present disclosure relates to a method of treating a genetic disorder in a subject, the method comprising administering to the subject an effective amount of the pharmaceutical composition according to any of the aspects or embodiments herein.

BRIEF DESCRIPTION OF THE DRAWINGS

Embodiments of the present disclosure, briefly summarized above and discussed in greater detail below, can be understood by reference to the illustrative embodiments of the disclosure depicted in the appended drawings. However, the appended drawings illustrate only typical embodiments of the disclosure and are therefore not to be considered limiting of scope, for the disclosure may admit to other equally effective embodiments.

DETAILED DESCRIPTION

Figure 1B:
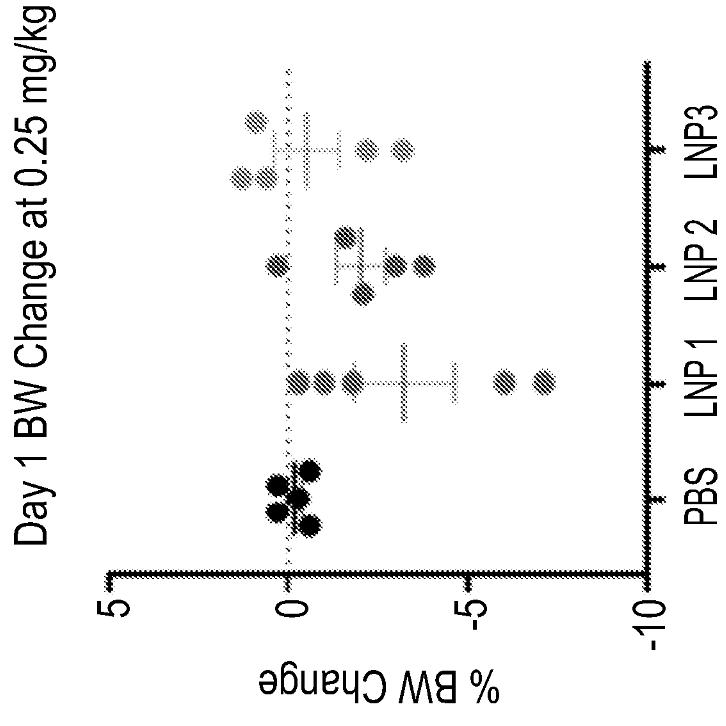
FIG. 1B is a graph showing the body weight changes at day 1 in the mice administered ceDNA encoding luciferase formulated in LNP1, LNP2, LNP3 and PBS as described above.

The present disclosure provides a lipid-based platform for delivering therapeutic nucleic acid (TNA) such as non-viral (e.g., closed-ended DNA) or synthetic viral vectors, which can be taken up by the cells and maintain high levels of expression. For example, the immunogenicity associated with viral vector-based gene therapies has limited the number of patients who can be treated due to pre-existing background immunity, as well as prevented the re-dosing of patients either to titrate to effective levels in each patient, or to maintain effects over the longer term. Furthermore, other nucleic acid modalities greatly suffer from immunogenicity due to an innate DNA or RNA sensing mechanism that triggers a cascade of immune responses. Because of the lack of pre-existing immunity, the presently described TNA lipid particles (e.g., lipid nanoparticles) allow for additional doses of TNA, such as mRNA, siRNA, synthetic viral vector or ceDNA as necessary, and further expands patient access, including into pediatric populations who may require a subsequent dose upon tissue growth. Moreover, it is a finding of the present disclosure that the TNA lipid particles (e.g., lipid nanoparticles), comprising, in particular, lipid compositions comprising one or more tertiary amino groups, and a disulfide bond provide more efficient delivery of the TNA (e.g., ceDNA), better tolerability and an improved safety profile. Because the presently described TNA lipid particles (e.g., lipid nanoparticles) have no packaging constraints imposed by the space within the viral capsid, in theory, the only size limitation of the TNA lipid particles (e.g., lipid nanoparticles) resides in the expression (e.g., DNA replication, or RNA translation) efficiency of the host cell.

One of the biggest hurdles in the development of therapeutics, particularly in rare diseases, is the large number of individual conditions. Around 350 million people on earth are living with rare disorders, defined by the National Institutes of Health as a disorder or condition with fewer than 200,000 people diagnosed. About 80 percent of these rare disorders are genetic in origin, and about 95 percent of them do not have treatment approved by the FDA (rarediseases.info.nih.gov/diseases/pages/31/faqs-about-rare-diseases). Among the advantages of the TNA lipid particles (e.g., lipid nanoparticles) described herein is in providing an approach that can be rapidly adapted to multiple diseases that can be treated with a specific modality of TNA, and particularly to rare monogenic diseases that can meaningfully change the current state of treatments for many of the genetic disorder or diseases.

I. Definitions

The term "alkyl" refers to a monovalent radical of a saturated, straight (i.e., unbranched) or branched chain hydrocarbon. Unless it is specifically described that an alkyl is unbranched, e.g., $C_1$-$C_{16}$ unbranched alkyl, the term "alkyl" as used herein applies to both branched and unbranched alkyl groups. Exemplary alkyl groups include, but are not limited to, $C_1$-$C_{16}$ unbranched alkyl, $C_7$-$C_{16}$ alkyl, $C_5$-$C_{14}$ alkyl, $C_2$-$C_{14}$ unbranched alkyl, $C_2$-$C_{12}$ unbranched alkyl, $C_2$-$C_{10}$ unbranched alkyl, $C_2$-$C_7$ unbranched alkyl, $C_1$-$C_6$ alkyl, $C_1$-$C_4$ alkyl, $C_1$-$C_3$ alkyl, $C_1$-$C_2$ alkyl, $C_7$ unbranched alkyl, $C_8$ unbranched alkyl, $C_9$ unbranched alkyl, $C_{10}$ unbranched alkyl, $C_{11}$ unbranched alkyl, $C_8$ alkyl, $C_{10}$ alkyl, $C_{12}$ alkyl, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, nonyl, decanyl, undecanyl, dodecanyl, tridecanyl, tetradecanyl, pentadecanyl, hexadecanyl, heptadecanyl, octadecanyl, nonadecanyl, eicosanyl, etc.

The term "alkylene" refers to a bivalent radical of a saturated, straight, or branched chain hydrocarbon. Unless it is specifically described that an alkylene is unbranched, e.g., $C_1$-$C_{12}$ unbranched alkylene, the term "alkylene" as used herein applies to both branched and unbranched alkylene groups. Exemplary alkylene groups include, but are not limited to, $C_1$-$C_{12}$ alkylene, $C_1$-$C_9$ alkylene, $C_1$-$C_8$ alkylene, $C_1$-$C_6$ alkylene, $C_1$-$C_4$ alkylene, $C_2$-$C_8$ alkylene, $C_3$-$C_7$ alkylene, $C_5$-$C_7$ alkylene, $C_7$ alkylene, $C_5$ alkylene, and a corresponding alkenylene to any of the exemplary alkyl groups described above.

The term "alkenyl" refers to a monovalent radical of a straight or branched chain hydrocarbon having one or more (e.g., one or two) carbon-carbon double bonds, wherein the alkenyl radical includes radicals having "cis" and "trans" orientations, or by an alternative nomenclature, "E" and "Z" orientations. Unless it is specifically described that an alkenyl is unbranched, e.g., $C_2$-$C_{16}$ unbranched alkenyl, the term "alkenyl" as used herein applies to both branched and unbranched alkenyl groups. Exemplary alkenyl groups include, but are not limited to, $C_2$-$C_{16}$ unbranched alkenyl, $C_7$-$C_{16}$ alkenyl, $C_5$-$C_{14}$ alkenyl, $C_2$-$C_{14}$ unbranched alkenyl, $C_2$-$C_{12}$ unbranched alkenyl, $C_2$-$C_{10}$ unbranched alkenyl, $C_2$-$C_7$ unbranched alkenyl, $C_2$-$C_6$ alkenyl, $C_2$-$C_4$ alkenyl, $C_2$-$C_3$ alkenyl, $C_8$ alkenyl, $C_{10}$ alkenyl, $C_{12}$ alkenyl, and a corresponding alkenyl to any of the exemplary alkyl groups described above that contain two carbon atoms and above.

The term "alkenylene" refers to a bivalent radical of a straight or branched chain hydrocarbon having one or more (e.g., one or two) carbon-carbon double bonds, wherein the alkenyl radical includes radicals having "cis" and "trans" orientations, or by an alternative nomenclature, "E" and "Z" orientations. Unless it is specifically described that an alkenylene is unbranched, e.g., $C_2$-$C_{12}$ unbranched alkylene, the term "alkenylene" as used herein applies to both branched and unbranched alkenylene groups. Exemplary alkenylene groups include, but are not limited to, $C_2$-$C_{12}$ alkenylene, $C_2$-$C_9$ alkenylene, $C_2$-$C_8$ alkenylene, $C_2$-$C_6$ alkenylene, $C_3$-$C_7$ alkenylene, $C_5$-$C_7$ alkenylene, $C_2$-$C_4$ alkenylene, $C_1$-$C_8$ alkylene, $C_2$-$C_8$ alkylene, $C_3$-$C_7$ alkylene, $C_5$-$C_7$ alkylene, $C_7$ alkylene, $C_5$ alkylene, and a corresponding alkenyl to any of the exemplary alkyl groups described above that contain two carbon atoms and above.

The term "pharmaceutically acceptable salt" as used herein refers to pharmaceutically acceptable organic or inorganic salts of a cationic lipid of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

As used in this specification and the appended claims, the term "about," when referring to a measurable value such as an amount, a temporal duration, and the like, is meant to encompass variations of ±20% or ±10%, or ±5%, or ±1%, or ±0.5%, and still more preferably ±0.1% from the specified value, as such variations are appropriate to perform the disclosed methods.

As used herein, "comprise," "comprising," and "comprises" and "comprised of" are meant to be synonymous with "include", "including", "includes" or "contain", "containing", "contains" and are inclusive or open-ended terms that specify the presence of what follows, e.g. component and do not exclude or preclude the presence of additional, non-recited components, features, element, members, steps, known in the art or disclosed therein.

The term "consisting of" refers to compositions, methods, processes, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein the terms, "administration," "administering" and variants thereof refers to introducing a composition or agent (e.g., nucleic acids, in particular ceDNA) into a subject and includes concurrent and sequential introduction of one or more compositions or agents. The introduction of a composition or agent into a subject is by any suitable route, including orally, pulmonarily, intranasally, parenterally (intravenously, intramuscularly, intraperitoneally, or subcutaneously), rectally, intralymphatically, intratumorally, or topically. Administration includes self-administration and the administration by another. Administration can be carried out by any suitable route. A suitable route of administration allows the composition or the agent to perform its intended function. For example, if a suitable route is intravenous, the composition is administered by introducing the composition or agent into a vein of the subject. In one aspect of any of the aspects or embodiments herein, "administration" refers to therapeutic administration.

As used herein, the phrase "anti-therapeutic nucleic acid immune response", "anti-transfer vector immune response", "immune response against a therapeutic nucleic acid", "immune response against a transfer vector", or the like is meant to refer to any undesired immune response against a therapeutic nucleic acid, viral or non-viral in its origin. In some embodiments of any of the aspects and embodiments herein, the undesired immune response is an antigen-specific immune response against the viral transfer vector itself. In some embodiments of any of the aspects and embodiments herein, the immune response is specific to the transfer vector which can be double stranded DNA, single stranded RNA, or double stranded RNA. In other embodiments, the immune response is specific to a sequence of the transfer vector. In other embodiments, the immune response is specific to the CpG content of the transfer vector.

As used herein, the terms "carrier" and "excipient" are used interchangeably and are meant to include any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutically active substances is well known in the art. Supplementary active ingredients can also be incorporated into the compositions. The phrase "pharmaceutically-acceptable" refers to molecular entities and compositions that do not produce a toxic, an allergic, or similar untoward reaction when administered to a host.

As used herein, the term "ceDNA" is meant to refer to capsid-free closed-ended linear double stranded (ds) duplex DNA for non-viral gene transfer, synthetic or otherwise. Detailed description of ceDNA is described in International Patent Application No. PCT/US2017/020828, filed Mar. 3, 2017, the entire contents of which are expressly incorporated herein by reference. Certain methods for the production of ceDNA comprising various inverted terminal repeat (ITR) sequences and configurations using cell-based methods are described in Example 1 of International Patent Application Nos. PCT/US2018/049996, filed Sep. 7, 2018, and PCT/US2018/064242, filed Dec. 6, 2018, the contents of each of which are incorporated herein by reference in their entirety. Certain methods for the production of synthetic ceDNA vectors comprising various ITR sequences and configurations are described, e.g., in International Patent Application No. PCT/US2019/14122, filed Jan. 18, 2019, the entire content of which are hereby incorporated herein by reference. As used herein, the terms "ceDNA vector" and "ceDNA" are used interchangeably. According to some embodiments of any of the aspects or embodiments herein, the ceDNA is a closed-ended linear duplex (CELiD) CELiD DNA. According to some embodiments of any of the aspects or embodiments herein, the ceDNA is a DNA-based minicircle. According to some embodiments of any of the aspects or embodiments herein, the ceDNA is a minimalistic immunological-defined gene expression (MIDGE)-vector. According to some embodiments of any of the aspects or embodiments herein, the ceDNA is a ministring DNA. According to some embodiments of any of the aspects or embodiments herein, the ceDNA is a dumbbell shaped linear duplex closed-ended DNA comprising two hairpin structures of ITRs in the 5' and 3' ends of an expression cassette. According to some embodiments of any of the aspects or embodiments herein, the ceDNA is a Doggybone™ DNA.

As used herein, the term "ceDNA-bacmid" is meant to refer to an infectious baculovirus genome comprising a ceDNA genome as an intermolecular duplex that is capable of propagating in *E. coli* as a plasmid, and so can operate as a shuttle vector for baculovirus.

As used herein, the term "ceDNA-baculovirus" is meant to refer to a baculovirus that comprises a ceDNA genome as an intermolecular duplex within the baculovirus genome.

As used herein, the terms "ceDNA-baculovirus infected insect cell" and "ceDNA-BIIC" are used interchangeably and are meant to refer to an invertebrate host cell (including, but not limited to an insect cell (e.g., an Sf9 cell)) infected with a ceDNA-baculovirus.

As used herein, the term "ceDNA genome" is meant to refer to an expression cassette that further incorporates at least one inverted terminal repeat region. A ceDNA genome may further comprise one or more spacer regions. In some embodiments of any of the aspects and embodiments herein the ceDNA genome is incorporated as an intermolecular duplex polynucleotide of DNA into a plasmid or viral genome.

As used herein, the terms "DNA regulatory sequences," "control elements," and "regulatory elements," are used interchangeably herein, and are meant to refer to transcriptional and translational control sequences, such as promoters, enhancers, polyadenylation signals, terminators, protein degradation signals, and the like, that provide for and/or regulate transcription of a non-coding sequence (e.g., DNA-targeting RNA) or a coding sequence (e.g., site-directed modifying polypeptide, or Cas9/Csn1 polypeptide) and/or regulate translation of an encoded polypeptide.

As used herein, the term "exogenous" is meant to refer to a substance present in a cell other than its native source. The term "exogenous" when used herein can refer to a nucleic acid (e.g., a nucleic acid encoding a polypeptide) or a polypeptide that has been introduced by a process involving the hand of man into a biological system such as a cell or organism in which it is not normally found, and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, as used herein, the term "endogenous" refers to a substance that is native to the biological system or cell.

As used herein, the term "expression" is meant to refer to the cellular processes involved in producing RNA and proteins and as appropriate, secreting proteins, including where applicable, but not limited to, for example, transcription, transcript processing, translation and protein folding, modification and processing. As used herein, the phrase "expression products" include RNA transcribed from a gene (e.g., transgene), and polypeptides obtained by translation of mRNA transcribed from a gene.

As used herein, the term "expression vector" is meant to refer to a vector that directs expression of an RNA or polypeptide from sequences linked to transcriptional regulatory sequences on the vector. The sequences expressed will often, but not necessarily, be heterologous to the host cell. An expression vector may comprise additional elements, for example, the expression vector may have two replication systems, thus allowing it to be maintained in two organisms, for example in human cells for expression and in a prokaryotic host for cloning and amplification. The expression vector may be a recombinant vector.

As used herein, the terms "expression cassette" and "expression unit" are used interchangeably and are meant to refer to a heterologous DNA sequence that is operably linked to a promoter or other DNA regulatory sequence sufficient to direct transcription of a transgene of a DNA vector, e.g., synthetic AAV vector. Suitable promoters include, for example, tissue specific promoters. Promoters can also be of AAV origin.

As used herein, the term "flanking" is meant to refer to a relative position of one nucleic acid sequence with respect to another nucleic acid sequence. Generally, in the sequence ABC, B is flanked by A and C. The same is true for the arrangement A×B×C. Thus, a flanking sequence precedes or follows a flanked sequence but need not be contiguous with, or immediately adjacent to the flanked sequence. In one embodiment of any of the aspects or embodiments herein, the term flanking refers to terminal repeats at each end of the linear single strand synthetic AAV vector.

As used herein, the term "gene" is used broadly to refer to any segment of nucleic acid associated with expression of a given RNA or protein, in vitro or in vivo. Thus, genes include regions encoding expressed RNAs (which typically include polypeptide coding sequences) and, often, the regulatory sequences required for their expression. Genes can be obtained from a variety of sources, including cloning from a source of interest, or synthesizing from known or predicted sequence information, and may include sequences designed to have specifically desired parameters.

As used herein, the phrase "genetic disease" or "genetic disorder" is meant to refer to a disease or deficiency, partially or completely, directly, or indirectly, caused by one or more abnormalities in the genome, including and especially a condition that is present from birth. The abnormality may be a mutation, an insertion, or a deletion in a gene. The abnormality may affect the coding sequence of the gene or its regulatory sequence.

As used herein, the term "heterologous," is meant to refer to a nucleotide or polypeptide sequence that is not found in the native nucleic acid or protein, respectively. A heterologous nucleic acid sequence may be linked to a naturally occurring nucleic acid sequence (or a variant thereof) (e.g., by genetic engineering) to generate a chimeric nucleotide sequence encoding a chimeric polypeptide. A heterologous nucleic acid sequence may be linked to a variant polypeptide (e.g., by genetic engineering) to generate a nucleotide sequence encoding a fusion variant polypeptide.

As used herein, the term "host cell" refers to any cell type that is susceptible to transformation, transfection, transduction, and the like with nucleic acid therapeutics of the present disclosure. As non-limiting examples, a host cell can be an isolated primary cell, pluripotent stem cells, $CD34^+$ cells, induced pluripotent stem cells, or any number of immortalized cell lines (e.g., HepG2 cells). Alternatively, a host cell can be an in situ or in vivo cell in a tissue, organ, or organism. Furthermore, a host cell can be a target cell of, for example, a mammalian subject (e.g., human patient in need of gene therapy).

As used herein, an "inducible promoter" is meant to refer to a promoter that is capable of initiating or enhancing transcriptional activity when in the presence of, influenced by, or contacted by an inducer or inducing agent. An "inducer" or "inducing agent," as used herein, can be endogenous, or a normally exogenous compound or protein that is administered in such a way as to be active in inducing transcriptional activity from the inducible promoter. In some embodiments of any of the aspects and embodiments herein, the inducer or inducing agent, i.e., a chemical, a compound, or a protein, can itself be the result of transcription or expression of a nucleic acid sequence (i.e., an inducer can be an inducer protein expressed by another component or module), which itself can be under the control or an inducible promoter. In some embodiments of any of the aspects and embodiments herein, an inducible promoter is induced in the absence of certain agents, such as a repressor. Examples of inducible promoters include but are not limited to, tetracycline, metallothionine, ecdysone, mammalian viruses (e.g., the adenovirus late promoter; and the mouse mammary tumor virus long terminal repeat (MMTV-LTR)) and other steroid-responsive promoters, rapamycin responsive promoters and the like.

As used herein, the term "in vitro" is meant to refer to assays and methods that do not require the presence of a cell with an intact membrane, such as cellular extracts, and can refer to the introducing of a programmable synthetic biological circuit in a non-cellular system, such as a medium not comprising cells or cellular systems, such as cellular extracts.

As used herein, the term "in vivo" is meant to refer to assays or processes that occur in or within an organism, such as a multicellular animal. In some of the aspects described herein, a method or use can be said to occur "in vivo" when a unicellular organism, such as a bacterium, is used. The term "ex vivo" refers to methods and uses that are performed using a living cell with an intact membrane that is outside of the body of a multicellular animal or plant, e.g., explants, cultured cells, including primary cells and cell lines, transformed cell lines, and extracted tissue or cells, including blood cells, among others.

As used herein, the term "lipid" is meant to refer to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

As used herein, the term "encapsulated" is meant to refer to a lipid particle that provides an active agent or therapeutic agent, such as a nucleic acid (e.g., an ASO, mRNA, siRNA, ceDNA, viral vector), with full encapsulation, partial encapsulation, or both. In a preferred embodiment, the nucleic acid is fully encapsulated in the lipid particle (e.g., to form a nucleic acid containing lipid particle).

As used herein, the terms "lipid particle" or "lipid nanoparticle" is meant to refer to a lipid formulation that can be used to deliver a therapeutic agent such as nucleic acid therapeutics (TNA) to a target site of interest (e.g., cell, tissue, organ, and the like) (referred to as "TNA lipid particle", "TNA lipid nanoparticle" or "TNA LNP"). In one embodiment of any of the aspects or embodiments herein, the lipid particle of the invention is a LNP containing one or more therapeutic nucleic acids, wherein the LNP is typically composed of a cationic lipid, a sterol, a non-cationic lipid, and optionally a PEGylated lipid that prevents aggregation of the particle, and further optionally a tissue-specific targeting ligand for the delivery of the LNP to a target site of interest. In other preferred embodiments, a therapeutic agent such as a therapeutic nucleic acid may be encapsulated in the lipid portion of the particle, thereby protecting it from enzymatic degradation. In one embodiment of any of the aspects or embodiments herein, the LNP comprises a nucleic acid (e.g., ceDNA) and LNP formulated with a cationic lipid described herein.

As used herein, the term "ionizable lipid" is meant to refer to a lipid, e.g., "cationic lipid," having at least one protonatable or deprotonatable group, such that the lipid is positively charged at a pH at or below physiological pH (e.g., pH 7.4), and neutral at a second pH, preferably at or above physiological pH. It will be understood by one of ordinary skill in the art that the addition or removal of protons as a function of pH is an equilibrium process, and that the reference to a charged or a neutral lipid refers to the nature of the predominant species and does not require that all lipids be present in the charged or neutral form. Generally, cationic lipids have a pKa of the protonatable group in the range of about 4 to about 7. Accordingly, the term "cationic" as used herein encompasses both ionized (or charged) and neutral forms of the lipids of the invention.

As used herein, the term "neutral lipid" is meant to refer to any lipid species that exists either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

As used herein, the term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

As used herein, the term "non-cationic lipid" is meant to refer to any amphipathic lipid as well as any other neutral lipid or anionic lipid.

As used herein, the term "organic lipid solution" is meant to refer to a composition comprising in whole, or in part, an organic solvent having a lipid.

As used herein, the term "liposome" is meant to refer to lipid molecules assembled in a spherical configuration encapsulating an interior aqueous volume that is segregated from an aqueous exterior. Liposomes are vesicles that possess at least one lipid bilayer. Liposomes are typical used as carriers for drug/therapeutic delivery in the context of pharmaceutical development. They work by fusing with a cellular membrane and repositioning its lipid structure to deliver a drug or active pharmaceutical ingredient. Liposome compositions for such delivery are typically composed of phospholipids, especially compounds having a phosphatidylcholine group, however these compositions may also include other lipids.

As used herein, the term "local delivery" is meant to refer to delivery of an active agent such as an interfering RNA (e.g., siRNA) directly to a target site within an organism. For example, an agent can be locally delivered by direct injection into a disease site such as a tumor or other target site such as a site of inflammation or a target organ such as the liver, heart, pancreas, kidney, and the like.

As used herein, the term "neDNA" or "nicked ceDNA" is meant to refer to a closed-ended DNA having a nick or a gap of 2-100 base pairs in a stem region or spacer region 5' upstream of an open reading frame (e.g., a promoter and transgene to be expressed).

As used herein, the term "nucleic acid," is meant to refer to a polymer containing at least two nucleotides (i.e., deoxyribonucleotides or ribonucleotides) in either single- or double-stranded form and includes DNA, RNA, and hybrids thereof. DNA may be in the form of, e.g., antisense molecules, plasmid DNA, DNA-DNA duplexes, pre-condensed DNA, PCR products, vectors (P1, PAC, BAC, YAC, artificial chromosomes), expression cassettes, chimeric sequences, chromosomal DNA, or derivatives and combinations of these groups. DNA may be in the form of minicircle, plasmid, bacmid, minigene, ministring DNA (linear covalently closed DNA vector), closed-ended linear duplex DNA (CELiD or ceDNA), Doggybone™ DNA, dumbbell shaped DNA, minimalistic immunological-defined gene expression (MIDGE)-vector, viral vector or non-viral vectors. RNA may be in the form of small interfering RNA (siRNA), Dicer-substrate dsRNA, small hairpin RNA (shRNA), asymmetrical interfering RNA (aiRNA), microRNA (miRNA), mRNA, rRNA, tRNA, viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs and/or modified residues include, without limitation, phosphorothioates, phosphorodiamidate morpholino oligomer (morpholino), phosphoramidates, methyl phosphonates, chiral-methyl phosphonates, 2'-O-methyl ribonucleotides, locked nucleic acid (LNA™), and peptide nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated.

As used herein, the phrases "nucleic acid therapeutics", "therapeutic nucleic acid" and "TNA" are used interchangeably and refer to any modality of therapeutic using nucleic acids as an active component of therapeutic agent to treat a disease or disorder. As used herein, these phrases refer to RNA-based therapeutics and DNA-based therapeutics. Non-limiting examples of RNA-based therapeutics include mRNA, antisense RNA and oligonucleotides, ribozymes, aptamers, interfering RNAs (RNAi), dicer-substrate dsRNA, small hairpin RNA (shRNA), asymmetrical interfering RNA (aiRNA), and microRNA (miRNA). Non-limiting examples of DNA-based therapeutics include minicircle DNA, minigene, viral DNA (e.g., Lentiviral or AAV genome) or non-viral DNA vectors, closed-ended linear duplex DNA (ceDNA/CELiD), plasmids, bacmids, Doggybone™ DNA vectors, minimalistic immunological-defined gene expression (MIDGE)-vector, nonviral ministring DNA vector (linear-covalently closed DNA vector), and dumbbell-shaped DNA minimal vector ("dumbbell DNA"). As used herein, the term "TNA LNP" refers to a lipid particle containing at least one of the TNA as described above.

As used herein, "nucleotides" contain a sugar deoxyribose (DNA) or ribose (RNA), a base, and a phosphate group. Nucleotides are linked together through the phosphate groups.

As used herein, "operably linked" is meant to refer to a juxtaposition wherein the components so described are in a relationship permitting them to function in their intended manner. For instance, a promoter is operably linked to a coding sequence if the promoter affects its transcription or expression. A promoter can be said to drive expression or drive transcription of the nucleic acid sequence that it regulates. The phrases "operably linked," "operatively positioned," "operatively linked," "under control," and "under transcriptional control" indicate that a promoter is in a correct functional location and/or orientation in relation to a nucleic acid sequence it regulates to control transcriptional initiation and/or expression of that sequence. An "inverted promoter," as used herein, refers to a promoter in which the nucleic acid sequence is in the reverse orientation, such that what was the coding strand is now the non-coding strand, and vice versa. Inverted promoter sequences can be used in various embodiments to regulate the state of a switch. In addition, in various embodiments, a promoter can be used in conjunction with an enhancer.

As used herein, the term "promoter" is meant to refer to any nucleic acid sequence that regulates the expression of another nucleic acid sequence by driving transcription of the nucleic acid sequence, which can be a heterologous target gene encoding a protein or an RNA. Promoters can be constitutive, inducible, repressible, tissue-specific, or any combination thereof. A promoter is a control region of a nucleic acid sequence at which initiation and rate of transcription of the remainder of a nucleic acid sequence are controlled. A promoter can also contain genetic elements at which regulatory proteins and molecules can bind, such as RNA polymerase and other transcription factors. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the expression of transgenes in the synthetic AAV vectors disclosed herein. A promoter sequence may be bounded at its 3' terminus by the transcription initiation site and extends upstream (5' direction) to include the minimum number of bases or elements necessary to initiate transcription at levels detectable above background.

A promoter can be one naturally associated with a gene or sequence, as can be obtained by isolating the 5' non-coding sequences located upstream of the coding segment and/or exon of a given gene or sequence. Such a promoter can be referred to as "endogenous." Similarly, in some embodiments of any of the aspects and embodiments herein, an enhancer can be one naturally associated with a nucleic acid sequence, located either downstream or upstream of that sequence. In some embodiments of any of the aspects and embodiments herein, a coding nucleic acid segment is positioned under the control of a "recombinant promoter" or "heterologous promoter," both of which refer to a promoter that is not normally associated with the encoded nucleic acid sequence that it is operably linked to in its natural environment. Similarly, a "recombinant or heterologous enhancer" refers to an enhancer not normally associated with a given nucleic acid sequence in its natural environment. Such promoters or enhancers can include promoters or enhancers of other genes; promoters or enhancers isolated from any other prokaryotic, viral, or eukaryotic cell; and synthetic promoters or enhancers that are not "naturally occurring," i.e., comprise different elements of different transcriptional regulatory regions, and/or mutations that alter expression through methods of genetic engineering that are known in the art. In addition to producing nucleic acid sequences of promoters and enhancers synthetically, promoter sequences can be produced using recombinant cloning and/or nucleic acid amplification technology, including PCR, in connection with the synthetic biological circuits and modules disclosed herein (see, e.g., U.S. Pat. Nos. 4,683,202, 5,928,906, each incorporated herein by reference in its entirety). Furthermore, it is contemplated that control sequences that direct transcription and/or expression of sequences within non-nuclear organelles such as mitochondria, chloroplasts, and the like, can be employed as well.

As used herein, the terms "Rep binding site" ("RBS") and "Rep binding element" ("RBE") are used interchangeably and are meant to refer to a binding site for Rep protein (e.g., AAV Rep 78 or AAV Rep 68) which upon binding by a Rep protein permits the Rep protein to perform its site-specific endonuclease activity on the sequence incorporating the RBS. An RBS sequence and its inverse complement together form a single RBS. RBS sequences are well known in the art, and include, for example, 5'-GCGCGCTCGCTCGCTC-3', an RBS sequence identified in AAV2.

As used herein, the phrase "recombinant vector" is meant to refer to a vector that includes a heterologous nucleic acid sequence, or "transgene" that is capable of expression in vivo. It is to be understood that the vectors described herein can, in some embodiments of any of the aspects and embodiments herein, be combined with other suitable compositions and therapies. In some embodiments of any of the aspects and embodiments herein, the vector is episomal. The use of a suitable episomal vector provides a means of maintaining the nucleotide of interest in the subject in high copy number extra chromosomal DNA thereby eliminating potential effects of chromosomal integration.

As used herein, the term "reporter" is meant to refer to a protein that can be used to provide a detectable read-out. A reporter generally produces a measurable signal such as fluorescence, color, or luminescence. Reporter protein coding sequences encode proteins whose presence in the cell or organism is readily observed.

As used herein, the terms "sense" and "antisense" are meant to refer to the orientation of the structural element on the polynucleotide. The sense and antisense versions of an element are the reverse complement of each other.

As used herein, the term "sequence identity" is meant to refer to the relatedness between two nucleotide sequences. For purposes of the present disclosure, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows: (Identical Deoxyribonucleotides-.times.100)/(Length of Alignment-Total Number of Gaps in Alignment). The length of the alignment is preferably at least 10 nucleotides, preferably at least 25 nucleotides more preferred at least 50 nucleotides and most preferred at least 100 nucleotides.

As used herein, the term "spacer region" is meant to refer to an intervening sequence that separates functional elements in a vector or genome. In some embodiments of any of the aspects and embodiments herein, AAV spacer regions keep two functional elements at a desired distance for optimal functionality. In some embodiments of any of the aspects and embodiments herein, the spacer regions provide or add to the genetic stability of the vector or genome. In some embodiments of any of the aspects and embodiments herein, spacer regions facilitate ready genetic manipulation of the genome by providing a convenient location for cloning sites and a gap of design number of base pair. For example, in certain aspects, an oligonucleotide "polylinker" or "poly cloning site" containing several restriction endonuclease sites, or a non-open reading frame sequence designed to have no known protein (e.g., transcription factor) binding sites can be positioned in the vector or genome to separate the cis—acting factors, e.g., inserting a 6mer, 12mer, 18mer, 24mer, 48mer, 86mer, 176mer, etc.

As used herein, the term "subject" is meant to refer to a human or animal, to whom treatment, including prophylactic treatment, with the therapeutic nucleic acid according to the present invention, is provided. Usually, the animal is a vertebrate such as, but not limited to a primate, rodent, domestic animal, or game animal. Primates include but are not limited to, chimpanzees, cynomolgus monkeys, spider monkeys, and macaques, e.g., Rhesus. Rodents include mice, rats, woodchucks, ferrets, rabbits, and hamsters. Domestic and game animals include, but are not limited to, cows, horses, pigs, deer, bison, buffalo, feline species, e.g., domestic cat, canine species, e.g., dog, fox, wolf, avian species, e.g., chicken, emu, ostrich, and fish, e.g., trout, catfish, and salmon. In certain embodiments of the aspects described herein, the subject is a mammal, e.g., a primate or a human. A subject can be male or female. Additionally, a subject can be an infant or a child. In some embodiments of any of the aspects and embodiments herein, the subject can be a neonate or an unborn subject, e.g., the subject is in utero. Preferably, the subject is a mammal. The mammal can be a human, non-human primate, mouse, rat, dog, cat, horse, or cow, but is not limited to these examples. Mammals other than humans can be advantageously used as subjects that represent animal models of diseases and disorders. In addition, the methods and compositions described herein can be used for domesticated animals and/or pets. A human subject can be of any age, gender, race, or ethnic group, e.g., Caucasian (white), Asian, African, black, African American, African European, Hispanic, Mideastern, etc. In some embodiments of any of the aspects and embodiments herein, the subject can be a patient or other subject in a clinical setting. In some embodiments of any of the aspects and embodiments herein, the subject is already undergoing treatment. In some embodiments of any of the aspects and embodiments herein, the subject is an embryo, a fetus, neonate, infant, child, adolescent, or adult. In some embodiments of any of the aspects and embodiments herein, the subject is a human fetus, human neonate, human infant, human child, human adolescent, or human adult. In some embodiments of any of the aspects and embodiments herein, the subject is an animal embryo, or non-human embryo or non-human primate embryo. In some embodiments of any of the aspects and embodiments herein, the subject is a human embryo.

As used herein, the phrase "subject in need" refers to a subject that (i) will be administered a TNA lipid particle (or pharmaceutical composition comprising a TNA lipid particle) according to the described invention, (ii) is receiving a TNA lipid particle (or pharmaceutical composition comprising a TNA lipid particle) according to the described invention; or (iii) has received a TNA lipid particle (or pharmaceutical composition comprising a TNA lipid particle) according to the described invention, unless the context and usage of the phrase indicates otherwise.

As used herein, the term "suppress," "decrease," "interfere," "inhibit" and/or "reduce" (and like terms) generally refers to the act of reducing, either directly or indirectly, a concentration, level, function, activity, or behavior relative to the natural, expected, or average, or relative to a control condition.

As used herein, the terms "synthetic AAV vector" and "synthetic production of AAV vector" are meant to refer to an AAV vector and synthetic production methods thereof in an entirely cell-free environment.

As used herein, the term "systemic delivery" is meant to refer to delivery of lipid particles that leads to a broad biodistribution of an active agent such as an interfering RNA (e.g., siRNA) within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles (e.g., lipid nanoparticles) can be by any means known in the art including, for example, intravenous, subcutaneous, and intraperitoneal. In a preferred embodiment, systemic delivery of lipid particles (e.g., lipid nanoparticles) is by intravenous delivery.

As used herein, the terms "terminal resolution site" and "TRS" are used interchangeably herein and meant to refer to a region at which Rep forms a tyrosine-phosphodiester bond with the 5' thymidine generating a 3'-OH that serves as a substrate for DNA extension via a cellular DNA polymerase, e.g., DNA pol delta or DNA pol epsilon. Alternatively, the Rep-thymidine complex may participate in a coordinated ligation reaction.

As used herein, the terms "therapeutic amount", "therapeutically effective amount", an "amount effective", "effective amount", or "pharmaceutically effective amount" of an active agent (e.g., a TNA lipid particle as described herein) are used interchangeably to refer to an amount that is sufficient to provide the intended benefit of treatment or effect e.g., inhibition of expression of a target sequence in comparison to the expression level detected in the absence of a therapeutic nucleic acid. Suitable assays for measuring expression of a target gene or target sequence include, e.g., examination of protein or RNA levels using techniques known to those of skill in the art such as dot blots, northern blots, in situ hybridization, ELISA, immunoprecipitation, enzyme function, as well as phenotypic assays known to those of skill in the art. Dosage levels are based on a variety of factors, including the type of injury, the age, weight, sex, medical condition of the patient, the severity of the condition, the route of administration, and the particular active agent employed. Thus, the dosage regimen may vary widely, but can be determined routinely by a physician using standard methods. Additionally, the terms "therapeutic amount," "effective amount," "therapeutically effective amount" and "pharmaceutically effective amount" include prophylactic or preventative amounts of the compositions of the described invention. In prophylactic or preventative applications of the described invention, pharmaceutical compositions or medicaments are administered to a patient susceptible to, or otherwise at risk of, a disease, disorder or condition in an amount sufficient to eliminate or reduce the risk, lessen the severity, or delay the onset of the disease, disorder or condition, including biochemical, histologic and/or behavioral symptoms of the disease, disorder or condition, its complications, and intermediate pathological phenotypes presenting during development of the disease, disorder or condition. It is generally preferred that a maximum dose be used, that is, the highest safe dose according to some medical judgment. The terms "dose" and "dosage" are used interchangeably herein. In one aspect of any of the aspects or embodiments herein, "therapeutic amount", "therapeutically effective amounts" and "pharmaceutically effective amounts" refer to non-prophylactic or non-preventative applications.

As used herein the term "therapeutic effect" refers to a consequence of treatment, the results of which are judged to be desirable and beneficial. A therapeutic effect can include, directly or indirectly, the arrest, reduction, or elimination of a disease manifestation. A therapeutic effect can also include, directly or indirectly, the arrest reduction or elimination of the progression of a disease manifestation.

For any therapeutic agent described herein therapeutically effective amount may be initially determined from preliminary in vitro studies and/or animal models. A therapeutically effective dose may also be determined from human data. The applied dose may be adjusted based on the relative bioavailability and potency of the administered compound. Adjusting the dose to achieve maximal efficacy based on the methods described above and other well-known methods is within the capabilities of the ordinarily skilled artisan. General principles for determining therapeutic effectiveness, which may be found in Chapter 1 of Goodman and Gilman's The Pharmacological Basis of Therapeutics, 10th Edition, McGraw-Hill (New York) (2001), incorporated herein by reference, are summarized below.

Pharmacokinetic principles provide a basis for modifying a dosage regimen to obtain a desired degree of therapeutic efficacy with a minimum of unacceptable adverse effects. In situations where the drug's plasma concentration can be measured and related to therapeutic window, additional guidance for dosage modification can be obtained.

As used herein, the terms "treat," "treating," and/or "treatment" include abrogating, inhibiting, slowing, or reversing the progression of a condition, ameliorating clinical symptoms of a condition, or preventing the appearance of clinical symptoms of a condition, obtaining beneficial or desired clinical results. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s). In one aspect of any of the aspects or embodiments herein, the terms "treat," "treating," and/or "treatment" include abrogating, inhibiting, slowing or reversing the progression of a condition, or ameliorating clinical symptoms of a condition.

Beneficial or desired clinical results, such as pharmacologic and/or physiologic effects include, but are not limited to, preventing the disease, disorder or condition from occurring in a subject that may be predisposed to the disease, disorder or condition but does not yet experience or exhibit symptoms of the disease (prophylactic treatment), alleviation of symptoms of the disease, disorder or condition, diminishment of extent of the disease, disorder or condition, stabilization (i.e., not worsening) of the disease, disorder or condition, preventing spread of the disease, disorder or condition, delaying or slowing of the disease, disorder or condition progression, amelioration or palliation of the disease, disorder or condition, and combinations thereof, as well as prolonging survival as compared to expected survival if not receiving treatment.

As used herein, the terms "vector" or "expression vector" are meant to refer to a replicon, such as plasmid, bacmid, phage, virus, virion, or cosmid, to which another DNA segment, i.e., an "insert" "transgene" or "expression cassette", may be attached, so as to bring about the expression or replication of the attached segment ("expression cassette") in a cell. A vector can be a nucleic acid construct designed for delivery to a host cell or for transfer between different host cells. As used herein, a vector can be viral or non-viral in origin in the final form. However, for the purpose of the present disclosure, a "vector" generally refers to synthetic AAV vector or a nicked ceDNA vector. Accordingly, the term "vector" encompasses any genetic element that is capable of replication when associated with the proper control elements and that can transfer gene sequences to cells. In some embodiments of any of the aspects and embodiments herein, a vector can be a recombinant vector or an expression vector.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

II. Lipids

In a first embodiment, provided are cationic lipids represented by Formula I:

I

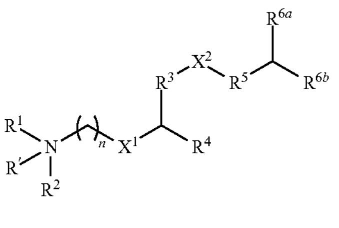

or a pharmaceutically acceptable salt thereof, wherein:

R' is absent, hydrogen, or $C_1$-$C_6$ alkyl; provided that when R' is hydrogen or $C_1$-$C_6$ alkyl, the nitrogen atom to which R', $R^1$, and $R^2$ are all attached is protonated;

$R^1$ and $R^2$ are each independently hydrogen or $C_1$-$C_6$ alkyl;

$R^3$ is $C_1$-$C_{12}$ alkylene or $C_2$-$C_{12}$ alkenylene;

$R^4$ is $C_1$-$C_{16}$ unbranched alkyl, $C_2$-$C_{16}$ unbranched alkenyl, or

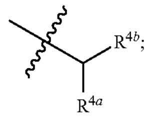

wherein:

$R^{4a}$ and $R^{4b}$ are each independently $C_1$-$C_{16}$ unbranched alkyl or $C_2$-$C_{16}$ unbranched alkenyl;

$R^5$ is absent, $C_1$-$C_8$ alkylene, or $C_2$-$C_8$ alkenylene;

$R^{6a}$ and $R^{6b}$ are each independently $C_7$-$C_{16}$ alkyl or $C_7$-$C_{16}$ alkenyl; provided that the total number of carbon atoms in $R^{6a}$ and $R^{6b}$ as combined is greater than 15;

$X^1$ and $X^2$ are each independently —OC(═O)—, —SC(═O)—, —OC(═S)—, —C(═O)O—, —C(═O)S—, —S—S—, —C($R^a$)═N—, —N═C($R^a$)—, —C($R^a$)═NO—, —O—N═C($R^a$)—, —C(═O)N$R^a$—, —N$R^a$C(═O)—, —N$R^a$C(═O)N$R^a$—, —OC(═O)O—, —OSi$(R^a)_2$O—, —C(═O)(C$R^{a2}$)C(═O)O—, or OC(═O)(C$R^{a2}$)C(═O)—; wherein:

$R^a$, for each occurrence, is independently hydrogen or $C_1$-$C_6$ alkyl; and n is an integer selected from 1, 2, 3, 4, 5, and 6.

In a second embodiment, in the cationic lipid according to the first embodiment, or a pharmaceutically acceptable salt thereof, $X^1$ and $X^2$ are the same; and all other remaining variables are as described for Formula I or the first embodiment.

In a third embodiment, in the cationic lipid according to the first or second embodiment, or a pharmaceutically acceptable salt thereof, $X^1$ and $X^2$ are each independently —OC(═O)—, —SC(═O)—, —OC(═S)—, —C(═O)O—, —C(═O)S—, or —S—S—; or $X^1$ and $X^2$ are each independently —C(═O)O—, —C(═O)S—, or —S—S—; or $X^1$ and $X^2$ are each independently —C(═O)O— or —S—S—; and all other remaining variables are as described for Formula I or any one of the preceding embodiments.

In a fourth embodiment, the cationic lipid of the present disclosure is represented by Formula II:

II

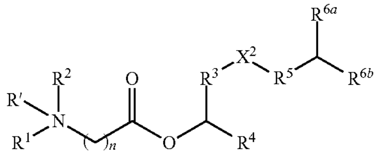

or a pharmaceutically acceptable salt thereof, wherein n is an integer selected from 1, 2, 3, and 4; and all other remaining variables are as described for Formula I or any one of the preceding embodiments.

In a fifth embodiment, the cationic lipid of the present disclosure is represented by Formula III:

III

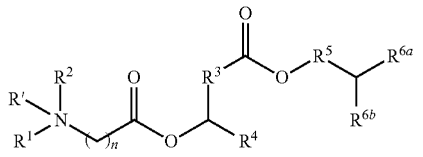

or a pharmaceutically acceptable salt thereof, wherein n is an integer selected from 1, 2, and 3; and all other remaining variables are as described for Formula I, Formula II or any one of the preceding embodiments.

In a sixth embodiment, the cationic lipid of the present disclosure is represented by Formula IV:

IV

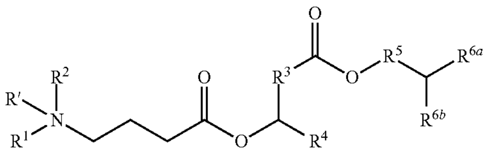

or a pharmaceutically acceptable salt thereof; and all other remaining variables are as described for Formula I, Formula II, Formula III or any one of the preceding embodiments.

In a seventh embodiment, in the cationic lipid according to Formula I, Formula II, Formula III, Formula IV or any one of the preceding embodiments, or a pharmaceutically acceptable salt thereof, $R^1$ and $R^2$ are each independently hydrogen, $C_1$-$C_6$ alkyl or $C_2$-$C_6$ alkenyl, or $C_1$-$C_5$ alkyl or $C_2$-$C_5$ alkenyl, or $C_1$-$C_4$ alkyl or $C_2$-$C_4$ alkenyl, or $C_1$-$C_3$ alkyl or $C_2$-$C_3$ alkenyl, or $C_1$-$C_2$ alkyl, or $C_6$ alkyl, or $C_5$ alkyl, or $C_4$ alkyl, or $C_3$ alkyl, or $C_2$ alkyl, or $C_1$ alkyl, or $C_6$ alkenyl, or $C_5$ alkenyl, or $C_4$ alkenyl, or $C_3$ alkenyl, or $C_2$ alkenyl; and all other remaining variables are as described for Formula I, Formula II, Formula III, Formula IV or any one of the preceding embodiments.

In an eighth embodiment, the cationic lipid of the present disclosure is represented by Formula V:

V

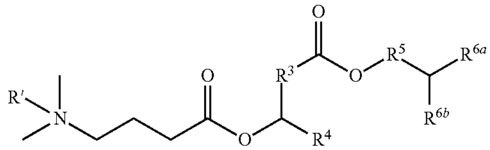

or a pharmaceutically acceptable salt thereof; and all other remaining variables are as described for Formula I, Formula II, Formula III, Formula IV or any one of the preceding embodiments.

In a ninth embodiment, in the cationic lipid according to Formula I, Formula II, Formula III, Formula IV, Formula V or any one of the preceding embodiments, or a pharmaceutically acceptable salt thereof, $R^3$ is $C_1$-$C_9$ alkylene or $C_2$-$C_9$ alkenylene, $C_1$-$C_7$ alkylene or $C_2$-$C_7$ alkenylene, $C_1$-$C_5$ alkylene or $C_2$-$C_5$ alkenylene, or $C_2$-$C_8$ alkylene or $C_2$-$C_8$ alkenylene, or $C_3$-$C_7$ alkylene or $C_3$-$C_7$ alkenylene, or $C_5$-$C_7$ alkylene or $C_5$-$C_7$ alkenylene; or $R^3$ is $C_{12}$ alkylene, $C_{11}$ alkylene, $C_{10}$ alkylene, $C_9$ alkylene, or $C_8$ alkylene, or $C_7$ alkylene, or $C_6$ alkylene, or $C_5$ alkylene, or $C_4$ alkylene, or $C_3$ alkylene, or $C_2$ alkylene, or $C_1$ alkylene, or $C_{12}$ alkenylene, $C_{11}$ alkenylene, $C_{10}$ alkenylene, $C_9$ alkenylene, or $C_8$ alkenylene, or $C_7$ alkenylene, or $C_6$ alkenylene, or $C_5$ alkenylene, or $C_4$ alkenylene, or $C_3$ alkenylene, or $C_2$ alkenylene; and all other remaining variables are as described for Formula I, Formula II, Formula III, Formula IV, Formula V or any one of the preceding embodiments. Alternatively, as part of a ninth embodiment, in the cationic lipid according to Formula I, Formula II, Formula III, Formula IV, Formula V or any one of the preceding embodiments, or a pharmaceutically acceptable salt thereof, $R^3$ is $C_1$-$C_9$ alkylene or $C_2$-$C_9$ alkenylene, $C_1$-$C_7$ alkylene or $C_2$-$C_7$ alkenylene, $C_1$-$C_6$ alkylene or $C_2$-$C_6$ alkenylene, $C_1$-$C_5$ alkylene or $C_2$-$C_8$ alkenylene, or $C_2$-$C_8$ alkylene or $C_2$-$C_8$ alkenylene, or $C_3$-$C_7$ alkylene or $C_3$-$C_7$ alkenylene, or $C_5$-$C_7$ alkylene or $C_5$-$C_7$ alkenylene; or $R^3$ is $C_{12}$ alkylene, $C_{11}$ alkylene, $C_{10}$ alkylene, $C_9$ alkylene, or $C_8$ alkylene, or $C_7$ alkylene, or $C_6$ alkylene, or $C_5$ alkylene, or $C_4$ alkylene, or $C_3$ alkylene, or $C_2$ alkylene, or $C_1$ alkylene, or $C_{12}$ alkenylene, $C_{11}$ alkenylene, $C_{10}$ alkenylene, $C_9$ alkenylene, or $C_8$ alkenylene, or $C_7$ alkenylene, or $C_6$ alkenylene, or $C_5$ alkenylene, or $C_4$ alkenylene, or $C_3$ alkenylene, or $C_2$ alkenylene; and all other remaining variables are as described for Formula I, Formula II, Formula III, Formula IV, Formula V or any one of the preceding embodiments.

In a tenth embodiment, in the cationic lipid according to Formula I, Formula II, Formula III, Formula IV, Formula V or any one of the preceding embodiments, or a pharmaceutically acceptable salt thereof, $R^5$ is absent, $C_1$-$C_6$ alkylene, or $C_2$-$C_6$ alkenylene; or $R^5$ is absent, $C_1$-$C_4$ alkylene, or $C_2$-$C_4$ alkenylene; or $R^5$ is absent; or $R^5$ is $C^8$ alkylene, $C_7$ alkylene, $C_6$ alkylene, $C_5$ alkylene, $C_4$ alkylene, $C_3$ alkylene, $C_2$ alkylene, $C_1$ alkylene, $C_8$ alkenylene, $C_7$ alkenylene, $C_6$ alkenylene, $C_5$ alkenylene, $C_4$ alkenylene, $C_3$ alkenylene, or $C_2$ alkenylene; and all other remaining variables are as described for Formula I, Formula II, Formula III, Formula IV, Formula V or any one of the preceding embodiments.

In an eleventh embodiment, in the cationic lipid according to Formula I, Formula II, Formula III, Formula IV, Formula V or any one of the preceding embodiments, or a pharmaceutically acceptable salt thereof, $R^4$ is $C_1$-$C_{14}$ unbranched alkyl, $C_2$-$C_{14}$ unbranched alkenyl, or

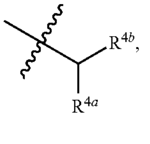

wherein $R^{4a}$ and $R^{4b}$ are each independently $C_1$-$C_{12}$ unbranched alkyl or $C_2$-$C_{12}$ unbranched alkenyl; or $R^4$ is $C_2$-$C_{12}$ unbranched alkyl or $C_2$-$C_{12}$ unbranched alkenyl; or $R^4$ is $C_2$-$C_7$ unbranched alkyl or $C_2$-$C_7$ unbranched alkenyl; or $R^4$ is $C_3$-$C_7$ unbranched alkyl or $C_3$-$C_7$ unbranched alkenyl; or $R^4$ is $C_4$-$C_7$ unbranched alkyl or $C_4$-$C_7$ unbranched alkenyl; or $R^4$ is $C_5$-$C_7$ unbranched alkyl or $C_5$-$C_7$ unbranched alkenyl; or $R^4$ is $C_6$-$C_7$ unbranched alkyl or $C_6$-$C_7$ unbranched alkenyl; or $R^4$ is $C_{16}$ unbranched alkyl, $C_{15}$ unbranched alkyl, $C_{14}$ unbranched alkyl, $C_{13}$ unbranched alkyl, $C_{12}$ unbranched alkyl, $C_{11}$ unbranched alkyl, $C_{10}$ unbranched alkyl, $C_9$ unbranched alkyl, $C_8$ unbranched alkyl, $C_7$ unbranched alkyl, $C_6$ unbranched alkyl, $C_5$ unbranched alkyl, $C_4$ unbranched alkyl, $C_3$ unbranched alkyl, $C_2$ unbranched alkyl, $C_1$ unbranched alkyl, $C_{16}$ unbranched alkenyl, $C_{15}$ unbranched alkenyl, $C_{14}$ unbranched alkenyl, $C_{13}$ unbranched alkenyl, $C_{12}$ unbranched alkenyl, $C_{11}$ unbranched alkenyl, $C_{10}$ unbranched alkenyl, $C_9$ unbranched alkenyl, $C_8$ unbranched alkenyl, $C_7$ unbranched alkenyl, $C_6$ unbranched alkenyl, $C_5$ unbranched alkenyl, $C_4$ unbranched alkenyl, $C_3$ unbranched alkenyl, or $C_2$ alkenyl; or $R^4$ is

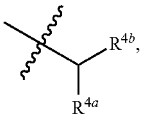

wherein $R^{4a}$ and $R^{4b}$ are each independently $C_2$-$C_{10}$ unbranched alkyl or $C_2$-$C_{10}$ unbranched alkenyl; or $R^4$ is

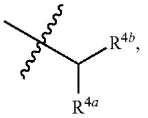

wherein $R^{4a}$ and $R^{4b}$ are each independently $C_{16}$ unbranched alkyl, $C_{15}$ unbranched alkyl, $C_{14}$ unbranched alkyl, $C_{13}$ unbranched alkyl, $C_{12}$ unbranched alkyl, $C_{11}$ unbranched alkyl, $C_{10}$ unbranched alkyl, $C_9$ unbranched alkyl, $C_8$ unbranched alkyl, $C_7$ unbranched alkyl, $C_6$ unbranched alkyl, $C_5$ unbranched alkyl, $C_4$ unbranched alkyl, $C_3$ unbranched alkyl, $C_2$ alkyl, $C_1$ alkyl, $C_{16}$ unbranched alkenyl, $C_{15}$ unbranched alkenyl, $C_{14}$ unbranched alkenyl, $C_{13}$ unbranched alkenyl, $C_{12}$ unbranched alkenyl, $C_{11}$ unbranched alkenyl, $C_{10}$ unbranched alkenyl, $C_9$ unbranched alkenyl, $C_8$ unbranched alkenyl, $C_7$ unbranched alkenyl, $C_6$ unbranched alkenyl, $C_5$ unbranched alkenyl, $C_4$ unbranched alkenyl, $C_3$ unbranched alkenyl, or $C_2$ alkenyl; and all other remaining variables are as described for Formula I, Formula II, Formula III, Formula IV, Formula V or any one of the preceding embodiments.

In a twelfth embodiment, in the cationic lipid according to Formula I, Formula II, Formula III, Formula IV, Formula V or any one of the preceding embodiments, or a pharmaceutically acceptable salt thereof, $R^{6a}$ and $R^{6b}$ are each independently $C_7$-$C_{14}$ alkyl or $C_7$-$C_{14}$ alkenyl; or $R^{6a}$ and $R^{6b}$ are each independently $C_8$-$C_{12}$ alkyl or $C_8$-$C_{12}$ alkenyl; or $R^{6a}$ and $R^{6b}$ are each independently $C_{16}$ alkyl, $C_{15}$ alkyl, $C_{14}$ alkyl, $C_{13}$ alkyl, $C_{12}$ alkyl, $C_{11}$ alkyl, $C_{10}$ alkyl, $C_9$ alkyl, $C_8$ alkyl, $C_7$ alkyl, $C_{16}$ alkenyl, $C_{15}$ alkenyl, $C_{14}$ alkenyl, $C_{13}$ alkenyl, $C_{12}$ alkenyl, $C_{11}$ alkenyl, $C_{10}$ alkenyl, $C_9$ alkenyl, $C_8$ alkenyl, or $C_7$ alkenyl; provided that the total number of carbon atoms in $R^{6a}$ and $R^{6b}$ as combined is greater than 15; and all other remaining variables are as described for Formula I, Formula II, Formula III, Formula IV, Formula V or any one of the preceding embodiments.

In a thirteenth embodiment, in the cationic lipid according to Formula I, Formula II, Formula III, Formula IV, Formula V or any one of the preceding embodiments, or a pharmaceutically acceptable salt thereof, $R^{6a}$ and $R^{6b}$ are each greater than $C_8$ alkyl or $C_8$ alkenyl, i.e., $R^{6a}$ and $R^{6b}$ are each independently $C_9$-$C_{16}$ alkyl or $C_9$-$C_{16}$ alkenyl; or $R^{6a}$ and $R^{6b}$ are each independently $C_9$-$C_{15}$ alkyl or $C_9$-$C_{15}$ alkenyl; or $R^{6a}$ and $R^{6b}$ are each independently $C_9$-$C_{14}$ alkyl or $C_9$-$C_{14}$ alkenyl; or $R^{6a}$ and $R^{6b}$ are each independently $C_9$-$C_{13}$ alkyl or $C_9$-$C_{13}$ alkenyl; or $R^{6a}$ and $R^{6b}$ are each independently $C_9$-$C_{12}$ alkyl or $C_9$-$C_{12}$ alkenyl; or $R^{6a}$ and $R^{6b}$ are each independently $C_{10}$-$C_{12}$ alkyl or $C_{10}$-$C_{12}$ alkenyl; or $R^{6a}$ and $R^{6b}$ are each independently $C_{16}$ alkyl, $C_{15}$ alkyl, $C_{14}$ alkyl, $C_{13}$ alkyl, $C_{12}$ alkyl, $C_{11}$ alkyl, $C_{10}$ alkyl, $C_9$ alkyl, $C_{16}$ alkenyl, $C_{15}$ alkenyl, $C_{14}$ alkenyl, $C_{13}$ alkenyl, $C_{12}$ alkenyl, $C_{11}$ alkenyl, $C_{10}$ alkenyl, or $C_9$ alkenyl; provided that the total number of carbon atoms in $R^{6a}$ and $R^{6b}$ as combined is greater than 15; and all other remaining variables are as described for Formula I, Formula II, Formula III, Formula IV, Formula V or any one of the preceding embodiments. In a fourteenth embodiment, in the cationic lipid according to Formula I, Formula II, Formula III, Formula IV, Formula V or any one of the preceding embodiments, or a pharmaceutically acceptable salt thereof, $R^{6a}$ and $R^{6b}$ contain an equal number of carbon atoms with each other; or $R^{6a}$ and $R^{6b}$ are the same; or $R^{6a}$ and $R^{6b}$ are both $C_{16}$ alkyl, $C_{15}$ alkyl, $C_{14}$ alkyl, $C_{13}$ alkyl, $C_{12}$ alkyl, $C_{11}$ alkyl, $C_{10}$ alkyl, $C_9$ alkyl, $C_8$ alkyl, $C_7$ alkyl, $C_{16}$ alkenyl, $C_{15}$ alkenyl, $C_{14}$ alkenyl, $C_{13}$ alkenyl, $C_{12}$ alkenyl, $C_{11}$ alkenyl, $C_{10}$ alkenyl, $C_9$ alkenyl, $C_8$ alkenyl, or $C_7$ alkenyl; provided that the total number of carbon atoms in $R^{6a}$ and $R^{6b}$ as combined is greater than 15; and all other remaining variables are as described for Formula I, Formula II, Formula III, Formula IV, Formula V or any one of the preceding embodiments.

In a fifteenth embodiment, in the cationic lipid according to Formula I, Formula II, Formula III, Formula IV, Formula V or any one of the preceding embodiments, or a pharmaceutically acceptable salt thereof, $R^{6a}$ and $R^{6b}$ as defined in any one of the preceding embodiments each contain a different number of carbon atoms with each other; or the number of carbon atoms $R^{6a}$ and $R^{6b}$ differs by one or two carbon atoms; or the number of carbon atoms $R^{6a}$ and $R^{6b}$ differs by one carbon atom; or $R^{6a}$ is $C_7$ alkyl and $R^{6a}$ is $C_8$ alkyl, $R^{6a}$ is $C_8$ alkyl and $R^{6a}$ is $C_7$ alkyl, $R^{6a}$ is $C_8$ alkyl and $R^{6a}$ is $C_9$ alkyl, $R^{6a}$ is $C_9$ alkyl and $R^{6a}$ is $C_8$ alkyl, $R^{6a}$ is $C_9$ alkyl and $R^{6a}$ is $C_{10}$ alkyl, $R^{6a}$ is $C_{10}$ alkyl and $R^{6a}$ is $C_9$ alkyl, $R^{6a}$ is $C_{10}$ alkyl and $R^{6a}$ is $C_{11}$ alkyl, $R^{6a}$ is $C_{11}$ alkyl and $R^{6a}$ is $C_{10}$ alkyl, $R^{6a}$ is $C_{11}$ alkyl and $R^{6a}$ is $C_{12}$ alkyl, $R^{6a}$ is $C_{12}$ alkyl and $R^{6a}$ is $C_{11}$ alkyl, $R^{6a}$ is $C_7$ alkyl and $R^{6a}$ is $C_9$ alkyl, $R^{6a}$ is $C_9$ alkyl and $R^{6a}$ is $C_7$ alkyl, $R^{6a}$ is $C_8$ alkyl and $R^{6a}$ is $C_{10}$ alkyl, $R^{6a}$ is $C_{10}$ alkyl and $R^{6a}$ is $C_8$ alkyl, $R^{6a}$ is $C_9$ alkyl and $R^{6a}$ is $C_{11}$ alkyl, $R^{6a}$ is $C_{11}$ alkyl and $R^{6a}$ is $C_9$ alkyl, $R^{6a}$ is $C_{10}$ alkyl and $R^{6a}$ is $C_{12}$ alkyl, $R^{6a}$ is $C_{12}$ alkyl and $R^{6a}$ is $C_{10}$ alkyl, $R^{6a}$ is $C_{11}$ alkyl and $R^{6a}$ is $C_{13}$ alkyl, or $R^{6a}$ is $C_{13}$ alkyl and $R^{6a}$ is $C_{11}$ alkyl, etc.; and all other remaining variables are as described for Formula I, Formula II, Formula III, Formula IV, Formula V or any one of the preceding embodiments.

In a sixteenth embodiment, in the cationic lipid according to Formula I, Formula II, Formula III, Formula IV, Formula V or any one of the preceding embodiments, or a pharmaceutically acceptable salt thereof, R' is absent.

In a seventeenth embodiment, in the cationic lipid according to Formula I, Formula II, Formula III, Formula IV, Formula V or any one of the preceding embodiments, or a pharmaceutically acceptable salt thereof, $R^4$ is an alkyl that is no greater than $C_7$ unbranched alkyl or an alkenyl that is no greater than $C_7$ unbranched alkenyl; and $R^{6a}$ and $R^{6b}$ are each an alkyl greater than $C_8$ alkyl or an alkenyl greater than $C_8$ alkenyl; i.e., or $R^4$ is $C_2$-$C_7$ unbranched alkyl or $C_2$-$C_7$ unbranched alkenyl; or $R^4$ is $C_3$-$C_7$ unbranched alkyl or $C_3$-$C_7$ unbranched alkenyl; or $R^4$ is $C_4$-$C_7$ unbranched alkyl or $C_4$-$C_7$ unbranched alkenyl; or $R^4$ is $C_5$-$C_7$ unbranched alkyl or $C_5$-$C_7$ unbranched alkenyl; or $R^4$ is $C_6$-$C_7$ unbranched alkyl or $C_6$-$C_7$ unbranched alkenyl; or $R^4$ is $C_7$ unbranched alkyl, $C_6$ unbranched alkyl, $C_5$ unbranched alkyl, $C_4$ unbranched alkyl, $C_3$ unbranched alkyl, $C_2$ unbranched alkyl, $C_1$ unbranched alkyl, $C_7$ unbranched alkenyl, $C_6$ unbranched alkenyl, $C_5$ unbranched alkenyl, $C_4$ unbranched alkenyl, $C_3$ unbranched alkenyl, or $C_2$ alkenyl; or $R^{6a}$ and $R^{6b}$ are each independently $C_9$-$C_{16}$ alkyl or $C_9$-$C_{16}$ alkenyl; or $R^{6a}$ and $R^{6b}$ are each independently $C_9$-$C_{15}$ alkyl or $C_9$-$C_{15}$ alkenyl; or $R^{6a}$ and $R^{6b}$ are each independently $C_9$-$C_{14}$ alkyl or $C_9$-$C_{14}$ alkenyl; or $R^{6a}$ and $R^{6b}$ are each independently $C_9$-$C_{13}$ alkyl or $C_9$-$C_{13}$ alkenyl; or $R^{6a}$ and $R^{6b}$ are each independently $C_9$-$C_{12}$ alkyl or $C_9$-$C_{12}$ alkenyl; or $R^{6a}$ and $R^{6b}$ are each independently $C_{10}$-$C_{12}$ alkyl or $C_{10}$-$C_{12}$ alkenyl; or $R^{6a}$ and $R^{6b}$ are each independently $C_{16}$ alkyl, $C_{15}$ alkyl, $C_{14}$ alkyl, $C_{13}$ alkyl, $C_{12}$ alkyl, $C_{11}$ alkyl, $C_{10}$ alkyl, $C_9$ alkyl, $C_{16}$ alkenyl, $C_{15}$ alkenyl, $C_{14}$ alkenyl, $C_{13}$ alkenyl, $C_{12}$ alkenyl, $C_{11}$ alkenyl, $C_{10}$ alkenyl, or $C_9$ alkenyl; provided that the total number of carbon atoms in $R^{6a}$ and $R^{6b}$ as combined is greater than 15; and all other remaining variables are as described for Formula I, Formula II, Formula III, Formula IV, Formula V or any one of the preceding embodiments.

In some embodiments, in the cationic lipid according to Formula I, Formula II, Formula III, Formula IV, Formula V or any one of the preceding embodiments, wherein R' is hydrogen or $C_1$-$C_6$ alkyl, the nitrogen atom to which R', $R^1$, and $R^2$ are all attached is protonated in that the nitrogen atom is positively charged.

In some embodiments, in the cationic lipid according to Formula I, Formula II, Formula III, Formula IV, Formula V or any one of the preceding embodiments, wherein R', $R^1$ and $R^2$ are each $C_1$-$C_6$ alkyl, and wherein R', $R^1$ and $R^2$ together with the nitrogen atom attached thereto form a quaternary ammonium cation or a quaternary amine.

In an eighteenth embodiment, provided are cationic lipids represented by Formula Ia:

Ia

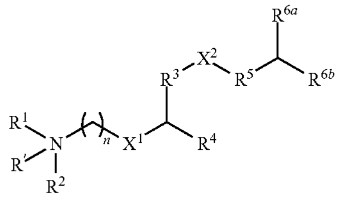

or a pharmaceutically acceptable salt thereof, wherein:

R' is absent or is $C_1$-$C_6$ alkyl;

$R^1$ and $R^2$ are each independently hydrogen or $C_1$-$C_6$ alkyl;

$R^3$ is $C_1$-$C_{12}$ alkylene or $C_2$-$C_{12}$ alkenylene;

$R^4$ is $C_1$-$C_{16}$ unbranched alkyl, $C_2$-$C_{16}$ unbranched alkenyl, or

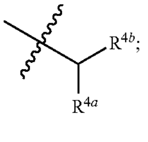

wherein:

$R^{4a}$ and $R^{4b}$ are each independently $C_1$-$C_{16}$ unbranched alkyl or $C_2$-$C_{16}$ unbranched alkenyl;

$R^5$ is absent, $C_1$-$C_8$ alkylene, or $C_2$-$C_8$ alkenylene;

$R^{6a}$ and $R^{6b}$ are each independently $C_7$-$C_{16}$ alkyl or $C_7$-$C_{16}$ alkenyl; provided that the total number of carbon atoms in $R^{6a}$ and $R^{6b}$ as combined is greater than 15;

$X^1$ and $X^2$ are each independently —OC(═O)—, —SC(═O)—, —OC(═S)—, —C(═O)O—, —C(═O)S—, —S—S—, —C($R^a$)═N—, —N═C($R^a$)—, —C($R^a$)═NO—, —O—N═C($R^a$)—, —C(═O)N$R^a$—, —N$R^a$C(═O)—, —N$R^a$C(═O)N$R^a$—, —OC(═O)O—, —OSi($R^a$)$_2$O—, —C(═O)(C$R^{a2}$)C(═O)O—, or OC(═O)(C$R^{a2}$)C(═O)—; wherein:

$R^a$, for each occurrence, is independently hydrogen or $C_1$-$C_6$ alkyl; and n is an integer selected from 1, 2, 3, 4, 5, and 6.

In a nineteenth embodiment, in the cationic lipid according to the eighteenth embodiment, or a pharmaceutically acceptable salt thereof, $X^1$ and $X^2$ in Formula Ia are the same; and all other remaining variables are as described for Formula Ia or the eighteenth embodiment.

In a twentieth embodiment, in the cationic lipid according to the eighteenth or nineteenth embodiment, or a pharmaceutically acceptable salt thereof, $X^1$ and $X^2$ in Formula Ia are each independently —OC(═O)—, —SC(═O)—, —OC(═S)—, —C(═O)O—, —C(═O)S—, or —S—S—; or $X^1$ and $X^2$ are each independently —C(═O)O—, —C(═O)S—, or —S—S—; or $X^1$ and $X^2$ are each independently —C(═O)O— or —S—S—; and all other remaining variables are as described for Formula Ia or any one of the eighteenth or nineteenth embodiments.

In a twenty-first embodiment, the cationic lipid of the present disclosure is represented by Formula IIa:

IIa

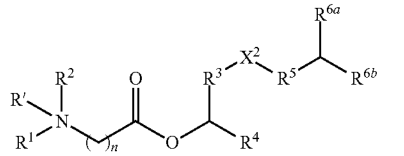

or a pharmaceutically acceptable salt thereof, wherein n is an integer selected from 1, 2, 3, and 4; and all other remaining variables are as described for Formula Ia or any one of the eighteenth, nineteenth or twentieth embodiments.

In a twenty-second embodiment, the cationic lipid of the present disclosure is represented by Formula IIIa:

IIIa

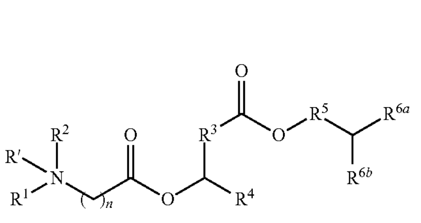

or a pharmaceutically acceptable salt thereof, wherein n is an integer selected from 1, 2, and 3; and all other remaining variables are as described for Formula Ia, Formula IIa or any one of the eighteenth, nineteenth, twentieth or twenty-first embodiments.

In a twenty-third embodiment, the cationic lipid of the present disclosure is represented by Formula IVa:

IVa

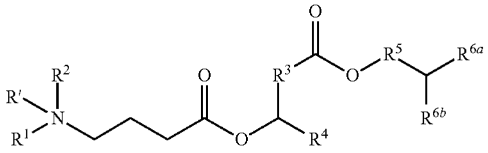

or a pharmaceutically acceptable salt thereof; and all other remaining variables are as described for Formula Ia, Formula IIa, Formula IIIa or any one of the eighteenth, nineteenth, twentieth, twenty-first or twenty-second embodiments.

In a twenty-fourth embodiment, in the cationic lipid according to Formula Ia, Formula IIa, Formula IIIa, Formula IVa or any one of the eighteenth, nineteenth, twentieth, twenty-first or twenty-second embodiments, or a pharmaceutically acceptable salt thereof, $R^1$ and $R^2$ are each independently hydrogen, $C_1$-$C_6$ alkyl or $C_2$-$C_6$ alkenyl, or $C_1$-$C_5$ alkyl or $C_2$-$C_5$ alkenyl, or $C_1$-$C_4$ alkyl or $C_2$-$C_4$ alkenyl, or $C_1$-$C_3$ alkyl or $C_2$-$C_3$ alkenyl, or $C_1$-$C_2$ alkyl, or $C_6$ alkyl, or $C_5$ alkyl, or $C_4$ alkyl, or $C_3$ alkyl, or $C_2$ alkyl, or $C_1$ alkyl, or $C_6$ alkenyl, or $C_5$ alkenyl, or $C_4$ alkenyl, or $C_3$ alkenyl, or $C_2$ alkenyl; and all other remaining variables are as described for Formula Ia, Formula IIa, Formula IIIa, Formula IVa or any one of the eighteenth, nineteenth, twentieth, twenty-first, twenty-second or twenty-third embodiments.

In a twenty-fifth embodiment, the cationic lipid of the present disclosure is represented by Formula Va:

Va

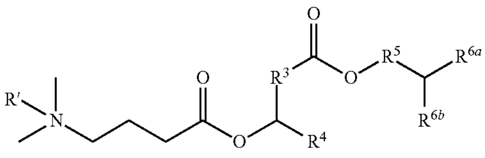

or a pharmaceutically acceptable salt thereof; and all other remaining variables are as described for Formula Ia, Formula IIa, Formula IIIa, Formula IVa or any one of the eighteenth, nineteenth, twentieth, twenty-first, twenty-second, twenty-third or twenty-fourth embodiments.

In a twenty-sixth embodiment, in the cationic lipid according to Formula Ia, Formula IIa, Formula IIIa, Formula IVa, Formula Va or any one of the eighteenth, nineteenth, twentieth, twenty-first, twenty-second, twenty-third, twenty-fourth or twenty-fifth embodiments, or a pharmaceutically acceptable salt thereof, $R^3$ is $C_1$-$C_9$ alkylene or $C_2$-$C_9$ alkenylene, $C_1$-$C_7$ alkylene or $C_2$-$C_7$ alkenylene, $C_1$-$C_5$ alkylene or $C_2$-$C_5$ alkenylene, or $C_2$-$C_8$ alkylene or $C_2$-$C_8$ alkenylene, or $C_3$-$C_7$ alkylene or $C_3$-$C_7$ alkenylene, or $C_5$-$C_7$ alkylene or $C_5$-$C_7$ alkenylene; or $R^3$ is $C_{12}$ alkylene, $C_{11}$ alkylene, $C_{10}$ alkylene, $C_9$ alkylene, or $C_8$ alkylene, or $C_7$ alkylene, or $C_6$ alkylene, or $C_5$ alkylene, or $C_4$ alkylene, or $C_3$ alkylene, or $C_2$ alkylene, or $C_1$ alkylene, or $C_{12}$ alkenylene, $C_{11}$ alkenylene, $C_{10}$ alkenylene, $C_9$ alkenylene, or $C_8$ alkenylene, or $C_7$ alkenylene, or $C_6$ alkenylene, or $C_5$ alkenylene, or $C_4$ alkenylene, or $C_3$ alkenylene, or $C_2$ alkenylene; and all other remaining variables are as described for Formula Ia, Formula IIa, Formula IIIa, Formula IVa, Formula Va or any one of the eighteenth, nineteenth, twentieth, twenty-first, twenty-second, twenty-third, twenty-fourth or twenty-fifth embodiments. Alternatively, as part of a twenty-sixth embodiment, in the cationic lipid according to Formula Ia, Formula IIa, Formula IIIa, Formula IVa, Formula Va or any one of the eighteenth, nineteenth, twentieth, twenty-first, twenty-second, twenty-third, twenty-fourth or twenty-fifth embodiments, or a pharmaceutically acceptable salt thereof, $R^3$ is $C_1$-$C_9$ alkylene or $C_2$-$C_9$ alkenylene, $C_1$-$C_7$ alkylene or $C_2$-$C_7$ alkenylene, $C_1$-$C_6$ alkylene or $C_2$-$C_6$ alkenylene, $C_1$-$C_5$ alkylene or $C_2$-$C_5$ alkenylene, or $C_2$-$C_8$ alkylene or $C_2$-$C_8$ alkenylene, or $C_3$-$C_7$ alkylene or $C_3$-$C_7$ alkenylene, or $C_5$-$C_7$ alkylene or $C_5$-$C_7$ alkenylene; or $R^3$ is $C_{12}$ alkylene, $C_{11}$ alkylene, $C_{10}$ alkylene, $C_9$ alkylene, or $C_8$ alkylene, or $C_7$ alkylene, or $C_6$ alkylene, or $C_5$ alkylene, or $C_4$ alkylene, or $C_3$ alkylene, or $C_2$ alkylene, or $C_1$ alkylene, or $C_{12}$ alkenylene, $C_{11}$ alkenylene, $C_{10}$ alkenylene, $C_9$ alkenylene, or $C_8$ alkenylene, or $C_7$ alkenylene, or $C_6$ alkenylene, or $C_5$ alkenylene, or $C_4$ alkenylene, or $C_3$ alkenylene, or $C_2$ alkenylene; and all other remaining variables are as described for Formula Ia, Formula IIa, Formula IIIa, Formula IVa, Formula Va or any one of the eighteenth, nineteenth, twentieth, twenty-first, twenty-second, twenty-third, twenty-fourth or twenty-fifth embodiments.

In a twenty-seventh embodiment, in the cationic lipid according to Formula Ia, Formula IIa, Formula IIIa, Formula IVa, Formula Va or any one of the eighteenth, nineteenth, twentieth, twenty-first, twenty-second, twenty-third, twenty-fourth, twenty-fifth or twenty-sixth embodiments, or a pharmaceutically acceptable salt thereof, $R^5$ is absent, $C_1$-$C_6$ alkylene, or $C_2$-$C_6$ alkenylene; or $R^5$ is absent, $C_1$-$C_4$ alkylene, or $C_2$-$C_4$ alkenylene; or $R^5$ is absent; or $R^5$ is $C^8$ alkylene, $C_7$ alkylene, $C_6$ alkylene, $C_5$ alkylene, $C_4$ alkylene, $C_3$ alkylene, $C_2$ alkylene, $C_1$ alkylene, $C_8$ alkenylene, $C_7$ alkenylene, $C_6$ alkenylene, $C_5$ alkenylene, $C_4$ alkenylene, $C_3$ alkenylene, or $C_2$ alkenylene; and all other remaining variables are as described for Formula Ia, Formula IIa, Formula IIIa, Formula IVa, Formula Va or any one of the eighteenth, nineteenth, twentieth, twenty-first, twenty-second, twenty-third, twenty-fourth, twenty-fifth or twenty-sixth embodiments.

In a twenty-eighth embodiment, in the cationic lipid according to Formula Ia, Formula IIa, Formula IIIa, Formula IVa, Formula Va or any one of the eighteenth, nineteenth, twentieth, twenty-first, twenty-second, twenty-third, twenty-fourth, twenty-fifth, twenty-sixth or twenty-seventh embodiments, or a pharmaceutically acceptable salt thereof, $R^4$ is $C_1$-$C_{14}$ unbranched alkyl, $C_2$-$C_{14}$ unbranched alkenyl, or

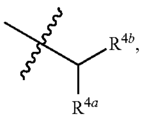

wherein $R^{4a}$ and $R^{4b}$ are each independently $C_1$-$C_{12}$ unbranched alkyl or $C_2$-$C_{12}$ unbranched alkenyl; or $R^4$ is $C_2$-$C_{12}$ unbranched alkyl or $C_2$-$C_{12}$ unbranched alkenyl; or $R^4$ is $C_2$-$C_7$ unbranched alkyl or $C_2$-$C_7$ unbranched alkenyl; or $R^4$ is $C_3$-$C_7$ unbranched alkyl or $C_3$-$C_7$ unbranched alkenyl; or $R^4$ is $C_4$-$C_7$ unbranched alkyl or $C_4$-$C_7$ unbranched alkenyl; or $R^4$ is $C_5$-$C_7$ unbranched alkyl or $C_5$-$C_7$ unbranched alkenyl; or $R^4$ is $C_6$-$C_7$ unbranched alkyl or $C_6$-$C_7$ unbranched alkenyl; or $R^4$ is $C_{16}$ unbranched alkyl, $C_{15}$ unbranched alkyl, $C_{14}$ unbranched alkyl, $C_{13}$ unbranched alkyl, $C_{12}$ unbranched alkyl, $C_{11}$ unbranched alkyl, $C_{10}$ unbranched alkyl, $C_9$ unbranched alkyl, $C_8$ unbranched alkyl, $C_7$ unbranched alkyl, $C_6$ unbranched alkyl, $C_5$ unbranched alkyl, $C_4$ unbranched alkyl, $C_3$ unbranched alkyl, $C_2$ unbranched alkyl, $C_1$ unbranched alkyl, $C_{16}$ unbranched alkenyl, $C_{15}$ unbranched alkenyl, $C_{14}$ unbranched alkenyl, $C_{13}$ unbranched alkenyl, $C_{12}$ unbranched alkenyl, $C_{11}$ unbranched alkenyl, $C_{10}$ unbranched alkenyl, $C_9$ unbranched alkenyl, $C_8$ unbranched alkenyl, $C_7$ unbranched alkenyl, $C_6$ unbranched alkenyl, $C_5$ unbranched alkenyl, $C_4$ unbranched alkenyl, $C_3$ unbranched alkenyl, or $C_2$ alkenyl; or $R^4$ is

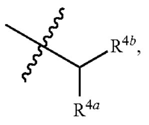

(wherein $R^{4a}$ and $R^{4b}$ are each independently $C_2$-$C_{10}$ unbranched alkyl or $C_2$-$C_{10}$ unbranched alkenyl; or $R^4$ is

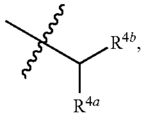

wherein $R^{4a}$ and $R^{4b}$ are each independently $C_{16}$ unbranched alkyl, $C_{15}$ unbranched alkyl, $C_{14}$ unbranched alkyl, $C_{13}$ unbranched alkyl, $C_{12}$ unbranched alkyl, $C_{11}$ unbranched alkyl, $C_{10}$ unbranched alkyl, $C_9$ unbranched alkyl, $C_8$ unbranched alkyl, $C_7$ unbranched alkyl, $C_6$ unbranched alkyl, $C_5$ unbranched alkyl, $C_4$ unbranched alkyl, $C_3$ unbranched alkyl, $C_2$ alkyl, $C_1$ alkyl, $C_{16}$ unbranched alkenyl, $C_{15}$ unbranched alkenyl, $C_{14}$ unbranched alkenyl, $C_{13}$ unbranched alkenyl, $C_{12}$ unbranched alkenyl, $C_{11}$ unbranched alkenyl, $C_{10}$ unbranched alkenyl, $C_9$ unbranched alkenyl, $C_8$ unbranched alkenyl, $C_7$ unbranched alkenyl, $C_6$ unbranched alkenyl, $C_5$ unbranched alkenyl, $C_4$ unbranched alkenyl, $C_3$ unbranched alkenyl, or $C_2$ alkenyl; and all other remaining variables are as described for Formula Ia, Formula IIa, Formula IIIa, Formula IVa, Formula Va or any one of the eighteenth, nineteenth, twentieth, twenty-first, twenty-second, twenty-third, twenty-fourth, twenty-fifth, twenty-sixth or twenty-seventh embodiments.

In a twenty-ninth embodiment, in the cationic lipid according to Formula Ia, Formula IIa, Formula IIIa, Formula IVa, Formula Va or any one of the eighteenth, nineteenth, twentieth, twenty-first, twenty-second, twenty-third, twenty-fourth, twenty-fifth, twenty-sixth, twenty-seventh or twenty-eighth embodiments, or a pharmaceutically acceptable salt thereof, $R^{6a}$ and $R^{6b}$ are each independently $C_7$-$C_{14}$ alkyl or $C_7$-$C_{14}$ alkenyl; or $R^{6a}$ and $R^{6b}$ are each independently $C_8$-$C_{12}$ alkyl or $C_8$-$C_{12}$ alkenyl; or $R^{6a}$ and $R^{6b}$ are each independently $C_{16}$ alkyl, $C_{15}$ alkyl, $C_{14}$ alkyl, $C_{13}$ alkyl, $C_{12}$ alkyl, $C_{11}$ alkyl, $C_{10}$ alkyl, $C_9$ alkyl, $C_8$ alkyl, $C_7$ alkyl, $C_{16}$ alkenyl, $C_{15}$ alkenyl, $C_{14}$ alkenyl, $C_{13}$ alkenyl, $C_{12}$ alkenyl, $C_{11}$ alkenyl, $C_{10}$ alkenyl, $C_9$ alkenyl, $C_8$ alkenyl, or $C_7$ alkenyl; provided that the total number of carbon atoms in $R^{6a}$ and $R^{6b}$ as combined is greater than 15; and all other remaining variables are as described for Formula Ia, Formula IIa, Formula IIIa, Formula IVa, Formula Va or any one of the eighteenth, nineteenth, twentieth, twenty-first, twenty-second, twenty-third, twenty-fourth, twenty-fifth, twenty-sixth, twenty-seventh or twenty-eighth embodiments.

In a thirtieth embodiment, in the cationic lipid according to Formula Ia, Formula IIa, Formula IIIa, Formula IVa, Formula Va or any one of the eighteenth, nineteenth, twentieth, twenty-first, twenty-second, twenty-third, twenty-fourth, twenty-fifth, twenty-sixth, twenty-seventh, twenty-eighth or twenty-ninth embodiments, or a pharmaceutically acceptable salt thereof, $R^{6a}$ and $R^{6b}$ are each greater than $C_8$ alkyl or $C_8$ alkenyl, i.e., $R^{6a}$ and $R^{6b}$ are each independently $C_9$-$C_{16}$ alkyl or $C_9$-$C_{16}$ alkenyl; or $R^{6a}$ and $R^{6b}$ are each independently $C_9$-$C_{15}$ alkyl or $C_9$-$C_{15}$ alkenyl; or $R^{6a}$ and $R^{6b}$ are each independently $C_9$-$C_{14}$ alkyl or $C_9$-$C_{14}$ alkenyl; or $R^{6a}$ and $R^{6b}$ are each independently $C_9$-$C_{13}$ alkyl or $C_9$-$C_{13}$ alkenyl; or $R^{6a}$ and $R^{6b}$ are each independently $C_9$-$C_{12}$ alkyl or $C_9$-$C_{12}$ alkenyl; or $R^{6a}$ and $R^{6b}$ are each independently $C_{10}$-$C_{12}$ alkyl or $C_{10}$-$C_{12}$ alkenyl; or $R^{6a}$ and $R^{6b}$ are each independently $C_{16}$ alkyl, $C_{15}$ alkyl, $C_{14}$ alkyl, $C_{13}$ alkyl, $C_{12}$ alkyl, $C_{11}$ alkyl, $C_{10}$ alkyl, $C_9$ alkyl, $C_{16}$ alkenyl, $C_{15}$ alkenyl, $C_{14}$ alkenyl, $C_{13}$ alkenyl, $C_{12}$ alkenyl, $C_{11}$ alkenyl, $C_{10}$ alkenyl, or $C_9$ alkenyl; provided that the total number of carbon atoms in $R^{6a}$ and $R^{6b}$ as combined is greater than 15; and all other remaining variables are as described for Formula Ia, Formula IIa, Formula IIIa, Formula IVa, Formula Va or any one of the eighteenth, nineteenth, twentieth, twenty-first, twenty-second, twenty-third, twenty-fourth, twenty-fifth, twenty-sixth, twenty-seventh, twenty-eighth or twenty-ninth embodiments.

In a thirty-first embodiment, in the cationic lipid according to Formula Ia, Formula IIa, Formula IIIa, Formula IVa, Formula Va or or any one of the eighteenth, nineteenth, twentieth, twenty-first, twenty-second, twenty-third, twenty-fourth, twenty-fifth, twenty-sixth, twenty-seventh, twenty-eighth, twenty-ninth or thirtieth embodiments, or a pharmaceutically acceptable salt thereof, $R^{6a}$ and $R^{6b}$ contain an equal number of carbon atoms with each other; or $R^{6a}$ and $R^{6b}$ are the same; or $R^{6a}$ and $R^{6b}$ are both $C_{16}$ alkyl, $C_{15}$ alkyl, $C_{14}$ alkyl, $C_{13}$ alkyl, $C_{12}$ alkyl, $C_{11}$ alkyl, $C_{10}$ alkyl, $C_9$ alkyl, $C_8$ alkyl, $C_7$ alkyl, $C_{16}$ alkenyl, $C_{15}$ alkenyl, $C_{14}$ alkenyl, $C_{13}$ alkenyl, $C_{12}$ alkenyl, $C_{11}$ alkenyl, $C_{10}$ alkenyl, $C_9$ alkenyl, $C_8$ alkenyl, or $C_7$ alkenyl; provided that the total number of carbon atoms in $R^{6a}$ and $R^{6b}$ as combined is greater than 15; and all other remaining variables are as described for Formula Ia, Formula IIa, Formula IIIa, Formula IVa, Formula Va or or any one of the eighteenth, nineteenth, twentieth, twenty-first, twenty-second, twenty-third, twenty-fourth, twenty-fifth, twenty-sixth, twenty-seventh, twenty-eighth, twenty-ninth or thirtieth embodiments.

In a thirty-second embodiment, in the cationic lipid according to Formula Ia, Formula IIa, Formula IIIa, Formula IVa, Formula Va or or any one of the eighteenth, nineteenth, twentieth, twenty-first, twenty-second, twenty-third, twenty-fourth, twenty-fifth, twenty-sixth, twenty-seventh, twenty-eighth, twenty-ninth, thirtieth or thirty-first embodiments, or a pharmaceutically acceptable salt thereof, $R^{6a}$ and $R^{6b}$ as defined in any one of the eighteenth, nineteenth, twentieth, twenty-first, twenty-second, twenty-third, twenty-fourth, twenty-fifth, twenty-sixth, twenty-seventh, twenty-eighth, twenty-ninth, thirtieth or thirty-first embodiments each contain a different number of carbon atoms with each other; or the number of carbon atoms $R^{6a}$ and $R^{6b}$ differs by one or two carbon atoms; or the number of carbon atoms $R^{6a}$ and $R^{6b}$ differs by one carbon atom; or $R^{6a}$ is $C_7$ alkyl and $R^{6a}$ is $C_8$ alkyl, $R^{6a}$ is $C_8$ alkyl and $R^{6a}$ is $C_7$ alkyl, $R^{6a}$ is $C_8$ alkyl and $R^{6a}$ is $C_9$ alkyl, $R^{6a}$ is $C_9$ alkyl and $R^{6a}$ is $C_8$ alkyl, $R^{6a}$ is $C_9$ alkyl and $R^{6a}$ is $C_{10}$ alkyl, $R^{6a}$ is $C_{10}$ alkyl and $R^{6a}$ is $C_9$ alkyl, $R^{6a}$ is $C_{10}$ alkyl and $R^{6a}$ is $C_{11}$ alkyl, $R^{6a}$ is $C_{11}$ alkyl and $R^{6a}$ is $C_{10}$ alkyl, $R^{6a}$ is $C_{11}$ alkyl and $R^{6a}$ is $C_{12}$ alkyl, $R^{6a}$ is $C_{12}$ alkyl and $R^{6a}$ is $C_{11}$ alkyl, $R^{6a}$ is $C_7$ alkyl and $R^{6a}$ is $C_9$ alkyl, $R^{6a}$ is $C_9$ alkyl and $R^{6a}$ is $C_7$ alkyl, $R^{6a}$ is $C_8$ alkyl and $R^{6a}$ is $C_{10}$ alkyl, $R^{6a}$ is $C_{10}$ alkyl and $R^{6a}$ is $C_8$ alkyl, $R^{6a}$ is $C_9$ alkyl and $R^{6a}$ is $C_{11}$ alkyl, $R^{6a}$ is $C_{11}$ alkyl and $R^{6a}$ is $C_9$ alkyl, $R^{6a}$ is $C_{10}$ alkyl and $R^{6a}$ is $C_{12}$ alkyl, $R^{6a}$ is $C_{12}$ alkyl and $R^{6a}$ is $C_{10}$ alkyl, $R^{6a}$ is $C_{11}$ alkyl and $R^{6a}$ is $C_{13}$ alkyl, or $R^{6a}$ is $C_{13}$ alkyl and $R^{6a}$ is $C_{11}$ alkyl, etc.; and all other remaining variables are as described for Formula Ia, Formula IIa, Formula IIIa, Formula IVa, Formula Va or or any one of the eighteenth, nineteenth, twentieth, twenty-first, twenty-second, twenty-third, twenty-fourth, twenty-fifth, twenty-sixth, twenty-seventh, twenty-eighth, twenty-ninth, thirtieth or thirty-first embodiments.

In a thirty-third embodiment, in the cationic lipid according to Formula Ia, Formula IIa, Formula IIIa, Formula IVa, Formula Va or or any one of the eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first or thirty-second embodiments, or a pharmaceutically acceptable salt thereof, R' is absent.

In a thirty-fourth embodiment, in the cationic lipid according to Formula Ia, Formula IIa, Formula IIIa, Formula IVa, Formula Va or any one of the eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second or thirty-third embodiments, or a pharmaceutically acceptable salt thereof, $R^4$ is an alkyl that is no greater than $C_7$ unbranched alkyl or an alkenyl that is no greater than $C_7$ unbranched alkenyl; and $R^{6a}$ and $R^{6b}$ are each an alkyl greater than $C_8$ alkyl or an alkenyl greater than $C_8$ alkenyl; i.e., or $R^4$ is $C_2$-$C_7$ unbranched alkyl or $C_2$-$C_7$ unbranched alkenyl; or $R^4$ is $C_3$-$C_7$ unbranched alkyl or $C_3$-$C_7$ unbranched alkenyl; or $R^4$ is $C_4$-$C_7$ unbranched alkyl or $C_4$-$C_7$ unbranched alkenyl; or $R^4$ is $C_5$-$C_7$ unbranched alkyl or $C_5$-$C_7$ unbranched alkenyl; or $R^4$ is $C_6$-$C_7$ unbranched alkyl or $C_6$-$C_7$ unbranched alkenyl; or $R^4$ is $C_7$ unbranched alkyl, $C_6$ unbranched alkyl, $C_5$ unbranched alkyl, $C_4$ unbranched alkyl, $C_3$ unbranched alkyl, $C_2$ unbranched alkyl, $C_1$ unbranched alkyl, $C_7$ unbranched alkenyl, $C_6$ unbranched alkenyl, $C_5$ unbranched alkenyl, $C_4$ unbranched alkenyl, $C_3$ unbranched alkenyl, or $C_2$ alkenyl; or $R^{6a}$ and $R^{6b}$ are each independently $C_9$-$C_{16}$ alkyl or $C_9$-$C_{16}$ alkenyl; or $R^{6a}$ and $R^{6b}$ are each independently $C_9$-$C_{15}$ alkyl or $C_9$-$C_{15}$ alkenyl; or $R^{6a}$ and $R^{6b}$ are each independently $C_9$-$C_{14}$ alkyl or $C_9$-$C_{14}$ alkenyl; or $R^{6a}$ and $R^{6b}$ are each independently $C_9$-$C_{13}$ alkyl or $C_9$-$C_{13}$ alkenyl; or $R^{6a}$ and $R^{6b}$ are each independently $C_9$-$C_{12}$ alkyl or $C_9$-$C_{12}$ alkenyl; or $R^{6a}$ and $R^{6b}$ are each independently $C_{10}$-$C_{12}$ alkyl or $C_{10}$-$C_{12}$ alkenyl; or $R^{6a}$ and $R^{6b}$ are each independently $C_{16}$ alkyl, $C_{15}$ alkyl, $C_{14}$ alkyl, $C_{13}$ alkyl, $C_{12}$ alkyl, $C_{11}$ alkyl, $C_{10}$ alkyl, $C_9$ alkyl, $C_{16}$ alkenyl, $C_{15}$ alkenyl, $C_{14}$ alkenyl, $C_{13}$ alkenyl, $C_{12}$ alkenyl, $C_{11}$ alkenyl, $C_{10}$ alkenyl, or $C_9$ alkenyl; provided that the total number of carbon atoms in $R^{6a}$ and $R^{6b}$ as combined is greater than 15; and all other remaining variables are as described for Formula Ia, Formula IIa, Formula IIIa, Formula IVa, Formula Va or any one of the eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second or thirty-third embodiments.

In some embodiments, in the cationic lipid according to Formula Ia, Formula IIa, Formula IIIa, Formula IVa, Formula Va or any one of the eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third or thirty-fourth embodiments, wherein R' is absent, the nitrogen atom to which R', $R^1$, and $R^2$ are all attached is protonated when the lipid is present at physiological conditions, e.g., at a pH of about 7.4 or lower, such as pH of about 7.4.

In some embodiments, in the cationic lipid according to Formula Ia, Formula IIa, Formula IIIa, Formula IVa, Formula Va or any one of the eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third or thirty-fourth embodiments, wherein R' is absent, the nitrogen atom to which R', $R^1$, and $R^2$ are all attached is protonated when the lipid is present in an aqueous solution.

In some embodiments, in the cationic lipid according to Formula Ia, Formula IIa, Formula IIIa, Formula IVa, Formula Va or any one of the eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third or thirty-fourth embodiments, wherein R' is absent, the nitrogen atom to which R', $R^1$, and $R^2$ are all attached is protonated when the lipid is present at a pH of about 7.4 or lower.

In some embodiments, in the cationic lipid according to Formula Ia, Formula IIa, Formula IIIa, Formula IVa, Formula Va or any one of the eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third or thirty-fourth embodiments, wherein R' is absent, the nitrogen atom to which R', $R^1$, and $R^2$ are all attached is protonated when the lipid is present in an aqueous solution and at a pH of about 7.4 or lower (e.g., pH of about 7.4).

In some embodiments, in the cationic lipid according to Formula Ia, Formula IIa, Formula IIIa, Formula IVa, Formula Va or any one of the eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third or thirty-fourth embodiments, wherein R', $R^1$ and $R^2$ are each $C_1$-$C_6$ alkyl, and wherein R', $R^1$ and $R^2$ together with the nitrogen atom attached thereto form a quaternary ammonium cation or a quaternary amine.

In one embodiment, the cationic lipid of the present disclosure or the cationic lipid of Formula I or Formula Ia is any one lipid selected from:

(Lipid 1)

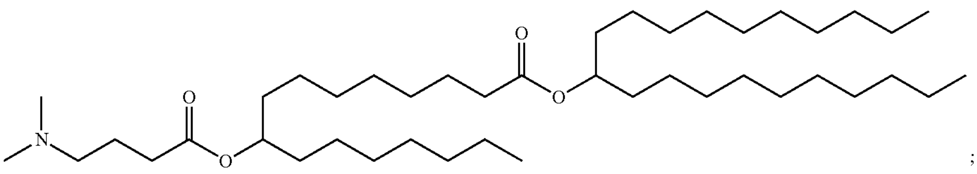

;

henicosan-11-yl 9-((4-(dimethylamino)butanoyl)oxy)hexadecanoate (Lipid 2)

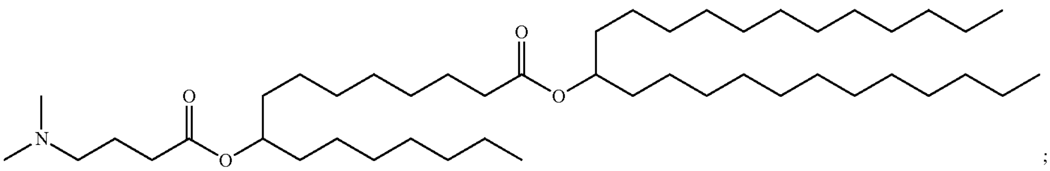

;

pentacosan-13-yl 9-((4-(dimethylamino)butanoyl)oxy)hexadecanoate (Lipid 3)

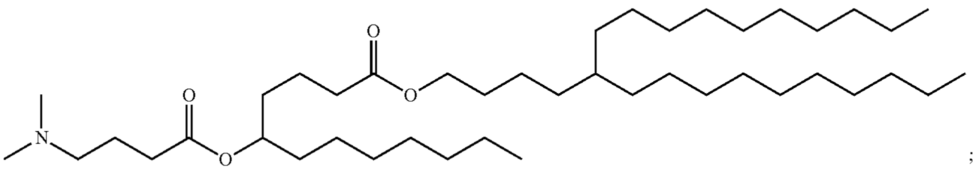

;

5-decylpentadecyl 5-((4-(dimethylamino)butanoyl)oxy)dodecanoate (Lipid 4)

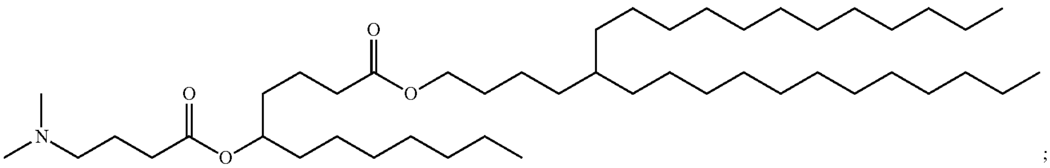

;

5-dodecylheptadecyl 5-((4-(dimethylamino)butanoyl)oxy)dodecanoate

-continued
(Lipid 5)
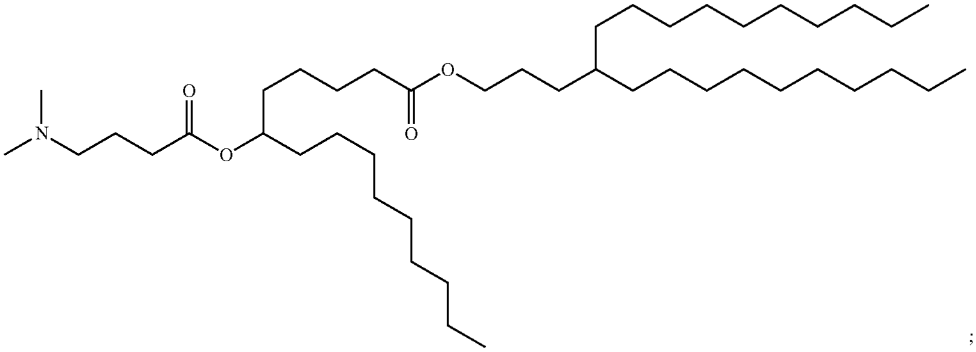
;
4-decyltetradecyl 6-((4-(dimethylamino)butanoyl)oxy)tridecanoate
(Lipid 6)
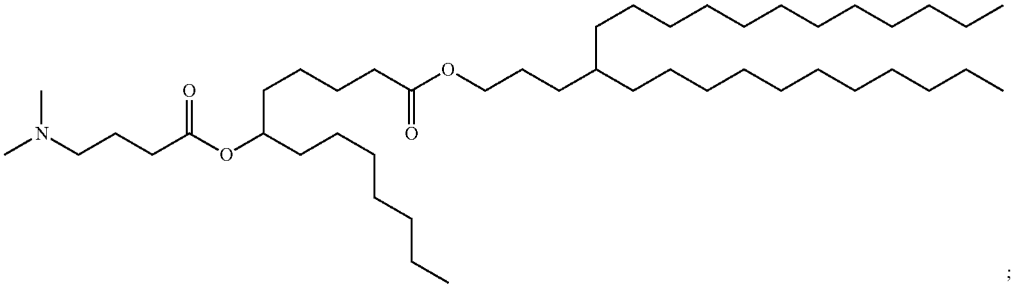
;
4-dodecylhexadecyl 6-((4-(dimethylamino)butanoyl)oxy)tridecanoate
(Lipid 7)
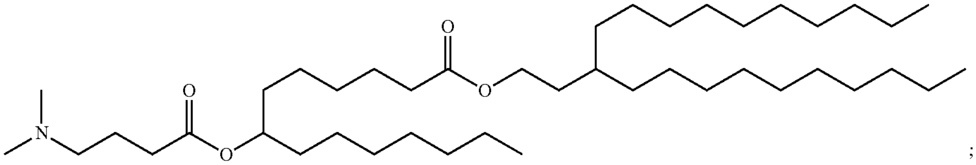
;
3-decyltridecyl 7-((4-(dimethylamino)butanoyl)oxy)tetradecanoate
(Lipid 8)
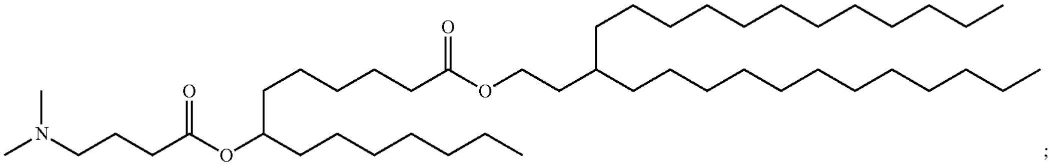
;
3-dodecylpentadecyl 7-((4-(dimethylamino)butanoyl)oxy)tetradecanoate
(Lipid 9)
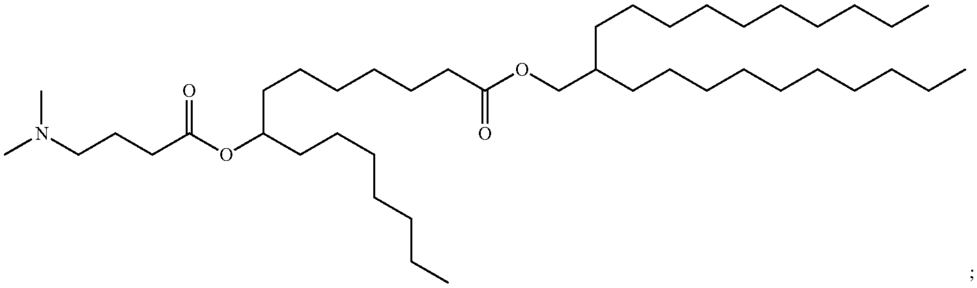
;
2-decyldodecyl 8-((4-(dimethylamino)butanoyl)oxy)pentadecanoate -continued
(Lipid 10)
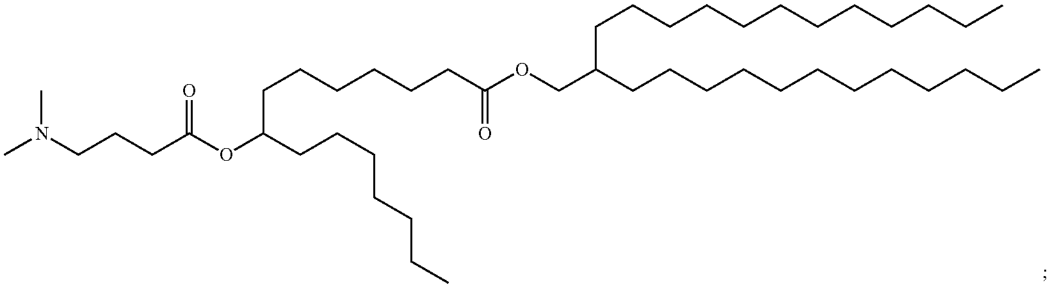
;
2-dodecyltetradecyl 8-((4-(dimethylamino)butanoyl)oxy)pentadecanoate
(Lipid 11)
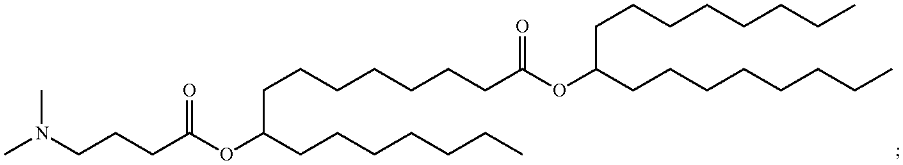
;
heptadecan-9-yl 9-((4-(dimethylamino)butanoyl)oxy)hexadecanoate
(Lipid 12)
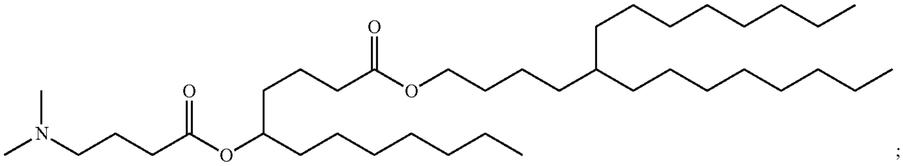
;
5-octyltridecyl 5-((4-(dimethylamino)butanoyl)oxy)dodecanoate
(Lipid 13)
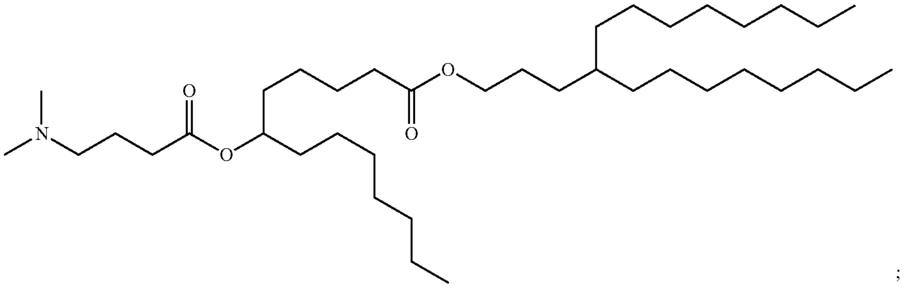
;
4-octyldodecyl 6-((4-(dimethylamino)butanoyl)oxy)tridecanoate
(Lipid 14)
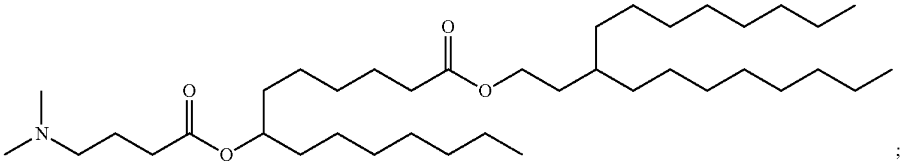
;
3-octylundecyl 7-((4-(dimethylamino)butanoyl)oxy)tetradecanoate -continued (Lipid 15)

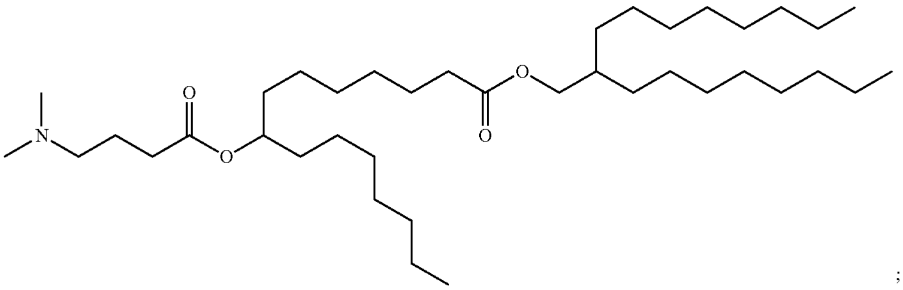

;

2-octyldecyl 8-((4-(dimethylamino)butanoyl)oxy)pentadecanoate (Lipid 16)

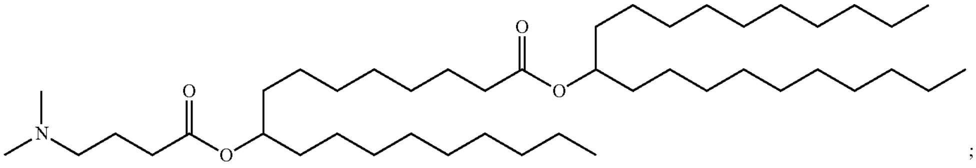

;

henicosan-11-yl 9-((4-(dimethylamino)butanoyl)oxy)octadecanoate (Lipid 17)

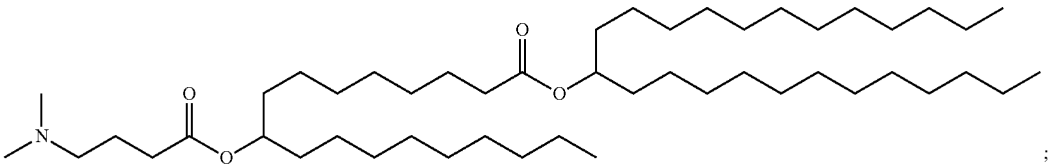

;

pentacosan-13-yl 9-((4-(dimethylamino)butanoyl)oxy)octadecanoate (Lipid 18)

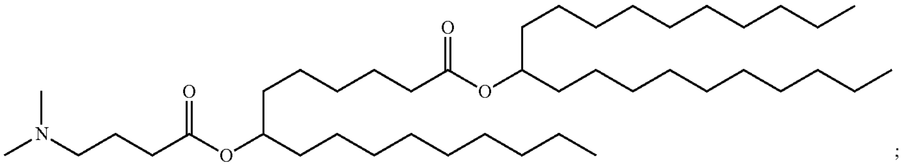

;

henicosan-11-yl 7-((4-(dimethylamino)butanoyl)oxy)hexadecanoate (Lipid 19)

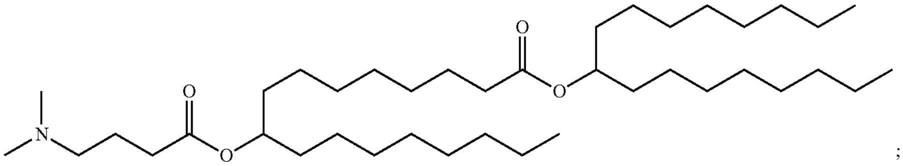

;

heptadecan-9-yl 9-((4-(dimethylamino)butanoyl)oxy)heptadecanoate (Lipid 20)

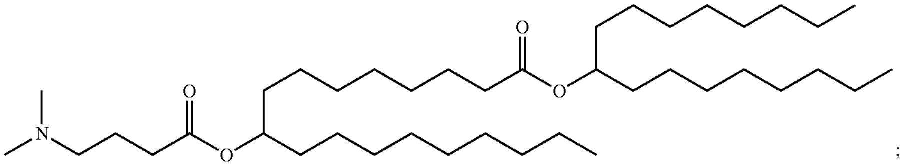

;

heptadecan-9-yl 9-((4-(dimethylamino)butanoyl)oxy)octadecanoate

-continued (Lipid 21)

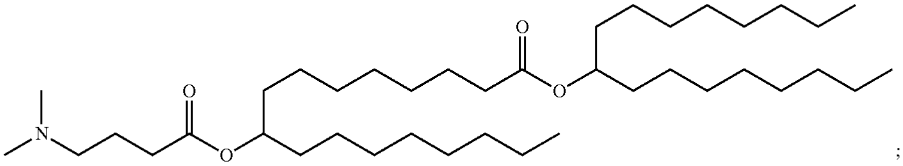

;

heptadecan-9-yl 9-((4-(dimethylamino)butanoyl)oxy)nonadecanoate (Lipid 22)

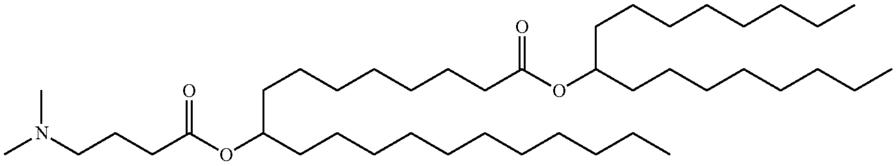

heptadecan-9-yl 9-((4-(dimethylamino)butanoyl)oxy)icosanoate (Lipid 23)

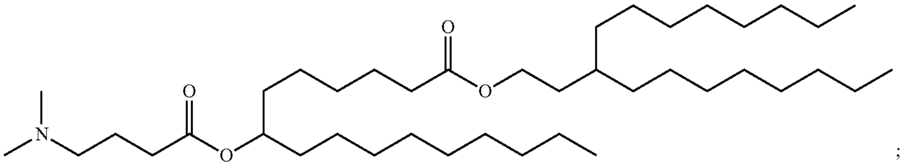

;

3-octylundecyl 7-((4-(dimethylamino)butanoyl)oxy)hexadecanoate (Lipid 24)

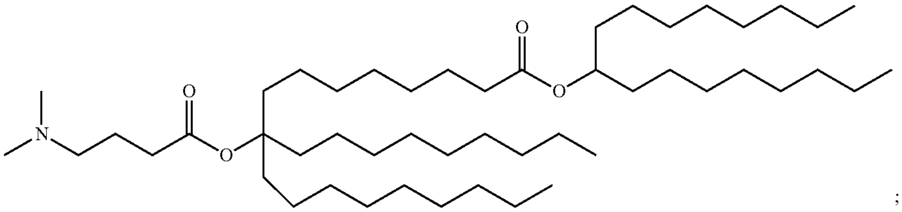

; and heptadecan-9-yl 9-((4-(dimethylamino)butanoyl)oxy)-9-nonyloctadecanoate (Lipid 25)

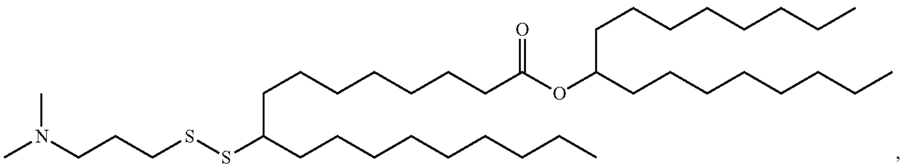

, heptadecan-9-yl 9-((3-(dimethylamino)propyl)disulfaneyl)octadecanoate or a pharmaceutically acceptable salt thereof.

Moreover, a lipid of Formula I, Formula II, Formula III, Formula IV, Formula V, Formula Ia, Formula IIa, Formula IIIa, Formula IVa, Formula Va, or a pharmaceutically acceptable salt thereof (e.g., quaternary ammonium salt), or any of the exemplary lipids disclosed herein may be converted to corresponding lipids comprising a quaternary amine or a quaternary ammonium cation, i.e., R', $R^1$ and $R^2$ are each $C_1$-$C_6$ alkyl (all contemplated in this disclosure), for example, by treatment with chloromethane ($CH_3Cl$) in acetonitrile ($CH_3CN$) and chloroform ($CHCl_3$). The quaternary ammonium cations in such lipids are permanently charged, independently of the pH of their solution.

In some embodiments, the nitrogen atom of any of Lipid 1, Lipid 2, Lipid 3, Lipid 4, Lipid 5, Lipid 6, Lipid 7, Lipid 8, Lipid 9, Lipid 10, Lipid 11, Lipid 12, Lipid 13, Lipid 14, Lipid 15, Lipid 16, Lipid 17, Lipid 18, Lipid 19, Lipid 20, Lipid 21, Lipid 22, Lipid 23, Lipid 24, or Lipid 25 is protonated when the lipid is present a physiological conditions, e.g., at a pH of about 7.4 or lower, such as pH of about 7.4.

In some embodiments, the nitrogen atom of any of Lipid 1, Lipid 2, Lipid 3, Lipid 4, Lipid 5, Lipid 6, Lipid 7, Lipid 8, Lipid 9, Lipid 10, Lipid 11, Lipid 12, Lipid 13, Lipid 14, Lipid 15, Lipid 16, Lipid 17, Lipid 18, Lipid 19, Lipid 20, Lipid 21, Lipid 22, Lipid 23, Lipid 24, or Lipid 25 is protonated when the lipid is present in an aqueous solution.

In some embodiments, the nitrogen atom of any of Lipid 1, Lipid 2, Lipid 3, Lipid 4, Lipid 5, Lipid 6, Lipid 7, Lipid 8, Lipid 9, Lipid 10, Lipid 11, Lipid 12, Lipid 13, Lipid 14, Lipid 15, Lipid 16, Lipid 17, Lipid 18, Lipid 19, Lipid 20, Lipid 21, Lipid 22, Lipid 23, Lipid 24 or Lipid 25 is protonated when the lipid is present at a pH of about 7.4 or lower (e.g., pH of about 7.4).

In some embodiments, the nitrogen atom of any of Lipid 1, Lipid 2, Lipid 3, Lipid 4, Lipid 5, Lipid 6, Lipid 7, Lipid 8, Lipid 9, Lipid 10, Lipid 11, Lipid 12, Lipid 13, Lipid 14, Lipid 15, Lipid 16, Lipid 17, Lipid 18, Lipid 19, Lipid 20, Lipid 21, Lipid 22, Lipid 23, Lipid 24, or Lipid 25 is protonated when the lipid is present in an aqueous solution and at a pH of about 7.4 or lower (e.g., pH of about 7.4).

III. Lipid Nanoparticles (LNP)

LNP as Delivery Vehicle of Nucleic Acid

Lipid nanoparticles (LNPs), or pharmaceutical compositions thereof, comprising a cationic lipid described herein and a capsid free, non-viral vector or therapeutic nucleic acid (TNA) (e.g., ceDNA) can be used to deliver the capsid-free, non-viral DNA vector to a target site of interest (e.g., cell, tissue, organ, and the like). Accordingly, another aspect of this disclosure relates to a lipid nanoparticle (LNP) comprising one or more cationic lipids described herein, or a pharmaceutically acceptable salt thereof, and a therapeutic nucleic acid (TNA).

Generally, a cationic lipid is typically employed to condense the nucleic acid cargo, e.g., ceDNA at low pH and to drive membrane association and fusogenicity. Generally, cationic lipids are lipids comprising at least one amino group that is positively charged or becomes protonated under acidic conditions, for example at pH of 6.5 or lower, to form lipids comprising quaternary amines.

In one embodiment of any of the aspects or embodiments herein, in a lipid nanoparticle, the cationic lipid as provided herein or a pharmaceutically acceptable salt thereof is present at a molar percentage of about 30% to about 80%, e.g., about 35% to about 80%, about 40% to about 80%, about 45% to about 80%, about 50% to about 80%, about 55% to about 80%, about 60% to about 80%, about 65% to about 80%, about 70% to about 80%, about 75% to about 80%, 30% to about 75%, about 35% to about 75%, about 40% to about 75%, about 45% to about 75%, about 50% to about 75%, about 55% to about 75%, about 60% to about 75%, about 65% to about 75%, about 70% to about 75%, 30% to about 70%, about 35% to about 70%, about 40% to about 70%, about 45% to about 70%, about 50% to about 70%, about 55% to about 70%, about 60% to about 70%, about 65% to about 70%, about 30% to about 65%, about 35% to about 65%, about 40% to about 65%, about 45% to about 65%, about 50% to about 65%, about 55% to about 65%, about 60% to about 65%, about 30% to about 60%, about 35% to about 60%, about 40% to about 60%, about 45% to about 60%, about 50% to about 60%, about 55% to about 60%, about 30% to about 55%, about 35% to about 55%, about 40% to about 55%, about 45% to about 55%, about 50% to about 55%, about 30% to about 50%, about 35% to about 50%, about 40% to about 50%, about 45% to about 50%, about 30% to about 45%, about 35% to about 45%, about 40% to about 45%, about 30% to about 40%, or about 35% to about 40%. In one embodiment of any of the aspects or embodiments herein, in a lipid nanoparticle, the cationic lipid as provided herein or a pharmaceutically acceptable salt thereof is present at a molar percentage of about 40% to about 60%, or about 45% to about 60%, or about 45% to about 55%, or about 45% to about 50%, or about 50% to about 55%, or about 40% to about 50%; such as but not limited to about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60%.

Sterol

In one embodiment of any of the aspects or embodiments herein, in addition to the more cationic lipids described herein, or a pharmaceutically acceptable salt thereof, and a TNA, the LNP described herein further comprises at least one sterol, to provide membrane integrity and stability of the lipid particle. In one embodiment of any of the aspects or embodiments herein, an exemplary sterol that can be used in the lipid particle is cholesterol, or a derivative thereof. Non-limiting examples of cholesterol derivatives include polar analogues such as 5α-cholestanol, 5-βcoprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5-βcholestanone, and cholesteryl decanoate; and mixtures thereof. In some embodiments of any of the aspects and embodiments herein, the cholesterol derivative is a polar analogue such as cholesteryl-(4'-hydroxy)-butyl ether. In some embodiments of any of the aspects and embodiments herein, cholesterol derivative is cholestryl hemisuccinate (CHEMS).

Exemplary cholesterol derivatives are described in International Patent Application Publication No. WO2009/127060 and U.S. Patent Application Publication No. US2010/0130588, the contents of each of which hereby are incorporated herein by reference in their entirety.

Further exemplary sterols include betasitosterol, campesterol, stigmasterol, ergosterol, brassicasterol, lopeol, cycloartenol, and derivatives thereof. In one embodiment of any of the aspects or embodiments herein, an exemplary sterol that can be used in the lipid particle is betasitosterol.

In one embodiment of any of the aspects or embodiments herein, in a lipid nanoparticle, the sterol is present at a molar percentage of about 20% to about 50%, e.g., about 25% to about 50%, about 30% to about 50%, about 35% to about 50%, about 40% to about 50%, about 45% to about 50%, about 20% to about 45%, about 25% to about 45%, about 30% to about 45%, about 35% to about 45%, about 40% to about 45%, about 20% to about 40%, about 25% to about 40%, about 30% to about 40%, about 35% to about 40%, about 20% to about 35%, about 25% to about 35%, about 30% to about 35%, about 20% to about 30%, or about 25% to about 35%. In one embodiment of any of the aspects or embodiments herein, in a lipid nanoparticle, the sterol is present at a molar percentage of about 35% to about 45%, or about 40% to about 45%, or about 35% to about 40%; such as but not limited to about 35%, about 36%, about 37%, about 38%, about 39%, about 40%, about 41%, about 42%, about 43%, about 44%, or about 45%.

Non-Cationic Lipids

In one embodiment of any of the aspects or embodiments herein, a lipid nanoparticle (LNP) described herein further comprises at least one non-cationic lipid. Non-cationic lipids are also known as structural lipids and may serve to increase fusogenicity and also increase stability of the LNP during formation to provide membrane integrity and stability of the lipid particle. Non-cationic lipids include amphipathic lipids, neutral lipids and anionic lipids. Accordingly, the non-cationic lipid can be a neutral uncharged, zwitterionic, or anionic lipid.

Exemplary non-cationic lipids include, but are not limited to, phospholipids such as distearoyl-sn-glycero-phosphoethanolamine, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), monomethyl-phosphatidylethanolamine (such as 16-O-monomethyl PE), dimethyl-phosphatidylethanolamine (such as 16-O-dimethyl PE), 18-1-trans PE, 1-stearoyl-2-oleoyl-phosphatidyethanolamine (SOPE), hydrogenated soy phosphatidylcholine (HSPC), egg phosphatidylcholine (EPC), dioleoylphosphatidylserine (DOPS), sphingomyelin (SM), dimyristoyl phosphatidylcholine (DMPC), dimyristoyl phosphatidylglycerol (DMPG), distearoylphosphatidylglycerol (DSPG), dierucoylphosphatidylcholine (DEPC), palmitoyloleyolphosphatidylglycerol (POPG), dielaidoyl-phosphatidylethanolamine (DEPE), 1,2-dilauroyl-sn-glycero-3-phosphoethanolamine (DLPE); 1,2-diphytanoyl-sn-glycero-3-phosphoethanolamine (DPHyPE); lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidicacid, cerebrosides, dicetylphosphate, lysophosphatidylcholine, dilinoleoylphosphatidylcholine, or mixtures thereof. It is to be understood that other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl. In one embodiment of any of the aspects or embodiments herein, the non-cationic lipid is any one or more selected from dioleoylphosphatidylcholine (DOPC), distearoylphosphatidylcholine (DSPC), and dioleoyl-phosphatidylethanolamine (DOPE).

Other examples of non-cationic lipids suitable for use in the lipid particles (e.g., lipid nanoparticles) include non-phosphorous lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, sphingomyelin, and the like.

Additional exemplary non-cationic lipids are described in International Patent Application Publication No. WO2017/099823 and U.S. Patent Application Publication No. US2018/0028664, the contents of each of which are hereby incorporated herein by reference in their entirety.

In one embodiment of any of the aspects or embodiments herein, in a lipid nanoparticle, the non-cationic lipid is present at a molar percentage of about 2% to about 20%, e.g., about 3% to about 20%, about 5% to about 20%, about 7% to about 20%, about 8% to about 20%, about 10% to about 20%, about 12% to about 20%, about 13% to about 20%, about 15% to about 20%, about 17% to about 20%, about 18% to about 20%, about 2% to about 18%, about 3% to about 18%, about 5% to about 18%, about 7% to about 18%, about 8% to about 18%, about 10% to about 18%, about 12% to about 18%, about 13% to about 18%, about 15% to about 18%, about 17% to about 18%, about 2% to about 17%, about 3% to about 17%, about 5% to about 17%, about 7% to about 17%, about 8% to about 17%, about 10% to about 17%, about 12% to about 17%, about 13% to about 17%, about 15% to about 17%, about 2% to about 15%, about 3% to about 15%, about 5% to about 15%, about 7% to about 15%, about 8% to about 15%, about 10% to about 15%, about 12% to about 15%, about 13% to about 15%, about 2% to about 13%, about 3% to about 13%, about 5% to about 13%, about 7% to about 13%, about 8% to about 13%, about 10% to about 13%, about 12% to about 13%, about 2% to about 12%, about 3% to about 12%, about 5% to about 12%, about 7% to about 12%, about 8% to about 12%, about 10% to about 12%, about 2% to about 10%, about 3% to about 10%, about 5% to about 10%, about 7% to about 10%, about 8% to about 10%, about 2% to about 8%, about 3% to about 8%, about 5% to about 8%, about 7% to about 8%, about 2% to about 7%, about 3% to about 7%, about 5% to about 7%, about 2% to about 5%, about 3% to about 5%, or about 2% to about 3%. In one embodiment of any of the aspects or embodiments herein, in a lipid nanoparticle, the non-cationic lipid is present at a molar percentage of about 5% to about 15%, about 7% to about 15%, about 8% to about 15%, about 10% to about 15%, about 12% to about 15%, about 13% to about 15%, 5% to about 13%, about 7% to about 13%, about 8% to about 13%, about 10% to about 13%, about 12% to about 13%, about 5% to about 12%, about 7% to about 12%, about 8% to about 12%, about 10% to about 12%, about 5% to about 10%, about 7% to about 10%, about 8% to about 10%, about 5% to about 8%, about 7% to about 8%, or about 5% to about 7%; such as but not limited to about 5%, about 6%, about 7%, about 8%, about 9%, about 10%, about 11%, about 11%, about 12%, about 13%, about 14%, or about 15%.

PEGylated Lipids

In one embodiment of any of the aspects or embodiments herein, a lipid nanoparticle (LNP) described herein further comprises at least one PEGylated lipid (e.g., one, two, or three). A PEGylated lipid is a lipid as defined herein that is covalently or non-covalently linked to one or more polyethylene glycol (PEG) polymer chains and is therefore a class of conjugated lipids. Generally, PEGylated lipids are incorporated in LNPs to inhibit aggregation of the particle and/or provide steric stabilization. In one embodiment of any of the aspects or embodiments herein, the lipid is covalently linked to the one or more PEG polymer chains.

Suitable PEG molecules for use in a PEGylated lipid include but are not limited to those having a molecular weight of between about 500 and about 10,000, or between about 1,000 and about 7,500, or about between about 1,000 and about 5,000, or between about 2,000 and about 5,000, or between about 2,000 and about 4,000, or between about 2,000 and about 3,500, or between about 2,000 and about 3,000; e.g., PEG2000, PEG2500, PEG3000, PEG3350, PEG3500, and PEG4000.

The lipid to which the one or more PEG chains are linked to can be a sterol, a non-cationic lipid, or a phospholipid. Exemplary PEGylated lipids include, but are not limited to, PEG-diacylglycerol (DAG) (such as 1-(monomethoxy-polyethyleneglycol)-2,3-dimyristoylglycerol (PEG-DMG)), PEG-dialkyloxypropyl (DAA), PEG-phospholipid, PEG-ceramide (Cer), a PEGylated phosphatidylethanoloamine (PEG-PE), PEG succinate diacylglycerol (PEGS-DAG) (such as 4-0-(2',3'-di(tetradecanoyloxy)propyl-1-0-(w-methoxy(polyethoxy)ethyl) butanedioate (PEG-S-DMG)), PEG dialkoxypropylcarbam, N-(carbonyl-methoxypoly ethylene glycol 2000)-1,2-distearoyl-sn-glycero-3-phosphoethanolamine sodium salt, or a mixture thereof. Additional exemplary PEGylated lipids are described, for example, in U.S. Pat. Nos. 5,885,613 and 6,287,591 and U.S. Patent Application Publication Nos. US2003/0077829, US2003/0077829, US2005/0175682, US2008/0020058, US2011/0117125, US2010/0130588, US2016/0376224, and US2017/0119904, the contents of each of which are hereby incorporated herein by reference in their entirety.

In one embodiment of any of the aspects or embodiments herein, the at least one PEGylated lipid in a lipid nanoparticle (LNP) provided herein is selected from the group consisting of PEG-dilauryloxypropyl; PEG-dimyristyloxypropyl; PEG-dipalmityloxypropyl, PEG-distearyloxypropyl; 1-(monomethoxy-polyethyleneglycol)-2,3-dimyristoylglycerol (DMG-PEG); PEG-dilaurylglycerol; PEG-dipalmitoylglycerol; PEG-disterylglycerol; PEG-dilaurylglycamide; PEG-dimyristylglycamide; PEG-dipalmitoylglycamide; PEG-disterylglycamide; (1-[8'-(Cholest-5-en-3[beta]-oxy)carboxamido-3',6'-dioxaoctanyl] carbamoyl-[omega]-methyl-poly(ethylene glycol) (PEG-cholesterol); 3,4-ditetradecoxylbenzyl-[omega]-methyl-poly(ethylene glycol) ether (PEG-DMB), 1,2-dimyristoyl-sn-glycero-3-phosphoethanolamine-N-[methoxy (polyethylene glycol) (DSPE-PEG), 1,2-dimyristoyl-sn-glycero-3-phosphoethanolamine-N-[methoxy(polyethylene glycol)-hydroxyl (DSPE-PEG-OH); and polyethylene glycol (mono)octadecyl (mPEG-C18). In one embodiment of any of the aspects or embodiments herein, the at least one PEGylated lipid is DMG-PEG, DSPE-PEG, or both. In one embodiment of any of the aspects or embodiments herein, the at least one PEGylated lipid is DMG-PEG, DSPE-PEG, DSPE-PEG-OH, mPEG-C18, or any combination thereof such as a combination of two or three thereof. In one embodiment of any of the aspects or embodiments herein, the at least one PEGylated lipid is DMG-PEG2000, DSPE-PEG2000, or both. In one embodiment of any of the aspects or embodiments herein, the at least one PEGylated lipid is DMG-PEG2000, DSPE-PEG2000, DSPE-PEG2000-OH, or mPEG-C18, or any combination thereof such as a combination of two or three thereof. In one embodiment of any of the aspects or embodiments herein, a lipid nanoparticle (LNP) provided herein comprises DMP-PEG2000 and DSPE-PEG2000. In one embodiment of any of the aspects or embodiments herein, a lipid nanoparticle (LNP) provided herein comprises DMG-PEG2000, DSPE-PEG2000, and DSPE-PEG2000-OH, or mPEG-C18, or any combination thereof such as a combination of two or three thereof. In one embodiment of any of the aspects or embodiments herein, in a lipid nanoparticle, the at least one PEGylated lipid is present, in total, at a molar percentage of about 1% to 10%, e.g., about 1.5% to about 10%, about 2% to about 10%, about 2.5% to about 10%, about 3% to about 10%, about 3.5% to about 10%, about 4% to about 10%, about 4.5% to about 10%, about 5% to about 10%, about 5.5% to about 10%, about 6% to about 10%, about 6.5% to about 10%, about 7% to about 10%, about 7.5% to about 10%, about 8% to about 10%, about 8.5% to about 10%, about 9% to about 10%, about 9.5% to about 10%, about 1% to about 5%, about 1.5% to about 5%, about 2% to about 5%, about 2.5% to about 5%, about 3% to about 5%, about 3.5% to about 5%, about 4% to about 5%, about 4.5% to about 5%, about 1% to about 4%, about 1.5% to about 4%, about 2% to about 4%, about 2.5% to about 4%, about 3% to about 4%, about 3.5% to about 4%, about 1% to about 3.5%, about 1.5% to about 3.5%, about 2% to about 3.5%, about 2.5% to about 3.5%, about 3% to about 3.5%, about 1% to about 3%, about 1.5% to about 3%, about 2% to about 3%, about 2.5% to about 3%, about 1% to about 2.5%, about 1.5% to about 2.5%, about 2% to about 2.5%, about 1% to about 2%, about 1.5% to about 2%, or about 1% to about 1.5%. In one embodiment of any of the aspects or embodiments herein, in a lipid nanoparticle, the at least one PEGylated lipid is present, in total, at a molar percentage of about 1% to about 2%, about 1.5% to about 2%, or about 1% to about 1.5%; such as but not limited to about 1%, about 1.1%, about 1.2%, about 1.3%, about 1.4%, about 1.5%, about 1.6%, about 1.7%, about 1.8%, about 1.9%, or about 2%.

In one embodiment of any of the aspects or embodiments herein, in a lipid nanoparticle, the at least one PEGylated lipid is present, in total, at a molar percentage of about 2.1% to about 10%, e.g., about 2.5% to about 10%, about 3% to about 10%, about 3.5% to about 10%, about 4% to about 10%, about 4.5% to about 10%, about 5% to about 10%, about 5.5% to about 10%, about 6% to about 10%, about 6.5% to about 10%, about 7% to about 10%, about 7.5% to about 10%, about 8% to about 10%, about 8.5% to about 10%, about 9% to about 10%, about 9.5% to about 10%, about 2.1% to about 7%, about 2.5% to about 7%, about 3% to about 7%, about 3.5% to about 7%, about 4% to about 7%, about 4.5% to about 7%, about 5% to about 7%, about 5.5% to about 7%, about 6% to about 7%, about 6.5% to about 7%, about 2.1% to about 5%, about 2.5% to about 5%, about 3% to about 5%, about 3.5% to about 5%, about 4% to about 5%, about 4.5% to about 5%, about 2.1% to about 4%, about 2.5% to about 4%, about 3% to about 4%, about 3.5% to about 4%, about 2.1% to about 3.5%, about 2.5% to about 3.5%, about 3% to about 3.5%, about 2.1% to about 3%, about 2.5% to about 3%, or about 2.1% to about 2.5%. In one embodiment of any of the aspects or embodiments herein, in a lipid nanoparticle, the at least one PEGylated lipid is present, in total, at a molar percentage of about 2.1% to about 5%, about 2.5% to about 5%, about 3% to about 5%, about 3.5% to about 5%, about 4% to about 5%, about 4.5% to about 5%, about 2.1% to about 4%, about 2.5% to about 4%, about 3% to about 4%, about 3.5% to about 4%, about 2.1% to about 3.5%, about 2.5% to about 3.5%, about 3% to about 3.5%, about 2.1% to about 3%, about 2.5% to about 3%, or about 2.1% to about 2.5%; such as but not limited to about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, or about 5%.

Tissue-Specific Targeting Ligands and PEGylated Lipid Conjugates

In one embodiment of any of the aspects or embodiments herein, a lipid nanoparticle (LNP) described herein further comprises at least one tissue-specific targeting ligand for the purpose of aiding, enhancing and/or increasing the delivery of the LNP to a target site of interest. The ligand may be any biological molecule such as a peptide, a protein, an antibody, a glycan, a sugar, a nucleic acid, a lipid, or a conjugate comprising any of the foregoing, that recognizes a receptor or a surface antigen that is unique to certain cells and tissues.

In one embodiment of any of the aspects or embodiments herein, the at least one tissue-specific targeting ligand is N-Acetylgalactosamine (GalNAc) or a GalNAc derivative. The term "GalNAc derivative" encompasses modified GalNAc, functionalized GalNAc, and GalNAc conjugates wherein one or more GalNAc molecules (native or modified) is covalently linked to one or more functional groups or one or more classes of exemplary biological molecules such as but not limited to a peptide, a protein, an antibody, a glycan, a sugar, a nucleic acid, a lipid. The biological molecule itself, to which the one or more GalNAc molecules may be conjugated to, typically help to increase the stability and/or to inhibit aggregation. In one embodiment of any of the aspects or embodiments herein, the mol ratio between a tissue-specific target ligand, such as GalNAc, and the biological molecule to which the ligand is conjugated to is 1:1, 2:1, 3:1, 4:1, 5:1, 6:1, 7:1, 8:1, 9:1, 10:1, 1:2, 1:3, 1:4, 1:5, 1:6, 1:7, 1:8, 1:9, and 1:10. In one embodiment of any of the aspects or embodiments herein, the mol ratio between a tissue-specific target ligand, such as GalNAc, and the biological molecule to which the ligand is conjugated to is 1:1 (e.g., mono-antennary GalNAc), 2:1 (bi-antennary GalNAc), 3:1 (tri-antennary GalNAc), and 4:1 (tetra-antennary GalNAc). Conjugated GalNAc such as tri-antennary GalNAc (GalNAc3) or tetra-antennary GalNAc (GalNAc4) can be synthesized as known in the art (see, WO2017/084987 and WO2013/166121) and chemically conjugated to lipid or PEG as well-known in the art (see, Resen et al., J. Biol. Chem. (2001) "Determination of the Upper Size Limit for Uptake and Processing of Ligands by the Asialoglycoprotein Receptor on Hepatocytes in Vitro and in Vivo" 276:375577-37584).

In one embodiment of any of the aspects or embodiments herein, the tissue-specific targeting ligand is covalently linked to a PEGylated lipid as defined and described herein to form a PEGylated lipid conjugate. Exemplary PEGylated lipids are described above, and include PEG-dilauryloxypropyl; PEG-dimyristyloxypropyl; PEG-dipalmityloxypropyl, PEG-distearyloxypropyl; 1-(monomethoxy-polyethyleneglycol)-2,3-dimyristoylglycerol (DMG-PEG); PEG-dilaurylglycerol; PEG-dipalmitoylglycerol; PEG-disterylglycerol; PEG-dilaurylglycamide; PEG-dimyristylglycamide; PEG-dipalmitoylglycamide; PEG-disterylglycamide; (1-[8'-(Cholest-5-en-3[beta]-oxy) carboxamido-3',6'-dioxaoctanyl]carbamoyl-[omega]-methyl-poly(ethylene glycol) (PEG-cholesterol); 3,4-ditetradecoxylbenzyl-[omega]-methyl-poly(ethylene glycol) ether (PEG-DMB), and 1,2-dimyristoyl-sn-glycero-3-phosphoethanolamine-N-[methoxy(polyethylene glycol) (DSPE-PEG). In one embodiment of any of the aspects or embodiments herein, the tissue-specific targeting ligand is covalently linked to GalNAc or a GalNAc derivative. In one embodiment of any of the aspects or embodiments herein, the PEGylated lipid conjugate is mono-, bi-, tri-, or tetra-antennary GalNAc-DSPE-PEG. In one embodiment of any of the aspects or embodiments herein, the PEGylated lipid conjugate is mono-, bi-, tri-, or tetra-antennary GalNAc-DSPE-PEG2000. In one embodiment of any of the aspects or embodiments herein, the PEGylated lipid conjugate is tetra-antennary GalNAc-DSPE-PEG2000.

In one embodiment of any of the aspects or embodiments herein, in a lipid nanoparticle, the PEGylated lipid conjugate is present at a molar percentage of about 0.1% to about 10%, e.g., about 0.2% to about 10%, about 0.3% to about 10%, about 0.4% to about 10%, about 0.5% to about 10%, about 0.6% to about 10%, about 0.7% to about 10%, about 0.8% to about 10%, about 0.9% to about 10%, about 1% to about 10%, about 1.5% to about 10%, about 2% to about 10%, about 2.5% to about 10%, about 3% to about 10%, about 3.5% to about 10%, about 4% to about 10%, about 4.5% to about 10%, about 5% to about 10%, about 5.5% to about 10%, about 6% to about 10%, about 6.5% to about 10%, about 7% to about 10%, about 7.5% to about 10%, about 8% to about 10%, about 8.5% to about 10%, about 9% to about 10%, about 9.5% to about 10%, about 0.1% to about 5%, about 0.2% to about 5%, about 0.3% to about 5%, about 0.4% to about 5%, about 0.5% to about 5%, about 0.6% to about 5%, about 0.7% to about 5%, about 0.8% to about 5%, about 0.9% to about 10%, about 1% to about 5%, about 1.5% to about 5%, about 2% to about 5%, about 2.5% to about 5%, about 3% to about 5%, about 3.5% to about 5%, about 4% to about 5%, about 4.5% to about 5%, about 0.1% to about 3%, about 0.2% to about 3%, about 0.3% to about 3%, about 0.4% to about 3%, about 0.5% to about 3%, about 0.6% to about 3%, about 0.7% to about 3%, about 0.8% to about 3%, about 0.9% to about 3%, about 1% to about 3%, about 1.5% to about 3%, about 2% to about 3%, about 2.5% to about 3%, about 0.1% to about 2%, about 0.2% to about 2%, about 0.3% to about 2%, about 0.4% to about 2%, about 0.5% to about 2%, about 0.6% to about 2%, about 0.7% to about 2%, about 0.8% to about 2%, about 0.9% to about 2%, about 1% to about 2%, about 1.5% to about 2%, about 0.1% to about 1.5%, 0.2% to about 1.5%, about 0.3% to about 1.5%, about 0.4% to about 1.5%, about 0.5% to about 1.5%, about 0.6% to about 1.5%, about 0.7% to about 1.5%, about 0.8% to about 1.5%, about 0.9% to about 1.5%, about 1% to about 1.5%, about 0.1% to about 1%, 0.2% to about 1%, about 0.3% to about 1%, about 0.4% to about 1%, about 0.5% to about 1%, about 0.6% to about 1%, about 0.7% to about 1%, about 0.8% to about 1%, or about 0.9% to about 1%. In one embodiment of any of the aspects or embodiments herein, in a lipid nanoparticle, the PEGylated lipid conjugate is present at a molar percentage of about 0.1% to about 1.5%, 0.2% to about 1.5%, about 0.3% to about 1.5%, about 0.4% to about 1.5%, about 0.5% to about 1.5%, about 0.6% to about 1.5%, about 0.7% to about 1.5%, about 0.8% to about 1.5%, about 0.9% to about 1.5%, about 1% to about 1.5%, about 0.1% to about 1%, 0.2% to about 1%, about 0.3% to about 1%, about 0.4% to about 1%, about 0.5% to about 1%, about 0.6% to about 1%, about 0.7% to about 1%, about 0.8% to about 1%, or about 0.9% to about 1%; such as but not limited to about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, or about 1.5%.

Other Components of Lipid Nanoparticles (LNP)

Additional components of LNP such as conjugated lipids are also contemplated in this disclosure. Exemplary conjugated lipids include, but are not limited to, polyoxazoline (POZ)-lipid conjugates, polyamide-lipid conjugates (such as ATTA-lipid conjugates), cationic-polymer lipid (CPL) conjugates, and mixtures thereof.

Furthermore, in one embodiment of any of the aspects or embodiments herein, a lipid nanoparticle (LNP) described herein further comprises, for example, by co-encapsulation within the LNP or by conjugation to a therapeutic nucleic acid or any one of the components of the LNP as described above, an immune-modulating compound. The immune-modulating compound, such as dexamethasone or a modified dexamethasone, may aid in of minimizing immune response. In one embodiment of any of the aspects or embodiments herein, a lipid nanoparticle (LNP) described herein further comprises dexamethasone palmitate.

In some embodiments of any of the aspects and embodiments herein, in addition to the cationic lipid, the lipid nanoparticle comprises an agent for condensing and/or encapsulating nucleic acid cargo, such as ceDNA. Such an agent is also referred to as a condensing or encapsulating agent herein. Without limitations, any compound known in the art for condensing and/or encapsulating nucleic acids can be used as long as it is non-fusogenic. In other words, an agent capable of condensing and/or encapsulating the nucleic acid cargo, such as ceDNA, but having little or no fusogenic activity. Without wishing to be bound by a theory, a condensing agent may have some fusogenic activity when not condensing/encapsulating a nucleic acid, such as ceDNA, but a nucleic acid encapsulating lipid nanoparticle formed with said condensing agent can be non-fusogenic.

Total Lipid to Nucleic Acid Ratio

Generally, the lipid particles (e.g., lipid nanoparticles) are prepared such that the final particle has a total lipid to therapeutic nucleic acid (mass or weight) ratio of from about 10:1 to 60:1, e.g., about 15:1 to about 60:1, about 20:1 to about 60:1, about 25:1 to about 60:1, about 30:1 to about 60:1, about 35:1 to about 60:1, about 40:1 to about 60:1, about 45:1 to about 60:1, about 50:1 to about 60:1, about 55:1 to about 60:1, about 10:1 to about 55:1, about 15:1 to about 55:1, about 20:1 to about 55:1, about 25:1 to about 55:1, about 30:1 to about 55:1, about 35:1 to about 55:1, about 40:1 to about 55:1, about 45:1 to about 55:1, about 50:1 to about 55:1, about 10:1 to about 50:1, about 15:1 to about 50:1, about 20:1 to about 50:1, about 25:1 to about 50:1, about 30:1 to about 50:1, about 35:1 to about 50:1, about 40:1 to about 50:1, about 45:1 to about 50:1, about 10:1 to about 45:1, about 15:1 to about 45:1, about 20:1 to about 45:1, about 25:1 to about 45:1, about 30:1 to about 45:1, about 35:1 to about 45:1, about 40:1 to about 45:1, about 10:1 to about 40:1, about 15:1 to about 40:1, about 20:1 to about 40:1, about 25:1 to about 40:1, about 30:1 to about 40:1, about 35:1 to about 40:1, about 10:1 to about 35:1, about 15:1 to about 35:1, about 20:1 to about 35:1, about 25:1 to about 35:1, about 30:1 to about 35:1, about 10:1 to about 30:1, about 15:1 to about 30:1, about 20:1 to about 30:1, about 25:1 to about 30:1, about 10:1 to about 25:1, about 15:1 to about 25:1, about 20:1 to about 25:1, about 10:1 to about 20:1, about 15:1 to about 20:1, or about 10:1 to about 15:1.

The amounts of lipids and nucleic acid can be adjusted to provide a desired N/P ratio (i.e., ratio of positively charged polymer amine (N=nitrogen) groups to negatively charged nucleic acid phosphate (P) groups), for example, an N/P ratio of 3, 4, 5, 6, 7, 8, 9, 10, 11, 12, 13, 14 15, 16, 17, 18, 19, 20, or higher. Generally, the lipid particle formulation's overall lipid content can range from about 5 mg/ml to about 30 mg/mL.

Size of Lipid Nanoparticles (LNP)

According to some embodiments of any of the aspects or embodiments herein, the LNP has a diameter ranging from about 40 nm to about 120 nm, e.g., about 45 nm to about 120 nm, about 50 nm to about 120 nm, about 55 nm to about 120 nm, about 60 nm to about 120 nm, about 65 nm to about 120 nm, about 70 nm to about 120 nm, about 75 nm to about 120 nm, about 80 nm to about 120 nm, about 85 nm to about 120 nm, about 90 nm to about 120 nm, about 95 nm to about 120 nm, about 100 nm to about 120 nm, about 105 nm to about 120 nm, about 110 nm to about 120 nm, about 115 nm to about 120 nm, about 40 nm to about 110 nm, about 45 nm to about 110 nm, about 50 nm to about 110 nm, about 55 nm to about 110 nm, about 60 nm to about 110 nm, about 65 nm to about 110 nm, about 70 nm to about 110 nm, about 75 nm to about 110 nm, about 80 nm to about 110 nm, about 85 nm to about 110 nm, about 90 nm to about 110 nm, about 95 nm to about 110 nm, about 100 nm to about 110 nm, about 105 nm to about 110 nm, about 40 nm to about 100 nm, about 45 nm to about 100 nm, about 50 nm to about 100 nm, about 55 nm to about 100 nm, about 60 nm to about 100 nm, about 65 nm to about 100 nm, about 70 nm to about 100 nm, about 75 nm to about 100 nm, about 80 nm to about 100 nm, about 85 nm to about 100 nm, about 90 nm to about 100 nm, or about 95 nm to about 100 nm.

According to some embodiments of any of the aspects or embodiments herein, the LNP has a diameter of less than about 100 nm, e.g., about 40 nm to about 90 nm, about 45 nm to about 90 nm, about 50 nm to about 90 nm, about 55 nm to about 90 nm, about 60 nm to about 90 nm, about 65 nm to about 90 nm, about 70 nm to about 90 nm, about 75 nm to about 90 nm, about 80 nm to about 90 nm, about 85 nm to about 90 nm, about 40 nm to about 85 nm, about 45 nm to about 85 nm, about 50 nm to about 85 nm, about 55 nm to about 85 nm, about 60 nm to about 85 nm, about 65 nm to about 85 nm, about 70 nm to about 85 nm, about 75 nm to about 85 nm, about 80 nm to about 85 nm, about 40 nm to about 80 nm, about 45 nm to about 80 nm, about 50 nm to about 80 nm, about 55 nm to about 80 nm, about 60 nm to about 80 nm, about 65 nm to about 80 nm, about 70 nm to about 80 nm, about 75 nm to about 80 nm, about 40 nm to about 75 nm, about 45 nm to about 75 nm, about 50 nm to about 75 nm, about 55 nm to about 75 nm, about 60 nm to about 75 nm, about 65 nm to about 75 nm, about 70 nm to about 75 nm, about 40 nm to about 70 nm, about 45 nm to about 70 nm, about 50 nm to about 70 nm, about 55 nm to about 70 nm, about 60 nm to about 70 nm, or about 65 nm to about 70 nm. In one embodiment of any of the aspects or embodiments herein, the LNP has a diameter of about 60 nm to about 85 nm, about 65 nm to about 85 nm, about 70 nm to about 85 nm, about 75 nm to about 85 nm, about 80 nm to about 85 nm, about 60 nm to about 80 nm, about 65 nm to about 80 nm, about 70 nm to about 80 nm, about 75 nm to about 80 nm, about 60 nm to about 75 nm, about 65 nm to about 75 nm, about 70 nm to about 75 nm, about 60 nm to about 70 nm, or about 65 nm to about 70 nm; such as but not limited to about 60 mm, about 61 mm, about 62 mm, about 63 mm, about 64 mm, about 65 mm, about 66 mm, about 67 mm, about 68 mm, about 69 mm, about 70 mm, about 71 mm, about 72 mm, about 73 mm, about 74 mm, about 75 mm, about 76 mm, about 77 mm, about 78 mm, about 79 mm, about 80 mm, about 81 mm, about 82 mm, about 83 mm, about 84 mm, or about 85 mm.

In one embodiment of any of the aspects or embodiments herein, lipid particle (e.g., lipid nanoparticle) size can be determined by quasi-elastic light scattering using, for example, a Malvern Zetasizer Nano ZS (Malvern, UK) system.

LNP Comprising Cationic Lipid, Sterol, Non-Cationic Lipid, PEGylated Lipid, and Optionally Tissue-Specific Targeting Ligand According to some embodiments of any of the aspects or embodiments herein, a lipid nanoparticle provided herein comprises at least one cationic lipid as described herein, at least one sterol, at least one non-cationic lipid, and at least one PEGylated lipid. In one embodiment of any of the aspects or embodiments herein, a lipid nanoparticle provided herein consists essentially of at least one cationic lipid as described herein, at least one sterol, at least one non-cationic lipid, and at least one PEGylated lipid. In one embodiment of any of the aspects or embodiments herein, a lipid nanoparticle provided herein consists of at least one cationic lipid as described herein, at least one sterol, at least one non-cationic lipid, and at least one PEGylated lipid. In one embodiment of any of the aspects or embodiments herein, the molar ratio of cationic lipid:sterol:non-cationic lipid:PEGylated lipid is about 48 (±5) 20:10 (±3):41 (±5):2 (±2), e.g., about 47.5:10.0:40.7:1.8 or about 47.5:10.0:40.7:3.0.

According to some embodiments of any of the aspects or embodiments herein, a lipid nanoparticle provided herein comprises at least one cationic lipid as described herein, at least one sterol, at least one non-cationic lipid, at least one PEGylated lipid, and a tissue-specific targeting ligand. In one embodiment of any of the aspects or embodiments herein, the tissue-specific targeting ligand is GalNAc. In one embodiment of any of the aspects or embodiments herein, a lipid nanoparticle provided herein consists essentially of at least one cationic lipid as described herein, at least one sterol, at least one non-cationic lipid, at least one PEGylated lipid, and a tissue-specific targeting ligand. In one embodiment of any of the aspects or embodiments herein, a lipid nanoparticle provided herein consists of at least one cationic lipid as described herein, at least one sterol, at least one non-cationic lipid, at least one PEGylated lipid, and a tissue-specific targeting ligand. In one embodiment of any of the aspects or embodiments herein, the tissue-specific targeting ligand is conjugated to a PEGylated lipid to form a PEGylated lipid conjugate. In one embodiment of any of the aspects or embodiments herein, the PEGylated lipid conjugate is mono-, bi-, tri-, or tetra-antennary GalNAc-DSPE-PEG2000. In one embodiment of any of the aspects or embodiments herein, the PEGylated lipid conjugate is tetra-antennary GalNAc-DSPE-PEG2000. In one embodiment of any of the aspects or embodiments herein, the molar ratio of cationic lipid:sterol:non-cationic lipid:PEGylated lipid:PEGylated lipid conjugate is about 48 (±5):10 (±3):41 (±5):2 (±2):1.5 (±1), e.g., 47.5:10.0:40.2:1.8:0.5 or 47.5:10.0:39.5:2.5:0.5.

IV. Therapeutic Nucleic Acid (TNA)

The present disclosure provides a lipid-based platform for delivering therapeutic nucleic acid (TNA). Non-limiting examples of RNA-based therapeutics include mRNA, antisense RNA and oligonucleotides, ribozymes, aptamers, interfering RNAs (RNAi), dicer-substrate dsRNA, small hairpin RNA (shRNA), asymmetrical interfering RNA (aiRNA), microRNA (miRNA). Non-limiting examples of DNA-based therapeutics include minicircle DNA, minigene, viral DNA (e.g., Lentiviral or AAV genome) or non-viral DNA vectors, closed-ended linear duplex DNA (ceDNA/CELiD), plasmids, bacmids, Doggybone™ DNA vectors, minimalistic immunological-defined gene expression (MIDGE)-vector, nonviral ministring DNA vector (linear-covalently closed DNA vector), or dumbbell-shaped DNA minimal vector ("dumbbell DNA"). As such, aspects of the present disclosure generally provide ionizable lipid particles (e.g., lipid nanoparticles) comprising a TNA.

siRNA or miRNA that can downregulate the intracellular levels of specific proteins through a process called RNA interference (RNAi) are also contemplated by the present invention to be nucleic acid therapeutics. After siRNA or miRNA is introduced into the cytoplasm of a host cell, these double-stranded RNA constructs can bind to a protein called RISC. The sense strand of the siRNA or miRNA is removed by the RISC complex. The RISC complex, when combined with the complementary mRNA, cleaves the mRNA and release the cut strands. RNAi is by inducing specific destruction of mRNA that results in downregulation of a corresponding protein.

Antisense oligonucleotides (ASO) and ribozymes that inhibit mRNA translation into protein can be nucleic acid therapeutics. For antisense constructs, these single stranded deoxynucleic acids have a complementary sequence to the sequence of the target protein mRNA and are capable of binding to the mRNA by Watson-Crick base pairing. This binding prevents translation of a target mRNA, and/or triggers RNaseH degradation of the mRNA transcript. As a result, the antisense oligonucleotide has increased specificity of action (i.e., down-regulation of a specific disease-related protein).

In any of the methods and compositions provided herein, the therapeutic nucleic acid (TNA) can be a therapeutic RNA. Said therapeutic RNA can be an inhibitor of mRNA translation, agent of RNA interference (RNAi), catalytically active RNA molecule (ribozyme), transfer RNA (tRNA) or an RNA that binds an mRNA transcript (ASO), protein or other molecular ligand (aptamer). In any of the methods provided herein, the agent of RNAi can be a double-stranded RNA, single-stranded RNA, micro-RNA, short interfering RNA, short hairpin RNA, or a triplex-forming oligonucleotide.

In any of the methods composition provided herein, the therapeutic nucleic acid (TNA) is a therapeutic DNA such as closed ended double stranded DNA (e.g., ceDNA, CELiD, linear covalently closed DNA ("ministring"), Doggybone™, protelomere closed ended DNA, dumbbell linear DNA, plasmid, minicircle or the like). Some embodiments of the disclosure are based on methods and compositions comprising closed-ended linear duplexed (ceDNA) that can express a transgene (e.g., a therapeutic nucleic acid). The ceDNA vectors as described herein have no packaging constraints imposed by the limiting space within the viral capsid. ceDNA vectors represent a viable eukaryotically-produced alternative to prokaryote-produced plasmid DNA vectors.

ceDNA vectors preferably have a linear and continuous structure rather than a non-continuous structure. The linear and continuous structure is believed to be more stable from attack by cellular endonucleases, as well as less likely to be recombined and cause mutagenesis. Thus, a ceDNA vector in the linear and continuous structure is a preferred embodiment. The continuous, linear, single strand intramolecular duplex ceDNA vector can have covalently bound terminal ends, without sequences encoding AAV capsid proteins. These ceDNA vectors are structurally distinct from plasmids (including ceDNA plasmids described herein), which are circular duplex nucleic acid molecules of bacterial origin. The complimentary strands of plasmids may be separated following denaturation to produce two nucleic acid molecules, whereas in contrast, ceDNA vectors, while having complimentary strands, are a single DNA molecule and therefore even if denatured, remain a single molecule. In some embodiments of any of the aspects and embodiments herein, ceDNA vectors can be produced without DNA base methylation of prokaryotic type, unlike plasmids. Therefore, the ceDNA vectors and ceDNA-plasmids are different both in term of structure (in particular, linear versus circular) and also in view of the methods used for producing and purifying these different objects, and also in view of their DNA methylation which is of prokaryotic type for ceDNA-plasmids and of eukaryotic type for the ceDNA vector.

Provided herein are non-viral, capsid-free ceDNA molecules with covalently closed ends (ceDNA). These non-viral capsid free ceDNA molecules can be produced in permissive host cells from an expression construct (e.g., a ceDNA-plasmid, a ceDNA-bacmid, a ceDNA-baculovirus, or an integrated cell-line) containing a heterologous gene (e.g., a transgene, in particular a therapeutic transgene) positioned between two different inverted terminal repeat (ITR) sequences, where the ITRs are different with respect to each other. In some embodiments of any of the aspects and embodiments herein, one of the ITRs is modified by deletion, insertion, and/or substitution as compared to a wild-type ITR sequence (e.g., AAV ITR); and at least one of the ITRs comprises a functional terminal resolution site (TRS) and a Rep binding site. The ceDNA vector is preferably duplex, e.g., self-complementary, over at least a portion of the molecule, such as the expression cassette (e.g., ceDNA is not a double stranded circular molecule). The ceDNA vector has covalently closed ends, and thus is resistant to exonuclease digestion (e.g., exonuclease I or exonuclease III), e.g., for over an hour at 37° C.

In one aspect of any of the aspects or embodiments herein, a ceDNA vector comprises, in the 5' to 3' direction: a first adeno-associated virus (AAV) inverted terminal repeat (ITR), a nucleotide sequence of interest (for example an expression cassette as described herein) and a second AAV ITR. In one embodiment of any of the aspects or embodiments herein, the first ITR (5' ITR) and the second ITR (3' ITR) are asymmetrical with respect to each other—that is, they have a different 3D-spatial configuration from one another. As an exemplary embodiment, the first ITR can be a wild-type ITR and the second ITR can be a mutated or modified ITR, or vice versa, where the first ITR can be a mutated or modified ITR and the second ITR a wild-type ITR. In one embodiment of any of the aspects or embodiments herein, the first ITR and the second ITR are both modified but are different sequences, or have different modifications, or are not identical modified ITRs, and have different 3D spatial configurations. Stated differently, a ceDNA vector with asymmetrical ITRs have ITRs where any changes in one ITR relative to the WT-ITR are not reflected in the other ITR; or alternatively, where the asymmetrical ITRs have a the modified asymmetrical ITR pair can have a different sequence and different three-dimensional shape with respect to each other.

In one embodiment of any of the aspects or embodiments herein, a ceDNA vector comprises, in the 5' to 3' direction: a first adeno-associated virus (AAV) inverted terminal repeat (ITR), a nucleotide sequence of interest (for example an expression cassette as described herein) and a second AAV ITR, where the first ITR (5' ITR) and the second ITR (3' ITR) are symmetric, or substantially symmetrical with respect to each other—that is, a ceDNA vector can comprise ITR sequences that have a symmetrical three-dimensional spatial organization such that their structure is the same shape in geometrical space, or have the same A, C—C' and B—B' loops in 3D space. In such an embodiment, a symmetrical ITR pair, or substantially symmetrical ITR pair can be modified ITRs (e.g., mod-ITRs) that are not wild-type ITRs. A mod-ITR pair can have the same sequence which has one or more modifications from wild-type ITR and are reverse complements (inverted) of each other. In one embodiment of any of the aspects or embodiments herein, a modified ITR pair are substantially symmetrical as defined herein, that is, the modified ITR pair can have a different sequence but have corresponding or the same symmetrical three-dimensional shape. In some embodiments of any of the aspects and embodiments herein, the symmetrical ITRs, or substantially symmetrical ITRs can be wild type (WT-ITRs) as described herein. That is, both ITRs have a wild-type sequence, but do not necessarily have to be WT-ITRs from the same AAV serotype. In one embodiment of any of the aspects or embodiments herein, one WT-ITR can be from one AAV serotype, and the other WT-ITR can be from a different AAV serotype. In such an embodiment, a WT-ITR pair are substantially symmetrical as defined herein, that is, they can have one or more conservative nucleotide modification while still retaining the symmetrical three-dimensional spatial organization.

The wild-type or mutated or otherwise modified ITR sequences provided herein represent DNA sequences included in the expression construct (e.g., ceDNA-plasmid, ceDNA Bacmid, ceDNA-baculovirus) for production of the ceDNA vector. Thus, ITR sequences actually contained in the ceDNA vector produced from the ceDNA-plasmid or other expression construct may or may not be identical to the ITR sequences provided herein as a result of naturally occurring changes taking place during the production process (e.g., replication error).

In one embodiment of any of the aspects or embodiments herein, a ceDNA vector described herein comprising the expression cassette with a transgene which is a therapeutic nucleic acid sequence, can be operatively linked to one or more regulatory sequence(s) that allows or controls expression of the transgene. In one embodiment of any of the aspects or embodiments herein, the polynucleotide comprises a first ITR sequence and a second ITR sequence, wherein the nucleotide sequence of interest is flanked by the first and second ITR sequences, and the first and second ITR sequences are asymmetrical relative to each other, or symmetrical relative to each other.

In one embodiment of any of the aspects or embodiments herein, an expression cassette is located between two ITRs comprised in the following order with one or more of: a promoter operably linked to a transgene, a posttranscriptional regulatory element, and a polyadenylation and termination signal. In one embodiment of any of the aspects or embodiments herein, the promoter is regulatable—inducible or repressible. The promoter can be any sequence that facilitates the transcription of the transgene. In one embodiment of any of the aspects or embodiments herein the promoter is a CAG promoter, or variation thereof. The posttranscriptional regulatory element is a sequence that modulates expression of the transgene, as a non-limiting example, any sequence that creates a tertiary structure that enhances expression of the transgene which is a therapeutic nucleic acid sequence.

In one embodiment of any of the aspects or embodiments herein, the posttranscriptional regulatory element comprises WPRE. In one embodiment of any of the aspects or embodiments herein, the polyadenylation and termination signal comprise BGHpolyA. Any cis regulatory element known in the art, or combination thereof, can be additionally used e.g., SV40 late polyA signal upstream enhancer sequence (USE), or other posttranscriptional processing elements including, but not limited to, the thymidine kinase gene of herpes simplex virus, or hepatitis B virus (HBV). In one embodiment of any of the aspects or embodiments herein, the expression cassette length in the 5' to 3' direction is greater than the maximum length known to be encapsidated in an AAV virion. In one embodiment of any of the aspects or embodiments herein, the length is greater than 4.6 kb, or greater than 5 kb, or greater than 6 kb, or greater than 7 kb. Various expression cassettes are exemplified herein.

In one embodiment of any of the aspects or embodiments herein, the expression cassette can comprise more than 4000 nucleotides, 5000 nucleotides, 10,000 nucleotides or 20,000 nucleotides, or 30,000 nucleotides, or 40,000 nucleotides or 50,000 nucleotides, or any range between about 4000-10,000 nucleotides or 10,000-50,000 nucleotides, or more than 50,000 nucleotides.

In one embodiment of any of the aspects or embodiments herein, the expression cassette can also comprise an internal ribosome entry site (IRES) and/or a 2A element. The cis-regulatory elements include, but are not limited to, a promoter, a riboswitch, an insulator, a mir-regulatable element, a post-transcriptional regulatory element, a tissue- and cell type-specific promoter and an enhancer. In some embodiments of any of the aspects and embodiments herein the ITR can act as the promoter for the transgene. In some embodiments of any of the aspects and embodiments herein, the ceDNA vector comprises additional components to regulate expression of the transgene, for example, a regulatory switch, for controlling and regulating the expression of the transgene, and can include if desired, a regulatory switch which is a kill switch to enable controlled cell death of a cell comprising a ceDNA vector.

In one embodiment of any of the aspects or embodiments herein, ceDNA vectors are capsid-free and can be obtained from a plasmid encoding in this order: a first ITR, expressible transgene cassette and a second ITR, where at least one of the first and/or second ITR sequence is mutated with respect to the corresponding wild type AAV2 ITR sequence.

In one embodiment of any of the aspects or embodiments herein, the ceDNA vectors disclosed herein are used for therapeutic purposes (e.g., for medical, diagnostic, or veterinary uses) or immunogenic polypeptides.

The expression cassette can comprise any transgene which is a therapeutic nucleic acid sequence. In certain embodiments, the ceDNA vector comprises any gene of interest in the subject, which includes one or more polypeptides, peptides, ribozymes, peptide nucleic acids, siRNAs, RNAis, antisense oligonucleotides, antisense polynucleotides, antibodies, antigen binding fragments, or any combination thereof.

In one embodiment of any of the aspects or embodiments herein, sequences provided in the expression cassette, expression construct, or donor sequence of a ceDNA vector described herein can be codon optimized for the host cell. As used herein, the term "codon optimized" or "codon optimization" refers to the process of modifying a nucleic acid sequence for enhanced expression in the cells of the vertebrate of interest, e.g., mouse or human, by replacing at least one, more than one, or a significant number of codons of the native sequence (e.g., a prokaryotic sequence) with codons that are more frequently or most frequently used in the genes of that vertebrate. Various species exhibit particular bias for certain codons of a particular amino acid.

Typically, codon optimization does not alter the amino acid sequence of the original translated protein. Optimized codons can be determined using e.g., Aptagen's Gene Forge® codon optimization and custom gene synthesis platform (Aptagen, Inc., 2190 Fox Mill Rd. Suite 300, Herndon, Va. 20171) or another publicly available database.

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage (Nakamura, Y., et al. "Codon usage tabulated from the international DNA sequence databases: status for the year 2000" Nucl. Acids Res. 28:292 (2000)).

Inverted Terminal Repeats (ITRs)

As described herein, the ceDNA vectors are capsid-free, linear duplex DNA molecules formed from a continuous strand of complementary DNA with covalently closed ends (linear, continuous and non-encapsidated structure), which comprise a 5' inverted terminal repeat (ITR) sequence and a 3' ITR sequence that are different, or asymmetrical with respect to each other. At least one of the ITRs comprises a functional terminal resolution site and a replication protein binding site (RPS) (sometimes referred to as a replicative protein binding site), e.g., a Rep binding site. Generally, the ceDNA vector contains at least one modified AAV inverted terminal repeat sequence (ITR), i.e., a deletion, insertion, and/or substitution with respect to the other ITR, and an expressible transgene.

In one embodiment of any of the aspects or embodiments herein, at least one of the ITRs is an AAV ITR, e.g., a wild type AAV ITR. In one embodiment of any of the aspects or embodiments herein, at least one of the ITRs is a modified ITR relative to the other ITR—that is, the ceDNA comprises ITRs that are asymmetrical relative to each other. In one embodiment of any of the aspects or embodiments herein, at least one of the ITRs is a non-functional ITR.

In one embodiment of any of the aspects or embodiments herein, the ceDNA vector comprises: (1) an expression cassette comprising a cis-regulatory element, a promoter and at least one transgene; or (2) a promoter operably linked to at least one transgene, and (3) two self-complementary sequences, e.g., ITRs, flanking said expression cassette, wherein the ceDNA vector is not associated with a capsid protein. In some embodiments of any of the aspects and embodiments herein, the ceDNA vector comprises two self-complementary sequences found in an AAV genome, where at least one comprises an operative Rep-binding element (RBE) and a terminal resolution site (TRS) of AAV or a functional variant of the RBE, and one or more cis-regulatory elements operatively linked to a transgene. In some embodiments of any of the aspects and embodiments herein, the ceDNA vector comprises additional components to regulate expression of the transgene, for example, regulatory switches for controlling and regulating the expression of the transgene and can include a regulatory switch which is a kill switch to enable controlled cell death of a cell comprising a ceDNA vector.

In one embodiment of any of the aspects or embodiments herein, the two self-complementary sequences can be ITR sequences from any known parvovirus, for example a dependovirus such as AAV (e.g., AAV1-AAV12). Any AAV serotype can be used, including but not limited to a modified AAV2 ITR sequence, that retains a Rep-binding site (RBS) such as 5'-GCGCGCTCGCTCGCTC-3' and a terminal resolution site (TRS) in addition to a variable palindromic sequence allowing for hairpin secondary structure formation. In some embodiments of any of the aspects and embodiments herein, an ITR may be synthetic. In one embodiment of any of the aspects or embodiments herein, a synthetic ITR is based on ITR sequences from more than one AAV serotype. In another embodiment, a synthetic ITR includes no AAV-based sequence. In yet another embodiment, a synthetic ITR preserves the ITR structure described above although having only some or no AAV-sourced sequence. In some aspects, a synthetic ITR may interact preferentially with a wildtype Rep or a Rep of a specific serotype, or in some instances will not be recognized by a wild-type Rep and be recognized only by a mutated Rep. In some embodiments of any of the aspects and embodiments herein, the ITR is a synthetic ITR sequence that retains a functional Rep-binding site (RBS) such as 5'-GCGCGCTCGCTCGCTC-3' and a terminal resolution site (TRS) in addition to a variable palindromic sequence allowing for hairpin secondary structure formation. In some examples, a modified ITR sequence retains the sequence of the RBS, TRS and the structure and position of a Rep binding element forming the terminal loop portion of one of the ITR hairpin secondary structure from the corresponding sequence of the wild-type AAV2 ITR. Exemplary ITR sequences for use in the ceDNA vectors are disclosed in Tables 2-9, 10A and 10B, SEQ ID NO: 2, 52, 101-449 and 545-547, and the partial ITR sequences shown in FIGS. 26A-26B of International Patent Application No. PCT/US2018/049996, filed Sep. 7, 2018. In some embodiments of any of the aspects and embodiments herein, a ceDNA vector can comprise an ITR with a modification in the ITR corresponding to any of the modifications in ITR sequences or ITR partial sequences shown in any one or more of Tables 2, 3, 4, 5, 6, 7, 8, 9, 10A and 10B International Patent Application No. PCT/US2018/49996, filed Sep. 7, 2018.

In one embodiment of any of the aspects or embodiments herein, the ceDNA vectors can be produced from expression constructs that further comprise a specific combination of cis-regulatory elements. The cis-regulatory elements include, but are not limited to, a promoter, a riboswitch, an insulator, a mir-regulatable element, a post-transcriptional regulatory element, a tissue- and cell type-specific promoter and an enhancer. In some embodiments of any of the aspects and embodiments herein the ITR can act as the promoter for the transgene. In some embodiments of any of the aspects and embodiments herein, the ceDNA vector comprises additional components to regulate expression of the transgene, for example, regulatory switches as described in International Patent Application No. PCT/US2018/049996, filed Sep. 7, 2018, to regulate the expression of the transgene or a kill switch, which can kill a cell comprising the ceDNA vector.

In one embodiment of any of the aspects or embodiments herein, the expression cassettes can also include a post-transcriptional element to increase the expression of a transgene. In one embodiment of any of the aspects or embodiments herein, Woodchuck Hepatitis Virus (WHP) posttranscriptional regulatory element (WPRE) is used to increase the expression of a transgene. Other posttranscriptional processing elements such as the post-transcriptional element from the thymidine kinase gene of herpes simplex virus, or hepatitis B virus (HBV) can be used. Secretory sequences can be linked to the transgenes, e.g., VH-02 and VK-A26 sequences. The expression cassettes can include a poly-adenylation sequence known in the art or a variation thereof, such as a naturally occurring sequence isolated from bovine BGHpA or a virus SV40 pA, or a synthetic sequence. Some expression cassettes can also include SV40 late polyA signal upstream enhancer (USE) sequence. The USE can be used in combination with SV40 pA or heterologous poly-A signal.

Figure 1A:
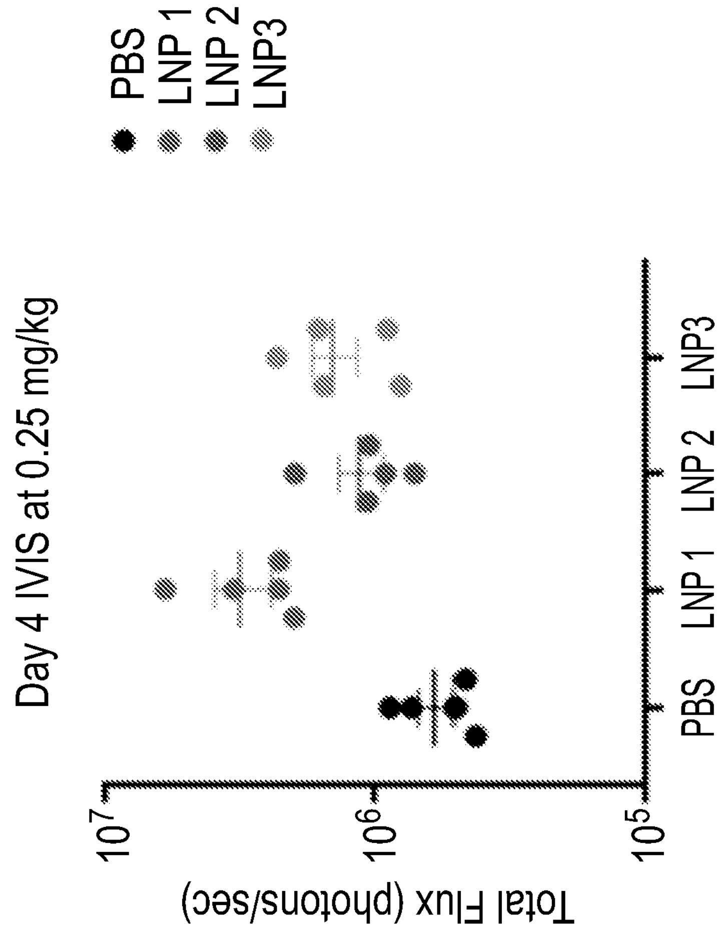
FIG. 1A is a graph showing the total amount of luciferase expression as measured by fluorescence in mice on day 4 after administration of ceDNA encoding luciferase formulated in LNP1, LNP2 and LNP3. LNP1 is a lipid nanoparticle formulated with Reference Lipid A and used as a positive control, while LNP2 and LNP3 are lipid nanoparticles formulated with Lipid 20 as described in Table 4. PBS was used as a negative control.

FIGS. 1A-1C of International Patent Application No. PCT/US2018/050042, filed on Sep. 7, 2018, and incorporated herein by reference in its entirety herein, show schematics of nonlimiting, exemplary ceDNA vectors, or the corresponding sequence of ceDNA plasmids. ceDNA vectors are capsid-free and can be obtained from a plasmid encoding in this order: a first ITR, expressible transgene cassette and a second ITR, where at least one of the first and/or second ITR sequence is mutated with respect to the corresponding wild type AAV2 ITR sequence. The expressible transgene cassette preferably includes one or more of, in this order: an enhancer/promoter, an ORF reporter (transgene), a post-transcription regulatory element (e.g., WPRE), and a polyadenylation and termination signal (e.g., BGH polyA).

Promoters

Suitable promoters, including those described above, can be derived from viruses, and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVTE), a rous sarcoma virus (RSV) promoter, a human U6 small nuclear promoter (U6, e.g., (Miyagishi el al., Nature Biotechnology 20, 497-500 (2002)), an enhanced U6 promoter (e.g., Xia et al., Nucleic Acids Res. 2003 Sep. 1; 31(17)), a human H1 promoter (H1), a CAG promoter, a human alpha 1-antitrypsin (HAAT) promoter (e.g., and the like). In one embodiment of any of the aspects or embodiments herein, these promoters are altered at their downstream intron containing end to include one or more nuclease cleavage sites. In one embodiment of any of the aspects or embodiments herein, the DNA containing the nuclease cleavage site(s) is foreign to the promoter DNA.

In one embodiment of any of the aspects or embodiments herein, a promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to the cell, tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter, as well as the promoters listed below. Such promoters and/or enhancers can be used for expression of any gene of interest, e.g., therapeutic proteins). For example, the vector may comprise a promoter that is operably linked to the nucleic acid sequence encoding a therapeutic protein. In one embodiment of any of the aspects or embodiments herein, the promoter operably linked to the therapeutic protein coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. In one embodiment of any of the aspects or embodiments herein, the promoter may also be a promoter from a human gene such as human ubiquitin C (hUbC), human actin, human myosin, human hemoglobin, human muscle creatine, or human metallothionein. The promoter may also be a tissue specific promoter, such as a liver specific promoter, such as human alpha 1-antitrypsin (HAAT) or transthyretin (TTR), natural or synthetic. In one embodiment of any of the aspects or embodiments herein, delivery to the liver can be achieved using endogenous ApoE specific targeting of the composition comprising a ceDNA vector to hepatocytes via the low-density lipoprotein (LDL) receptor present on the surface of the hepatocyte.

In one embodiment of any of the aspects or embodiments herein, the promoter used is the native promoter of the gene encoding the therapeutic protein. The promoters and other regulatory sequences for the respective genes encoding the therapeutic proteins are known and have been characterized. The promoter region used may further include one or more additional regulatory sequences (e.g., native) such as enhancers (e.g., Serpin Enhancer) known in the art.

Non-limiting examples of suitable promoters for use in accordance with the present invention include the CAG promoter of, for example, the HAAT promoter, the human EF1-α promoter or a fragment of the EF1-α promoter and the rat EF1-α promoter.

Polyadenylation Sequences

A sequence encoding a polyadenylation sequence can be included in the ceDNA vector to stabilize the mRNA expressed from the ceDNA vector, and to aid in nuclear export and translation. In one embodiment of any of the aspects or embodiments herein, the ceDNA vector does not include a polyadenylation sequence. In other embodiments, the vector includes at least 1, at least 2, at least 3, at least 4, at least 5, at least 10, at least 15, at least 20, at least 25, at least 30, at least 40, least 45, at least 50 or more adenine dinucleotides. In some embodiments of any of the aspects and embodiments herein, the polyadenylation sequence comprises about 43 nucleotides, about 40-50 nucleotides, about 40-55 nucleotides, about 45-50 nucleotides, about 35-50 nucleotides, or any range there between.

In one embodiment of any of the aspects or embodiments herein, the ceDNA can be obtained from a vector polynucleotide that encodes a heterologous nucleic acid operatively positioned between two different inverted terminal repeat sequences (ITRs) (e.g. AAV ITRs), wherein at least one of the ITRs comprises a terminal resolution site and a replicative protein binding site (RPS), e.g. a Rep binding site (e.g. wt AAV ITR), and one of the ITRs comprises a deletion, insertion, and/or substitution with respect to the other ITR, e.g., functional ITR.

In one embodiment of any of the aspects or embodiments herein, the host cells do not express viral capsid proteins and the polynucleotide vector template is devoid of any viral capsid coding sequences. In one embodiment of any of the aspects or embodiments herein, the polynucleotide vector template is devoid of AAV capsid genes but also of capsid genes of other viruses). In one embodiment of any of the aspects or embodiments herein, the nucleic acid molecule is also devoid of AAV Rep protein coding sequences. Accordingly, in some embodiments of any of the aspects and embodiments herein, the nucleic acid molecule of the invention is devoid of both functional AAV cap and AAV rep genes.

In one embodiment of any of the aspects or embodiments herein, the ceDNA vector does not have a modified ITRs.

In one embodiment of any of the aspects or embodiments herein, the ceDNA vector comprises a regulatory switch as disclosed herein (or in International Patent Application No. PCT/US2018/049996, filed Sep. 7, 2018).

V. Production of a ceDNA Vector

Methods for the production of a ceDNA vector as described herein comprising an asymmetrical ITR pair or symmetrical ITR pair as defined herein is described in section IV of PCT/US 18/49996 filed Sep. 7, 2018, which is incorporated herein in its entirety by reference. As described herein, the ceDNA vector can be obtained, for example, by the process comprising the steps of: a) incubating a population of host cells (e.g. insect cells) harboring the polynucleotide expression construct template (e.g., a ceDNA-plasmid, a ceDNA-Bacmid, and/or a ceDNA-baculovirus), which is devoid of viral capsid coding sequences, in the presence of a Rep protein under conditions effective and for a time sufficient to induce production of the ceDNA vector within the host cells, and wherein the host cells do not comprise viral capsid coding sequences; and b) harvesting and isolating the ceDNA vector from the host cells. The presence of Rep protein induces replication of the vector polynucleotide with a modified ITR to produce the ceDNA vector in a host cell.

However, no viral particles (e.g., AAV virions) are expressed. Thus, there is no size limitation such as that naturally imposed in AAV or other viral-based vectors.

The presence of the ceDNA vector isolated from the host cells can be confirmed by digesting DNA isolated from the host cell with a restriction enzyme having a single recognition site on the ceDNA vector and analyzing the digested DNA material on a non-denaturing gel to confirm the presence of characteristic bands of linear and continuous DNA as compared to linear and non-continuous DNA.

In one embodiment of any of the aspects or embodiments herein, the invention provides for use of host cell lines that have stably integrated the DNA vector polynucleotide expression template (ceDNA template) into their own genome in production of the non-viral DNA vector, e.g., as described in Lee, L. et al. (2013) Plos One 8(8): e69879. Preferably, Rep is added to host cells at an MOI of about 3. When the host cell line is a mammalian cell line, e.g., HEK293 cells, the cell lines can have polynucleotide vector template stably integrated, and a second vector such as herpes virus can be used to introduce Rep protein into cells, allowing for the excision and amplification of ceDNA in the presence of Rep and helper virus.

In one embodiment of any of the aspects or embodiments herein, the host cells used to make the ceDNA vectors described herein are insect cells, and baculovirus is used to deliver both the polynucleotide that encodes Rep protein and the non-viral DNA vector polynucleotide expression construct template for ceDNA. In some embodiments of any of the aspects and embodiments herein, the host cell is engineered to express Rep protein.

The ceDNA vector is then harvested and isolated from the host cells. The time for harvesting and collecting ceDNA vectors described herein from the cells can be selected and optimized to achieve a high-yield production of the ceDNA vectors. For example, the harvest time can be selected in view of cell viability, cell morphology, cell growth, etc. In one embodiment of any of the aspects or embodiments herein, cells are grown under sufficient conditions and harvested a sufficient time after baculoviral infection to produce ceDNA vectors but before most cells start to die due to the baculoviral toxicity. The DNA vectors can be isolated using plasmid purification kits such as Qiagen Endo-Free Plasmid kits. Other methods developed for plasmid isolation can be also adapted for DNA vectors. Generally, any nucleic acid purification methods can be adopted.

The DNA vectors can be purified by any means known to those of skill in the art for purification of DNA. In one embodiment of any of the aspects or embodiments herein, ceDNA vectors are purified as DNA molecules. In one embodiment of any of the aspects or embodiments herein, the ceDNA vectors are purified as exosomes or microparticles. The presence of the ceDNA vector can be confirmed by digesting the vector DNA isolated from the cells with a restriction enzyme having a single recognition site on the DNA vector and analyzing both digested and undigested DNA material using gel electrophoresis to confirm the presence of characteristic bands of linear and continuous DNA as compared to linear and non-continuous DNA.

VI. Preparation of Lipid Particles

Lipid particles (e.g., lipid nanoparticles) can form spontaneously upon mixing of TNA (e.g., ceDNA) and the lipid(s). Depending on the desired particle size distribution, the resultant nanoparticle mixture can be extruded through a membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration.

Generally, lipid particles (e.g., lipid nanoparticles) can be formed by any method known in the art. For example, the lipid particles (e.g., lipid nanoparticles) can be prepared by the methods described, for example, in U.S. Patent Application Publication Nos. US2013/0037977, US2010/0015218, US2013/0156845, US2013/0164400, US2012/0225129, and US2010/0130588, content of each of which is incorporated herein by reference in their entirety. In some embodiments of any of the aspects and embodiments herein, lipid particles (e.g., lipid nanoparticles) can be prepared using a continuous mixing method, a direct dilution process, or an in-line dilution process. The processes and apparatuses for apparatuses for preparing lipid nanoparticles using direct dilution and in-line dilution processes are described in US2007/0042031, the contents of which are incorporated herein by reference in its entirety. The processes and apparatuses for preparing lipid nanoparticles using step-wise dilution processes are described in U.S. Patent Application Publication No. US2004/0142025, the contents of which are hereby incorporated herein by reference in its entirety.

In one embodiment of any of the aspects or embodiments herein, the lipid particles (e.g., lipid nanoparticles) can be prepared by an impinging jet process. Generally, the particles are formed by mixing lipids dissolved in alcohol (e.g., ethanol) with ceDNA dissolved in a buffer, e.g, a citrate buffer, a sodium acetate buffer, a sodium acetate and magnesium chloride buffer, a malic acid buffer, a malic acid and sodium chloride buffer, or a sodium citrate and sodium chloride buffer. The mixing ratio of lipids to ceDNA can be about 45-55% lipid and about 65-45% ceDNA.

The lipid solution can contain a disclosed cationic lipid, a non-cationic lipid (e.g., a phospholipid, such as DSPC, DOPE, and DOPC), one or more PEGylated lipids, and a sterol (e.g., cholesterol) at a total lipid concentration of 5-30 mg/mL, more likely 5-15 mg/mL, most likely 9-12 mg/mL in an alcohol, e.g., in ethanol. In the lipid solution, mol ratio of the lipids can range from about 25-98% for the cationic lipid, such as about 35-65%; about 0-15% for the non-ionic lipid, such as about 0-12%; about 0-15% for the PEGylated lipid, such as about 1-6%; and about 0-75% for the sterol, such as about 30-50%.

The ceDNA solution can comprise the ceDNA at a concentration range from 0.3 to 1.0 mg/mL, preferably 0.3-0.9 mg/mL in buffered solution, with pH in the range of 3.5-5.

For forming the LNPs, in one exemplary but non-limiting embodiment, the two liquids are heated to a temperature in the range of about 15-40° C., preferably about 30-40° C., and then mixed, for example, in an impinging jet mixer, instantly forming the LNP. The mixing flow rate can range from 10-600 mL/min. The tube ID can have a range from 0.25 to 1.0 mm and a total flow rate from 10-600 mL/min. The combination of flow rate and tubing ID can have the effect of controlling the particle size of the LNPs between 30 nm and 200 nm. The solution can then be mixed with a buffered solution at a higher pH with a mixing ratio in the range of 1:1 to 1:3 vol:vol, preferably about 1:2 vol:vol. If needed this buffered solution can be at a temperature in the range of 15-40° C. or 30-40° C. The mixed LNPs can then undergo an anion exchange filtration step. Prior to the anion exchange, the mixed LNPs can be incubated for a period of time, for example, 30 min to 2 hours. The temperature during incubating can be in the range of 15-40° C. or 30-40° C. After incubating the solution is filtered through a filter, such as a 0.8 μm filter, containing an anion exchange separation step. This process can use tubing IDs ranging from 1 mm ID to 5 mm ID and a flow rate from 10 to 2000 mL/min.

After formation, the LNPs can be concentrated and diafiltered via an ultrafiltration process where the alcohol is removed and the buffer is exchanged for the final buffer solution, for example, phosphate buffered saline (PBS) at about pH 7, e.g., about pH 6.9, about pH 7.0, about pH 7.1, about pH 7.2, about pH 7.3, or about pH 7.4.

The ultrafiltration process can use a tangential flow filtration format (TFF) using a membrane nominal molecular weight cutoff range from 30-500 kD. The membrane format is hollow fiber or flat sheet cassette. The TFF processes with the proper molecular weight cutoff can retain the LNP in the retentate and the filtrate or permeate contains the alcohol; citrate buffer and final buffer wastes. The TFF process is a multiple step process with an initial concentration to a ceDNA concentration of 1-3 mg/mL. Following concentration, the LNPs solution is diafiltered against the final buffer for 10-20 volumes to remove the alcohol and perform buffer exchange. The material can then be concentrated an additional 1-3-fold. The concentrated LNP solution can be sterile filtered.

VII. Pharmaceutical Compositions and Formulations

Also provided herein is a pharmaceutical composition comprising the TNA lipid particle and a pharmaceutically acceptable carrier or excipient. In one embodiment of any of the aspects or embodiments herein, the present further relates to a pharmaceutical composition comprising the cationic lipid as described in any embodiment of any of the aspects or embodiments herein, or a lipid nanoparticle as described in any embodiment of any of the aspects or embodiments herein, and a pharmaceutical acceptable excipient.

Generally, the lipid particles (e.g., lipid nanoparticles) of the invention have a mean diameter selected to provide an intended therapeutic effect.

Depending on the intended use of the lipid particles (e.g., lipid nanoparticles), the proportions of the components can be varied and the delivery efficiency of a particular formulation can be measured using, for example, an endosomal release parameter (ERP) assay.

In one embodiment of any of the aspects or embodiments herein, the ceDNA can be complexed with the lipid portion of the particle or encapsulated in the lipid position of the lipid particle (e.g., lipid nanoparticle). In one embodiment of any of the aspects or embodiments herein, the ceDNA can be fully encapsulated in the lipid position of the lipid particle (e.g., lipid nanoparticle), thereby protecting it from degradation by a nuclease, e.g., in an aqueous solution. In one embodiment of any of the aspects or embodiments herein, the ceDNA in the lipid particle (e.g., lipid nanoparticle) is not substantially degraded after exposure of the lipid particle (e.g., lipid nanoparticle) to a nuclease at 37° C. for at least about 20, 30, 45, or 60 minutes. In some embodiments of any of the aspects and embodiments herein, the ceDNA in the lipid particle (e.g., lipid nanoparticle) is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours.

In one embodiment of any of the aspects or embodiments herein, the lipid particles (e.g., lipid nanoparticles) are substantially non-toxic to a subject, e.g., to a mammal such as a human.

In one embodiment of any of the aspects or embodiments herein, a pharmaceutical composition comprising a therapeutic nucleic acid of the present disclosure may be formulated in lipid particles (e.g., lipid nanoparticles). In some embodiments of any of the aspects and embodiments herein, the lipid particle comprising a therapeutic nucleic acid can be formed from a disclosed cationic lipid. In some other embodiments, the lipid particle comprising a therapeutic nucleic acid can be formed from non-cationic lipid. In a preferred embodiment, the lipid particle of the invention is a nucleic acid containing lipid particle, which is formed from a disclosed cationic lipid comprising a therapeutic nucleic acid selected from the group consisting of mRNA, antisense RNA and oligonucleotide, ribozymes, aptamer, interfering RNAs (RNAi), Dicer-substrate dsRNA, small hairpin RNA (shRNA), asymmetrical interfering RNA (aiRNA), microRNA (miRNA), minicircle DNA, minigene, viral DNA (e.g., Lentiviral or AAV genome) or non-viral synthetic DNA vectors, closed-ended linear duplex DNA (ceDNA/CELiD), plasmids, bacmids, Doggybone™ DNA vectors, minimalistic immunological-defined gene expression (MIDGE)-vector, nonviral ministring DNA vector (linear-covalently closed DNA vector), or dumbbell-shaped DNA minimal vector ("dumbbell DNA").

In another preferred embodiment, the lipid particle of the invention is a nucleic acid containing lipid particle, which is formed from a non-cationic lipid, and optionally a PEGylated lipid or other forms of conjugated lipids that prevent aggregation of the particle.

In one embodiment of any of the aspects or embodiments herein, the lipid particle formulation is an aqueous solution. In one embodiment of any of the aspects or embodiments herein, the lipid particle (e.g., lipid nanoparticle) formulation is a lyophilized powder.

According to some aspects, the disclosure provides for a lipid particle formulation further comprising one or more pharmaceutical excipients. In one embodiment of any of the aspects or embodiments herein, the lipid particle (e.g., lipid nanoparticle) formulation further comprises sucrose, tris, trehalose and/or glycine.

In one embodiment of any of the aspects or embodiments herein, the lipid particles (e.g., lipid nanoparticles) disclosed herein can be incorporated into pharmaceutical compositions suitable for administration to a subject for in vivo delivery to cells, tissues, or organs of the subject. Typically, the pharmaceutical composition comprises the TNA lipid particles (e.g., lipid nanoparticles) disclosed herein and a pharmaceutically acceptable carrier. In one embodiment of any of the aspects or embodiments herein, the TNA lipid particles (e.g., lipid nanoparticles) of the disclosure can be incorporated into a pharmaceutical composition suitable for a desired route of therapeutic administration (e.g., parenteral administration). Passive tissue transduction via high pressure intravenous or intraarterial infusion, as well as intracellular injection, such as intranuclear microinjection or intracytoplasmic injection, are also contemplated. Pharmaceutical compositions for therapeutic purposes can be formulated as a solution, microemulsion, dispersion, liposomes, or other ordered structure suitable for high ceDNA vector concentration. Sterile injectable solutions can be prepared by incorporating the ceDNA vector compound in the required amount in an appropriate buffer with one or a combination of ingredients enumerated above, as required, followed by filtered sterilization.

A lipid particle as disclosed herein can be incorporated into a pharmaceutical composition suitable for topical, systemic, intra-amniotic, intrathecal, intracranial, intraarterial, intravenous, intralymphatic, intraperitoneal, subcutaneous, tracheal, intra-tissue (e.g., intramuscular, intracardiac, intrahepatic, intrarenal, intracerebral), intrathecal, intravesical, conjunctival (e.g., extra-orbital, intraorbital, retroorbital, intraretinal, subretinal, choroidal, sub-choroidal, intrastromal, intracameral and intravitreal), intracochlear, and mucosal (e.g., oral, rectal, nasal) administration. Passive tissue transduction via high pressure intravenous or intraarterial infusion, as well as intracellular injection, such as intranuclear microinjection or intracytoplasmic injection, are also contemplated.

Pharmaceutically active compositions comprising TNA lipid particles (e.g., lipid nanoparticles) can be formulated to deliver a transgene in the nucleic acid to the cells of a recipient, resulting in the therapeutic expression of the transgene therein. The composition can also include a pharmaceutically acceptable carrier.

Pharmaceutical compositions for therapeutic purposes are typically sterile and stable under the conditions of manufacture and storage. The composition can be formulated as a solution, microemulsion, dispersion, liposomes, or other ordered structure suitable to high ceDNA vector concentration. Sterile injectable solutions can be prepared by incorporating the ceDNA vector compound in the required amount in an appropriate buffer with one or a combination of ingredients enumerated above, as required, followed by filtered sterilization.

In one embodiment of any of the aspects or embodiments herein, lipid particles (e.g., lipid nanoparticles) are solid core particles that possess at least one lipid bilayer. In one embodiment of any of the aspects or embodiments herein, the lipid particles (e.g., lipid nanoparticles) have a non-bilayer structure, i.e., a non-lamellar (i.e., non-bilayer) morphology. Without limitations, the non-bilayer morphology can include, for example, three dimensional tubes, rods, cubic symmetries, etc. The non-lamellar morphology (i.e., non-bilayer structure) of the lipid particles (e.g., lipid nanoparticles) can be determined using analytical techniques known to and used by those of skill in the art. Such techniques include, but are not limited to, Cryo-Transmission Electron Microscopy ("Cryo-TEM"), Differential Scanning calorimetry ("DSC"), X-Ray Diffraction, and the like. For example, the morphology of the lipid particles (lamellar vs. non-lamellar) can readily be assessed and characterized using, e.g., Cryo-TEM analysis as described in US2010/

0130588, the contents of which are hereby incorporated herein by reference in their entirety.

In one embodiment of any of the aspects or embodiments herein, the lipid particles (e.g., lipid nanoparticles) having a non-lamellar morphology are electron dense.

In one embodiment of any of the aspects or embodiments herein, the disclosure provides for a lipid particle (e.g., lipid nanoparticle) that is either unilamellar or multilamellar in structure. In some aspects, the disclosure provides for a lipid particle (e.g., lipid nanoparticle) formulation that comprises multi-vesicular particles and/or foam-based particles. By controlling the composition and concentration of the lipid components, one can control the rate at which a conjugated lipid exchanges out of the lipid particle and, in turn, the rate at which the lipid particle (e.g., lipid nanoparticle) becomes fusogenic. In addition, other variables including, for example, pH, temperature, or ionic strength, can be used to vary and/or control the rate at which the lipid particle (e.g., lipid nanoparticle) becomes fusogenic. Other methods which can be used to control the rate at which the lipid particle (e.g., lipid nanoparticle) becomes fusogenic will be apparent to those of ordinary skill in the art based on this disclosure. It will also be apparent that by controlling the composition and concentration of the conjugated lipid, one can control the lipid particle size.

In one embodiment of any of the aspects or embodiments herein, the pKa of formulated cationic lipids can be correlated with the effectiveness of the LNPs for delivery of nucleic acids (see Jayaraman et al., Angewandte Chemie, International Edition (2012), 51(34), 8529-8533; Semple et al., Nature Biotechnology 28, 172-176 (2010), both of which are incorporated by reference in their entireties). In one embodiment of any of the aspects or embodiments herein, the preferred range of pKa is about 5 to about 8. In one embodiment of any of the aspects or embodiments herein, the preferred range of pKa is about 6 to about 7. In one embodiment of any of the aspects or embodiments herein, the preferred pKa is about 6.5. In one embodiment of any of the aspects or embodiments herein, the pKa of the cationic lipid can be determined in lipid particles (e.g., lipid nanoparticles) using an assay based on fluorescence of 2-(p-toluidino)-6-napthalene sulfonic acid (TNS).

In one embodiment of any of the aspects or embodiments herein, encapsulation of ceDNA in lipid particles (e.g., lipid nanoparticles) can be determined by performing a membrane-impermeable fluorescent dye exclusion assay, which uses a dye that has enhanced fluorescence when associated with nucleic acid, for example, an Oligreen® assay or PicoGreen® assay. Generally, encapsulation is determined by adding the dye to the lipid particle formulation, measuring the resulting fluorescence, and comparing it to the fluorescence observed upon addition of a small amount of nonionic detergent. Detergent-mediated disruption of the lipid bilayer releases the encapsulated ceDNA, allowing it to interact with the membrane-impermeable dye. Encapsulation of ceDNA can be calculated as E=(Io−I)/Io, where I and Jo refers to the fluorescence intensities before and after the addition of detergent.

Unit Dosage

In one embodiment of any of the aspects or embodiments herein, the pharmaceutical compositions can be presented in unit dosage form. A unit dosage form will typically be adapted to one or more specific routes of administration of the pharmaceutical composition. In some embodiments of any of the aspects and embodiments herein, the unit dosage form is adapted for administration by inhalation. In some embodiments of any of the aspects and embodiments herein, the unit dosage form is adapted for administration by a vaporizer. In some embodiments of any of the aspects and embodiments herein, the unit dosage form is adapted for administration by a nebulizer. In some embodiments of any of the aspects and embodiments herein, the unit dosage form is adapted for administration by an aerosolizer. In some embodiments of any of the aspects and embodiments herein, the unit dosage form is adapted for oral administration, for buccal administration, or for sublingual administration. In some embodiments of any of the aspects and embodiments herein, the unit dosage form is adapted for intravenous, intramuscular, or subcutaneous administration. In some embodiments of any of the aspects and embodiments herein, the unit dosage form is adapted for intrathecal or intracerebroventricular administration. In some embodiments of any of the aspects and embodiments herein, the pharmaceutical composition is formulated for topical administration. The amount of active ingredient which can be combined with a carrier material to produce a single dosage form will generally be that amount of the compound which produces a therapeutic effect.

VIII. Methods of Treatment

The lipid nanoparticles and methods (e.g., TNA lipid particles, such as lipid nanoparticles) described herein can be used to introduce a nucleic acid sequence (e.g., a therapeutic nucleic acid sequence) in a host cell. In one embodiment of any of the aspects or embodiments herein, introduction of a nucleic acid sequence in a host cell using the TNA LNP (e.g., ceDNA vector lipid particles (e.g., lipid nanoparticles) as described herein) can be monitored with appropriate biomarkers from treated patients to assess gene expression.

The LNP compositions provided herein can be used to deliver a transgene (a nucleic acid sequence) for various purposes. In one embodiment of any of the aspects or embodiments herein, the ceDNA vectors (e.g., ceDNA vector lipid particles (e.g., lipid nanoparticles) as described herein) can be used in a variety of ways, including, for example, ex situ, in vitro and in vivo applications, methodologies, diagnostic procedures, and/or gene therapy regimens.

Provided herein are methods of treating a disease or disorder in a subject comprising introducing into a target cell in need thereof (for example, a liver cell, a muscle cell, a kidney cell, a neuronal cell, or other affected cell type) of the subject a therapeutically effective amount of TNA LNP (e.g., ceDNA vector lipid particles (e.g., lipid nanoparticles) as described herein), optionally with a pharmaceutically acceptable carrier. The TNA LNP (e.g., ceDNA vector lipid particles (e.g., lipid nanoparticles) as described herein) implemented comprises a nucleotide sequence of interest useful for treating the disease. In particular, the TNA may comprise a desired exogenous DNA sequence operably linked to control elements capable of directing transcription of the desired polypeptide, protein, or oligonucleotide encoded by the exogenous DNA sequence when introduced into the subject. The TNA LNP (e.g., ceDNA vector lipid particles (e.g., lipid nanoparticles) as described herein) can be administered via any suitable route as described herein and known in the art. In one embodiment of any of the aspects or embodiments herein, the target cells are in a human subject.

Provided herein are methods for providing a subject in need thereof with a diagnostically- or therapeutically-effective amount of TNA LNP (e.g., ceDNA vector lipid particles (e.g., lipid nanoparticles) as described herein), the method comprising providing to a cell, tissue or organ of a subject in need thereof, an amount of the TNA LNP (e.g., ceDNA vector lipid particles (e.g., lipid nanoparticles) as described herein); and for a time effective to enable expression of the transgene from the TNA LNP thereby providing the subject with a diagnostically- or a therapeutically-effective amount of the protein, peptide, nucleic acid expressed by the TNA LNP (e.g., ceDNA vector lipid particles (e.g., lipid nanoparticles) as described herein). In one embodiment of any of the aspects or embodiments herein, the subject is human.

Provided herein are methods for diagnosing, preventing, treating, or ameliorating at least one or more symptoms of a disease, a disorder, a dysfunction, an injury, an abnormal condition, or trauma in a subject. Generally, the method includes at least the step of administering to a subject in need thereof TNA LNP (e.g., ceDNA vector lipid particles (e.g., lipid nanoparticles) as described herein), in an amount and for a time sufficient to diagnose, prevent, treat or ameliorate the one or more symptoms of the disease, disorder, dysfunction, injury, abnormal condition, or trauma in the subject. In one embodiment of any of the aspects or embodiments herein, the subject is human.

Provided herein are methods for using the TNA LNP as a tool for treating one or more symptoms of a disease or disease states. There is a number of inherited diseases in which defective genes are known, and typically fall into two classes: deficiency states, usually of enzymes, which are generally inherited in a recessive manner, and unbalanced states, which may involve regulatory or structural proteins, and which are typically but not always inherited in a dominant manner. For deficiency state diseases, TNA LNP (e.g., ceDNA vector lipid particles (e.g., lipid nanoparticles) as described herein) can be used to deliver transgenes to bring a normal gene into affected tissues for replacement therapy, as well, in some embodiments of any of the aspects and embodiments herein, to create animal models for the disease using antisense mutations. For unbalanced disease states, TNA LNP (e.g., ceDNA vector lipid particles) can be used to create a disease state in a model system, which could then be used in efforts to counteract the disease state. Thus, the TNA LNP (e.g., ceDNA vector lipid particles (e.g., lipid nanoparticles)) and methods disclosed herein permit the treatment of genetic diseases. As used herein, a disease state is treated by partially or wholly remedying the deficiency or imbalance that causes the disease or makes it more severe.

In general, the TNA LNP (e.g., ceDNA vector lipid particles (e.g., lipid nanoparticles)) can be used to deliver any transgene in accordance with the description above to treat, prevent, or ameliorate the symptoms associated with any disorder related to gene expression. Illustrative disease states include, but are not-limited to: cystic fibrosis (and other diseases of the lung), hemophilia A, hemophilia B, thalassemia, anemia and other blood disorders, AIDS, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Hurler's disease, adenosine deaminase deficiency, metabolic defects, retinal degenerative diseases (and other diseases of the eye), mitochondriopathies (e.g., Leber's hereditary optic neuropathy (LHON), Leigh syndrome, and subacute sclerosing encephalopathy), myopathies (e.g., facioscapulohumeral myopathy (FSHD) and cardiomyopathies), diseases of solid organs (e.g., brain, liver, kidney, heart), and the like. In some embodiments of any of the aspects and embodiments herein, the ceDNA vectors as disclosed herein can be advantageously used in the treatment of individuals with metabolic disorders (e.g., ornithine transcarbamylase deficiency).

In one embodiment of any of the aspects or embodiments herein, the TNA LNPs described herein can be used to treat, ameliorate, and/or prevent a disease or disorder caused by mutation in a gene or gene product. Exemplary diseases or disorders that can be treated with the TNA LNPs (e.g., ceDNA vector lipid particles (e.g., lipid nanoparticles) as described herein)s include, but are not limited to, metabolic diseases or disorders (e.g., Fabry disease, Gaucher disease, phenylketonuria (PKU), glycogen storage disease); urea cycle diseases or disorders (e.g., ornithine transcarbamylase (OTC) deficiency); lysosomal storage diseases or disorders (e.g., metachromatic leukodystrophy (MLD), mucopolysaccharidosis Type II (MPSII; Hunter syndrome)); liver diseases or disorders (e.g., progressive familial intrahepatic cholestasis (PFIC); blood diseases or disorders (e.g., hemophilia A and B, thalassemia, and anemia); cancers and tumors, and genetic diseases or disorders (e.g., cystic fibrosis).

In one embodiment of any of the aspects or embodiments herein, the TNA LNPs (e.g., ceDNA vector lipid particles) may be employed to deliver a heterologous nucleotide sequence in situations in which it is desirable to regulate the level of transgene expression (e.g., transgenes encoding hormones or growth factors).

In one embodiment of any of the aspects or embodiments herein, the TNA LNPs (e.g., ceDNA vector lipid particles (e.g., lipid nanoparticles)) can be used to correct an abnormal level and/or function of a gene product (e.g., an absence of, or a defect in, a protein) that results in the disease or disorder. The TNA LNPs (e.g., ceDNA vector lipid particles (e.g., lipid nanoparticles)) can produce a functional protein and/or modify levels of the protein to alleviate or reduce symptoms resulting from, or confer benefit to, a particular disease or disorder caused by the absence or a defect in the protein. For example, treatment of OTC deficiency can be achieved by producing functional OTC enzyme; treatment of hemophilia A and B can be achieved by modifying levels of Factor VIII, Factor IX, and Factor X; treatment of PKU can be achieved by modifying levels of phenylalanine hydroxylase enzyme; treatment of Fabry or Gaucher disease can be achieved by producing functional alpha galactosidase or beta glucocerebrosidase, respectively; treatment of MFD or MPSII can be achieved by producing functional arylsulfatase A or iduronate-2-sulfatase, respectively; treatment of cystic fibrosis can be achieved by producing functional cystic fibrosis transmembrane conductance regulator; treatment of glycogen storage disease can be achieved by restoring functional G6Pase enzyme function; and treatment of PFIC can be achieved by producing functional ATP8B1, ABCB11, ABCB4, or TJP2 genes.

In one embodiment of any of the aspects or embodiments herein, the TNA LNP (e.g., ceDNA vector lipid particles (e.g., lipid nanoparticles)) can be used to provide an RNA-based therapeutic to a cell in vitro or in vivo. Examples of RNA-based therapeutics include, but are not limited to, mRNA, antisense RNA and oligonucleotides, ribozymes, aptamers, interfering RNAs (RNAi), Dicer-substrate dsRNA, small hairpin RNA (shRNA), asymmetrical interfering RNA (aiRNA), microRNA (miRNA). For example, the TNA LNP (e.g., ceDNA vector lipid particles (e.g., lipid nanoparticles)) can be used to provide an antisense nucleic acid to a cell in vitro or in vivo. For example, where the transgene is a RNAi molecule, expression of the antisense nucleic acid or RNAi in the target cell diminishes expression of a particular protein by the cell. Accordingly, transgenes which are RNAi molecules or antisense nucleic acids may be administered to decrease expression of a particular protein in a subject in need thereof. Antisense nucleic acids may also be administered to cells in vitro to regulate cell physiology, e.g., to optimize cell or tissue culture systems.

In one embodiment of any of the aspects or embodiments herein, the TNA LNP (e.g., ceDNA vector lipid particles (e.g., lipid nanoparticles)) can be used to provide a DNA-based therapeutic to a cell in vitro or in vivo. Examples of DNA-based therapeutics include, but are not limited to, minicircle DNA, minigene, viral DNA (e.g., Lentiviral or AAV genome) or non-viral synthetic DNA vectors, closed-ended linear duplex DNA (ceDNA/CELiD), plasmids, bacmids, Doggybone™ DNA vectors, minimalistic immunological-defined gene expression (MIDGE)-vector, nonviral ministring DNA vector (linear-covalently closed DNA vector), or dumbbell-shaped DNA minimal vector ("dumbbell DNA"). For example, in one embodiment of any of the aspects or embodiments herein, the ceDNA vectors (e.g., ceDNA vector lipid particles (e.g., lipid nanoparticles)) can be used to provide minicircle to a cell in vitro or in vivo. For example, where the transgene is a minicircle DNA, expression of the minicircle DNA in the target cell diminishes expression of a particular protein by the cell. Accordingly, transgenes which are minicircle DNAs may be administered to decrease expression of a particular protein in a subject in need thereof. Minicircle DNAs may also be administered to cells in vitro to regulate cell physiology, e.g., to optimize cell or tissue culture systems.

In one embodiment of any of the aspects or embodiments herein, exemplary transgenes encoded by a TNA vector comprising an expression cassette include, but are not limited to: X, lysosomal enzymes (e.g., hexosaminidase A, associated with Tay-Sachs disease, or iduronate sulfatase, associated, with Hunter Syndrome/MPS II), erythropoietin, angiostatin, endostatin, superoxide dismutase, globin, leptin, catalase, tyrosine hydroxylase, as well as cytokines (e.g., a interferon, β-interferon, interferon-γ, interleukin-2, interleukin-4, interleukin 12, granulocyte-macrophage colony stimulating factor, lymphotoxin, and the like), peptide growth factors and hormones (e.g., somatotropin, insulin, insulin-like growth factors 1 and 2, platelet derived growth factor (PDGF), epidermal growth factor (EGF), fibroblast growth factor (FGF), nerve growth factor (NGF), neurotrophic factor-3 and 4, brain-derived neurotrophic factor (BDNF), glial derived growth factor (GDNF), transforming growth factor-a and -b, and the like), receptors (e.g., tumor necrosis factor receptor). In some exemplary embodiments, the transgene encodes a monoclonal antibody specific for one or more desired targets. In some exemplary embodiments, more than one transgene is encoded by the ceDNA vector. In some exemplary embodiments, the transgene encodes a fusion protein comprising two different polypeptides of interest. In some embodiments of any of the aspects and embodiments herein, the transgene encodes an antibody, including a full-length antibody or antibody fragment, as defined herein. In some embodiments of any of the aspects and embodiments herein, the antibody is an antigen-binding domain or an immunoglobulin variable domain sequence, as that is defined herein. Other illustrative transgene sequences encode suicide gene products (thymidine kinase, cytosine deaminase, diphtheria toxin, cytochrome P450, oxycytidine kinase, and tumor necrosis factor), proteins conferring resistance to a drug used in cancer therapy, and tumor suppressor gene products.

In one embodiment of any of the aspects or embodiments herein, the present disclosure relates to a method of treating a genetic disorder in a subject (e.g., human), comprising administering to the subject an effective amount of the lipid nanoparticle or a pharmaceutical composition thereof as described in any of the aspects or embodiments herein. In one embodiment of any of the aspects or embodiments herein, the genetic disorder is selected from the group consisting of sickle-cell anemia, melanoma, hemophilia A (clotting factor VIII (FVIII) deficiency) and hemophilia B (clotting factor IX (FIX) deficiency), cystic fibrosis (CFTR), familial hypercholesterolemia (LDL receptor defect), hepatoblastoma, Wilson disease, phenylketonuria (PKU), congenital hepatic *porphyria*, inherited disorders of hepatic metabolism, Lesch Nyhan syndrome, sickle cell anemia, thalassaemias, xeroderma pigmentosum, Fanconi's anemia, retinitis pigmentosa, ataxia telangiectasia, Bloom's syndrome, retinoblastoma, mucopolysaccharide storage diseases (e.g., Hurler syndrome (MPS Type I), Scheie syndrome (MPS Type I S), Hurler-Scheie syndrome (MPS Type I H—S), Hunter syndrome (MPS Type II), Sanfilippo Types A, B, C, and D (MPS Types III A, B, C, and D), Morquio Types A and B (MPS IVA and MPS IVB), Maroteaux-Lamy syndrome (MPS Type VI), Sly syndrome (MPS Type VII), hyaluronidase deficiency (MPS Type IX)), Niemann-Pick Disease Types A/B, C1 and C2, Fabry disease, Schindler disease, GM2-gangliosidosis Type II (Sandhoff Disease), Tay-Sachs disease, Metachromatic Leukodystrophy, Krabbe disease, Mucolipidosis Type I, II/III and IV, Sialidosis Types I and II, Glycogen Storage disease Types I and II (Pompe disease), Gaucher disease Types I, II and III, cystinosis, Batten disease, Aspartylglucosaminuria, Salla disease, Danon disease (LAMP-2 deficiency), Lysosomal Acid Lipase (LAL) deficiency, neuronal ceroid lipofuscinoses (CLN1-8, INCL, and LINCL), sphingolipidoses, galactosialidosis, amyotrophic lateral sclerosis (ALS), Parkinson's disease, Alzheimer's disease, Huntington's disease, spinocerebellar ataxia, spinal muscular atrophy, Friedreich's ataxia, Duchenne muscular dystrophy (DMD), Becker muscular dystrophies (BMD), dystrophic epidermolysis bullosa (DEB), ectonucleotide pyrophosphatase 1 deficiency, generalized arterial calcification of infancy (GACI), Leber Congenital Amaurosis, Stargardt macular dystrophy (ABCA4), ornithine transcarbamylase (OTC) deficiency, Usher syndrome, age-related macular degeneration (AMD), alpha-1 antitrypsin deficiency, progressive familial intrahepatic cholestasis (PFIC) type I (ATP8B1 deficiency), type II (ABCB11), type III (ABCB4), or type IV (TJP2), and Cathepsin A deficiency. In one embodiment of any of the aspects or embodiments herein, the genetic disorder is hemophilia A. In one embodiment of any of the aspects or embodiments herein, the genetic disorder is hemophilia B. In one embodiment of any of the aspects or embodiments herein, the genetic disorder is phenylketonuria (PKU). In one embodiment of any of the aspects or embodiments herein, the genetic disorder is Wilson disease. In one embodiment of any of the aspects or embodiments herein, the genetic disorder is Gaucher disease Types I, II and III. In one embodiment of any of the aspects or embodiments herein, the genetic disorder is Stargardt macular dystrophy. In one embodiment of any of the aspects or embodiments herein, the genetic disorder is LCA10. In one embodiment of any of the aspects or embodiments herein, the genetic disorder is Usher syndrome. In one embodiment of any of the aspects or embodiments herein, the genetic disorder is wet AMD.

In one embodiment of any of the aspects or embodiments herein, the present disclosure relates to use of the lipid nanoparticle or a pharmaceutical composition thereof as described in any of the aspects or embodiments herein for the manufacture of a medicament for treating a genetic disorder in a subject (e.g., human), such as the exemplary genetic disorders are as described above. In one embodiment of any of the aspects or embodiments herein, the genetic disorder treated by the medicament is Stargardt macular dystrophy. In one embodiment of any of the aspects or embodiments herein, the genetic disorder treated by the medicament is LCA10. In one embodiment of any of the aspects or embodiments herein, the genetic disorder treated by the medicament is Usher syndrome. In one embodiment of any of the aspects or embodiments herein, the genetic disorder treated by the medicament is wet AMD.

In one embodiment of any of the aspects or embodiments herein, the present disclosure relates to the lipid nanoparticle or a pharmaceutical composition thereof as described in any of the aspects or embodiments herein for use in treating a genetic disorder in a subject (e.g., human), such as the exemplary genetic disorders are as described above. In one embodiment of any of the aspects or embodiments herein, the genetic disorder treated by the above use is Stargardt macular dystrophy. In one embodiment of any of the aspects or embodiments herein, the genetic disorder treated by the above use is LCA10. In one embodiment of any of the aspects or embodiments herein, the genetic disorder treated by the above use is Usher syndrome. In one embodiment of any of the aspects or embodiments herein, the genetic disorder treated by the above use is wet AMD.

Administration

In one embodiment of any of the aspects or embodiments herein, a TNA LNP (e.g., a ceDNA vector lipid particle as described herein) can be administered to an organism for transduction of cells in vivo. In one embodiment of any of the aspects or embodiments herein, TNA LNP (e.g., ceDNA vector lipid particles) can be administered to an organism for transduction of cells ex vivo.

Generally, administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route. Exemplary modes of administration of the TNA LNP (e.g., ceDNA vector lipid particles) includes oral, rectal, transmucosal, intranasal, inhalation (e.g., via an aerosol), buccal (e.g., sublingual), vaginal, intrathecal, intraocular, transdermal, intraendothelial, in utero (or in ovo), parenteral (e.g., intravenous, subcutaneous, intradermal, intracranial, intramuscular [including administration to skeletal, diaphragm and/or cardiac muscle], intrapleural, intracerebral, and intraarticular), topical (e.g., to both skin and mucosal surfaces, including airway surfaces, and transdermal administration), intralymphatic, and the like, as well as direct tissue or organ injection (e.g., to liver, eye, skeletal muscle, cardiac muscle, diaphragm muscle or brain).

Administration of the TNA LNP like ceDNA vector (e.g., a ceDNA LNP) can be to any site in a subject, including, without limitation, a site selected from the group consisting of the brain, a skeletal muscle, a smooth muscle, the heart, the diaphragm, the airway epithelium, the liver, the kidney, the spleen, the pancreas, the skin, and the eye. In one embodiment of any of the aspects or embodiments herein, administration of the ceDNA LNP can also be to a tumor (e.g., in or near a tumor or a lymph node). The most suitable route in any given case will depend on the nature and severity of the condition being treated, ameliorated, and/or prevented and on the nature of the particular ceDNA LNP that is being used. Additionally, ceDNA permits one to administer more than one transgene in a single vector, or multiple ceDNA vectors (e.g., a ceDNA cocktail).

In one embodiment of any of the aspects or embodiments herein, administration of the ceDNA LNP to skeletal muscle includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. The ceDNA vectors (e.g., ceDNA vector lipid particles (e.g., lipid nanoparticles)) can be delivered to skeletal muscle by intravenous administration, intra-arterial administration, intraperitoneal administration, limb perfusion, (optionally, isolated limb perfusion of a leg and/or arm; see, e.g., Arruda et al., (2005) Blood 105: 3458-3464), and/or direct intramuscular injection. In particular embodiments, the ceDNA LNP is administered to a limb (arm and/or leg) of a subject (e.g., a subject with muscular dystrophy such as DMD) by limb perfusion, optionally isolated limb perfusion (e.g., by intravenous or intra-articular administration. In one embodiment of any of the aspects or embodiments herein, the ceDNA LNP can be administered without employing "hydrodynamic" techniques.

Administration of the TNA LNPs (e.g., ceDNA LNP) to cardiac muscle includes administration to the left atrium, right atrium, left ventricle, right ventricle and/or septum. The TNA LNP (e.g., ceDNA LNP) can be delivered to cardiac muscle by intravenous administration, intra-arterial administration such as intra-aortic administration, direct cardiac injection (e.g., into left atrium, right atrium, left ventricle, right ventricle), and/or coronary artery perfusion. Administration to diaphragm muscle can be by any suitable method including intravenous administration, intra-arterial administration, and/or intra-peritoneal administration. Administration to smooth muscle can be by any suitable method including intravenous administration, intra-arterial administration, and/or intra-peritoneal administration. In one embodiment of any of the aspects or embodiments herein, administration can be to endothelial cells present in, near, and/or on smooth muscle.

In one embodiment of any of the aspects or embodiments herein, TNA LNPs (e.g., ceDNA LNP) are administered to skeletal muscle, diaphragm muscle and/or cardiac muscle (e.g., to treat, ameliorate, and/or prevent muscular dystrophy or heart disease (e.g., PAD or congestive heart failure).

TNA LNPs (e.g., ceDNA LNP) can be administered to the CNS (e.g., to the brain or to the eye). The TNA LNP (e.g., ceDNA LNP) may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and portaamygdala), limbic system, neocortex, corpus striatum, cerebrum, and inferior colliculus. The TNA LNPs (e.g., ceDNA LNP) may also be administered to different regions of the eye such as the retina, cornea and/or optic nerve. The TNA LNPs (e.g., ceDNA LNP) may be delivered into the cerebrospinal fluid (e.g., by lumbar puncture). The TNA LNPs (e.g., ceDNA vector lipid particles) may further be administered intravascularly to the CNS in situations in which the blood-brain barrier has been perturbed (e.g., brain tumor or cerebral infarct).

In one embodiment of any of the aspects or embodiments herein, the TNA LNPs (e.g., ceDNA LNP) can be administered to the desired region(s) of the CNS by any route known in the art, including but not limited to, intrathecal, intraocular, intracerebral, intraventricular, intravenous (e.g., in the presence of a sugar such as mannitol), intranasal, intraaural, intra-ocular (e.g., intra-vitreous, sub-retinal, anterior chamber) and peri-ocular (e.g., sub-Tenon's region) delivery as well as intramuscular delivery with retrograde delivery to motor neurons.

According to some embodiments of any of the aspects or embodiments herein, the TNA LNPs (e.g., ceDNA LNP) are administered in a liquid formulation by direct injection (e.g., stereotactic injection) to the desired region or compartment in the CNS. According to other embodiments, the TNA LNPs (e.g., ceDNA LNP) can be provided by topical application to the desired region or by intra-nasal administration of an aerosol formulation. Administration to the eye may be by topical application of liquid droplets. As a further alternative, the ceDNA vector can be administered as a solid, slow-release formulation (see, e.g., U.S. Pat. No. 7,201,898, incorporated by reference in its entirety herein). In one embodiment of any of the aspects or embodiments herein, the TNA LNPs (e.g., ceDNA LNP) can used for retrograde transport to treat, ameliorate, and/or prevent diseases and disorders involving motor neurons (e.g., amyotrophic lateral sclerosis (ALS); spinal muscular atrophy (SMA), etc.). For example, the TNA LNPs (e.g., ceDNA LNP) can be delivered to muscle tissue from which it can migrate into neurons.

In one embodiment of any of the aspects or embodiments herein, repeat administrations of the therapeutic product can be made until the appropriate level of expression has been achieved. Thus, in one embodiment of any of the aspects or embodiments herein, a therapeutic nucleic acid can be administered and re-dosed multiple times. For example, the therapeutic nucleic acid can be administered on day 0. Following the initial treatment at day 0, a second dosing (re-dose) can be performed in about 1 week, about 2 weeks, about 3 weeks, about 4 weeks, about 5 weeks, about 6 weeks, about 7 weeks, about 8 weeks, or about 3 months, about 4 months, about 5 months, about 6 months, about 7 months, about 8 months, about 9 months, about 10 months, about 11 months, or about 1 year, about 2 years, about 3 years, about 4 years, about 5 years, about 6 years, about 7 years, about 8 years, about 9 years, about 10 years, about 11 years, about 12 years, about 13 years, about 14 years, about 15 years, about 16 years, about 17 years, about 18 years, about 19 years, about 20 years, about 21 years, about 22 years, about 23 years, about 24 years, about 25 years, about 26 years, about 27 years, about 28 years, about 29 years, about 30 years, about 31 years, about 32 years, about 33 years, about 34 years, about 35 years, about 36 years, about 37 years, about 38 years, about 39 years, about 40 years, about 41 years, about 42 years, about 43 years is, about 44 years, about 45 years, about 46 years, about 47 years, about 48 years, about 49 years or about 50 years after the initial treatment with the therapeutic nucleic acid.

In one embodiment of any of the aspects or embodiments herein, one or more additional compounds can also be included. Those compounds can be administered separately, or the additional compounds can be included in the lipid particles (e.g., lipid nanoparticles) of the invention. In other words, the lipid particles (e.g., lipid nanoparticles) can contain other compounds in addition to the TNA or at least a second TNA, different than the first. Without limitations, other additional compounds can be selected from the group consisting of small or large organic or inorganic molecules, monosaccharides, disaccharides, trisaccharides, oligosaccharides, polysaccharides, peptides, proteins, peptide analogs and derivatives thereof, peptidomimetics, nucleic acids, nucleic acid analogs and derivatives, an extract made from biological materials, or any combinations thereof.

In one embodiment of any of the aspects or embodiments herein, the one or more additional compound can be a therapeutic agent. The therapeutic agent can be selected from any class suitable for the therapeutic objective. Accordingly, the therapeutic agent can be selected from any class suitable for the therapeutic objective. The therapeutic agent can be selected according to the treatment objective and biological action desired. For example, in one embodiment of any of the aspects or embodiments herein, if the TNA within the LNP is useful for treating cancer, the additional compound can be an anti-cancer agent (e.g., a chemotherapeutic agent, a targeted cancer therapy (including, but not limited to, a small molecule, an antibody, or an antibody-drug conjugate). In one embodiment of any of the aspects or embodiments herein, if the LNP containing the TNA is useful for treating an infection, the additional compound can be an antimicrobial agent (e.g., an antibiotic or antiviral compound). In one embodiment of any of the aspects or embodiments herein, if the LNP containing the TNA is useful for treating an immune disease or disorder, the additional compound can be a compound that modulates an immune response (e.g., an immunosuppressant, immunostimulatory compound, or compound modulating one or more specific immune pathways). In one embodiment of any of the aspects or embodiments herein, different cocktails of different lipid particles containing different compounds, such as a TNA encoding a different protein or a different compound, such as a therapeutic may be used in the compositions and methods of the invention. In one embodiment of any of the aspects or embodiments herein, the additional compound is an immune modulating agent. For example, the additional compound is an immunosuppressant. In some embodiments of any of the aspects and embodiments herein, the additional compound is immunostimulatory.

EXAMPLES

The following examples are provided by way of illustration not limitation. It will be appreciated by one of ordinary skill in the art that the scope of the lipids contemplated in disclosure can be designed and synthesized using general synthesis methods described below.

Example 1: General Synthesis

Lipids of Formula I were designed and synthesized using similar synthesis methods as depicted in Scheme 1 ($R^5$ is absent) and Scheme 2 ($R^5$ is $C_1$-$C_8$ alkylene or $C_2$-$C_8$ alkenylene) below. All other variables in the compounds shown in Scheme 1 and Scheme 2, i.e., $R^1$, $R^2$, $R^3$, $R^4$, $R^{6a}$, $R^{6b}$, $X^1$, $X^2$, and n, are as defined in Formula I. $X^{1'}$ is $X^1$ as defined but with an additional protecting group, such as benzyl or pyridine.

Scheme 1

Step 1

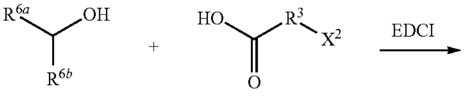

1 2

-continued
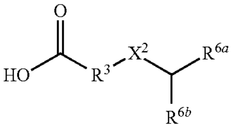
3
Step 2
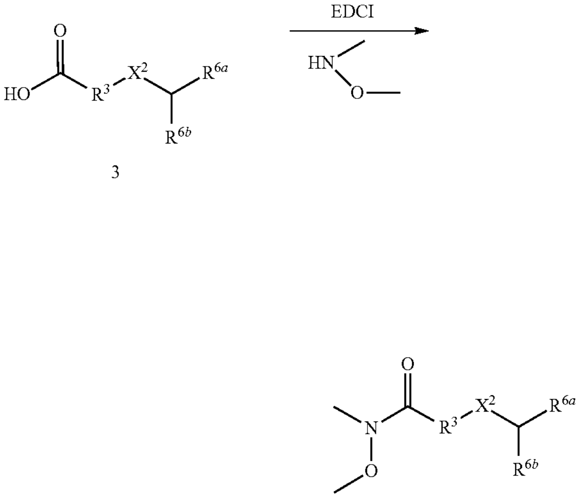
3
4
Step 3
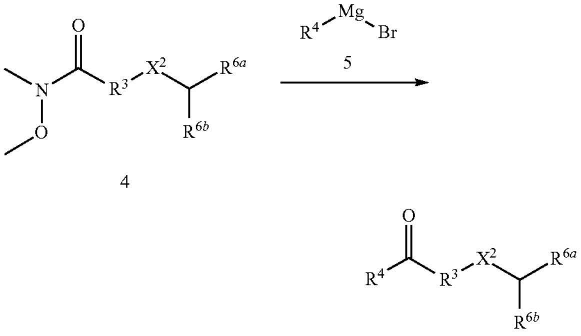
4
6
Step 4
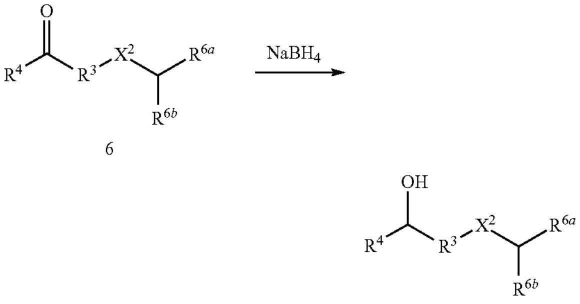
6
7
-continued
Step 5
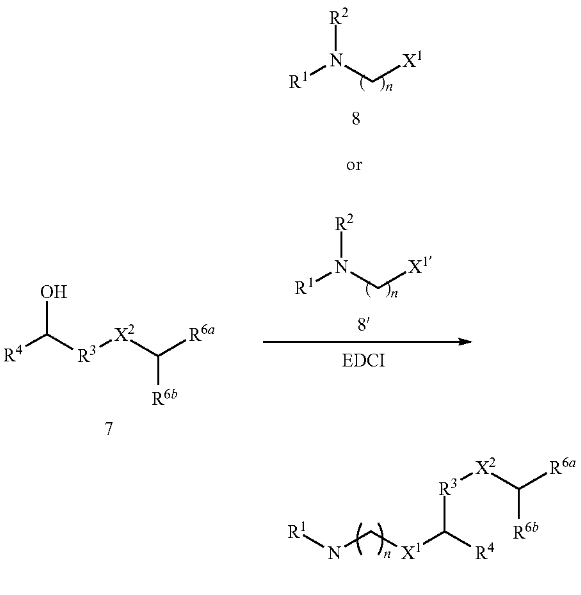
8
7
9
Scheme 2
Step 1
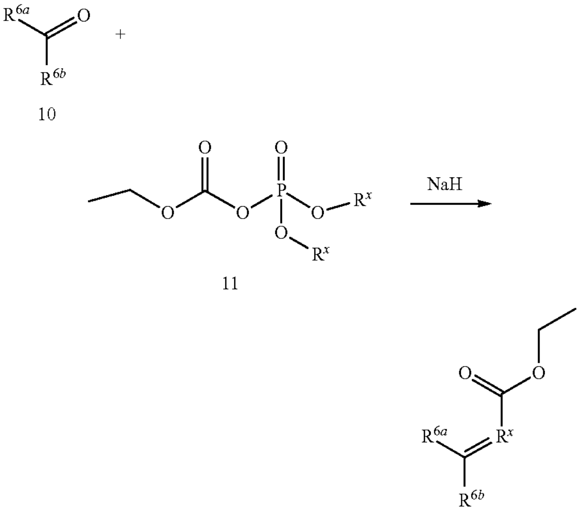
10
11
12
Step 2
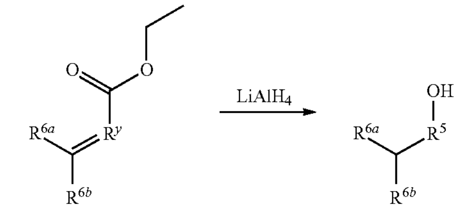
12
13

-continued

Step 3

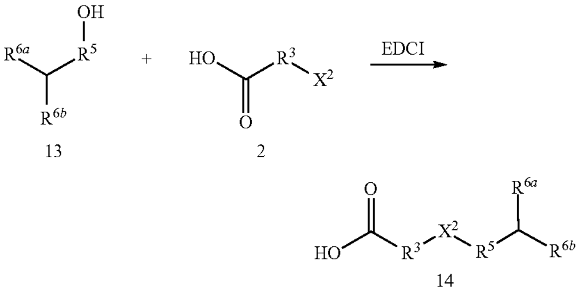

13 2

14

Step 4

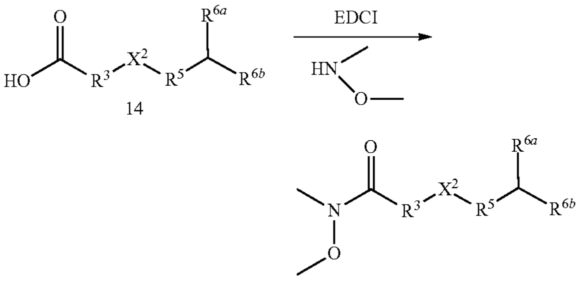

14

15

Step 5

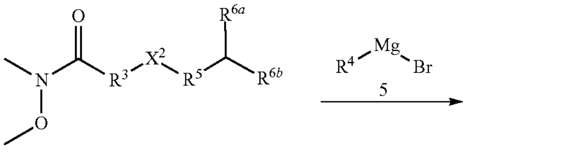

15 5

16

Step 6

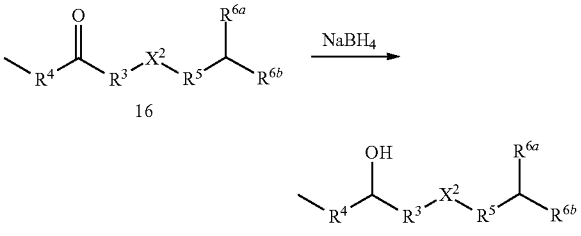

16

17

Step 7

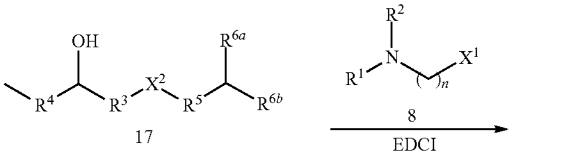

17 8

-continued

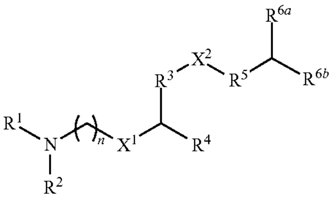

18

$R^x$ is alkylene or alkenylene having one less carbon atom than $R^5$.

Diester lipids of Formula III were designed and synthesized using similar synthesis methods as depicted in Scheme 3 ($R^5$ is absent) and Scheme 4 ($R^5$ is $C_1$-$C_8$ alkylene or $C_2$-$C_8$ alkenylene) below. All other variables in the compounds shown in Scheme 3 and Scheme 4, i.e., $R^1$, $R^2$, $R^3$, $R^4$, $R^{6a}$, $R^{6b}$, and n, are as defined in Formula III.

Scheme 3

Step 1

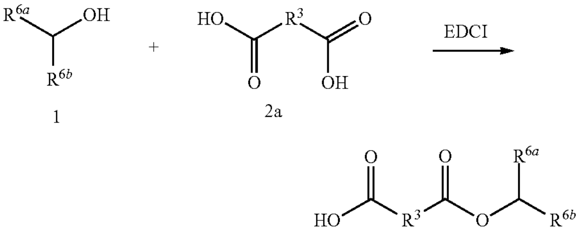

1 2a

3a

Step 2

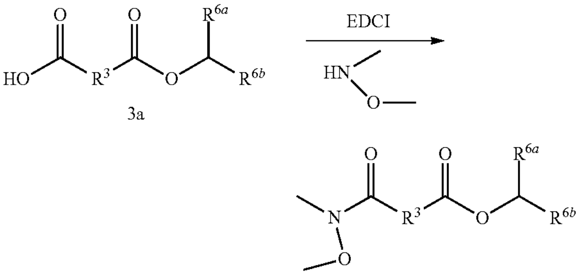

3a

4a

Step 3

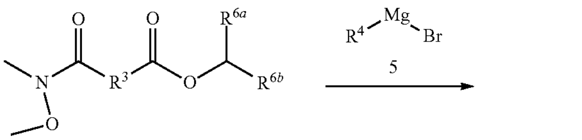

4a 5

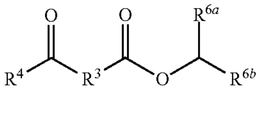

6a

-continued
Step 4
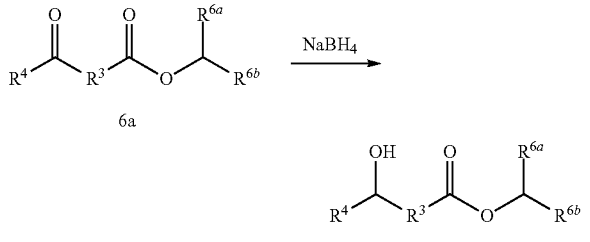
6a
7a
Step 5
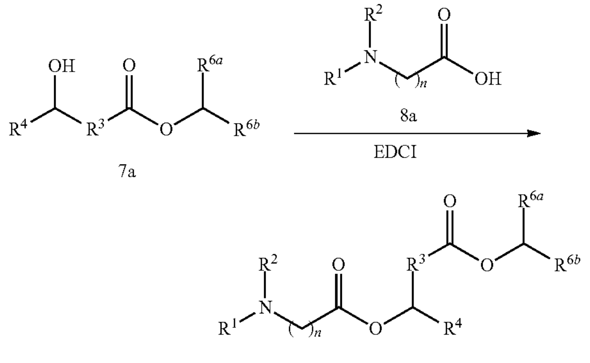
7a
8a
9a
Scheme 4
Step 1
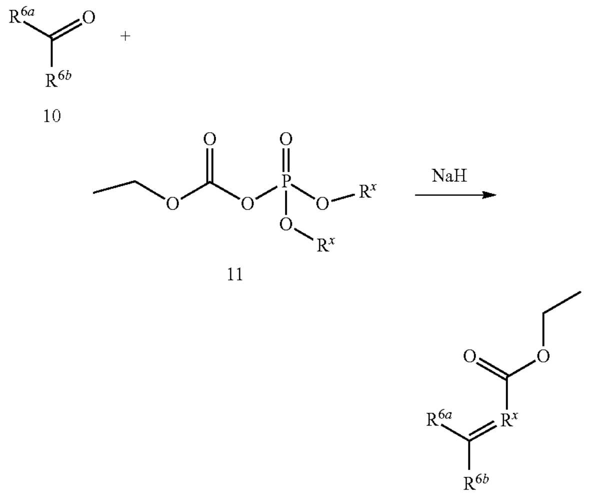
10
11
12
Step 2
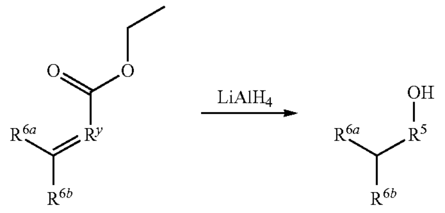
12
13
-continued
Step 3
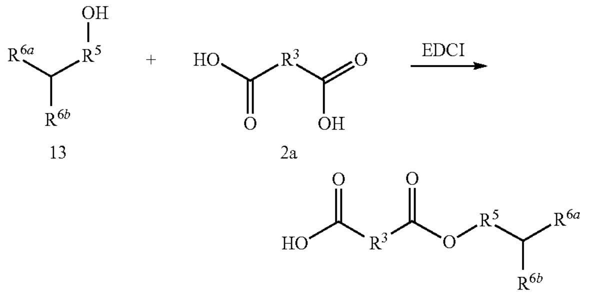
13
2a
14a
Step 4
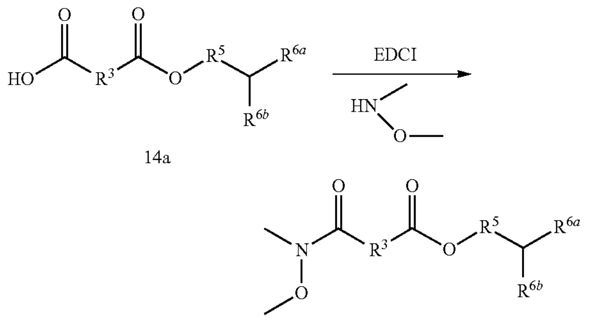
14a
15a
Step 5
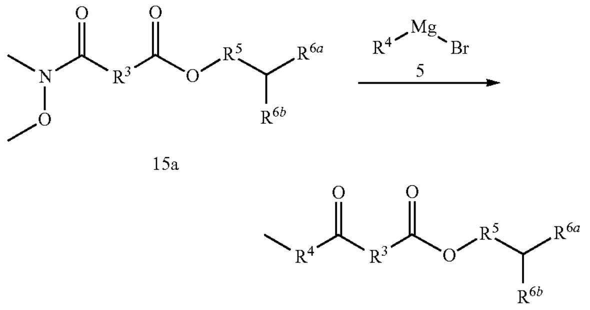
5
15a
16a
Step 6
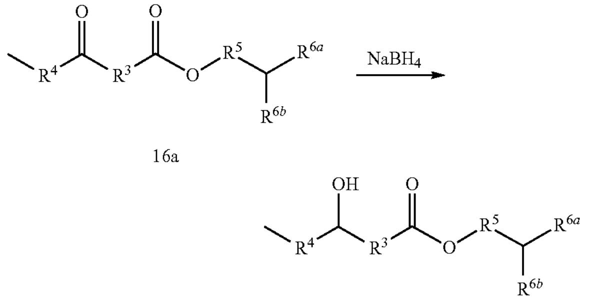
16a
17a -continued Step 7

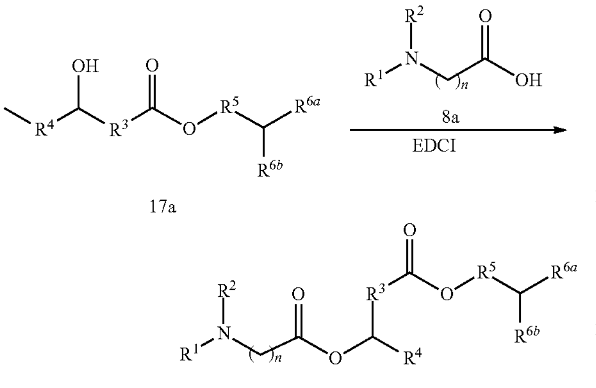

17a

18a $R^x$ is alkylene or alkenylene having one less carbon atom than $R^5$.

Scheme 1 and Scheme 3

Referring to Scheme 1 and Scheme 3, at Step 1, to a stirred solution of the acid 1 and alcohol 2 (or 2a) in dichloromethane (DCM), was added 4-dimethylaminopyridine (DMAP) followed by 1-ethyl-3-(3-dimethylaminopropyl)carbodiimide (EDCI). The resulting mixture was stirred at room temperature overnight, then washed with hydrochloric acid (HCl) and water. The organic layer was dried over magnesium sulfate ($MgSO_4$), evaporated to dryness, and purified by silica gel column chromatography using 0-10% methanol (MeOH) in DCM as eluent. The fractions containing the desired compound were pooled and evaporated to afford acid 3 as a white solid.

At Step 2, to a solution of acid 3 (or 3a) in DCM, EDCI and triethylamine (TEA) were added, and the mixture was stirred for 15 min at room temperature. Then, N,O-dimethylhydroxylamine hydrochloride and DMAP were added and the mixture was stirred overnight at room temperature. The next day, the reaction was quenched with an ammonium chloride aqueous solution ($NH_4Cl$ (aq)) and diluted with DCM. The organic layer was washed with $NH_4Cl$ and brine and dried over anhydrous sodium sulfate ($Na_2SO_4$). Solvent was evaporated under vacuo. The product 4 (or 4a) was used in next step without further purification.

At Step 3, the compound 4 (or 4a) was dissolved in anhydrous tetrahydrofuran (THF). Then 5, a magnesium bromide solution in diethyl ether ($Et_2O$) was added dropwise at 0° C. The resulting mixture was stirred at room temperature for 16 h under nitrogen gas ($N_2$). The reaction was quenched with saturated $NH_4Cl$ solution and extracted with ether. The organic layer was washed with brine and dried over anhydrous $Na_2SO_4$. Solvent was evaporated under vacuo and purified by column chromatography using 0-10% ethyl acetate (EtOAc) in hexane as eluent to afford 6 (or 6a).

At Step 4, to a solution of 6 (or 6a) in anhydrous THF was added sodium borohydride ($NaBH_4$) at 0° C. and the mixture was stirred overnight under $N_2$ atmosphere. The reaction was quenched with saturated $NH_4Cl$ solution and extracted with EtOAc. The organic phase was washed with brine and dried over anhydrous $Na_2SO_4$. Solvent was evaporated under vacuo and purified by column chromatography using 0-10% EtOAc in hexane as eluent to afford 7.

At Step 5, to a solution of compound 7 (or 7a) and compound 8 (or 8a) in DCM, N,N-diisopropylethylamine (DIPEA) was added. Then EDCI and DMAP (0.012 g, 0.1 mmol) were added, and the mixture was stirred overnight at room temperature under $N_2$ atmosphere. Next day reaction was diluted with DCM. The organic layer was washed with sodium bicarbonate aqueous solution ($NaHCO_3$(aq)) and dried over anhydrous $Na_2SO_4$. Solvent was evaporated under vacuo and purified by column chromatography using 0-5% MeOH in DCM as eluent to afford the final product 9 (or diester 9a).

Scheme 2 and Scheme 4

Referring to Scheme 2 and Scheme 4, at Step 1, to an ice-cold solution of 3 g (11.8 mmol) of ketone 10 in THF, the phosphoric anhydride solution 11 was added dropwise. The reaction was stirred for 30 min and then sodium hydride (NaH) was added. The reaction gave 12.

At Step 2, compound 2 in THF was reacted with lithium aluminum hydride solution ($LiAlH_4$). After 48 h, the crude was quenched with water and extracted with ether to give the alcohol 13.

The subsequent Step 3 through Step 7 of Scheme 2 and Scheme 4 were carried out similar procedures as described in Step 1 through Step 5 of Scheme 1 and Scheme 3, with the alcohol 13 as the appropriate starting material and with other modifications that would be within the knowledge of the person having ordinary skill in the art.

Example 2: Alternative General Synthesis

Lipids of Formula I may be synthesized using alternative synthesis procedures, such as the procedures described in this example.

Alternative General Synthesis (A)

At least Lipid 11, Lipid 1, and Lipid 2, and any lipid of Formula I where R' is absent, $R^1$ and $R^2$ are methyl, n is 3, $R^3$ is $C_6$ alkylene, $R^4$ is $C_7$ alkyl, $R^5$ is absent, and $X^1$ and $X^2$ are each independently —C(═O)O—, and where $R^{6a}$ and $R^{6b}$ are as defined in Formula I were or may be prepared using synthesis methods similar to those depicted in Scheme 5 provided below. Minor modifications may be applied to the general synthesis depicted in Scheme 5 to produce other lipids of Formula I, such as but not limited to substitution of compound 2b with compound 2a, substitution of heptylmagnesium bromide with compound 5, and/or substitution of 4-(dimethylamino)butanoic acid with compound 8a to produce lipids of Formula I.

Scheme 5

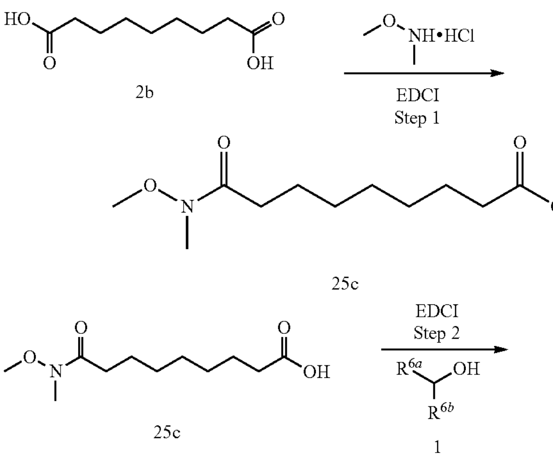

2b

25c

25c

1

-continued

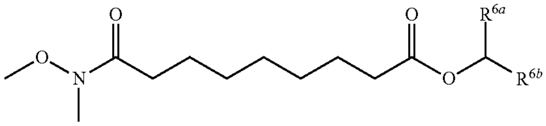

4f

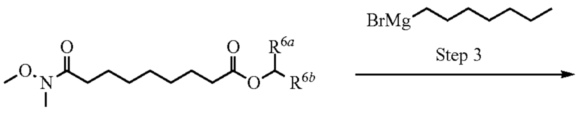

4f

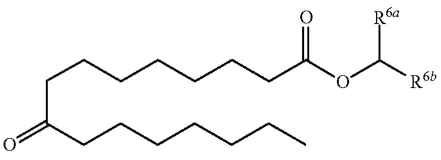

6g

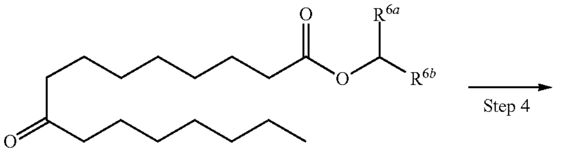

6g

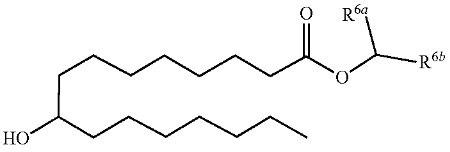

7h

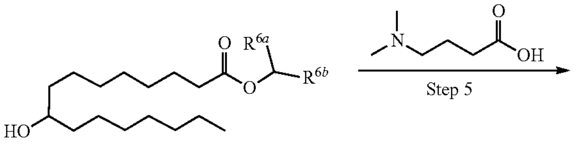

7h

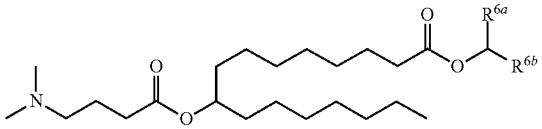

9c

Step 1: Synthesis of 9-(methoxy(methyl)amino)-9-oxononanoic acid (25c)

To a stirred mixture of nonanedioic acid (2b) (20 g, 106 mmol) and N,O-dimethylhydroxylamine hydrochoride (10.3 g, 106 mmol) in DCM (200 ml) was added triethylamine (20 ml) followed by EDCI (24.3 g, 127 mmol) and DMAP (0.5 g, 4 mmol). The resulting mixture was stirred at room temperature overnight, then washed with 150 ml 1 N HCl and 150 ml water. The organic layer was dried over $MgSO_4$, evaporated to dryness, and purified by silica gel column chromatography using 0-10% methanol in DCM as eluent. The fractions containing the desired compound were pooled and evaporated to afford compound 25c (12.8 g, 52%). $^1$H-NMR (300 MHz, d-chloroform): δ 3.67 (s, 3H), 3.17 (s, 3H), 2.39 (t, 2H), 2.32 (t, 2H), 1.55-1.70 (m, 4H), 1.24-1.36 (m, 6H).

Step 2: Synthesis of Compound 4f

To a stirred solution of acid 25c and alcohol 1 in DCM was added DMAP followed by EDCI. The resulting mixture was stirred at room temperature overnight, then washed with 1 N HCl and water. The organic layer was dried over $MgSO_4$, evaporated to dryness, and purified by silica gel column chromatography using 0-10% methanol in DCM as eluent. The fractions containing the desired compound were pooled and evaporated to afford compound 4f.

Step 3: Synthesis of Compound 6g

Compound 4f was dissolved in anhydrous THF. Then 1 M heptyl magnesium bromide solution in $Et_2O$ was added dropwise at 0° C. The resulted mixture was stirred at room temperature for 16 h under $N_2$. The reaction was quenched with saturated $NH_4Cl$ solution and extracted with ether. The organic layer was washed with brine and dried over anhydrous $Na_2SO_4$. Solvent was evaporated under vacuo. and purified by column chromatography using 0-30% EtOAc in hexane as eluent to afford compound 6g.

Step 4: Synthesis of Compound 7h

To a solution of 6 g in anhydrous THF was added $NaBH_4$ at 0° C. and stirred overnight under $N_2$ atmosphere. The reaction was quenched with saturated $NH_4Cl$ solution and extracted with EtOAc. The organic phase was washed with brine and dried over anhydrous $Na_2SO_4$. Solvent was evaporated under vacuo and purified by column chromatography using 0-50% EtOAc in hexane as eluent to afford compound 7h.

Step 5: Synthesis of Compound 9c

To a solution of compound 7h and 4-(dimethylamino) butanoic acid in DCM, DIPEA was added. Then EDCI and DMAP were added, and the mixture was stirred overnight at room temperature under $N_2$ atmosphere. Next day reaction was diluted with DCM. The organic layer was washed with $NaHCO_3$(aq) and dried over anhydrous $Na_2SO_4$. Solvent was evaporated under vacuo. and purified by column chromatography using 0-5% MeOH in DCM as eluent to afford compound 9c, which is a lipid of Formula I where R' is absent, $R^1$ and $R^2$ are methyl, n is 3, $R^3$ is $C_6$ alkylene, $R^4$ is $C_7$ alkyl, $R^5$ is absent, and $X^1$ and $X^2$ are each independently —C(═O)O—, and where $R^{6a}$ and $R^{6b}$ are as defined in Formula I.

Alternative General Synthesis (B)

At least Lipid 12, Lipid 3, and Lipid 4, and any lipid of Formula I where R' is absent, $R^1$ and $R^2$ are methyl, n is 3, $R^3$ is $C_3$ alkylene, $R^4$ is $C_7$ alkyl, $R^5$ is $C_4$ alkylene, and $X^1$ and $X^2$ are each independently —C(═O)O—, and where $R^{6a}$ and $R^{6b}$ are the same and as defined in Formula I and are equal to $R^6$ were or may be prepared using synthesis methods similar to those depicted in Scheme 6 as provided below. Minor modifications may be applied to the general synthesis depicted in Scheme 6 to produce other lipids of Formula I, such as but not limited to substitution of compound 2d with compound 2a, substitution of heptylmagnesium bromide with compound 5, substitution of 4-(dimethylamino)butanoic acid with compound 8a, substitution of compound 23 with an equivalent diol having different number of carbon atoms in the two aliphatic chain tails in accordance with the scope and definition of $R^{6a}$ and $R^{6b}$ in Formula I, and/or use of two different species compound 22 each having a different number of carbon atoms in the aliphatic chain to produce lipids of Formula I where $R^{6a}$ and $R^{6b}$ are different.

Scheme 6

Synthesis of compound 13b

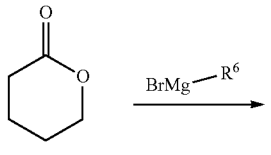

21

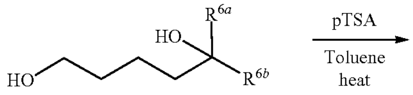

23

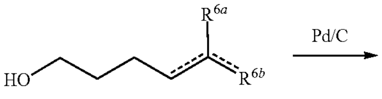

24

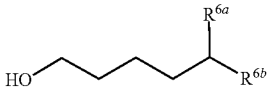

13b

Synthesis of compound 25

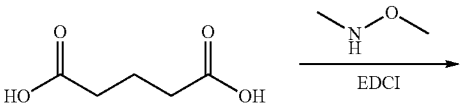

2d

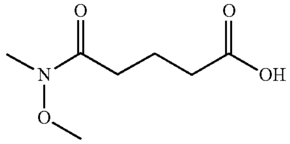

25

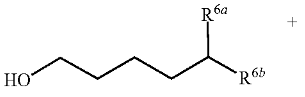

13b

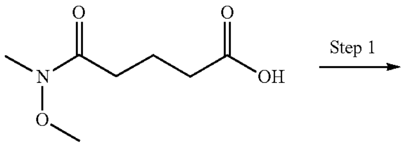

25

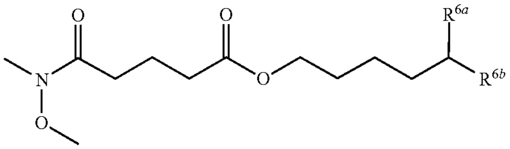

15c

-continued

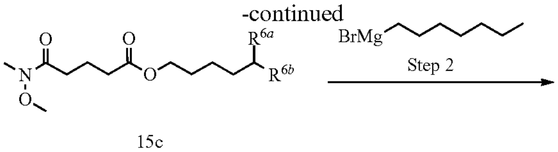

15c

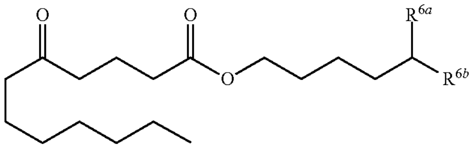

16c

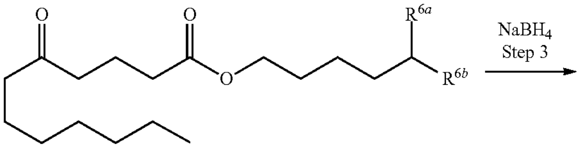

16c

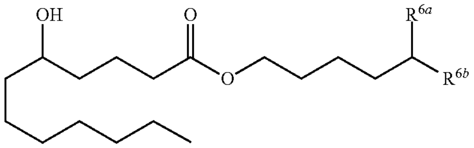

17c

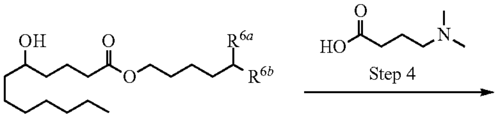

17c

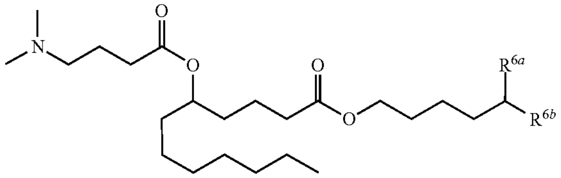

18b

Synthesis of Compound 13b

To a solution of alkyl magnesium bromide (22) in methyltetrahydrofuran (MeTHF) under nitrogen atmosphere and cooled down to 0° C., was added dropwise tetrahydro-2H-pyran-2-one (21) dissolved in anhydrous ethyl ether. After five minutes of stirring the ice bath was retrieved and the reaction was allowed to stir at room temperature overnight. The reaction was worked up as usual and the crude was purified by column chromatography using 0-25% ethyl acetate (EtOAc) in hexane as eluent to afford compound 23.

Compound 23 was dissolved in 5 ml of toluene and p-toluenesulfonic acid monohydrate (pTSA) added in a microwave tube and microwaved to 100° C. for one hour. Solvent was evaporated under vacuo and purified by column chromatography using 0-5% EtOAc in hexane as eluent to afford compound 24.

To a solution of compound 24 in EtOAc 200 mg of palladium (Pd) 10% on activated carbon, Pearlman (50-70% wet) was added and after degassing the mixture a hydrogen balloon was left over the mixture overnight. The mixture was filtered over celite, and the crude was purified using 0-10% EtOAc in hexane as eluent, to afford alcohol compound 13b.

Synthesis of 5-(methoxy(methy)amino)-5-oxopentanoic acid (25)

To a stirred solution of glutaric acid (2d) (5.4 g, 41 mmol) and N, O-dimethoxyamine hydrochloride (2 g, 20.5 mmol) in dichloromethane (DCM) (20 ml) was added 4-dimethylaminopyridine (DMAP) (0.25 g, 2 mmol) followed by 1-ethyl-3-(3-dimethylaminopropyl)carbodiimide (EDCI) and triethyl amine ($Et_3N$) (5.7 ml, 41 mmol). The resulting mixture was stirred at room temperature overnight, then washed with 50 ml $NH_4Cl$ aqueous solution and extracted with DCM (30 ml) and EtOAc (30 ml). The organic layer was dried over magnesium sulfate ($MgSO_4$), evaporated to dryness, and purified by silica gel column chromatography using 0-25% EtOAc in hexane as eluent. The fractions containing the desired compound were pooled and evaporated to afford 5-(methoxy(methy)amino)-5-oxopentanoic acid (25) (2.2 g, 60%) as an oil. $^1$H-NMR (300 MHz, d-chloroform): δ 3.67 (s, 3H), 3.17 (s, 3H), 2.55-1.9 (m, 4H), 1.94-2.00 (m, 2H).

Step 1: Synthesis of Compound 15c

Alcohol 13b and amide 25 were dissolved in anhydrous DCM followed by EDCI and DMAP. The reaction was stirred overnight under nitrogen and worked up adding $NH_4Cl$ aqueous solution and extracted with DCM and EtOAc. The organic layer was dried over $MgSO_4$. Solvent was evaporated under vacuo. and purified by column chromatography using 0-25% EtOAc in hexane as eluent to compound 15c.

Step 2: Synthesis of Compound 16c

To an ice-cold solution of 15c in anhydrous THF under nitrogen, heptyl magnesium bromide in ether was added dropwise. The reaction was allowed to stir overnight and was quenched using $NH_4Cl$ aqueous solution after cooling the reaction mixture to 0° C. The crude was extracted using hexane. The organic layer was dried over $MgSO_4$. Solvent was evaporated under vacuo and purified by column chromatography using 0-10% EtOAc in hexane as eluent to afford compound 16c.

Step 3: Synthesis of Compound 17c

To an ice-cold solution of 16c tetrahydrofuran/methanol (THF/MeOH) was dissolved in and sodium borohydride ($NaBH_4$) was added. The reduction reaction was followed by thin layer chromatography (TLC). After 1 h the starting material disappeared completely, and the reaction was quenched with $NH_4Cl$ aqueous solution. The crude was evaporated down to dryness then re-dissolved in DCM, washed once with water and the organic layer was dried over $MgSO_4$. The crude compound 17c was used in the next step without further purification.

Step 4: Synthesis of Compound 18b

To a solution of 17c and 4-dimethylamino butyric acid HCl in DCM was added EDCI, DMAP and finally triethyl amine. Reaction was allowed to stir overnight and quenched with saturated $NH_4Cl$ solution and extracted with DCM and EtOAc. The organic layer was dried over anhydrous $MgSO_4$. The solvent was evaporated under vacuo and purified by column chromatography using 0-5% MeOH in DCM as eluent to afford compound 18b, which is a lipid of Formula I where R' is absent, $R^1$ and $R^2$ are methyl, n is 3, $R^3$ is $C_3$ alkylene, $R^4$ is $C_7$ alkyl, $R^5$ is $C_4$ alkylene, and $X^1$ and $X^2$ are each independently —C(═O)O—, and where $R^{6a}$ and $R^{6b}$ are the same and as defined in Formula I.

Alternative Synthesis (C)

At least Lipid 13, Lipid 5, and Lipid 6, and any lipid of Formula I where R' is absent, $R^1$ and $R^2$ are methyl, n is 3, $R^3$ is $C_4$ alkylene, $R^4$ is $C_7$ alkyl, $R^5$ is $C_3$ alkylene, and $X^1$ and $X^2$ are each independently —C(═O)O—, and where $R^{6a}$ and $R^{6b}$ are the same and as defined in Formula I and are equal to $R^6$ were or may be prepared using synthesis methods similar to those depicted in Scheme 7 provided below. Minor modifications may be applied to the general synthesis depicted in Scheme 7 to produce other lipids of Formula I, such as but not limited to substitution of heptylmagnesium bromide with compound 5, substitution of 4-(dimethylamino)butanoic acid with compound 8a, substitution of compound 23a with an equivalent diol having different number of carbon atoms in the two aliphatic chain tails in accordance with the scope and definition of $R^{6a}$ and $R^{6b}$ in Formula I, and/or use of two different species of compound 22 each having a different number of carbon atoms in the aliphatic chain to produce lipids of Formula I where $R^{6a}$ and $R^{6b}$ are different.

Scheme 7

Synthesis of compound 13c

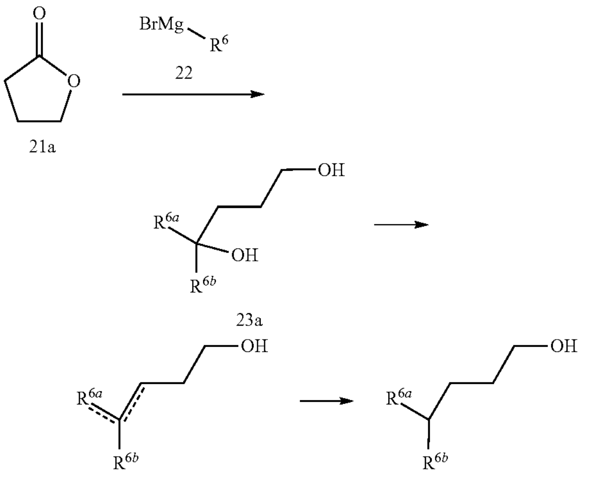

21a 22 23a 24a 13c

Synthesis of compound 29

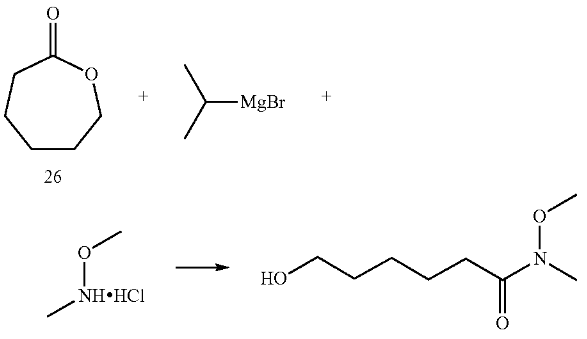

26 27

-continued

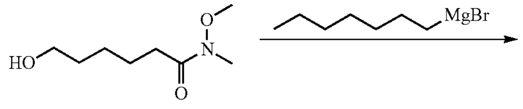

27

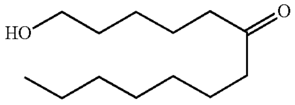

28

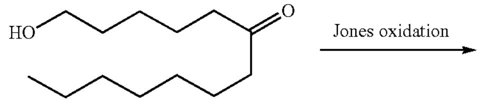

28

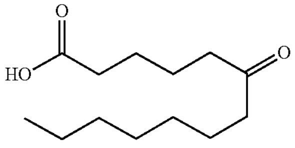

29

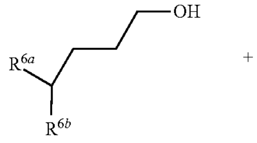

13c

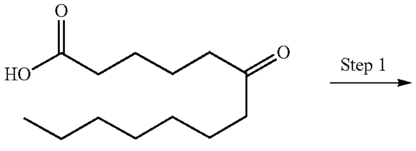

29

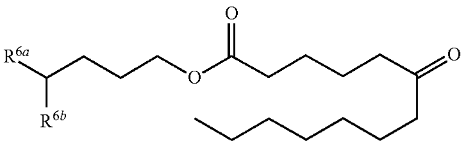

16i

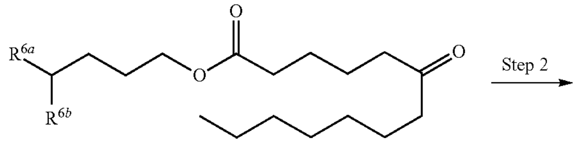

16i

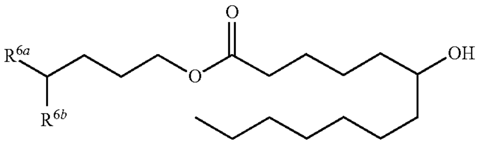

17i

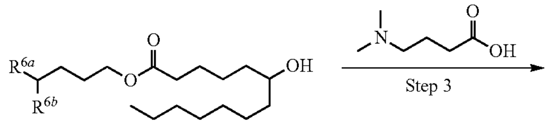

17i

-continued

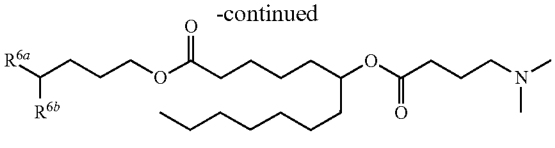

18c

Synthesis of Compound 13c

Alkyl magnesium bromide (22) was measured to an oven dried round bottom flask under nitrogen and cooled to 0° C. Then γ-butyrolactone (21a) solution in diethyl ether ($Et_2O$) was added dropwise at 0° C. The resulting mixture was stirred at room temperature for 16 h under nitrogen. The reaction was quenched with 3 M HCl solution and extracted with ether. The organic layer was washed with $H_2O$ and dried over anhydrous $Na_2SO_4$. Solvent was evaporated under vacuo and purified by column chromatography using 0-50% EtOAc in hexane as eluent to afford compound 23a.

Diol 23a and PTSA were dissolved in toluene and microwaved at 60° C. for 2 h. Then solvent was evaporated under vacuo and purified by column chromatography using 0-20% EtOAc in hexane as eluent to afford compound 24a.

Compound 24a was dissolved in EtOAc and degassed and 5% Pd/C was added and degassed again. Reaction was kept under hydrogen for 4 h. Then reaction mixture was filtered through celite. Solvent was evaporated under vacuo and purified by column chromatography using 0-20% EtOAc in hexane as eluent to afford compound 13c.

Synthesis of Compound 29

Isopropylmagnesium chloride solution (2.0 M solution in THF; 10 mL, 20 mmol) was added dropwise to a mixture of 2-oxepanone (26) (0.34 g, 3 mmol) and N,O-dimethylhydroxylamine hydrochloride (0.88 g, 9 mmol) in THF (15 mL) at 0° C. and allowed to reach room temperature. After stirring for 1 h at room temperature, the mixture was cooled to 0° C., and saturated $NH_4Cl$ solution was added. The phases were separated, and the aqueous layer was extracted with DCM. The organic phase was dried over anhydrous $Na_2SO_4$ and concentrated under reduced pressure to afford 6-hydroxy-N-methoxy-N-methylhexanamide (27), which was used in next step without further purification.

To a solution of compound 27 (3.96 g, 22.6 mmol) in THF (138 mL), was added heptyl magnesium bromide (45.2 mL, 45.2 mmol) at 0° C. The reaction mixture stirred under nitrogen overnight. Next day, the reaction was cooled to 0° C. and quenched with saturated $NH_4Cl$ aqueous solution and the product was extracted with DCM. Combined organic phases were dried over anhydrous $Na_2SO_4$ and concentrated under reduced pressure. The crude was purified by silica gel column chromatography using 0-50% EtOAc and hexane as eluent to afford 1-hydroxytridecan-6-one (28) (3.53 g, 75%). $^1H$ NMR (300 MHz, d-chloroform) δ 3.64 (dd, J=11.8, 6.3 Hz, 2H), 2.39 (dd, J=16.3, 7.5 Hz, 4H), 1.66-1.48 (m, 6H), 1.32-1.26 (m, 10H), 0.87 (t, J=6.7 Hz, 3H).

To stirred solution of compound 28 (0.17 g, 0.8 mmol) in acetone (4 mL) was added Jones reagent (i.e., solution of chromium trioxide in aqueous sulfuric acid) at 0° C., until the color remained orange (3 mmol, 1.5 mL). The reaction mixture was allowed to reach room temperature and diluted with EtOAc. Subsequently, the organic layer was washed with $H_2O$ and brine and dried over anhydrous $Na_2SO_4$ and concentrated under reduced pressure to provide compound 29, which was used in next step as a reagent in the synthesis of compound 17i without further purification. $^1$H NMR (300 MHz, d-chloroform) δ 2.50-2.28 (m, 5H), 1.67-1.48 (m, 6H), 1.26 (s, 8H), 0.87 (t, J=6.7 Hz, 3H).

Step 1: Synthesis of Compound 16i

To a solution of compound 33, DCM, EDCI, and DMAP were added and the mixture was stirred for 15 min under nitrogen atmosphere. Then compound 13c was added to the reaction mixture and stirred overnight. Next day, the reaction was diluted with DCM. The organic layer was washed with $H_2O$ and brine and dried over anhydrous $Na_2SO_4$. Solvent was evaporated under vacuo and purified by column chromatography using 0-30% EtOAc in hexane as eluent to afford compound 16i.

Step 2: Synthesis of Compound 17i

To a solution of compound 16i in THF:MeOH (1:1) was added $NaBH_4$ at 0° C. and stirred for 1 h, under nitrogen atmosphere. The reaction was quenched with saturated $NH_4Cl$ aqueous solution and extracted with EtOAc. The organic phase was washed with brine and dried over anhydrous $Na_2SO_4$. Solvent was evaporated under vacuo. and purified by column chromatography using 0-20% EtOAc in hexane as eluent to afford compound 17i.

Step 3: Synthesis of Compound 18c

To a solution of compound 17i and 4-(dimethylamino) butanoic acid in DCM (2 mL), N,N-diisopropylethylamine (DIPEA) was added. Then EDCI and DMAP were added, and the mixture was stirred overnight at room temperature under nitrogen atmosphere. Next day, the reaction was diluted with DCM. The organic layer was washed with sodium bicarbonate ($NaHCO_3$) aqueous solution and dried over anhydrous $Na_2SO_4$. Solvent was evaporated under vacuo and purified by column chromatography using 0-5% MeOH in DCM as eluent to afford compound 18c, which is a lipid of Formula I where R' is absent, $R^1$ and $R^2$ are methyl, n is 3, $R^3$ is $C_4$ alkylene, $R^4$ is $C_7$ alkyl, $R^5$ is $C_3$ alkylene, and $X^1$ and $X^2$ are each independently —C(═O)O—, and where $R^{6a}$ and $R^{6}$b are the same and as defined in Formula I and are equal to $R^{6a}$.

Alternative Synthesis (D)

At least Lipid 14, Lipid 7, and Lipid 8, and any lipid of Formula I where R' is absent, $R^1$ and $R^2$ are methyl, n is 3, $R^3$ is $C_5$ alkylene, $R^4$ is $C_7$ alkyl, $R^5$ is $C_2$ alkylene, and $X^1$ and $X^2$ are each independently —C(═O)O—, and where $R^{6a}$ and $R^{6b}$ are the same or different and as defined in Formula I were or may be prepared using synthesis methods similar to those depicted in Scheme 8 provided below. Minor modifications may be applied to the general synthesis depicted in Scheme 8 to produce other lipids of Formula I, such as but not limited to substitution of compound 2c with compound 2a, substitution of heptylmagnesium bromide with compound 5, and/or substitution of 4-(dimethylamino) butanoic acid with compound 8a.

Scheme 8

Synthesis of compound 25a

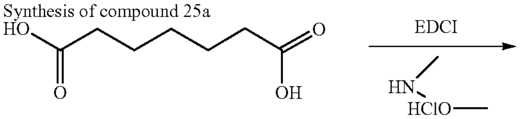

2c

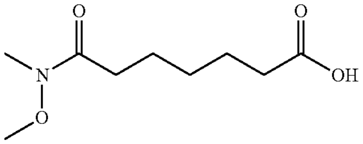

25a

Synthesis of compound 13d

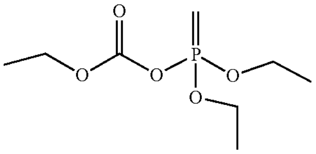

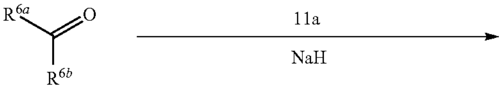

10

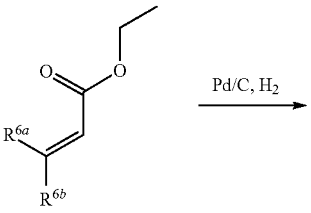

12b

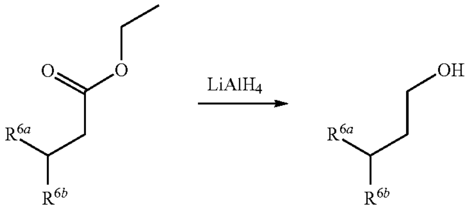

30 13d

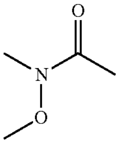

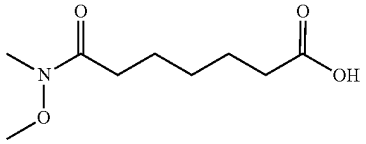

25a

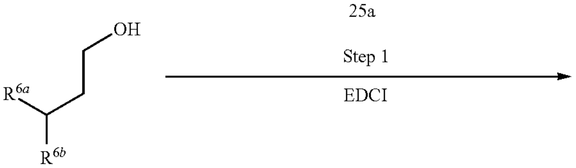

13d

-continued

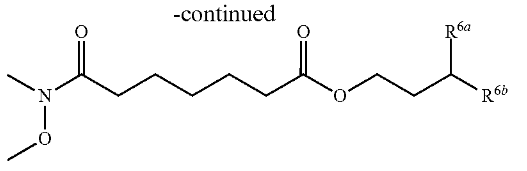

15d

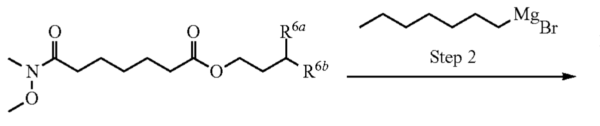

15d

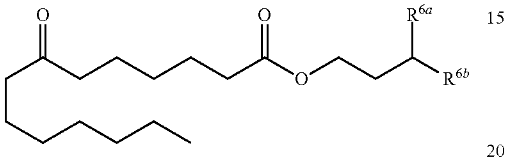

16d

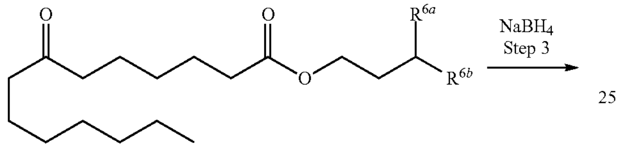

16d

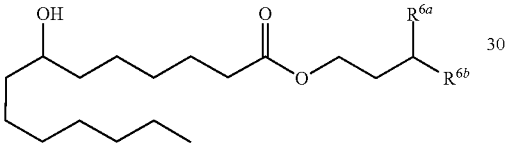

17d

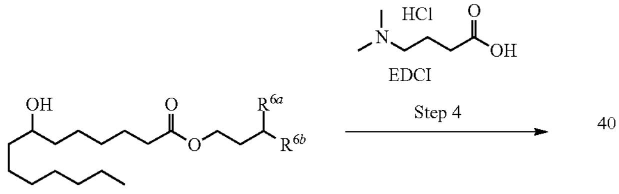

17d

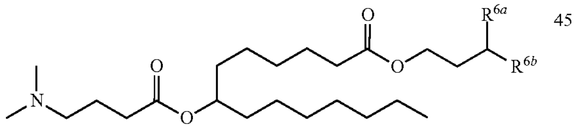

18d

Synthesis of 7-(methoxy(methyl)amino)-7-oxoheptanoic acid (25a)

Pimelic acid 2c (20.0 g, 0.125 mol) was dissolved in dichloromethane/DMF (120 mL/15 mL) followed by the addition of $Et_3N$ (58 mL, 0.50 mol) and N,O-dimethylhydroxylamine hydrochloride (10.1 g, 0.100 mol). The reaction mixture was cooled to 0° C. and EDCI (28.8 g, 0.15 mol) was added followed by the addition of DMAP (6.3 g, 0.050 mol). The ice bath was removed, and the reaction mixture was stirred at room temperature overnight. The light suspension was diluted with water and extracted with dichloromethane. Organic phase was washed with 0.5 M HCl, water, dried over $Na_2SO_4$ and concentrated. The crude was purified by column chromatography and afforded 2.8 g (11% yield) of pure compound 25a and 7.8 g of slightly impure material (with diamide as a byproduct) which was kept aside. $^1H$ NMR (300 MHz, d-chloroform) δ: 3.66 (s, 3H), 3.17 (s, 3H), 2.40-2.30 (m, 4H), 1.70-1.60 (m, 4H), 1.50-1.30 (m, 2H).

Synthesis of Compound 13d

To an ice-cold solution of ketone 10 in THF (anhydrous) was added neat (ethyl carbonic) (diethyl phosphoric) anhydride (11a) dropwise. The reaction was stirred for 30 min followed up by portionwise addition of NaH in oil. The reaction mixture was refluxed for 18 h, cooled to 0° C., quenched with 300 mL of water, and extracted with ether. The organic layer was washed several times with water, brine, dried over $Na_2SO_4$ and concentrated providing 7.5 g of crude material 13d which was used as is for the next step.

Step 1: Synthesis of Compound 15d

Compound 13d and 7-(methoxy(methyl)amino)-7-oxoheptanoic acid (25a) were dissolved in DCM and then DMAP and EDCI were added to this solution at room temperature. After stirring overnight, the reaction was quenched with $NH_4Cl$ (saturated aqueous solution) and extracted with DCM. Organic phase was washed with water, brine, dried over $Na_2SO_4$ and concentrated. Column chromatography purification (hexane-EtOAc) provided title compound 15d.

Step 2: Synthesis of Compound 16d

Compound 15d was co-evaporated several times with toluene and dried overnight over phosphorus pentoxide ($P_2O_5$) prior to the reaction. Dry compound 15d was dissolved in THF in a flame-dried round bottom flask, cooled to 0° C., and heptyl magnesium bromide in ether was added dropwise. The reaction mixture was stirred at room temperature for 3.5 h, then cooled to 0° C., quenched with $NH_4Cl$ (saturated) and extracted with hexanes several times. Organic phase was dried over $Na_2SO_4$, concentrated, and purified by column chromatography (0-10% EtOAc in hexane) providing title compound 16d.

Step 3: Synthesis of Compound 17d

To an ice-cold compound 16d dissolved in THF: MeOH=1:1 was added $NaBH_4$ in one portion. After 5 min the ice bath was removed, and the reaction mixture was stirred at room temperature overnight. After confirming full conversion by thin layer chromatography, the reaction mixture was quenched with $NH_4Cl$ (saturated) and concentrated to dryness. The residue was mixed with $CH_2Cl_2$, washed with water, dried over $Na_2SO_4$, concentrated, and purified by column chromatography (hexanes-EtOAc) providing compound 17d in quantitative yield.

Step 4: Synthesis of Compound 18d 4-(dimethylamino)butanoic acid hydrochloride was dissolved in a $CH_2Cl_2$/DMF mixture followed up addition of $Et_3N$, compound 17d, EDCI and DMAP. The reaction mixture was stirred overnight at room temperature, quenched with $NH_4Cl$ (saturated), and extracted with $CH_2Cl_2$. The organic phase was dried over $Na_2SO_4$, concentrated, and purified by column chromatography (0-15% MeOH in $CH_2Cl_2$) providing compound 18d, which is a lipid of Formula I where R' is absent, $R^1$ and $R^2$ are methyl, n is 3, $R^3$ is $C_5$ alkylene, $R^4$ is $C_7$ alkyl, $R^5$ is $C_2$ alkylene, and $X^1$ and $X^2$ are each independently —C(═O)O—, and where $R^{6a}$ and $R^{6b}$ are the same or different and as defined in Formula I.

Alternative Synthesis (E)

At least Lipid 15, Lipid 9, and Lipid 10, and any lipid of Formula I where R' is absent, $R^1$ and $R^2$ are methyl, n is 3, $R^3$ is $C_6$ alkylene, $R^4$ is $C_7$ alkyl, $R^5$ is $C_1$ alkylene, and $X^1$ and $X^2$ are each independently —C(═O)O—, and where $R^{6a}$ and $R^{6b}$ are the same and as defined in Formula I and are equal to $R^6$ were or may be prepared using similar synthesis methods depicted in Scheme 9 as provided below. Minor modifications may be applied to the general synthesis depicted in Scheme 9 to produce other lipids of Formula I, such as but not limited to substitution of compound 2e with compound 2a, substitution of heptylmagnesium bromide with compound 5, and/or substitution of 4-(dimethylamino) butanoic acid with compound 8a.

Scheme 9

Synthesis of compound 25b

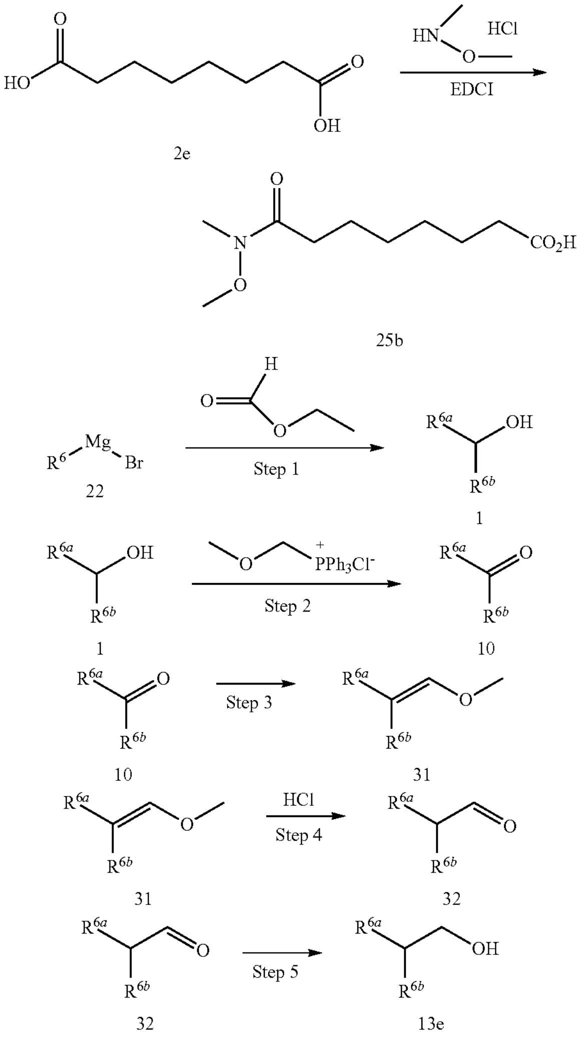

2e, 25b, 22, 1, 1, 10, 10, 31, 31, 32, 32, 13e

-continued

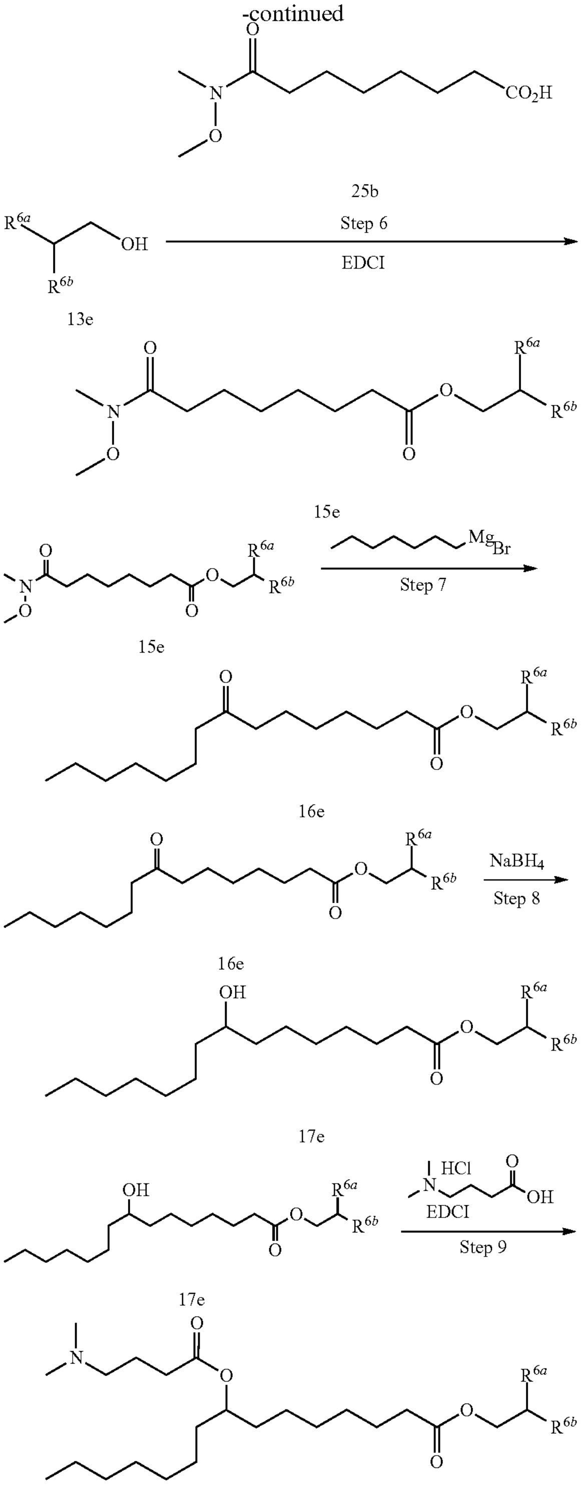

25b, 13e, 15e, 15e, 16e, 16e, 17e, 17e, 18e

Synthesis of 8-(methoxy(methyl)amino)-8-oxooctanoic acid (25b)

Suberic acid 2e (15.06 g, 86.45 mmol) was dissolved in dichloromethane/DMF (60 mL/15 mL) followed by the addition of TEA (18.1 mL, 129.8 mmol) and N,O-dimethylhydroxylamine hydrochloride (4.22 g, 43.26 mol). The reaction mixture was cooled to 0° C. and EDCI (10.36 g, 54.07 mol) was added followed by the addition of DMAP (2.64 g, 21.63 mol). The ice bath was removed, and the reaction mixture was stirred at room temperature overnight. The light suspension was diluted with water and extracted with dichloromethane. Organic phase was washed with 0.5 M HCl, water, dried over $Na_2SO_4$ and concentrated. The crude was purified by column chromatography and afforded 2.4 g (26% yield) of pure compound 25b. $^1H$ NMR (300 MHz, d-chloroform) δ: 3.67 (s, 3H), 3.17 (s, 3H), 2.42-2.30 (m, 4H), 1.70-1.60 (m, 4H), 1.40-1.30 (m, 4H).

Step 1: Synthesis of Compound 1

To an ice cold 0.5M/THF solution of alkyl magnesium bromide (22) in THF was added ethylformate in THF. After stirring overnight at room temperature, the reaction was quenched with −60 mL $NH_4Cl$ (saturated aqueous solution) and extracted with either. Organic phase was washed with brine, dried over $Na_2SO_4$ and concentrated. The crude was purified by recrystallization from dichloromethane-hexanes providing 2.82 g (82% yield) of pure compound 1.

Step 2: Synthesis of Compound 10

Alcohol 1 was mixed with 18 mL of dichloromethane, cooled to 0° C. and Dess-Martin periodinane was added to it in one portion. The reaction mixture was stirring at room temperature overnight, then cooled to 0° C. and quenched with 1:1 mixture of $NaHCO_3$ (saturated) and $Na_2S_2O_3$ (15% aq) (25:25 mL) and stirred at room temperature for 20 min. Layers were separated, the organic layer was washed with water, brine, dried over $Na_2SO_4$ and concentrated providing the crude compound 10 which was used for the next step without purification.

Step 3: Synthesis of Compound 31

To a suspension containing ketone 10 and methoxymethyl)triphenyl phosphonium chloride in THF was added 1 M solution of KOtBu in THF dropwise over 15 min. The reaction mixture was stirred overnight at room temperature, diluted with $Et_2O$ and washed with water, brine, dried over $Na_2SO_4$ and concentrated. The crude material was purified by column chromatography (0-2% EtOAc in hexanes) providing compound 31.

Step 4: Synthesis of Compound 32

To an ice cold cloudy solution of ketal 31 in dioxane/water was added 4 N HCl in dioxane dropwise, over 30 min. The reaction mixture was stirring at room temperature for 48 h. After confirming full conversion by thin layer chromatography, the reaction mixture was diluted with ether, cooled to 0° C. and quenched by slow addition of $NaHCO_3$ (saturated) and 10% $Na_2CO_3$. The layers were separated, and organic layer was washed with brine, dried over $Na_2SO_4$ and concentrated. The crude material was purified by column chromatography (0-5% EtOAc in hexanes) providing compound 32 in quantitative yield.

Step 5: Synthesis of Compound 13e

To an ice-cold compound 32 dissolved in THF: MeOH=1:1 was added $NaBH_4$ in one portion. The reaction mixture was stirred overnight at room temperature, then quenched with $NH_4Cl$ (saturated) at 0° C. and concentrated to dryness. The residue was mixed with $CH_2Cl_2$, washed with water, dried over $Na_2SO_4$, concentrated, and purified by column chromatography (hexanes-EtOAc) providing compound 13e in quantitative yield.

Step 6: Synthesis of Compound 15e

Compound 25b and 13e were dissolved in dichloromethane and then DMAP and EDCI were added to this solution at room temperature. After stirring overnight, the reaction was quenched with $NH_4Cl$ (saturated aqueous solution) and extracted with dichloromethane. Organic phase was washed with water, brine, dried over $Na_2SO_4$ and concentrated. Column chromatography purification (Hexane-EtOAc) provided pure compound 15e.

Step 7: Synthesis of Compound 16e

Compound 15e was co-evaporated several times with toluene and dried overnight over $P_2O_5$ prior to the reaction. Dry compound 15e was dissolved in THF in a flame-dried round bottom flask cooled to 0° C., and heptyl magnesium bromide (1 M in ether) was added dropwise. The reaction mixture was stirred at room temperature for 3.5 h, then cooled to 0° C., quenched with $NH_4Cl$ (saturated) and extracted with hexanes several times. Organic phase was dried over $Na_2SO_4$, concentrated, and purified by column chromatography (0-10% EtOAc in hexanes) providing compound 16e.

Step 8: Synthesis of Compound 17e

To an ice-cold compound 16e dissolved in THF: MeOH=1:1 was added $NaBH_4$ in one portion. The reaction mixture was stirred at room temperature for about 2 h until full conversion was confirmed by thin layer chromatography, and then quenched with 2 ml of $NH_4Cl$ (sat) and concentrated to dryness. The residue was mixed with $CH_2Cl_2$, washed with water, dried over $Na_2SO_4$, concentrated, and purified by column chromatography (hexanes-EtOAc) providing compound 17e.

Step 9: Synthesis of Compound 18e 4-(dimethylamino)butanoic acid hydrochloride was dissolved in a $CH_2Cl_2$/DMF mixture followed up addition of TEA, compound 17e, EDCI and DMAP. The reaction mixture was stirred overnight at room temperature, quenched with $NH_4Cl$ (saturated), and extracted with $CH_2Cl_2$. The organic phase was dried over $Na_2SO_4$, concentrated, and purified by column chromatography (0-15% MeOH in DCM) providing compound 18e, which is a lipid of Formula I where R' is absent, $R^1$ and $R^2$ are methyl, n is 3, $R^3$ is $C_6$ alkylene, $R^4$ is $C_7$ alkyl, $R^5$ is $C_1$ alkylene, and $X^1$ and $X^2$ are each independently —C(═O)O—, and where $R^{6a}$ and R b are the same and as defined in Formula I and are equal to $R^6$.

Example 3: Synthesis of Lipid 20, Lipid 21, Lipid 19 Lipid 22, and Lipid 11

Procedures for synthesizing Lipid 20, Lipid 21, Lipid 19, Lipid 22, and Lipid 11 are described below with reference to Scheme 10, provided below.

Scheme 10
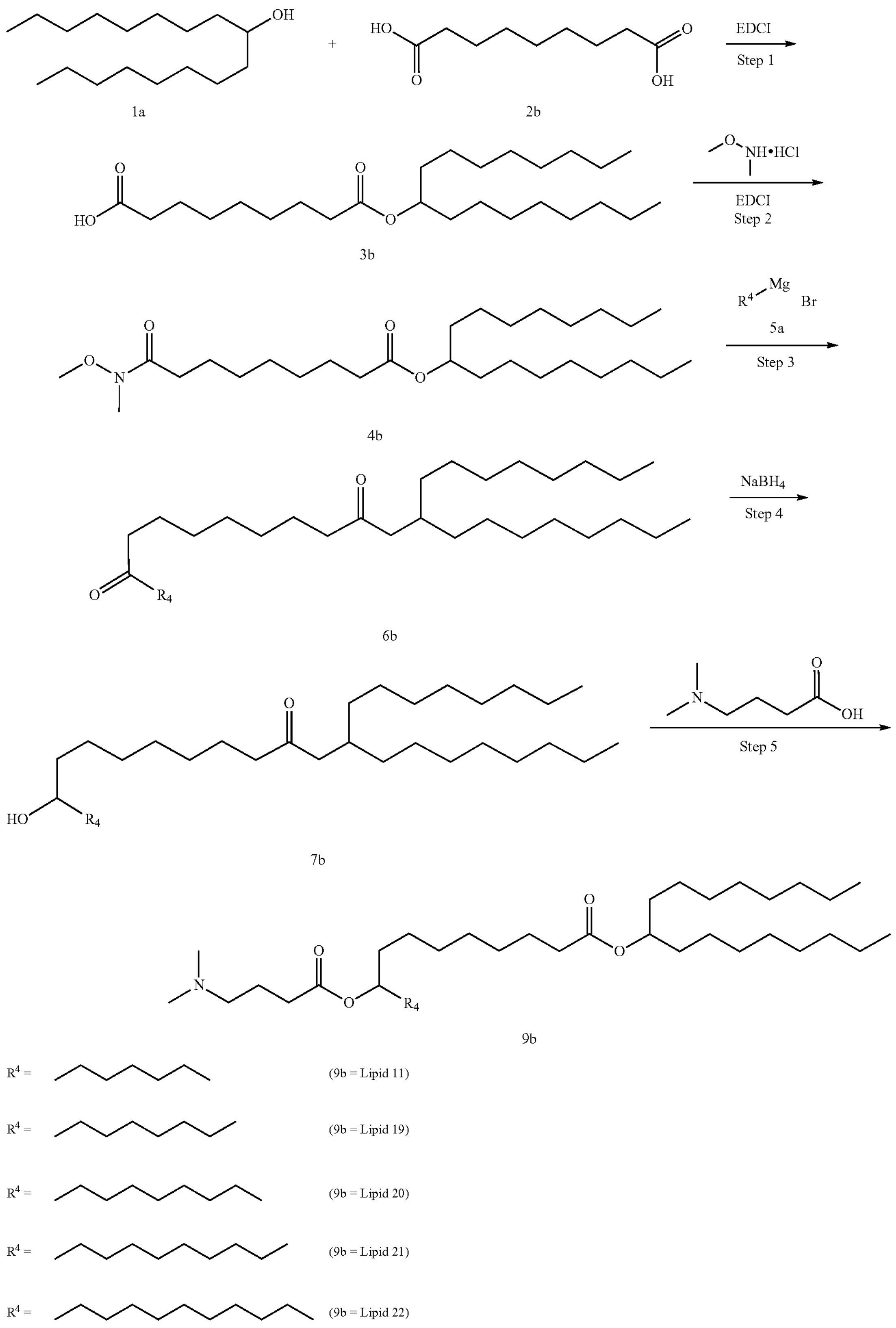
1a
2b
3b
4b
6b
7b
9b
(9b = Lipid 11)
(9b = Lipid 19)
(9b = Lipid 20)
(9b = Lipid 21)
(9b = Lipid 22)

Step 1: Synthesis of 9-(heptadecan-9-yloxy)-9-oxononanoic acid (3b)

To a stirred solution of nonanedioic acid (2b, also called azelaic acid) (7.34 g, 39 mmol) and heptadecan-9-ol (1a) (5 g, 19 mmol) in DCM (1000 ml) was added DMAP (2.37 g, 19 mmol) followed by EDCI (3 g, 19 mmol). The resulting mixture was stirred at room temperature overnight, then washed with 250 ml 1 N HCl and 250 ml water. The organic layer was dried over $MgSO_4$, evaporated to dryness, and purified by silica gel column chromatography using 0-10% methanol in DCM as eluent. The fractions containing the desired compound were pooled and evaporated to afford 3b (6.2 g, 75%) as a white solid. $^1$H-NMR (300 MHz, d-chloroform): δ 4.80-4.90 (m, 1H), 2.25-2.34 (m, 4H), 1.55-1.70 (m, 4H), 1.40-1.50 (m, 4H), 1.20-1.40 (m, 30H), 0.84-0.90 (t, 3H).

Step 2: Synthesis of heptadecan-9-yl 9-(methoxy(methyl)amino)-9-oxononanoate (4b)

To a solution of compound 3 (5.4 g, 12.7 mmol) in DCM (60 mL), EDCI (3.6 g, 19.7 mmol), and TEA (3.5 mL, 25.4 mmol) were added, and the mixture was stirred for 15 min at room temperature. Then N,O-dimethylhydroxylamine hydrochloride (1.36 g, 13.97 mmol) and DMAP (0.15 g, 1.27 mmol) were added and stirred overnight at room temperature. Next 20 day, the reaction was quenched with $NH_4Cl$ (aq) and diluted with DCM. The organic layer was washed with $NH_4Cl$ and brine and dried over anhydrous $Na_2SO_4$. Solvent was evaporated under vacuo. The product 4b was used in next step without further purification. $^1$H NMR (300 MHz, d-chloroform) δ 4.85 (t, J=6.2 Hz, 1H), 3.67 (s, 3H), 3.58 (s, 2H), 3.17 (s, 3H), 2.40 (t, J=7.6 Hz, 2H), 2.27 (t, J=7.5 Hz, 2H), 1.63 (dd, J=14.8, 5.5 Hz, 6H), 1.49 (d, J=5.4 Hz, 4H), 1.37-1.19 (m, 32H), 0.86 (d, J=6.8 Hz, 6H).

Step 3: Synthesis of heptadecan-9-yl 9-oxohexadecanoate (6b where $R^4$ is $C_7$ alkyl), heptadecan-9-yl 9-oxoheptadecanoate (6b where $R^4$ is $C_8$ alkyl), heptadecan-9-yl 9-oxooctadecanoate (6b where $R^4$ is $C_9$ alkyl), heptadecan-9-yl 9-oxononadecanoate (6b where $R^4$ is $C_{10}$ alkyl), or heptadecan-9-yl 9-oxoicosanoate (6b where $R^4$ is $C_7$ alkyl)

Heptadecan-9-yl 9-oxohexadecanoate (6b where $R^4$ is $C_7$ alkyl)

Compound 4b (1.0 g, 2.13 mmol) was dissolved in 10 ml of anhydrous THF. Then, 1 M heptyl magnesium bromide solution (Compound 5a where $R^4$ is $C_7$ alkyl) in $Et_2O$ (3.2 ml, 3.2 mmol) was added dropwise at 0° C. The resulting mixture was stirred at room temperature for 16 h under $N_2$. The reaction was quenched with saturated $NH_4Cl$ solution and extracted with ether. The organic layer was washed with brine and dried over anhydrous $Na_2SO_4$. Solvent was evaporated under vacuo and purified by column chromatography using 0-10% EtOAc in hexane as eluent to afford 6b where $R^4$ is $C_7$ alkyl (0.3 g, 30%). $^1$H NMR (300 MHz, d-chloroform) δ 4.85 (t, J=6.2 Hz, 1H), 2.37 (t, J=7.4 Hz, 4H), 2.27 (t, J=7.5 Hz, 2H), 1.64-1.43 (m, 12H), 1.27 (s, 36), 0.87 (t, J=6.7 Hz, 9H).

Heptadecan-9-yl 9-oxoheptadecanoate (6b where $R^4$ is $C_8$ alkyl)

Compound 4b (1.0 g, 2.13 mmol) was dissolved in 10 ml of anhydrous THF. Then 1 M octyl magnesium bromide solution (Compound 5 where $R^4$ is $C_8$ alkyl) in $Et_2O$ (1.6 ml, 3.2 mmol) was added dropwise at 0° C. The resulting mixture was stirred at room temperature for 16 h under $N_2$. The reaction was quenched with saturated $NH_4Cl$ solution and extracted with ether. The organic layer was washed with brine and dried over anhydrous $Na_2SO_4$. Solvent was evaporated under vacuo and purified by column chromatography using 0-10% EtOAc in hexane as eluent to afford 6b where $R^4$ is $C_8$ alkyl (0.41 g, 40%). $^1$H NMR (300 MHz, d-chloroform) δ 4.85 (t, J=6.2 Hz, 1H), 2.37 (t, J=7.4 Hz, 4H), 2.26 (t, J=7.5 Hz, 2H), 1.65-1.38 (m, 8H), 1.33-1.18 (m, 42H), 0.87 (t, J=6.5 Hz, 9H).

Heptadecan-9-yl 9-oxooctadecanoate (6b where $R^4$ is $C_9$ alkyl)

Compound 4b (1.1 g, 2.3 mmol) was dissolved in 20 ml of anhydrous THF. Then 1 M nonyl magnesium bromide solution (Compound 5 where $R^4$ is $C_9$ alkyl) in $Et_2O$ (6.13 ml, 3.2 mmol) was added dropwise at 0° C. The resulting mixture was allowed to reach room temperature over 2 h. The reaction was quenched with saturated $NH_4Cl$ solution and extracted with ether. The organic layer was washed with brine and dried over anhydrous $Na_2SO_4$. Solvent was evaporated under vacuo and purified by column chromatography using 0-30% EtOAc in hexane as eluent to afford 6b where $R^4$ is $C_9$ alkyl (1.2 g, 96%). $^1$H NMR (300 MHz, d-chloroform) δ 4.85 (t, J=6.2 Hz, 1H), 2.37 (t, J=7.4 Hz, 4H), 2.26 (t, J=7.5 Hz, 2H), 1.65-1.38 (m, 8H), 1.33-1.18 (m, 44H), 0.87 (t, J=6.5 Hz, 9H).

Heptadecan-9-yl 9-oxononadecanoate (6b where $R^4$ is $C_{10}$ alkyl)

Compound 4b (0.3 g, 0.64 mmol) was dissolved in 2 ml of anhydrous THF. Then 1M decyl magnesium bromide solution (Compound 5 where $R^4$ is $C_{10}$ alkyl) in $Et_2O$ (1.28 ml, 0.77 mmol) was added dropwise at 0° C. The resulting mixture was allowed to reach room temperature over 2 h. The reaction was quenched with saturated $NH_4Cl$ solution and extracted with hexane. The organic layer was washed with brine and dried over anhydrous $Na_2SO_4$. Solvent was evaporated under vacuo and purified by column chromatography using 0-10% EtOAc in hexane as eluent to afford 6b where $R^4$ is $C_{10}$ alkyl (0.2 g, 47%).

Heptadecan-9-yl 9-oxoicosanoate (6b where $R^4$ is $C_{11}$ alkyl)

To a solution of 1-bromoundecane (0.47 g, 2 mmol) and in 2 mL of anhydrous ether, was added Mg (0.072 g, 3 mmol) and 1 drop of 1,2-dibromoethane. The resulting mixture was stirred for 1 h and filtered and dried. The product undecylmagnesium bromide (Compound 5 where $R^4$ is $C_{11}$ alkyl) was used in next step without further purification.

Compound 4b (0.47 g, 1 mmol) was dissolved in 3 ml of anhydrous THF. Then undecylmagnesium bromide solution in THF (1.1 ml, 1 mmol) was added dropwise at 0° C. The resulting mixture was allowed to reach room temperature over 2 h. The reaction was quenched with saturated $NH_4Cl$ solution and extracted with hexane. The organic layer was washed with brine and dried over anhydrous $Na_2SO_4$. Solvent was evaporated under vacuo and purified by column chromatography using 0-10% EtOAc in hexane as eluent to afford (Compound 5 where $R^4$ is $C_{11}$ alkyl (0.27 g, 48%). $^1$H NMR (300 MHz, d-chloroform) δ 4.86 (t, J=6.2 Hz, 1H), 2.37 (t, J=7.4 Hz, 4H), 2.27 (t, J=7.5 Hz, 2H), 1.70-1.45 (m, 8H), 1.29-1.25 (m, 48H), 0.87 (t, J=6.6 Hz, 9H).

Step 4: Synthesis of heptadecan-9-yl 9-hydroxyhexadecanoate (7b where $R^4$ is $C_7$ alkyl), heptadecan-9-yl 9-hydroxyheptadecanoate (7b where $R^4$ is $C_8$ alkyl), heptadecan-9-yl 9-hydroxyoctadecanoate (7b where $R^4$ is $C_9$ alkyl), heptadecan-9-yl 9-hydroxynonadecanoate (7b where $R^4$ is $C_{10}$ alkyl), or heptadecan-9-yl 9-hydroxyicosanoate (7b where $R^4$ is $C_{11}$ alkyl)

Heptadecan-9-yl 9-hydroxyhexadecanoate (7b where $R^4$ is $C_7$ alkyl)

To a solution of heptadecan-9-yl 9-oxohexadecanoate (6b where $R^4$ is $C_7$ alkyl) (0.3 g, 0.6 mmol) in 10 mL of anhydrous THF was added $NaBH_4$ (0.09 g, 2.4 mmol) at 0° C. and stirred overnight under $N_2$ atmosphere. The reaction was quenched with saturated $NH_4Cl$ solution and extracted with EtOAc. The organic phase was washed with brine and dried over anhydrous $Na_2SO_4$. Solvent was evaporated under vacuo and purified by column chromatography using 0-10% EtOAc in hexane as eluent to afford 7b where $R^4$ is $C_7$ alkyl (0.25 g, 82%). $^1$H NMR (300 MHz, d-chloroform) δ 4.92-4.78 (m, 1H), 3.57 (m, 1H), 2.27 (t, J=7.5 Hz, 2H), 1.66-1.36 (m, 12H), 1.31-1.25 (m, 40H), 0.87 (t, J=6.1 Hz, 9H).

Heptadecan-9-yl 9-hydroxyheptadecanoate (7b where $R^4$ is $C_8$ alkyl)

To a solution of heptadecan-9-yl 9-oxoheptadecanoate (6b where $R^4$ is $C_8$ alkyl) (0.4 g, 0.77 mmol) in 10 mL of anhydrous THF was added $NaBH_4$ (0.04 g, 1.15 mmol) at 0° C. and stirred overnight under $N_2$ atmosphere. The reaction was quenched with saturated $NH_4Cl$ solution and extracted with EtOAc. The organic phase was washed with brine and dried over anhydrous $Na_2SO_4$. Solvent was evaporated under vacuo and purified by column chromatography using 0-10% EtOAc in hexane as eluent to afford 7b where $R^4$ is $C_8$ alkyl (0.21 g, 52%). $^1$H NMR (300 MHz, d-chloroform) δ 4.92-4.80 (m, 1H), 3.57 (m, 1H), 2.27 (t, J=7.5 Hz, 2H), 1.64-1.40 (m, 12H), 1.36-1.18 (m, 42H), 0.87 (t, J=6.5 Hz, 9H).

Heptadecan-9-yl 9-hydroxyoctadecanoate (7b where $R^4$ is $C_9$ alkyl)

To a solution of heptadecan-9-yl 9-oxooctadecanoate (6b where $R^4$ is $C_9$ alkyl) (1.1 g, 2.05 mmol) in 40 mL of DCM:MeOH (1:1) mixture was added $NaBH_4$ (0.3 g, 8 mmol) at 0° C. and stirred for 2 h under $N_2$ atmosphere. The reaction was quenched with 1 M HCl (aq) solution and extracted with DCM. The organic phase was washed with brine and dried over anhydrous $Na_2SO_4$. Solvent was evaporated under vacuo and purified by column chromatography using 5-40% EtOAc in hexane as eluent to afford 7b where $R^4$ is $C_9$ alkyl (0.9 g, 83%). $^1$H NMR (300 MHz, d-chloroform) δ 4.88-4.83 (m, 1H), 3.57 (m, 1H), 2.27 (t, J=7.5 Hz, 2H), 1.61 (t, J=7.5 Hz, 2H), 1.48-1.41 (m, 8H), 1.36-1.18 (m, 44H), 0.87 (t, J=6.5 Hz, 9H).

Heptadecan-9-yl 9-hydroxynonadecanoate (7b where $R^4$ is $C_{10}$ alkyl)

To a solution of heptadecan-9-yl 9-oxononadecanoate (6b where $R^4$ is $C_{10}$ alkyl) (0.2 g, 0.36 mmol) in 3 mL of THF:DCM:MeOH (1:1:1) mixture was added $NaBH_4$ (0.03 g, 0.8 mmol) at 0° C. and stirred for 3 h under $N_2$ atmosphere. The reaction was quenched with 0.5 mL of $H_2O$ and extracted with DCM. The organic phase was washed with brine and dried over anhydrous $MgSO_4$. Solvent was evaporated under vacuo and purified by column chromatography using 5-40% EtOAc in hexane as eluent to afford 7b where $R^4$ is $C_{10}$ alkyl (0.16 g, 80%). $^1$H NMR (300 MHz, d-chloroform) δ 4.86 (t, J=6.2 Hz, 1H), 3.58 (m, 1H), 2.27 (t, J=7.5 Hz, 2H), 1.61-1.37 (m, 12H), 1.32-1.18 (m, 46H), 0.87 (t, J=6.6 Hz, 9H).

Heptadecan-9-yl 9-hydroxyicosanoate (7b where $R^4$ is $C_{11}$ alkyl)

To a solution of heptadecan-9-yl 9-oxoicosanoate (6b where $R^4$ is $C_{11}$ alkyl) (0.27 g, 0.48 mmol) in 3 mL of THF:DCM:MeOH (1:1:1) mixture was added $NaBH_4$ (0.05 g, 1.35 mmol) at 0° C. and stirred for 3 h under $N_2$ atmosphere. The reaction was quenched with 0.5 mL of $H_2O$ and extracted with DCM. The organic phase was washed with brine and dried over anhydrous $MgSO_4$. Solvent was evaporated under vacuo and purified by column chromatography using 5-40% EtOAc in hexane as eluent to afford 7b where $R^4$ is $C_{11}$ alkyl (0.25 g, 92%). $^1$H NMR (301 MHz, d-chloroform) δ 4.86 (t, J=6.2 Hz, 1H), 3.57 (s, 1H), 2.27 (t, J=7.5 Hz, 2H), 1.69-1.37 (m, 12H), 1.29-1.17 (m, 48H), 0.87 (t, J=6.5 Hz, 9H).

Step 5: Synthesis of heptadecan-9-yl 9-((4-(dimethylamino)butanoyl)oxy)hexadecanoate (Lipid 11), heptadecan-9-yl 9-((4-(dimethylamino)butanoyl)oxy)heptadecanoate (Lipid 19), heptadecan-9-yl 9-((4-(dimethylamino)butanoyl)oxy)octadecenoate (Lipid 20), heptadecan-9-yl 9-((4-(dimethylamino)butanoyl)oxy)nonadecanoate (Lipid 21), or heptadecan-9-yl 9-((4-(dimethylamino)butanoyl)oxy)icosanoate (Lipid 22)

Heptadecan-9-yl 9-((4-(dimethylamino)butanoyl)oxy)hexadecanoate (Lipid 11)

To a solution of heptadecan-9-yl 9-hydroxyhexadecanoate (7b where $R^4$ is $C_7$ alkyl) (0.25 g, 0.49 mmol) and 4-(dimethylamino)butanoic acid (0.125 g, 0.75 mmol) in DCM (5 mL), 0.27 mL of DIPEA was added. Then EDCI (0.143 g, 0.75 mmol), and DMAP (0.012 g, 0.1 mmol) were added, and the mixture was stirred overnight at room temperature under $N_2$ atmosphere. Next day, the reaction was diluted with DCM. The organic layer was washed with $NaHCO_3$ (aq) and dried over anhydrous $Na_2SO_4$. Solvent was evaporated under vacuo and purified by column chromatography using 0-5% MeOH in DCM as eluent to afford Lipid 11 (0.14 g, 45%). $^1$H NMR (300 MHz, d-chloroform) δ 4.93-4.77 (m, 2H), 2.37-2.23 (m, 5H), 2.21 (s, 6H), 1.83-1.73 (m, 2H), 1.70-1.40 (m, 10H), 1.25 (s, 43H), 0.87 (t, J=6.6 Hz, 9H). MS found 624.5 $[M+H]^+$, calcd 623.59 for $[C_{39}H_{77}NO_4]$.

Heptadecan-9-yl 9-((4-(dimethylamino)butanoyl)oxy)heptadecanoate (Lipid 19)

To a solution of compound heptadecan-9-yl 9-hydroxyheptadecanoate (7b where $R^4$ is $C_8$ alkyl) (0.21 g, 0.4 mmol) and 4-(dimethylamino)butanoic acid (0.08 g, 0.45 mmol) in DCM (3 mL), 0.16 mL of DIPEA was added. Then EDCI (0.09 g, 0.45 mmol), and DMAP (0.008 g, 0.06 mmol) were added, and the mixture was stirred overnight at room temperature under $N_2$ atmosphere. Next day, the reaction was diluted with DCM. The organic layer was washed with $NaHCO_3$ (aq) and dried over anhydrous $Na_2SO_4$. The solvent was evaporated under vacuo and purified by column chromatography using 0-5% MeOH in DCM as eluent to afford Lipid 19 (0.112 g, 44%). $^1H$ NMR (300 MHz, d-chloroform) δ 4.86 (m, 2H), 2.34-2.24 (m, 5H), 2.21 (s, 6H), 1.78 (p, J=7.6 Hz, 2H), 1.68-1.56 (m, 2H), 1.54-1.40 (m, 8H), 1.25 (s, 45H), 0.87 (t, J=6.7 Hz, 9H). MS found 638.5 $[M+H]^+$, calcd 637.60 for $[C_{40}H_{79}NO_4]$.

Heptadecan-9-yl 9-((4-(dimethylamino)butanoyl)oxy)octadecenoate (Lipid 20)

To a solution of heptadecan-9-yl 9-hydroxyoctadecanoate (7b where $R^4$ is $C_9$ alkyl) (0.3 g, 0.56 mmol) in DCM (25 mL) and, EDCI (0.21 g, 1.12 mmol) and DMAP (0.07 g, 0.56 mmol) were added and stirred for 15 min under $N_2$ atmosphere. Then, 4-(dimethylamino)butanoic acid (0.25 g, 1.5 mmol) was added to the reaction mixture and stirred overnight. Next day, the solvent was evaporated and redissolved in EtOAc (300 mL). The organic layer was washed with $H_2O$ (300 mL), $NaHCO_3$ (aq) (200 mL) and brine (200 mL) and dried over anhydrous $Na_2SO_4$. The solvent was evaporated under vacuo and purified by column chromatography using 5-40% EtOAc in hexane as eluent to afford Lipid 20 (0.124 g, 34%). $^1H$ NMR (300 MHz, d-chloroform) δ 4.86 (m, 2H), 2.38-2.23 (m, 6H), 2.21 (s, 6H), 1.85-1.71 (m, 2H), 1.67-1.55 (m, 2H), 1.50-1.44 (m, 8H), 1.24 (s, 46H), 0.86 (t, J=6.5 Hz, 9H). MS found 652.7 $[M+H]^+$, calcd 651.62 for $[C_{41}H_{81}NO_4]$.

Heptadecan-9-yl 9-((4-(dimethylamino)butanoyl)oxy)nonadecanoate (Lipid 21)

To a solution of heptadecan-9-yl 9-hydroxynonadecanoate (7b where $R^4$ is $C_{10}$ alkyl) (0.16 g, 0.29 mmol) in 1 mL DCM, EDCI (0.052 g, 0.27 mmol), and DMAP (0.04 g, 0.0.33 mmol) were added and stirred for 15 min under $N_2$ atmosphere. Then, 4-(dimethylamino)butanoic acid (0.056 g, 0.33 mmol) was added to the reaction mixture and stirred overnight. Next day, the reaction was diluted with DCM. The organic layer was washed with $NaHCO_3$ (aq) and dried over anhydrous $MgSO_4$. The solvent was evaporated under vacuo and purified by column chromatography using 0-5% MeOH in DCM as eluent to afford Lipid 21 (0.07 g, 36%). $^1H$ NMR (300 MHz, d-chloroform) δ 4.93-4.81 (m, 2H), 2.34-2.24 (m, 5H), 2.22 (s, 6H), 1.85-1.67 (m, 4H), 1.63-1.57 (m, 2H), 1.48 (s, 7H), 1.24 (s, 47H), 0.87 (t, J=6.6 Hz, 9H). MS found 665.63 $[M+H]^+$, calcd 666.5 for $[C_{42}H_{83}NO_4]$.

Heptadecan-9-yl 9-((4-(dimethylamino)butanoyl)oxy)icosanoate (Lipid 22)

To a solution of compound heptadecan-9-yl 9-hydroxyicosanoate (7b where $R^4$ is $C_{11}$ alkyl) (0.25 g, 0.44 mmol) in DCM (1 mL) and, EDCI (0.068 g, 0.36 mmol), and DMAP (0.054 g, 0.0.44 mmol) were added and stirred for 15 min under $N_2$ atmosphere. Then 4-(dimethylamino)butanoic acid (0.074 g, 0.44 mmol) was added to the reaction mixture and stirred overnight. Next day, the reaction was diluted with DCM. The organic layer was washed with $NaHCO_3$ (aq) and dried over anhydrous $MgSO_4$. The solvent was evaporated under vacuo and purified by column chromatography using 0-5% MeOH in DCM as eluent to afford Lipid 22 (0.134 g, 45%). $^1H$ NMR (300 MHz, d-chloroform) δ 4.87-4.81 (m, 2H), 2.34-2.24 (m, 5H), 2.23 (d, J=7.2 Hz, 6H), 1.87-1.76 (m, 2H), 1.74-1.70 (m, 2H), 1.65-1.57 (m, 2H), 1.48 (s, 7H), 1.24 (s, 50H), 0.87 (t, J=6.6 Hz, 9H). MS found 680.6 $[M+H]^+$, calcd 679.65 for $[C_{43}H_{85}NO_4]$.

Example 4: Synthesis of Lipid 23

Procedures for synthesizing Lipid 23 are described below with reference to Scheme 11, also provided below.

Scheme 11

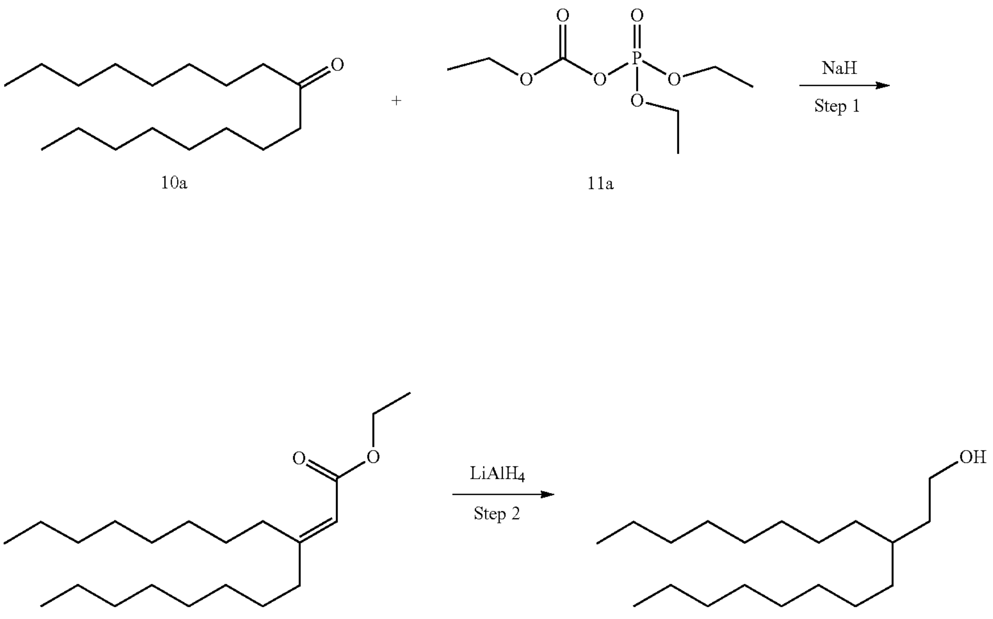

10a

11a

12a

13a

-continued
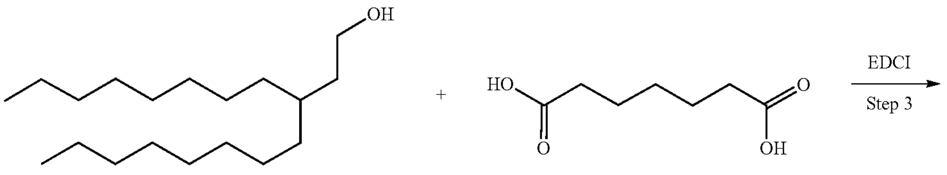
13a 2c
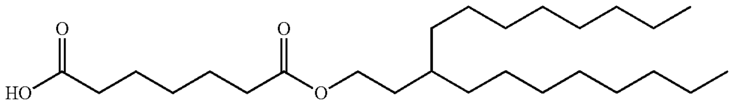
14b
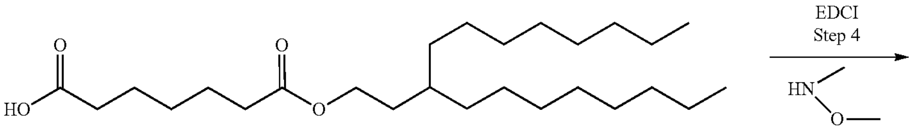
14b
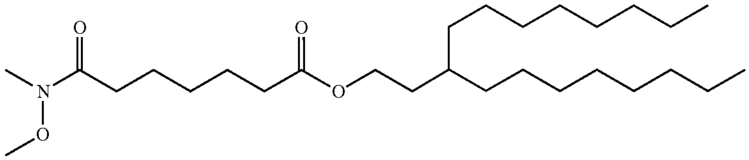
15b
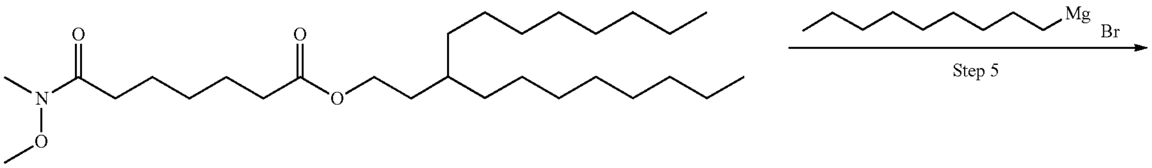
15b
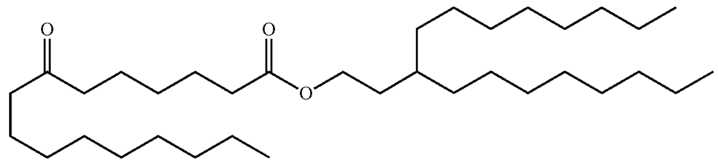
16b
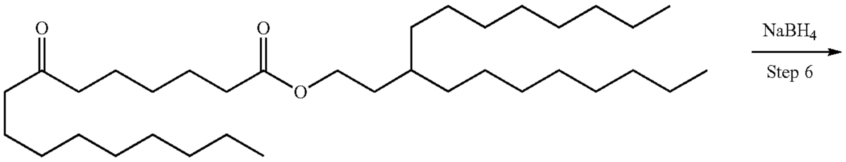
16b
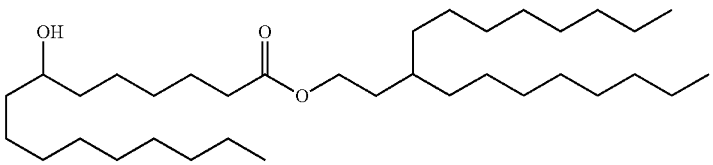
17b -continued

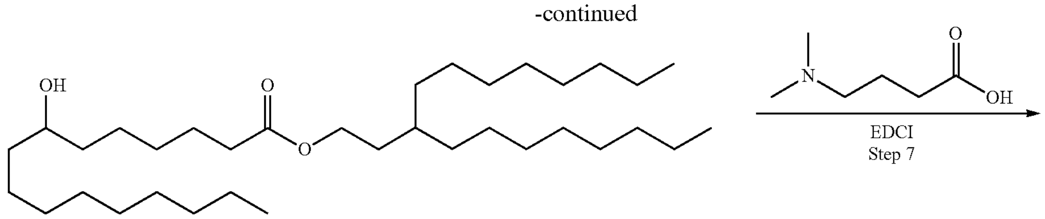

17b

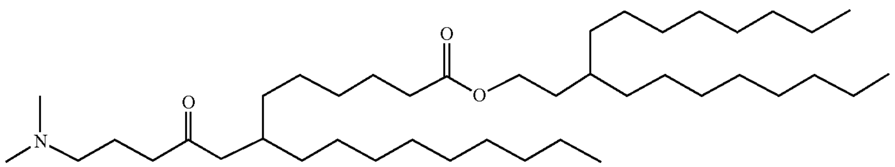

Lipid 23

Step 1 and Step 2: Synthesis of 3-octylundecan-1-ol (13a)

To an ice-cold solution of 3 g (11.8 mmol) of heptadecan-9-one (10a) in 120 ml of THF, 18 ml of (ethyl carbonic) (diethyl phosphoric) anhydride (11a) was added dropwise. The reaction was stirred for 30 min and then 3.2 g (80 mmol) of NaH were added. The reaction mixture refluxed for 18 h. The crude was quenched with water and extracted with ether to give 2. One gram of ethyl 3-octylundec-2-enoate (12a) in 5 ml of THF was reacted with 1 ml of $LiAlH_4$ (2 M solution). After 48 h, the crude was quenched with water and extracted with ether to give 0.6 g of 3-octylundecan-1-ol (13). $^1$H-NMR (300 MHz, d-chloroform): δ 0.86 (t, 6H), 1.20-1.40 (m, 27H), 1.50-1.60 (m, 2H), 1.81-1.87 (m, 1H), 1.88-2.00 (m, 1H), 3.50-3.68 (m, 2H), 3.70-3.77 (m, 1H).

Step 3: Synthesis of 7-((3-octylundecyl)oxy)-7-oxoheptanoic acid (14b)

0.6 g (2.1 mmol) of 3-octylundecan-1-ol (13) was dissolved in 30 ml of methylene chloride followed by 0.9 g (4.3 mmol) of pimelic acid. To this mixture 0.87 g (4.3 mmol) of 1-ethyl-3-(3-dimethylaminopropyl)carbodiimide (EDCI) was added followed by 0.69 g (4.3 mmol) of 4-dimethylaminopyridine (DMAP). The reaction was allowed to stir overnight. The reaction was quenched using aqueous 1 N HCl and purified in silica gel column to give 0.45 g (50% yield) of 7-((3-octylundecyl)oxy)-7-oxoheptanoic acid (14b). $^1$H-NMR (300 MHz, d-chloroform): δ 0.87 (t, 6H), 1.20-1.55 (m, 27H), 1.56-1.75 (m, 5H), 2.30 (dd, 2H), 2.36 (dd, 2H), 4.07 (dd, 2H).

Step 4: Synthesis of 3-octylundecyl 7-(methoxy(methyl)amino)-7-oxoheptanoate (15b)

To a solution of 0.45 g (1.1 mmol) of 7-((3-octylundecyl)oxy)-7-oxoheptanoic acid (14) in 10 ml of dichloromethane 0.25 g (1.6 mmol) of 1-ethyl-3-(3-dimethylaminopropyl)carbodiimide (EDCI) was added, followed by 0.16 g (1.6 mmol) N,O-dimethylhydroxylamine hydrochloride, 0.16 g (1.6 mmol) triethylamine and at last, 0.19 g (1.6 mmol) of 4-dimethylaminopyridine (DMAP). The reaction mixture was allowed to stir overnight and was then quenched with 1 N HCl solution. The organic phase was dried over magnesium sulfate to give 0.45 g (90% yield) of 3-octylundecyl 7-(methoxy(methyl)amino)-7-oxoheptanoate (15b). The crude was used in the next step with no further purification. $^1$H-NMR (300 MHz, d-chloroform): δ 0.87 (t, 6H), 1.20-1.55 (m, 32H), 1.56-1.80 (m, 4H), 2.30 (dd, 2H), 2.36 (dd, 2H), 3.17 (s, 3H), 3.67 (s, 3H), 4.07 (dd, 2H). MS found 470.3 $[M+H]^+$, calcd. 469.4 for $C_{28}H_{55}NO_4$ Step 5: Synthesis of 3-octylundecyl 7-oxohexadecanoate (16b)

1 ml of nonylmagnesium bromide (1 M in ether) was added dropwise to an ice-cold solution of 0.45 g (0.9 mmol) 3-octylundecyl 7-(methoxy(methyl)amino)-7-oxoheptanoate (15b) in 3 ml of anhydrous THF. After 1 hour of stirring at 0° C. the reaction mixture was warmed up to room temperature and allow to stir for 2 h. The reaction was cooled down again and quenched with aqueous ammonium chloride solution. The crude was extracted with hexanes, dried over magnesium sulfate and purified with silica gel (0-10% ethyl acetate/hexanes) to give 0.3 g (58% yield) of 3-octylundecyl 7-oxohexadecanoate (16b). $^1$H-NMR (300 MHz, d-chloroform): δ 0.87 (t, 9H), 1.10-1.40 (m, 38H), 1.45-1.70 (m, 7H), 2.27 (t, 2H), 2.32-2.39 (q, 4H), 4.07 (dd, 2H).

Step 6: Synthesis of 3-octylundecyl 7-hydroxyhexadecanoate (17b)

To an ice-cold solution of 0.3 g (0.56 mmol) of 3-octylundecyl 7-oxohexadecanoate (16b) dissolved in 3 ml mix THF/MeOH/methylene chloride (1/1/1) 50 mg (1.3 mmol) of sodium borohydride was added. The reaction was allowed to warm up to room temperature and after 3 h of stirring, it was quenched with water and evaporated down. The crude was re-dissolved in methylene chloride and washed with water. The organic phase was dried over magnesium sulfate and 220 mg of crude was used in the next step without further purification. $^1$H-NMR (300 MHz, d-chloroform): δ 0.88 (t, 9H), 1.10-1.45 (m, 46H), 1.50-1.70 (m, 2H), 2.31 (t, 2H), 3.65 (broad s, 1H), 4.07 (dd, 2H).

Step 7: Synthesis of 3-octylundecyl 7-((4-(dimethylamino)butanoyl)oxy)hexadecanoate (Lipid 23)

To a solution of 0.22 g (0.4 mmol) 3-octylundecyl 7-hydroxyhexadecanoate (17b) in 1 ml of methylene chloride, 0.068 g (0.43 mmol) of EDCI, 0.074 g (0.44 mmol) of 4-(dimethylamino)butanoic acid hydrochloride and 0.054 g (0.44 mmol) of DMAP were added together with 0.054 g (0.5 mmol) of triethylamine and after 16 h. The reaction was evaporated down. 3-octylundecyl 7-((4-(dimethylamino)butanoyl)oxy)hexadecanoate (Lipid 23) was obtained pure in the amount of 0.16 g (60% yield) after flash chromatography column 0-5% methanol/methylene chloride. $^1$H-NMR (300 MHz, d-chloroform): δ 0.87 (t, 9H), 1.10-1.40 (m, 48H), 1.41-1.70 (m, 6H), 1.72-1.85 (dd, 2H), 2.21 (s, 6H), 2.22-2.40 (m, 6H), 4.07 (dd, 2H), 4.80-4.90 (m, 1H). MS found 652.5 $[M+H]^+$, calcd. 651.6 for $C_{41}H_{81}NO_4$ Example 5: Synthesis of Lipid 16

Procedures for synthesizing Lipid 16 are described below with reference to Scheme 12, provided below.

Scheme 12

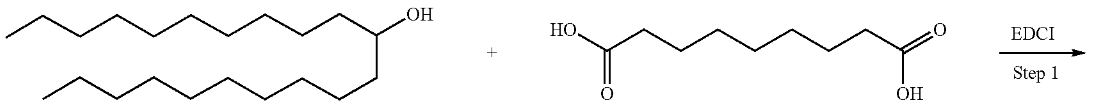

1b 2b

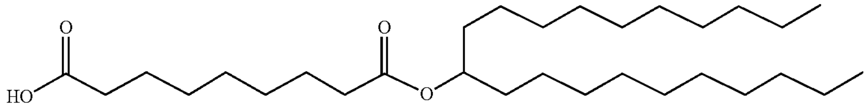

3c

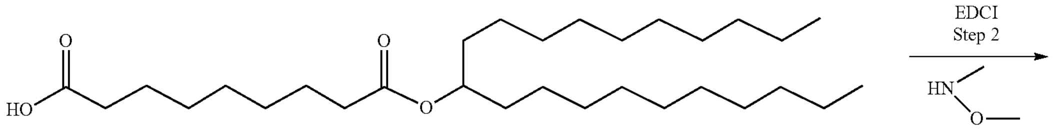

3c

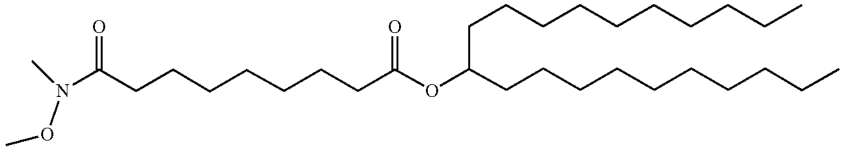

4c

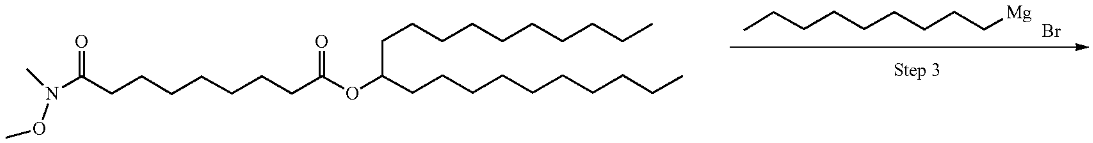

4c

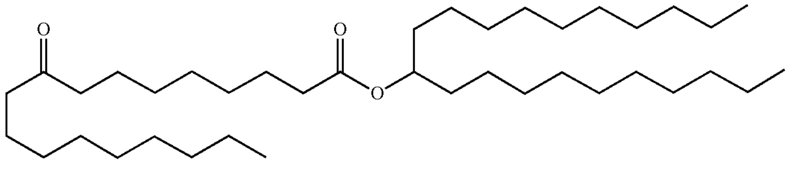

6c

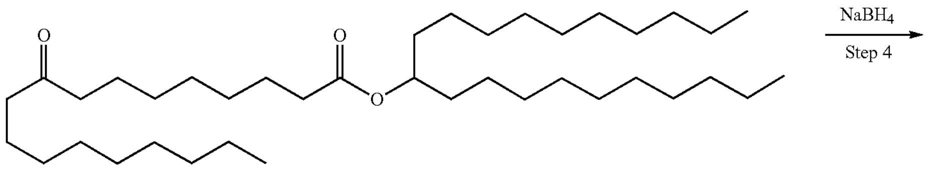

6c

-continued

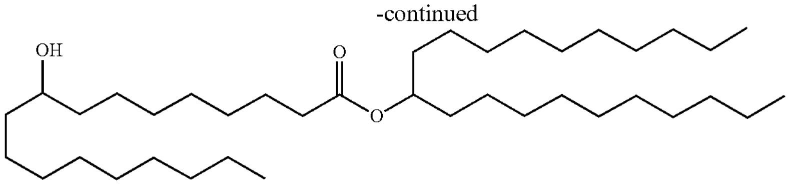

7c

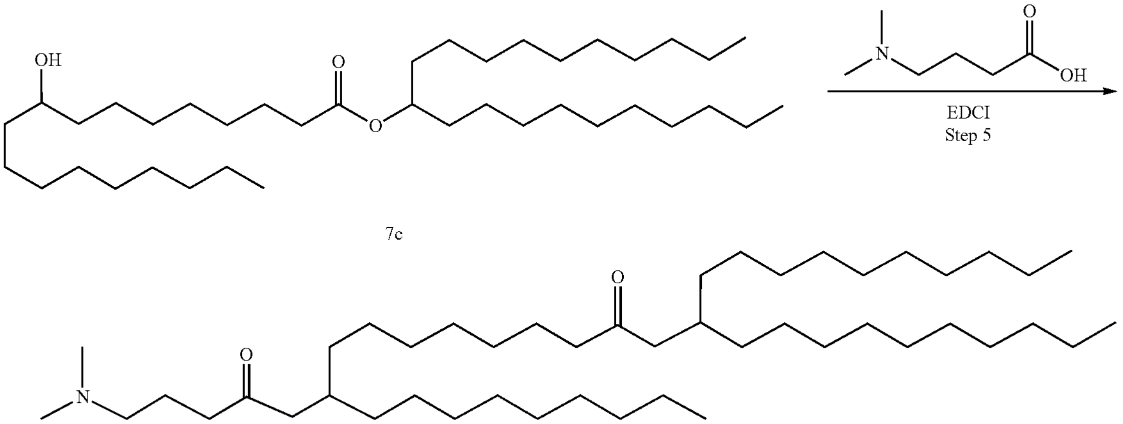

7c

Lipid 16

Step 1: Synthesis 9-(henicosan-11-yloxy)-9-oxononanoic acid (3c)

In a round bottom flask, 1.5 g (4.8 mmol) of henicosan-11-ol (1b) were dissolved in 60 ml of methylene chloride followed by 1.8 g (9.6 mmol) of azelaic acid (2b). To this mixture 1.48 g (9.6 mmol) of EDCI was added followed by 1.2 g (9.6 mmol) of DMAP. The reaction was allowed to stir overnight. The reaction was quenched using 1 N HCl (100 ml). The organic phases were dried over magnesium sulfate and purified in silica gel column (0-25% ethyl acetate-hexanes) to give 1.1 g (47% yield) of 9-(henicosan-11-yloxy)-9-oxononanoic acid (3c). $^1$H-NMR (300 MHz, d-chloroform): δ 0.86 (t, 6H), 1.20-1.80 (m, 62H), 2.20-2.40 (m, 4H), 4.82-4.94 (m, 1H). MS found 481.4 [M+H]$^+$, calcd. 482.4 for $C_{30}H_{58}O_4$.

Step 2: Synthesis of henicosan-11-yl 9-(methoxy(methyl)amino)-9-oxononanoate (4c)

To a solution of 1.1 g (2.3 mmol) of 9-(henicosan-11-yloxy)-9-oxononanoic acid (3c) in 20 ml of DCM 0.53 g (3.4 mmol) of EDCI was added, followed by 0.35 g (3.4 mmol) N,O-dimethylhydroxylamine hydrochloride and, at last, 0.42 g (3.4 mmol) of 4-dimethylaminopyridine (DMAP). The reaction mixture was allowed to stir for 16 h and was then quenched with 1 N HCl solution (2×5 ml). The organic phases were dried over magnesium sulfate and evaporated down to give 1 g (80% yield) of henicosan-11-yl 9-(methoxy(methyl)amino)-9-oxononanoate (4c). $^1$H-NMR (300 MHz, d-chloroform): δ 0.87 (t, 6H), 1.20-1.40 (m, 35H), 1.41-1.50 (m, 4H), 1.55-1.68 (m, 4H), 2.26 (dd, 2H), 2.37 (dd, 2H), 3.17 (s, 3H), 3.67 (s, 3H), 4.80-4.87 (m, 1H).

Step 3: Synthesis of henicosan-11-yl 9-oxooctadecanoate (6c)

2.3 ml of nonylmagnesium bromide (1 M in ether) was added dropwise to an ice-cold solution of 1 g (1.9 mmol) of henicosan-11-yl 9-(methoxy(methyl)amino)-9-oxononanoate (4c) in 6 ml of anhydrous THF, After 1 hour of stirring at 0° C. the reaction mixture was warmed up to room temperature and allowed to stir for 2 hours. The reaction was cooled down again and quenched with aqueous ammonium chloride solution. The crude was extracted with hexane, dried over magnesium sulfate, and purified with silica gel column (0-10% ethyl acetate/hexanes) to give 0.7 g (62% yield) of henicosan-11-yl 9-oxooctadecanoate (6c). $^1$H-NMR (300 MHz, d-chloroform): δ 0.87 (t, 9H), 1.10-1.40 (m, 45H), 1.45-1.61 (m, 11H), 2.26 (t, 2H), 2.37 (t, 4H), 4.83-4.87 (m, 1H).

Step 4: Synthesis of henicosan-11-yl 9-hydroxyoctadecanoate (7c)

To an ice-cold solution of 0.7 g (1.2 mmol) of henicosan-11-yl 9-oxooctadecanoate (6c), dissolved in a solution of 2 ml THF/2 ml MeOH/2 ml DCM, 0.2 g (5.3 mmol) of sodium borohydride was added. The reaction was allowed to warm up to room temperature and after 3 h of stirring, it was quenched with water and evaporated to dryness. The crude was redissolved in DCM and washed with water. After evaporation and column purification 0.6 g (86% yield) of henicosan-11-yl 9-hydroxyoctadecanoate (7c) were obtained. $^1$H-NMR (300 MHz, d-chloroform): δ 0.88 (t, 9H), 1.10-159 (m, 59H), 2.27 (t, 2H), 3.51-3.62 (m, 1H), 4.83-4.87 (m, 1H).

Step 5: Synthesis of henicosan-11-yl 9-((4-(dimethylamino)butanoyl)oxy)octadecanoate (Lipid 16)

To a solution of 0.24 g (0.41 mmol) henicosan-11-yl 9-hydroxyoctadecanoate (7c) in 1 ml of methylene chloride, 0.07 g (0.44 mmol) of EDCI, 0.074 g (0.44 mmol) of 4-(dimethylamino)butanoic acid hydrochloride, 0.054 g (0.44 mmol) of DMAP and 0.054 g (0.53 mmol) of triethylamine were added. After 16 h, the reaction was evaporated down and henicosan-11-yl 9-((4-(dimethylamino)butanoyl) oxy)octadecanoate (Lipid 16) was obtained pure in the amount of 0.160 g (55% yield) after flash chromatography column 0-5% Methanol/methylene chloride. $^1$H-NMR (300 MHz, d-chloroform): δ 0.87 (t, 9H), 1.10-1.35 (m, 55H), 1.40-1.54 (m, 7H), 1.55-1.70 (m, 2H) 1.77-1.85 (m, 2H), 2.21 (s, 6H) 2.22-2.40 (m, 6H), 4.82-4.87 (m, 2H). MS found 708.6 $[M+H]^+$, calcd. 707.7 for $C_{45}H_{89}NO_4$

Example 6: Synthesis of Lipid 18

Procedures for synthesizing Lipid 18 are described below with reference to Scheme 13, provided below.

Scheme 13

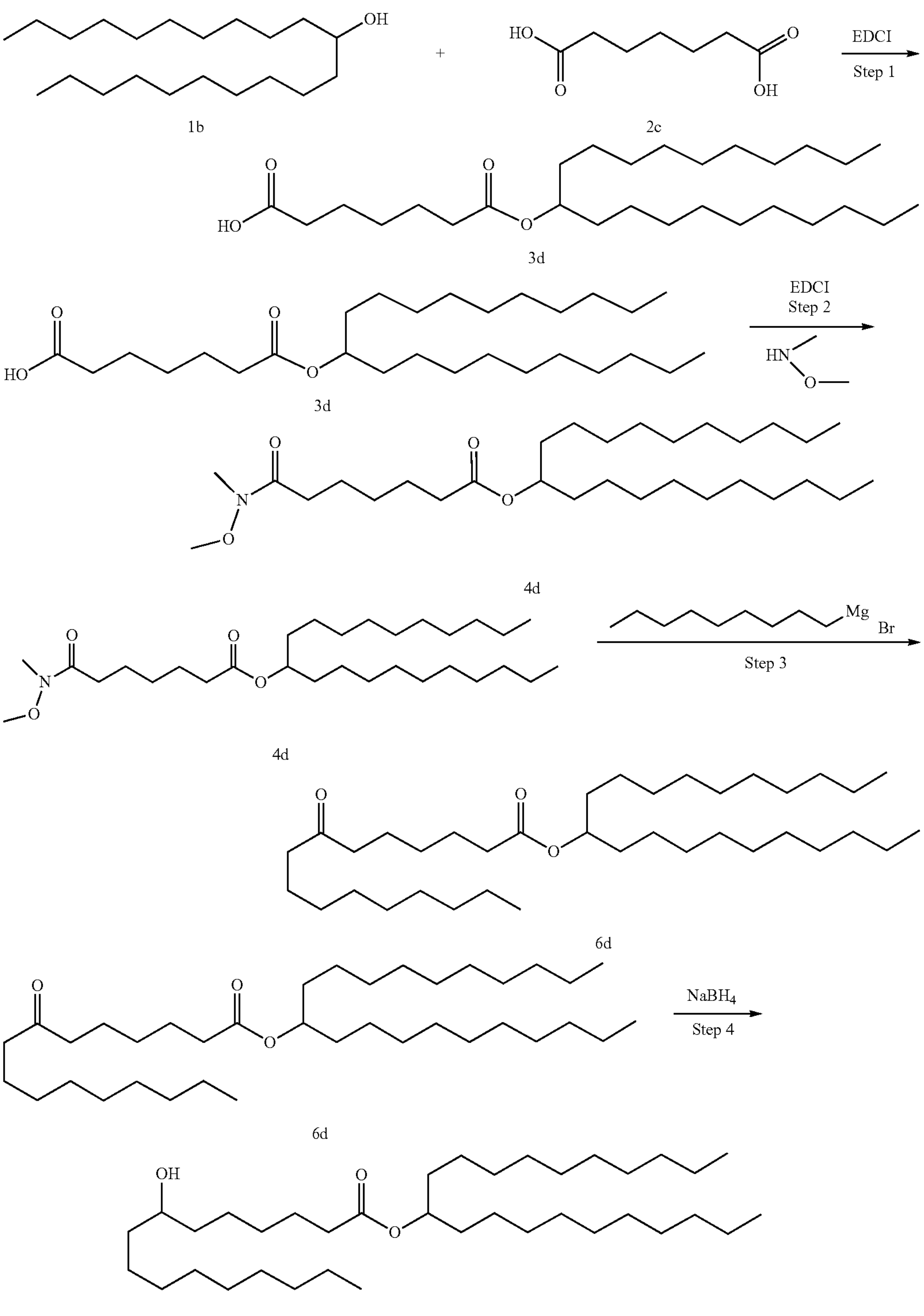

7d

-continued

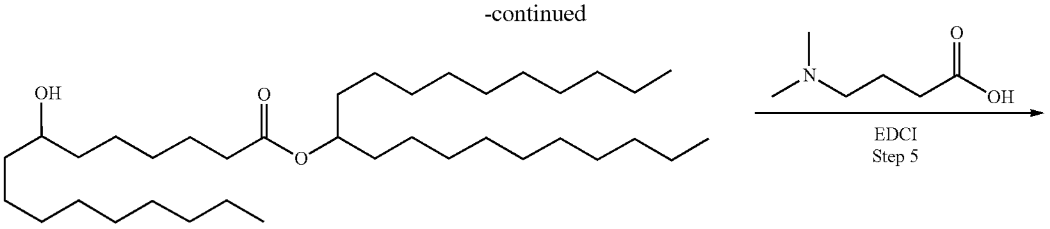

7d

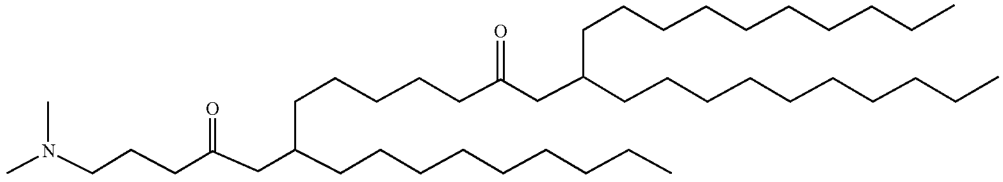

Lipid 18

Step 1: Synthesis of 7-(henicosan-11-yloxy)-7-oxoheptanoic acid (3d)

In a round bottom flask under nitrogen atmosphere, 2 g (6.3 mmol) of henicosan-11-ol (1b) were dissolved in 30 ml of anhydrous methylene chloride followed by 2.1 g (12.7 mmol) of pimelic acid (2c). To this mixture, 1.4 g (7.3 mmol) of EDCI was added followed by 1.6 g (13 mmol) of DMAP. The reaction was allowed to stir for 48 h. The reaction was quenched using aqueous ammonium chloride solution (100 ml) and extracted with methylene chloride. The organic phases were washed with brine (120 ml) dried over magnesium sulfate and purified in silica gel column (0-20% ethyl acetate-hexanes) to give 1.33 g (45% yield) of 7-(henicosan-11-yloxy)-7-oxoheptanoic acid (3d). $^1$H-NMR (300 MHz, d-chloroform): δ 0.87 (t, 6H), 1.18-1.42 (m, 32H), 1.42-1.55 (m, 3H), 1.60-1.69 (m, 4H), 2.29 (t, 2H), 2.36 (t, 2H) 4.84-4.88 (m, 1H). MS found 455.3 $[M+H]^+$, calcd. 454.4 for $C_{28}H_{54}O_4$.

Step 2: Synthesis of henicosan-11-yl 7-(methoxy (methyl)amino)-7-oxoheptanoate (4d)

To a solution of 1.33 g (2.9 mmol) of 7-(henicosan-11-yloxy)-7-oxoheptanoic acid (3d) in 10 ml of anhydrous DCM under nitrogen atmosphere, 0.84 g (4.4 mmol) of EDCI was added, followed by 0.82 ml (5.85 mmol) of triethyl amine, 0.34 g (3.5 mmol) N,O-dimethylhydroxylamine hydrochloride, and at last 36 mg (0.29 mmol) of DMAP. The reaction mixture was allowed to stir for 16 h, then quenched with ammonium chloride aqueous solution (100 ml) and extracted with methylene chloride (3×40 ml). The organic phases were washed with brine (100 ml) dried over magnesium sulfate and purified in silica gel column (0-10% ethyl acetate/hexanes) to give 0.91 g (64% yield) of henicosan-11-yl 7-(methoxy(methyl)amino)-7-oxoheptanoate (4d). $^1$H-NMR (300 MHz, d-chloroform): δ 0.87 (t, 6H), 1.24-1.29 (m, 38H), 1.30-1.52 (m, 8H), 1.55-1.75 (m, 5H), 2.29 (dd, 2H), 2.42 (dd, 2H), 3.17 (s, 3H), 3.67 (s, 3H), 4.83-4.87 (m, 1H).

Step 3: Synthesis of henicosan-11-yl 7-oxohexadecanoate (6d)

2.2 ml of nonylmagnesium bromide (1 M in ether) was added dropwise to an ice-cold solution of 0.86 g (0.1.7 mmol) henicosan-11-yl 7-(methoxy(methyl)amino)-7-oxoheptanoate (4d) in 5 ml of anhydrous THF. After 1 hour of stirring at 0° C., the reaction mixture was warmed up to room temperature and allow to stir for 4 hours. The reaction was cooled down again and quenched with aqueous ammonium chloride solution (5 ml). The crude was extracted with hexane (2×10 ml) and methylene chloride (2×15 ml) dried over magnesium sulfate and purified with silica gel (0-10% ethyl acetate/hexanes) to give 0.640 g (65% yield) of henicosan-11-yl 7-oxohexadecanoate (6d). $^1$H-NMR (300 MHz, d-chloroform): δ 0.87 (t, 9H), 1.10-1.35 (m, 44H), 1.40-1.60 (m, 12H), 2.28 (t, 2H), 2.31-2.38 (q, 4H), 4.83-4.87 (m, 1H). MS found 565.5 $[M+H]^+$, calcd. 564.6 for $C_{37}H_{72}O_3$.

Step 4: Synthesis of henicosan-11-yl 7-hydroxyhexadecanoate (7d)

To an ice-cold solution of 0.64 g (1.1 mmol) of henicosan-11-yl 7-oxohexadecanoate (7d) dissolved in 4 ml of 50% mix THF/MeOH 64 mg (1.7 mmol) of sodium borohydride was added. The reaction was allowed to warm up to room temperature and after 1 h of stirring, it was quenched with aqueous ammonium chloride (1 ml) and extracted the crude using methylene chloride (10 ml) and ethyl acetate (5 ml). The organic phases were dried over magnesium sulfate and used in the next step without further purification. $^1$H-NMR (300 MHz, d-chloroform): δ 0.87 (t, 9H), 1.10-154 (m, 63H), 1.54-1.55 (m, 2H), 2.28 (t, 2H), 3.50-3.60 (m, 1H), 4.83-4.88 (m, 1H). MS found 567.5 $[M+H]^+$, calcd. 566.56 for $C_{37}H_{74}O_3$.

Step 5: Synthesis of henicosan-11-yl 7-((4-(dimethylamino)butanoyl)oxy)hexadecanoate (Lipid 18)

To a solution of 0.57 g (1 mmol) henicosan-11-yl 7-hydroxyhexadecanoate (7d) in 4 ml of anhydrous methylene chloride under nitrogen atmosphere, 0.29 g (1.5 mmol) of EDCI, 0.20 g (1.2 mmol) of 4-(dimethylamino)butanoic acid hydrochloride and 0.186 g (1.5 mmol) of DMAP were added. After five minutes, 0.21 ml (1.5 mmol) of triethylamine were injected into the reaction mixture and after 16 h, the reaction was quenched with aqueous ammonium chloride (5 ml), extracted with methylene chloride (2×10 ml) and ethyl acetate (20 ml) and dried over magnesium sulfate. Henicosan-11-yl 7-((4-(dimethylamino)butanoyl)oxy)hexadecanoate (Lipid 18) was obtained pure in the amount of 0.296 g (28% yield) after flash chromatography column 0-5% Methanol/methylene chloride. $^1$H-NMR (300 MHz, d-chloroform): δ 0.87 (t, 9H), 1.10-1.30 (m, 47H), 1.40-1.84 (m, 15H), 2.23 (s, 6H), 2.24-2.4 (m, 6H), 4.81-4.88 (m, 2H). MS found 680.6 $[M+H]^+$, calcd. 679.7 for $C_{43}H_{85}NO_4$
Example 7: Synthesis of Lipid 17
Procedures for synthesizing Lipid 17 are described below with reference to Scheme 14, provided below.
Scheme 14
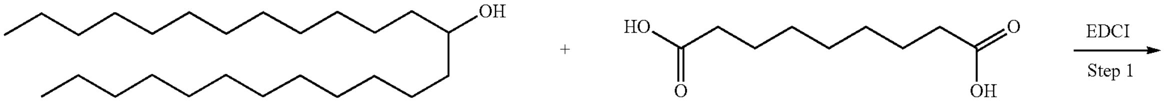
1c 2b
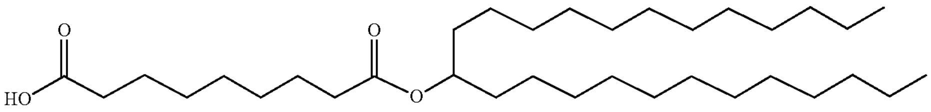
3e
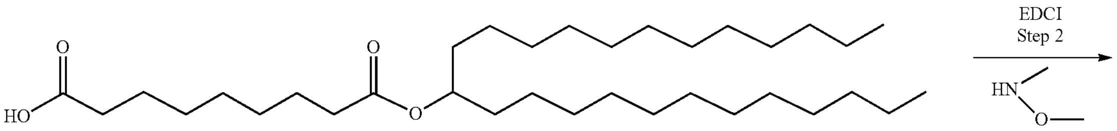
3e
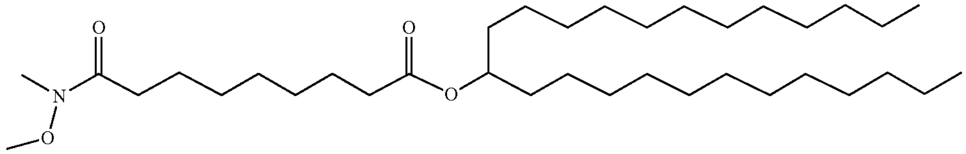
4e
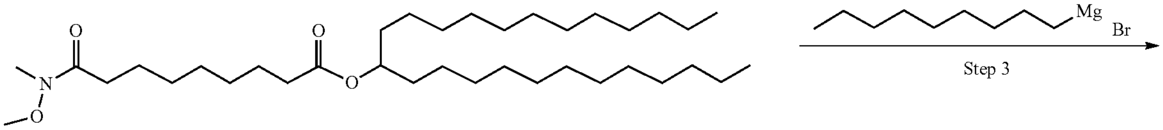
4e
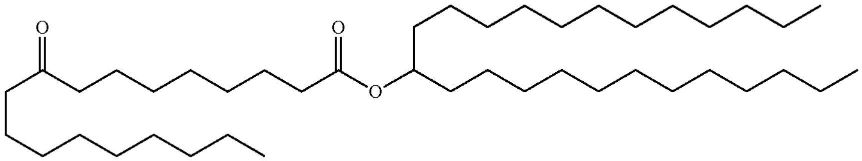
6e
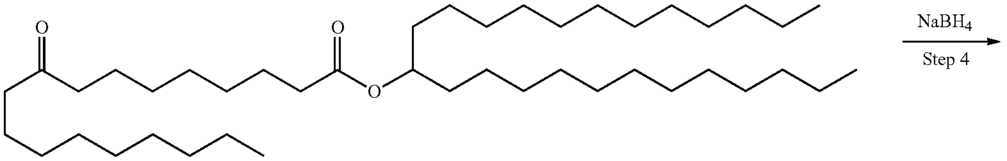
6e
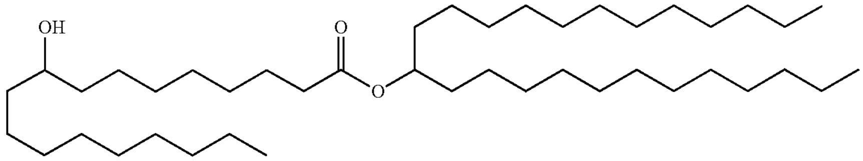
7e -continued

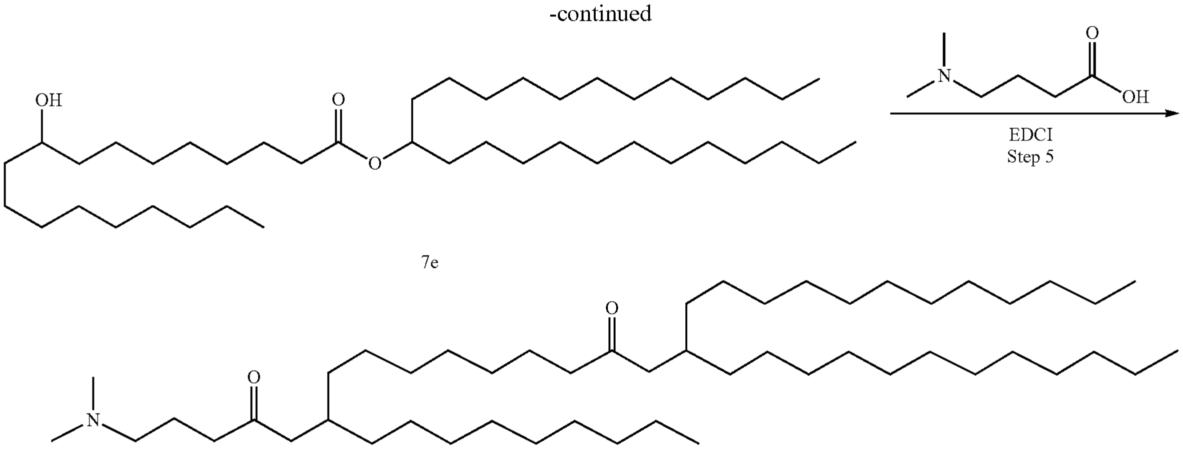

7e

Lipid 17

Step 1: Synthesis of 9-oxo-9-(pentacosan-13-yloxy) nonanoic acid (3e)

In a round bottom flask under nitrogen atmosphere, 0.9 g (2.4 mmol) of pentacosan-13-ol (1c) were dissolved in 50 ml of anhydrous methylene chloride followed by 0.9 g (4.3 mmol) of azelaic acid (2b). To this mixture 0.46 g (2.4 mmol) of EDCI was added followed by 0.6 g (4.6 mmol) of DMAP. The reaction was allowed to stir overnight. The reaction was quenched using aqueous ammonium chloride solution (100 ml) and extracted with methylene chloride. The organic phases were washed with brine (120 ml) dried over magnesium sulfate and purified in silica gel column (0-20% ethyl acetate-hexanes) to give 0.45 g (34% yield) of 9-oxo-9-(pentacosan-13-yloxy) nonanoic acid (3e). $^1$H-NMR (300 MHz, d-chloroform): δ 0.86 (t, 6H), 1.20-1.80 (m, 70H), 2.20-2.40 (m, 4H), 4.82-4.94 (m, 1H). MS found 539.4 $[M+H]^+$, calcd. 538.5 for $C_{34}H_{66}O_4$.

Step 2: Synthesis of pentacosan-13-yl 9-(methoxy (methyl)amino)-9-oxononanoate (4e)

To a solution of 0.45 g (0.8 mmol) of 9-oxo-9-(pentacosan-13-yloxy) nonanoic acid (3d) under nitrogen atmosphere in 30 ml of anhydrous DCM 0.24 g (1.25 mmol) of EDCI was added, followed by 0.2 ml (1.7 mmol) of triethylamine, 0.09 g (0.9 mmol) N,O-dimethylhydroxylamine hydrochloride and, at last, 10 mg (0.08 mmol) of DMAP. The reaction mixture was allowed to stir for 16 h and was then quenched with ammonium chloride aqueous solution (60 ml) and extracted with methylene chloride. The organic phases were washed with brine (100 ml) dried over magnesium sulfate and purified in silica gel column (0-10% ethyl acetate/hexanes) to give 0.35 g (70% yield) of pentacosan-13-yl 9-(methoxy(methyl)amino)-9-oxononanoate (4e). $^1$H-NMR (300 MHz, d-chloroform): δ 0.87 (t, 6H), 1.20-1.30 (m, 52H), 1.48-1.62 (m, 8H), 2.27 (dd, 2H), 2.29 (dd, 2H), 3.17 (s, 3H), 3.67 (s, 3H), 4.83-4.87 (m, 1H). MS found 582.4 $[M+H]^+$, calcd. 581.54 for $C_{36}H_{71}NO_4$.

Step 3: Synthesis of pentacosan-13-yl 9-oxooctadecanoate (6e)

0.9 ml of nonylmagnesium bromide (1 M in ether) was added dropwise to an ice-cold solution of 0.35 g (0.6 mmol) of pentacosan-13-yl 9-(methoxy(methyl)amino)-9-oxononanoate (4e) in 3 ml of anhydrous THF. After 1 hour of stirring at 0° C., the reaction mixture was warmed up to room temperature and allow to stir for 4 h. The reaction was cooled down again and quenched with aqueous ammonium chloride solution (3 ml). The crude was extracted with hexane (3×20 ml) and methylene chloride (1×10 ml) dried over magnesium sulfate and purified with silica gel (0-10% ethyl acetate/hexanes) to give 0.321 g (82% yield) of pentacosan-13-yl 9-oxooctadecanoate (6e). $^1$H-NMR (300 MHz, d-chloroform): δ 0.87 (t, 9H), 1.10-1.30 (m, 54H), 1.40-1.65 (m, 9H), 2.27 (t, 2H), 2.37 (t, 4H), 4.83-4.87 (m, 1H). MS found 649.5 $[M+H]^+$, calcd. 648.64 for $C_{43}H_{84}O_3$.

Step 4: Synthesis of pentacosan-13-yl 9-hydroxyoctadecanoate (7e)

To an ice-cold solution of 0.3 g (0.46 mmol) of pentacosan-13-yl 9-oxooctadecanoate (6e) dissolved in 2 ml of 50% mix THF/MeOH 26 mg (0.69 mmol) of sodium borohydride was added. The reaction was allowed to warm up to room temperature and after 1 h of stirring, it was quenched with aqueous ammonium chloride (1 ml) and extracted with methylene chloride (10 ml) and ethyl acetate (5 ml). The organic phases were dried over magnesium sulfate and used in the next step without further purification. $^1$H-NMR (300 MHz, d-chloroform): δ 0.88 (t, 9H), 1.10-154 (m, 72H), 1.55-1.70 (m, 2H), 2.27 (t, 2H), 3.51-3.62 (m, 1H), 4.83-4.87 (m, 1H). MS found 651.6 $[M+H]^+$, calcd. 650.66 for $C_{43}H_{86}O_3$.

Step 5: Synthesis of pentacosan-13-yl 9-((4-(dimethylamino)butanoyl)oxy)octadecenoate (Lipid 17)

To a solution of 0.29 g (0.45 mmol) pentacosan-13-yl 9-hydroxyoctadecanoate (6e) in 3 ml of anhydrous methylene chloride under nitrogen atmosphere, 0.128 g (0.67 mmol) of EDCI, 0.09 g (0.53 mmol) of 4-(dimethylamino) butanoic acid hydrochloride and 0.082 g (0.67 mmol) of DMAP were added. After five minutes, 0.09 ml (0.67 mmol) of triethylamine were injected into the reaction mixture and after 16 h, the reaction was quenched with aqueous ammonium chloride (3 ml) and extracted with methylene chloride (2×15 ml) and ethyl acetate (15 ml). The organic phases were dried over magnesium sulfate and concentrated. Pentacosan-13-yl 9-((4-(dimethylamino)butanoyl)oxy)octadecenoate (Lipid 17) was obtained pure in the amount of 0.135 g (34% yield) after flash chromatography column 0-5% Methanol/methylene chloride. $^1$H-NMR (300 MHz, d-chloroform): δ 0.87 (t, 9H), 1.10-1.35 (m, 64H), 1.40-1.76 (m, 11H), 1.77-1.85 (m, 2H), 2.23 (s, 6H) 2.24-2.32 (m, 6H), 4.82-4.87 (m, 2H). MS found 764.7 $[M+H]^+$, calcd. 763.74 for $C_{49}H_{97}NO_4$.

Example 8: Synthesis of Lipid 24

Procedures for synthesizing Lipid 24 are described below with reference to Scheme 15, provided below.

Scheme 15

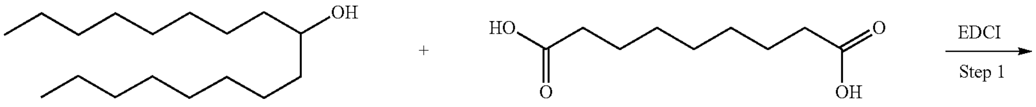

1a

2b

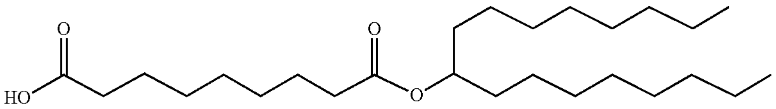

3b

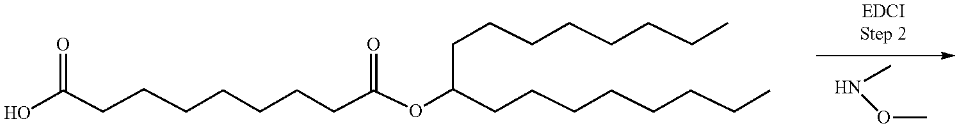

3b

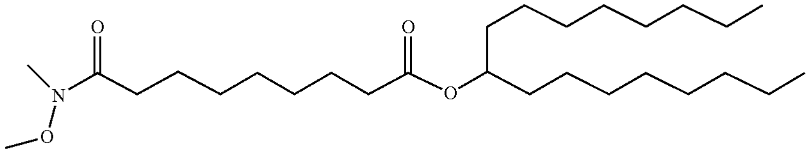

4b

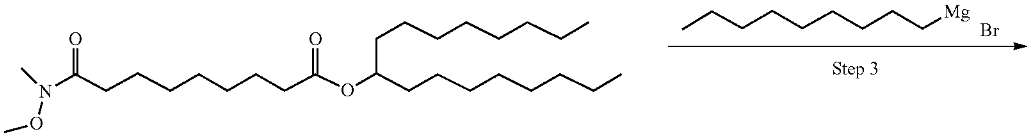

4b

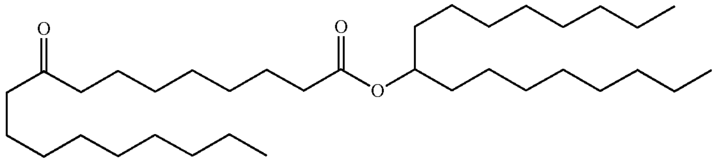

6f

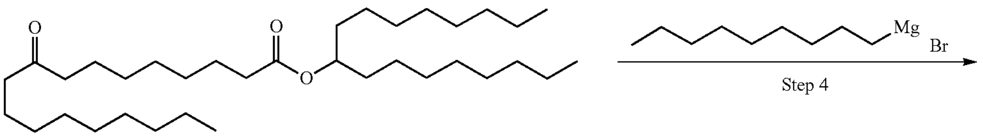

6f

-continued

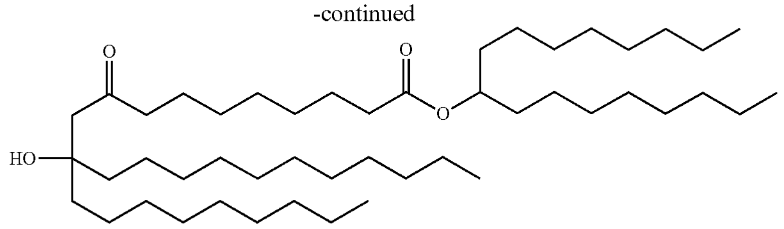

7f

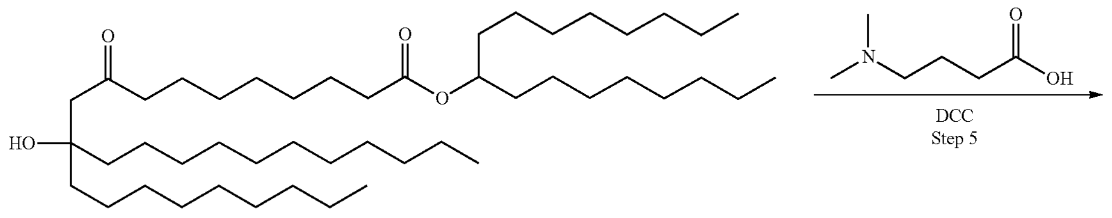

7f

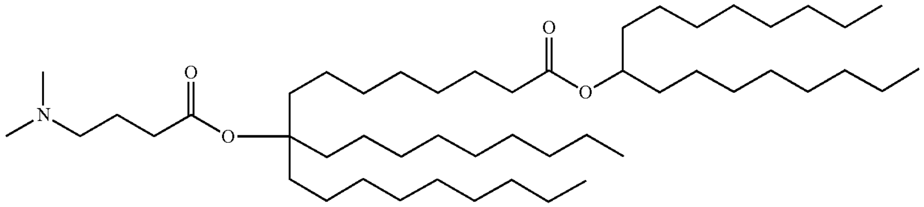

Lipid 24

Step 1: Synthesis of 9-(heptadecan-9-yloxy)-9-oxononanoic acid (3b)

In a round bottom flask under nitrogen atmosphere, 10 g (39 mmol) of heptadecan-9-ol (1a) were dissolved in 100 ml of anhydrous methylene chloride followed by 14.7 g (78 mmol) of azelaic acid (2b). To this mixture 9.7 g (50.7 mmol) of EDCI was added, followed by 9.5 g (78 mmol) of DMAP. The reaction was allowed to stir overnight. The reaction was quenched using aqueous ammonium chloride solution (100 ml) and extracted with methylene chloride (100 ml). The organic phases were washed with brine (120 ml) dried over magnesium sulfate and purified in silica gel column (0-20% ethyl acetate-hexanes) to give 7 g (42% yield) of 9-(heptadecan-9-yloxy)-9-oxononanoic acid (3b). $^1$H-NMR (300 MHz, d-chloroform): δ 0.87 (t, 6H), 1.20-1.33 (m, 30H), 1.40-1.50 (m, 4H), 1.50-1.64 (m, 4H), 2.27 (t, 2H), 2.32 (t, 2H), 4.82-4.88 (m, 1H). MS found 427.3 [M+H]$^+$, calcd. 426.37 for $C_{26}H_{50}O_4$.

Step 2: Synthesis of heptadecan-9-yl 9-(methoxy (methyl)amino)-9-oxononanoate (4b)

To a solution of 5 g (11.7 mmol) of of 9-(heptadecan-9-yloxy)-9-oxononanoic acid (3b) under nitrogen atmosphere in 40 ml of anhydrous dichloromethane 3.37 g (17.6 mmol) of EDCI was added, followed by 3.3 ml (23.5 mmol) of triethyl amine, 1.48 g (15.2 mmol) N,O-dimethylhydroxylamine hydrochloride and, at last, 143 mg (1.17 mmol) of DMAP. The reaction mixture was allowed to stir for 16 h and was then quenched with ammonium chloride aqueous solution (100 ml) and extracted with methylene chloride (150 ml). The organic phases were washed with brine (100 ml) dried over magnesium sulfate and purified in silica gel column (0-20% ethyl acetate/hexanes) to give 3.9 g (70% yield) of heptadecan-9-yl 9-(methoxy(methyl)amino)-9-oxononanoate (4b). $^1$H-NMR (300 MHz, d-chloroform): δ 0.87 (t, 6H), 1.10-1.40 (m, 29H), 1.41-1.57 (m, 10H), 2.27 (dd, 2H), 2.29 (dd, 2H), 3.17 (s, 3H), 3.67 (s, 3H), 4.83-4.88 (m, 1H). MS found 470.4 [M+H]$^+$, calcd. 469.41 for $C_{28}H_{55}NO_4$.

Step 3: Synthesis of heptadecan-9-yl 9-oxooctadecanoate (6f)

14.9 ml of nonylmagnesium bromide (1 M in ether) was added dropwise to an ice-cold solution of 5 g (10.6 mmol) of heptadecan-9-yl 9-(methoxy(methyl)amino)-9-oxononanoate (4b) in 24 ml of anhydrous THF After 1 hour of stirring at 0° C. the reaction mixture was warmed up to room temperature and allow to stir for 4 hours. The reaction was cooled down again and quenched with aqueous ammonium chloride solution (20 ml). The crude was extracted with ethyl acetate (3×30 ml) and washed with brine (30 ml) dried over magnesium sulfate and purified with silica gel (0-10% ethyl acetate/hexanes) to give 4 g (70% yield) of heptadecan-9-yl 9-oxooctadecanoate (6f). $^1$H-NMR (300 MHz, d-chloroform): δ 0.87 (t, 9H), 1.10-1.35 (m, 40H), 1.40-1.60 (m, 8H), 2.27 (t, 2H), 2.37 (t, 4H), 4.83-4.88 (m, 1H). MS found 537.5 [M+H]$^+$, calcd. 536.5 for $C_{35}H_{68}O_3$ Step 4: Synthesis of heptadecan-9-yl 9-hydroxy-9-nonyloctadecanoate (7f)

5.2 ml of nonylmagnesium bromide (1M in ether) was added dropwise to an ice-cold solution of 2 g (3.7 mmol) of heptadecan-9-yl 9-oxooctadecanoate (6f) in 8 ml of anhydrous THF. After 1 hour of stirring at 0° C. the reaction mixture was warmed up to room temperature and allow to stir for 4 hours. The reaction was cooled down again and quenched with aqueous ammonium chloride solution (8 ml). The crude was extracted with ethyl acetate (3×30 ml) and washed with brine (30 ml) dried over magnesium sulfate and purified with silica gel (0-10% ethyl acetate/hexanes) to give 1.1 g (44% yield) of heptadecan-9-yl 9-hydroxy-9-nonyloctadecanoate (7f). $^{1}$H-NMR (300 MHz, d-chloroform): δ 0.87 (t, 12H), 1.00-1.31 (m, 63H), 1.35-1.39 (m, 10H), 1.51-1.66 (m, 2H), 2.27 (t, 2H), 4.83-4.89 (m, 1H). $^{13}$C-NMR (300 MHz, d-chloroform): δ 14.2, 22.7, 23.6, 25.4, 29.3, 29.4, 29.6, 29.7, 30.4, 32.0, 34.0, 34.9, 39.4, 74.0, 74.2, 173.8.

Step 5: Synthesis of heptadecan-9-yl 9-((4-(dimethylamino)butanoyl)oxy)-9-nonyloctadecanoate (Lipid 24)

To a solution of 0.9 g (1.5 mmol) heptadecan-9-yl 9-hydroxy-9-nonyloctadecanoate (7f) in 8 ml of anhydrous methylene chloride under nitrogen atmosphere, 1 g (6 mmol) of 4-(dimethylamino)butanoic acid hydrochloride were added followed by 1.8 g (9 mmol) of 1N, N'-dicyclohexylcarbodiimide (DCC), and 0.182 g (1.5 mmol) of DMAP. After 16 h, the reaction was evaporated down and purified by column chromatography using 0-5% methanol/methylene chloride to recover 0.8 g of starting alcohol. The fraction containing the impure Lipid 24 was re-purified by C18 column using 0.1% TFA-water/0.1% TFA-acetonitrile. Heptadecan-9-yl 9-((4-(dimethylamino)butanoyl)oxy)-9-nonyloctadecanoate (Lipid 24) was obtained pure in the amount of 0.044 g (4% yield) $^{1}$H-NMR (300 MHz, d-chloroform): δ 0.87 (t, 12H), 1.10-1.30 (m, 63H), 1.40-1.80 (m, 15), 1.85-2.10 (m, 2H), 2.27 (t, 2H), 2.35 (t, 2H), 2.82-2.85 (s, s, 6H), 3.00-3.15 (m, 2H), 4.80-4.90 (m, 2H). ESI$^{+}$-MS found 778.6 [M+H]$^{+}$, calcd. 777.8 for $C_{50}H_{99}NO_4$.

Example 9: Synthesis of Lipid 25

Procedures for synthesizing Lipid 25 are described below with reference to Scheme 16, provided below.

Scheme 16

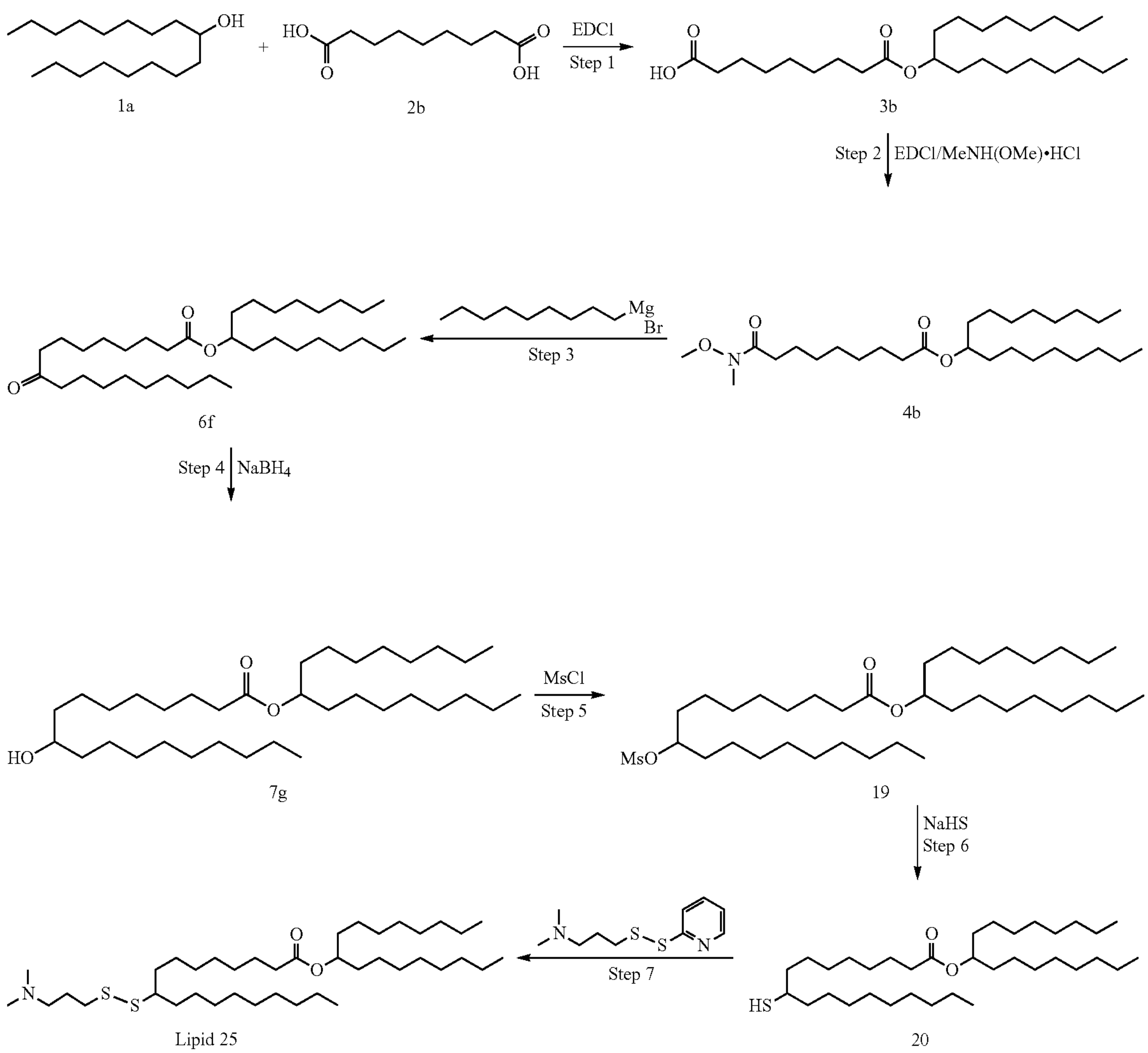

1a, 2b, 3b, 4b, 6f, 7g, 19, 20, Lipid 25

Step 1: Synthesis of 9-(heptadecan-9-yloxy)-9-oxononanoic acid (3b)

To a stirred solution of nonanedioic acid or azelaic acid (2b) (7.34 g, 39 mmol) and heptadecan-9-ol (1a) (5 g, 19 mmol) in DCM (1000 ml) was added DMAP (2.37 g, 19 mmol) followed by EDCI (3 g, 19 mmol). The resulting mixture was stirred at room temperature overnight, then washed with 250 ml 1 N HCl and 250 ml water. The organic layer was dried over $MgSO_4$, evaporated to dryness, and purified by silica gel column chromatography using 0-10% methanol in DCM as eluent. The fractions containing the desired compound were pooled and evaporated to afford 3b (6.2 g, 75%) as a white solid. $^1$H-NMR (300 MHz, d-chloroform): δ 4.80-4.90 (m, 1H), 2.25-2.34 (m, 4H), 1.55-1.70 (m, 4H), 1.40-1.50 (m, 4H), 1.20-1.40 (m, 30H), 0.84-0.90 (t, 3H).

Step 2: Synthesis of heptadecan-9-yl 9-(methoxy(methyl)amino)-9-oxononanoate (4b)

To a solution of compound 3b (5.4 g, 12.7 mmol) in DCM (60 mL), EDCI (3.6 g, 19.7 mmol), and TEA (3.5 mL, 25.4 mmol) were added, and the mixture was stirred for 15 min at room temperature. Then N,O-dimethylhydroxylamine hydrochloride (1.36 g, 13.97 mmol) and DMAP (0.15 g, 1.27 mmol) were added and stirred overnight at rt. Next day reaction was quenched with $NH_4Cl$ (aq) and diluted with DCM. The organic layer was washed with $NH_4Cl$ and brine and dried over anhydrous $Na_2SO_4$. Solvent was evaporated under vacuo. The product 4b was used in next step without further purification. $^1$H NMR (300 MHz, d-chloroform) δ 4.85 (t, J=6.2 Hz, 1H), 3.67 (s, 3H), 3.58 (s, 2H), 3.17 (s, 3H), 2.40 (t, J=7.6 Hz, 2H), 2.27 (t, J=7.5 Hz, 2H), 1.63 (dd, J=14.8, 5.5 Hz, 6H), 1.49 (d, J=5.4 Hz, 4H), 1.37-1.19 (m, 32H), 0.86 (d, J=6.8 Hz, 6H).

Step 3: Synthesis of heptadecan-9-yl 9-oxooctadecanoate (6g)

Compound 4b (1.1 g, 2.3 mmol) was dissolved in 20 ml of anhydrous THF. Then 1 M nonyl magnesium bromide solution in $Et_2O$ (6.13 ml, 3.2 mmol) was added dropwise at 0° C. The resulting mixture was allowed to reach room temperature over 2 h. The reaction was quenched with saturated $NH_4Cl$ solution and extracted with ether. The organic layer was washed with brine and dried over anhydrous $Na_2SO_4$. Solvent was evaporated under vacuo and purified by column chromatography using 0-30% EtOAc in hexane as eluent to afford 6f (1.2 g, 96%). $^1$H NMR (300 MHz, d-chloroform) δ 4.85 (t, J=6.2 Hz, 1H), 2.37 (t, J=7.4 Hz, 4H), 2.26 (t, J=7.5 Hz, 2H), 1.65-1.38 (m, 8H), 1.33-1.18 (m, 44H), 0.87 (t, J=6.5 Hz, 9H).

Step 4: Synthesis of heptadecan-9-yl 9-hydroxyoctadecanoate (7g)

To a solution of 6f (1.1 g, 2.05 mmol) in 40 mL of DCM:MeOH (1:1) mixture was added $NaBH_4$ (0.3 g, 8 mmol) at 0° C. and stirred for 2 h under $N_2$ atmosphere. The reaction was quenched with 1 M HCl (aq) solution and extracted with DCM. The organic phase was washed with brine and dried over anhydrous $Na_2SO_4$. Solvent was evaporated under vacuo and purified by column chromatography using 5-40% EtOAc in hexane as eluent to afford 7g (0.9 g, 83%). $^1$H NMR (300 MHz, d-chloroform) δ 4.88-4.83 (m, 1H), 3.57 (m, 1H), 2.27 (t, J=7.5 Hz, 2H), 1.61 (t, J=7.5 Hz, 2H), 1.48-1.41 (m, 8H), 1.36-1.18 (m, 44H), 0.87 (t, J=6.5 Hz, 9H).

Step 5: Synthesis of heptadecan-9-yl 9-((methylsulfonyl)oxy)octadecanoate (19)

To a solution of dry DCM (10 mL) was added compound 7g (0.48 g, 1.1 mmol) and cooled to 0° C. in an ice bath. Then, triethylamine or $Et_3N$ (0.45 mL, 3.3 mmol) was added, and the reaction mixture was stirred for 15 min at 0° C. Then methanesulfonyl chloride (MsCl) (0.25 mL, 2.2 mmol) dissolved in DCM was added and the reaction mixture was stirred at 0° C. for 30 min, the ice bath was removed, and the reaction was stirred for an additional 3 h at room temperature. The reaction mixture was quenched with $NaHCO_3$ (aq) (20 mL) and extracted with EtOAc (2×200 mL). The organic layer was washed with $NaHCO_3$ (200 mL) and brine, dried over anhydrous $Na_2SO_4$, and evaporated to dryness to afford the compound 19, which was used in next step without further purification.

Step 6: Synthesis of heptadecan-9-yl 9-mercaptooctadecanoate (20)

Compound 19 (0.2 g, 0.32 mmol) was dissolved in 1 ml of DMF to give a green color solution. To the reaction mixture, sodium hydrosulfide or NaHS (0.09 g, 1.62 mmol) was added in one portion and stirred at room temperature for 24 h. Next day, the reaction mixture was partitioned between $H_2O$ (5 mL) and $Et_2O$ (5 mL). The aqueous layer was washed with $Et_2O$ (5 mL). The combined organic layers were dried over $MgSO_4$ and evaporated to dryness to result product 20 (0.07 g) as a colorless oil and used in next step without further purification. $^1$H NMR (300 MHz, d-chloroform) δ 4.86 (q, J=6 Hz 1H), 2.27 (t, J=7.5 Hz, 2H), 1.71-1.43 (m, 10H), 1.36-1.12 (m, 46H), 0.87 (t, J=6.4 Hz, 9H).

Step 7: heptadecan-9-yl 9-((3-(dimethylamino)propyl)disulfaneyl)octadecenoate (Lipid 25)

Compound 20 (0.5 g, 0.9 mmol) and N,N-dimethyl-3-(pyridin-2-yldisulfaneyl)propan-1-amine (0.2 g, 0.8 mmol) were dissolved in DCM and stirred overnight at room temperature. Then solvent was evaporated under vacuo. and purified by column chromatography using 5% MeOH in DCM to yield Lipid 25 (0.4 g) as a light-yellow oil. $^1$H NMR (300 MHz, d-chloroform) δ 4.86 (q, J=6.1 Hz, 1H), 2.69-2.59 (m, 3H), 2.35 (t, J=7.2 Hz, 2H), 2.27 (q, J=7.5 Hz, 2H), 2.23 (s, 6H), 1.92-1.75 (m, 2H), 1.71-1.43 (m, 10H), 1.41-1.15 (m, 46H), 0.87 (t, J=6.4 Hz, 9H). MS found 672.5 $[M+H]^+$, calcd 671.57 for $[C_{40}H_{81}NO_2S_2]$.

Example 10: Alternative Synthesis of Lipid 11 and Synthesis of Lipids 1 and 2

Synthesis of Lipid 11 is provided in Example 3 above. Referring to Scheme 5 and Alternative Synthesis (A) in Example 2, this example describes an alternative synthesis of Lipid 11 and the synthesis of Lipid 1 and Lipid 2.

Step 1: Synthesis of 9-(methoxy(methyl)amino)-9-9oxononanoic acid (25c)

Please refer to Step 1 of Alternative Synthesis (A) in Example 2.

Step 2: Synthesis of heptadecan-9-yl 9-(methoxy(methyl)amino)-9-oxononanoate (4g), henicosan-11-yl 9-(methoxy(methyl)amino)-9-oxononanoate (4h), and pentacosan-13-yl 9-(methoxy(methyl)amino)-9-oxononanoate (4i)

Heptadecan-9-yl 9-(methoxy(methyl)amino)-9-oxononanoate (4f where $R^{6a}$ and $R^{6b}$ are each $C_8$ alkyl)

Scheme 17

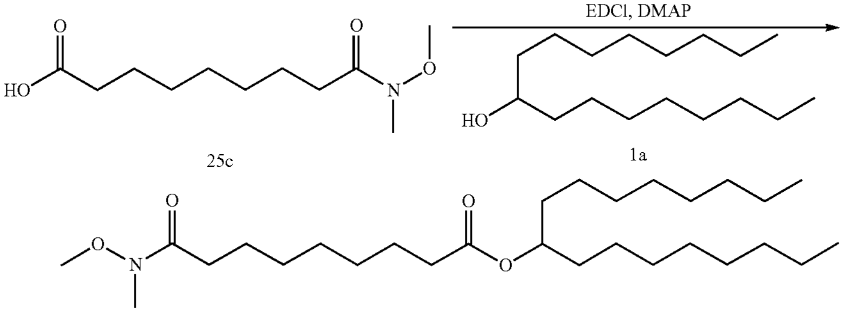

25c 1a
4c

To a stirred solution of acid 25c (4 mmol) and heptadecane-9-ol 1a (4 mmol) in DCM (30 ml) was added DMAP (590 mg, 4.8 mmol) followed by EDCI (916 mg, 4.8 mmol). The resulting mixture was stirred at room temperature overnight, then washed with 50 ml 1 N HCl and 50 ml water. The organic layer was dried over $MgSO_4$, evaporated to dryness, and purified by silica gel column chromatography using 0-10% methanol in DCM as eluent. The fractions containing the desired compound were pooled and evaporated to afford compound 4c in 57% yield. $^1H$ NMR (300 MHz, d-chloroform) δ 4.85 (t, J=6.2 Hz, 1H), 3.67 (s, 3H), 3.17 (s, 3H), 2.37 (t, J=7.5 Hz, 2H), 2.26 (t, J=7.5 Hz, 2H), 1.63 (m, 4H), 1.49 (m, 4H), 1.37-1.19 (m, 38), 0.86 (d, J=6.8 Hz, 6H).

Henicosan-11-yl 9-(methoxy(methyl)amino)-9-oxononanoate (4f where $R^{6a}$ and $R^{6b}$ are each $C_{10}$ alkyl)

Scheme 18

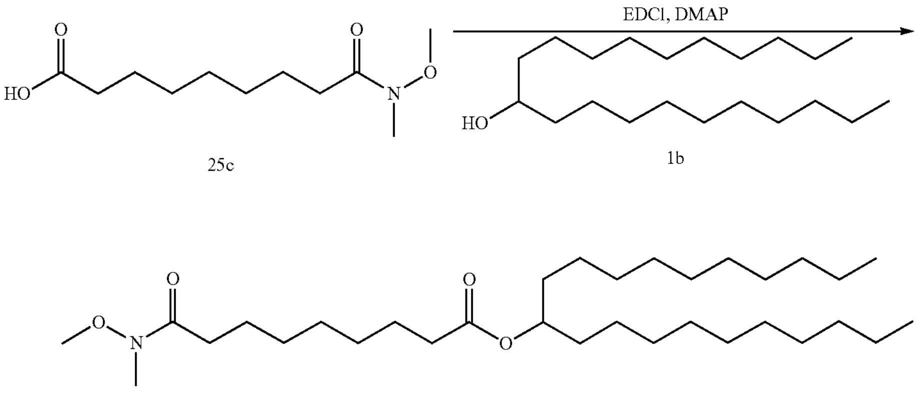

25c 1b
4d

Using the same reagents and conditions as described above for compound 4c with the exception of substituting heptadecane-9-ol 1a with henicosan-11-ol 1b, compound 4d was obtained from acid 25c in 58% yield. $^1$H-NMR (300 MHz, d-chloroform): δ 4.85 (m, 1H), 3.67 (s, 3H), 3.17 (s, 3H), 2.37 (t, J=7.4 Hz, 2H), 2.26 (t, J=7.4 Hz, 2H), 1.68-1.54 (m, 4H), 1.50-1.41 (m, 4H), 1.40-1.20 (m, 46H), 0.87 (t, J=6.8 Hz, 6H).

Pentacosan-13-yl 9-(methoxy(methyl)amino)-9-oxononanoate (4f where $R^{6a}$ and $R^{6b}$ are each $C_{12}$ alkyl)

Scheme 19

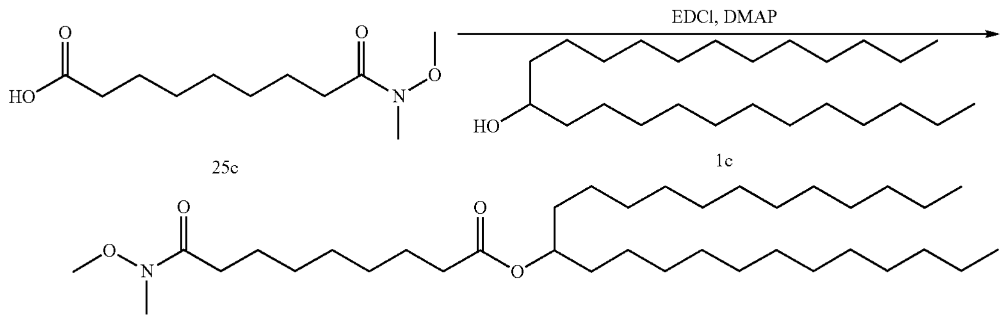

25c 1c

4e

Using the same reagents and conditions as described above for compound 4c with the exception of substituting heptadecane-9-ol 1a with pentacosan-13-ol 1c, compound 4e was obtained from acid 25c in 21% yield. $^1$H NMR (300 MHz, d-chloroform) δ 4.85 (m, 1H), 3.67 (s, 3H), 3.17 (s, 3H), 2.37 (t, J=7.5 Hz, 2H), 2.26 (t, J=7.5 Hz, 2H), 1.63 (m, 4H), 1.49 (m, 4H), 1.37-1.19 (m, 46), 0.86 (d, J=6.8 Hz, 6H).

Step 3: Synthesis of heptadecan-9-yl 9-oxohexadecanoate (6h), henicosan-11-yl 9-oxohexadecanoate (6i), and pentacosan-13-yl 9-oxohexadecanoate (6j)

Heptadecan-9-yl 9-oxohexadecanoate (6g where $R^{6a}$ and $R^{6b}$ are each $C_8$ alkyl)

Scheme 20

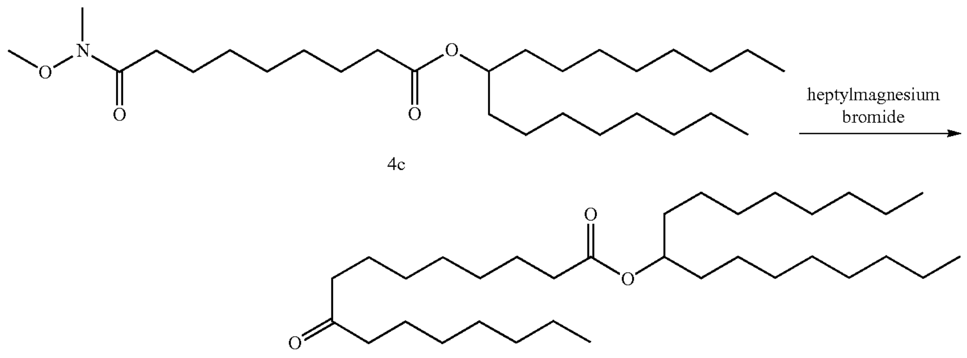

4c

6h

Compound 4c (2.13 mmol) was dissolved in 10 ml of anhydrous THF. Then 1 M heptyl magnesium bromide solution in $Et_2O$ (3.2 ml, 3.2 mmol) was added dropwise at 0° C. The resulting mixture was stirred at room temperature for 16 h under $N_2$. The reaction was quenched with saturated $NH_4Cl$ solution and extracted with ether. The organic layer was washed with brine and dried over anhydrous $Na_2SO_4$. Solvent was evaporated under vacuo and purified by column chromatography using 0-30% EtOAc in hexane as eluent to afford 6h in 57% yield. $^1H$ NMR (300 MHz, d-chloroform) δ 4.85 (t, J=6.2 Hz, 1H), 2.37 (t, J=7.4 Hz, 4H), 2.27 (t, J=7.5 Hz, 2H), 1.64-1.43 (m, 10H), 1.34-1.21 (m, 38H), 0.87 (t, J=6.7 Hz, 9H).

Henicosan-11-yl 9-oxohexadecanoate (6g: where $R^{6a}$ and $R^{6b}$ are each $C_{10}$ alkyl)

Scheme 21

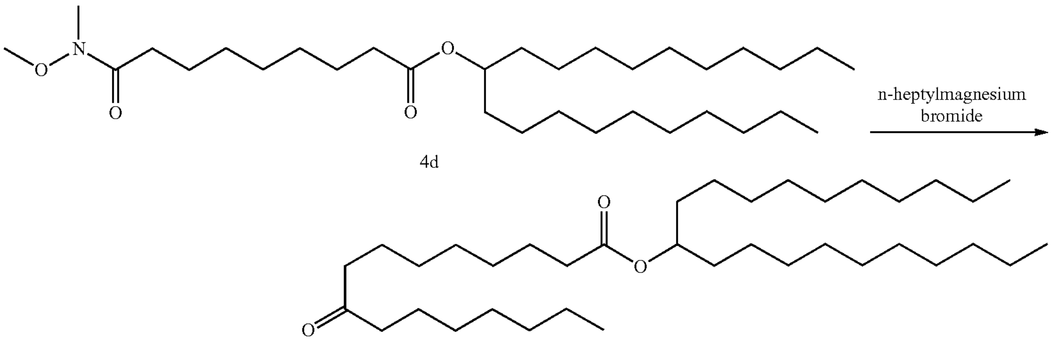

4d

6i

Using the same conditions as described above for compound 6h, compound 6i was obtained from 4d in 56% yield. $^1H$ NMR (300 MHz, d-chloroform) δ 4.85 (t, J=6.2 Hz, 1H), 2.37 (t, J=7.4 Hz, 4H), 2.27 (t, J=7.5 Hz, 2H), 1.64-1.43 (m, 8H), 1.34-1.24 (m, 46), 0.87 (t, J=6.7 Hz, 9H).

Pentacosan-13-yl 9-oxohexadecanoate (6g where $R^{6a}$ and $R^{6b}$ are each $C_{12}$ alkyl)

Scheme 22

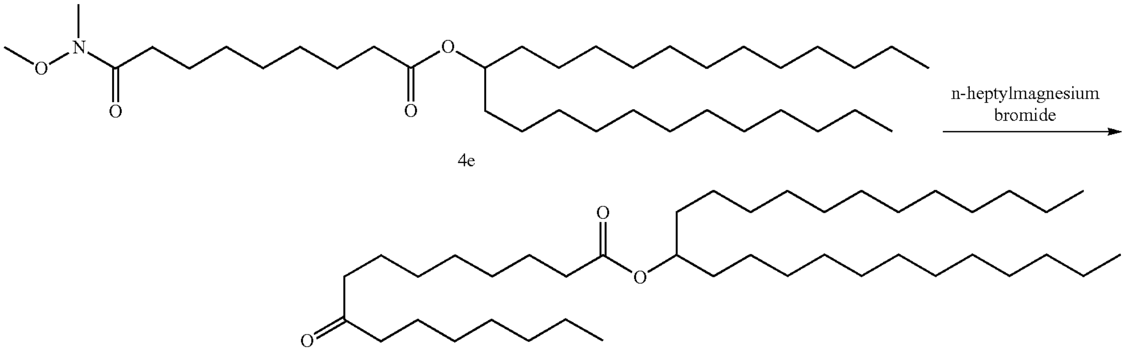

4e

6j

Using the same conditions as described above for compound 6h, compound 6j was obtained from 4e in 46% yield. $^1$H NMR (300 MHz, d-chloroform) δ 4.85 (t, J=6.2 Hz, 1H), 2.38 (t, J=7.4 Hz, 4H), 2.27 (t, J=7.4 Hz, 2H), 1.64-1.43 (m, 8H), 1.32-1.25 (m, 56H), 0.87 (t, J=6.7 Hz, 9H).

Step 4: Synthesis of heptadecan-9-yl 9-hydroxyhexadecanoate (7i), henicosan-11-yl 9-hydroxyhexadecanoate (7j), and pentacosan-13-yl 9-hydroxyhexadecanoate (7k)

Heptadecan-9-yl 9-hydroxyhexadecanoate (7h where $R^{6a}$ and $R^{6b}$ are each $C_8$ alkyl)

Scheme 23

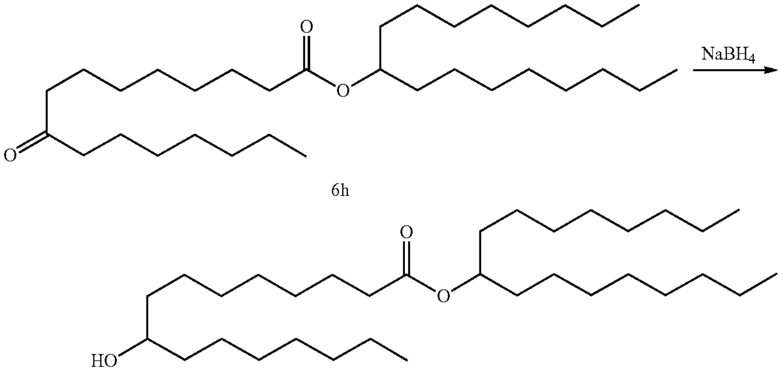

6h

7i

To a solution of 6h (0.6 mmol) in 10 mL of anhydrous THF was added $NaBH_4$ (0.09 g, 2.4 mmol) at 0° C. and stirred overnight under $N_2$ atmosphere. The reaction was quenched with saturated $NH_4Cl$ solution and extracted with EtOAc. The organic phase was washed with brine and dried over anhydrous $Na_2SO_4$. Solvent was evaporated under vacuo and purified by column chromatography using 0-50% EtOAc in hexane as eluent to afford 7i in 82% yield. $^1$H NMR (300 MHz, d-chloroform) δ 4.86 (m, 1H), 3.57 (m, 1H), 2.27 (t, J=7.5 Hz, 2H), 1.66-1.36 (m, 12H), 1.31-1.25 (m, 40H), 0.87 (t, J=6.1 Hz, 9H).

Henicosan-11-yl 9-hydroxyhexadecanoate (7h where $R^{6a}$ and $R^{6b}$ are each $C_{10}$ alkyl)

Scheme 24

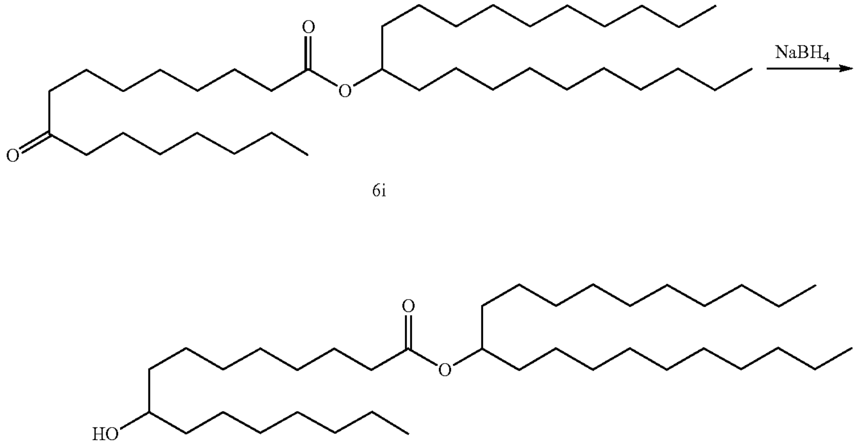

6i

7j

Using the same conditions as described above for compound 7i, compound 7j was obtained from compound 6i in 86% yield. $^1$H-NMR (300 MHz, d-chloroform): δ 4.85 (m, 1H), 3.57 (m, 1H), 2.27 (t, 2H), 1.10-1.59 (m, 60H), 0.88 (t, J=6.1 Hz, 9H).

Pentacosan-13-yl 9-hydroxyhexadecanoate (7h where $R^{6a}$ and $R^{6b}$ are each $C_{12}$ alkyl)

Scheme 25

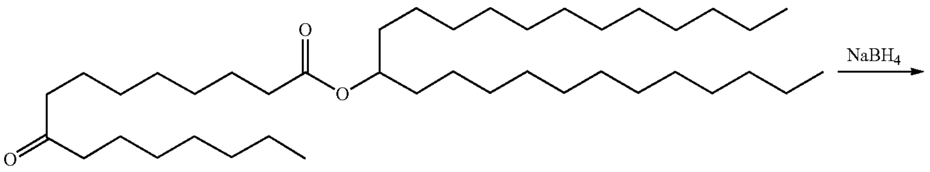

6j

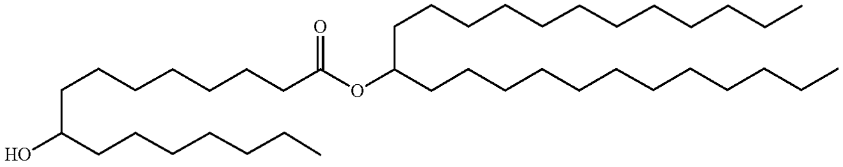

7k

Using the same conditions as described above for compound 7i, compound 7k was obtained from compound 6j in 78% yield. $^1$H-NMR (300 MHz, d-chloroform): δ 4.85 (m, 1H), 3.57 (m, 1H), 2.27 (t, 2H), 1.10-1.59 (m, 72H), 0.87 (t, J=6.1 Hz, 9H).

Step 5: Synthesis of heptadecan-9-yl 9-((4-(dimethylamino)butanoyl)oxy)hexadecanoate (Lipid 11), henicosan-11-9-yl 9-((4-(dimethylamino)butanoyl)oxy)hexadecanoate (Lipid 1), and pentacosan-13-yl 9-((4-(dimethylamino)butanoyl)oxy)hexadecanoate (Lipid 2)

Heptadecan-9-yl 9-((4-(dimethylamino)butanoyl)oxy)hexadecanoate (9c where $R^{6a}$ and $R^{6b}$ are each $C_8$ alkyl)

Scheme 26

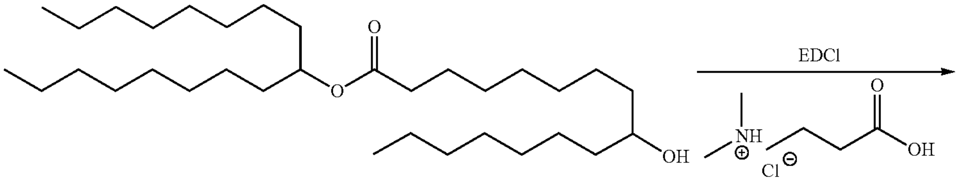

7i

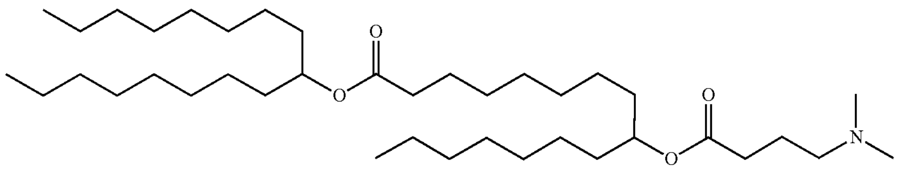

Lipid 11

To a solution of compound 7i (0.49 mmol) and 4-(dimethylamino)butanoic acid (0.125 g, 0.75 mmol) in DCM (5 mL), 0.27 mL of DIPEA was added. Then EDCI (0.143 g, 0.75 mmol), and DMAP (0.012 g, 0.1 mmol) were added, and the mixture was stirred overnight at room temperature under $N_2$ atmosphere. Next day reaction was diluted with DCM. The organic layer was washed with $NaHCO_3$ (aqueous) and dried over anhydrous $Na_2SO_4$. Solvent was evaporated under vacuo and purified by column chromatography using 0-5% MeOH in DCM as eluent to afford Lipid 1 in 45% yield. $^1$H NMR (300 MHz, d-chloroform) δ 4.87 (m, 2H), 2.37-2.23 (m, 6H), 2.21 (s, 6H), 1.78 (m, 2H), 1.70-1.40 (m, 10H), 1.36-1.22 (m, 42H), 0.87 (t, J=6.6 Hz, 9H). MS found 624.5 $[M+H]^+$, calcd 623.59 for $[C_{39}H_{77}NO_4]$.

Henicosan-11-9-yl 9-((4-(dimethylamino)butanoyl)oxy)hexadecanoate (9c where $R^{6a}$ and $R^{6b}$ are each $C_{10}$ alkyl)

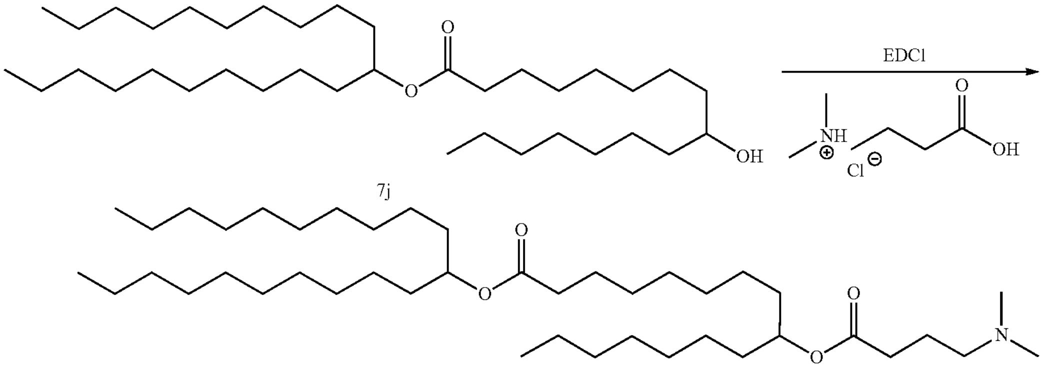

7j

Lipid 1

Using the same conditions as described above for compound Lipid 11, Lipid 1 was obtained from 7j in 45% yield. $^1$H NMR (300 MHz, d-chloroform) δ 4.85 (m, 2H), 2.37-2.23 (m, 6H), 2.21 (s, 6H), 1.79 (m, 2H), 1.70-1.40 (m, 10H), 1.36-1.21 (m, 52H), 0.87 (t, J=6.6 Hz, 9H). MS found 680.6 $[M+H]^+$, calcd 680.16 for $[C_{43}H_{85}NO_4]$.

Pentacosan-13-yl 9-((4-(dimethylamino)butanoyl)oxy)hexadecanoate (9c where $R^{6a}$ and $R^{6b}$ are each $C_{12}$ alkyl)

Scheme 27

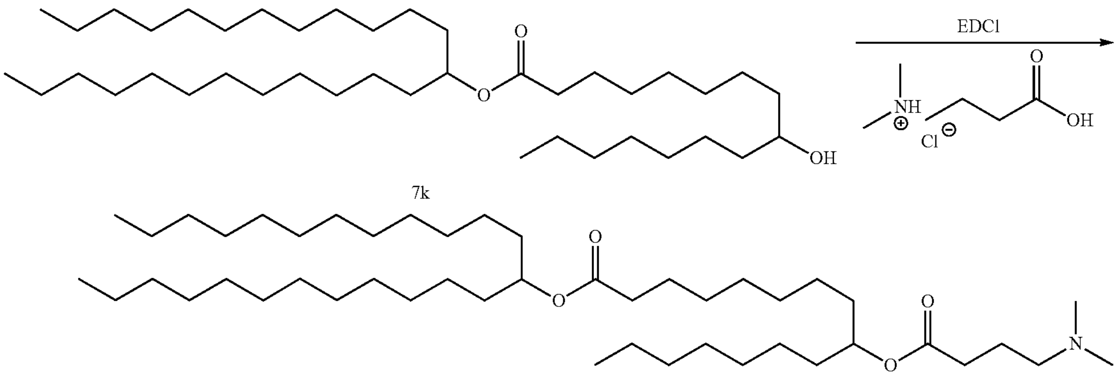

7k

Lipid 2

Using the same conditions as described above for compound Lipid 11, Lipid 2 was obtained from 7k in 45% yield. $^{1}$H NMR (300 MHz, d-chloroform) δ 4.85 (m, 2H), 2.37-2.23 (m, 6H), 2.21 (s, 6H), 1.79 (m, 2H), 1.52-1.43 (m, 10H), 1.36-1.21 (m, 60H), 0.87 (t, J=6.7 Hz, 9H). MS found 736.8 $[M+H]^+$, calcd 736.26 for $[C_{47}H_{93}NO_4]$.

Example 11: Synthesis of Lipid 12, Lipid 3, and Lipid 4

Referring to Scheme 6 and Alternative Synthesis (B) as described in Example 2, this example describes synthesis of Lipid 12, Lipid 3, and Lipid 4.

Synthesis of 5-(methoxy(methy)amino)-5-oxopentanoic acid (25)

Please refer to the synthesis procedure of compound 25 as described in Alternative Synthesis (B) in Example 2.

Synthesis of 5-octyltridecane-1,5-diol (23b), 5-decylpentadecane-1,5-diol (23c), and 5-dodecyl-heptadecane-1,5-diol (23d)

5-octyltridecane-1,5-diol (22 and 23 where $R^6$, $R^{6a}$ and $R^{6b}$ are each $C_8$ alkyl)

Scheme 28

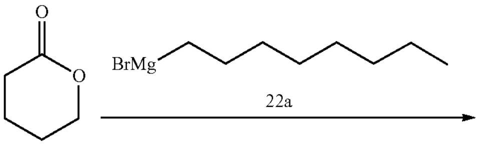

21

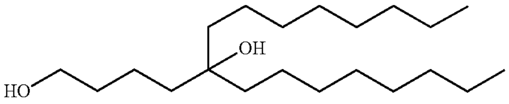

23b

To a solution of octyl magnesium bromide 22a (26 ml, 2 M in ether, 2.3 eq) under nitrogen atmosphere and cooled down to zero degrees, was added dropwise compound 21 (2 ml, 22 mmol, 1 eq) dissolved in 5 ml of anhydrous ethyl ether. After five minutes of stirring the ice bath was retrieved and the reaction was allowed to stir at room temperature overnight. The crude was dumped over 500 ml of ice diluted with concentrated HCl. The aqueous mixture was extracted with DCM (2×300 ml) and the organic phase was then washed once with water (300 ml) and dried over magnesium sulfate. Product 23b obtained was 8.5 g and used in the next step without further purification. $^{1}$H NMR (300 MHz, d-chloroform) δ 3.65 (t, 2H), 1.56-1.41 (m, 3H), 1.40-1.35 (m, 8H), 1.34-1.239 (m, 20H), 0.87 (t, 9H).

5-decylpentadecane-1,5-diol (22 and 23 where $R^6$, $R^{6a}$ and $R^{6b}$ are each $C_{10}$ alkyl)

Scheme 29

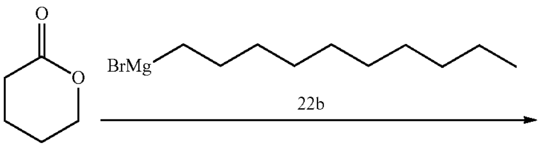

21

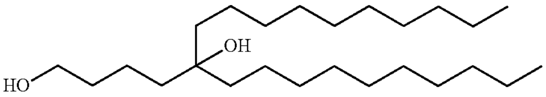

23c

To a solution of decyl magnesium bromide 22b (46 ml, 1 M in ether, 2.3 eq) under nitrogen atmosphere and cooled down to zero degrees, was added dropwise compound 21 (1.8 ml, 20 mmol, 1 eq) dissolved in 5 ml of anhydrous ethyl ether. After five minutes of stirring the ice bath was retrieved and the reaction was allowed to stir at room temperature overnight. The reaction was worked up as in the previous example and the product 23c obtained was 8 g and used in the next step without further purification. $^{1}$H NMR (300 MHz, d-chloroform) δ 3.64 (t, 2H), 1.60-1.35 (m, 10H), 1.30-1.20 (m, 26H), 0.87 (t, 6H).

5-dodecylheptadecane-1,5-diol (22 and 23 where $R^6$, $R^{6a}$ and $R^{6b}$ are each $C_{12}$ alkyl)

Scheme 30

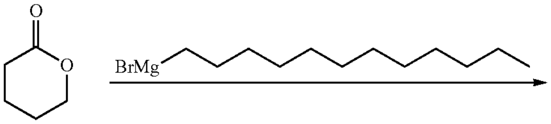

21

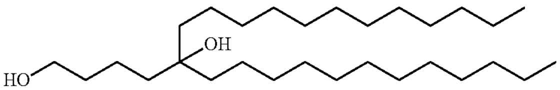

23d

To a solution of dodecyl magnesium bromide 22c (69 ml, 0.5M in MeTHF, 2.3 eq) under nitrogen atmosphere and cooled down to zero degrees, was added dropwise compound 21 (1.4 ml, 15 mmol, 1 eq) dissolved in 3 ml of anhydrous ethyl ether. After five minutes of stirring the ice bath was retrieved and the reaction was allowed to stir at room temperature overnight. The reaction was worked up as usual and the crude was purified by column chromatography using 0-25% EtOAc in hexane as eluent to afford 23d (5.6 g, 84%). $^{1}$H NMR (300 MHz, d-chloroform) δ 3.65 (t, 2H), 1.57-1.20 (m, 46H), 0.87 (t, 6H).

Synthesis of 5-octyltridec-4-en-1-ol (24a), 5-decylpentadec-4-en-1-ol (24b), and 5-dodecylheptadec-4-en-1-ol (24c)

5-octyltridec-4-en-1-ol (23 and 24 where $R^{6a}$ and $R^{6b}$ are each $C_8$ alkyl)

Scheme 31

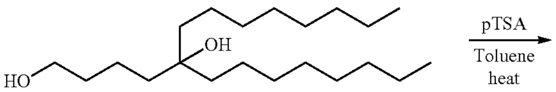

23b

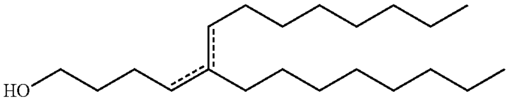

24b

Compound 23b (0.52 g, 1.6 mmol) was dissolved in 5 ml of toluene and p-Toluenesulfonic acid monohydrate (10 mg, 0.05 mmol) added in a microwave tube and microwaved to 100° C. for one hour. Solvent was evaporated under vacuo and purified by column chromatography using 0-5% EtOAc in hexane as eluent to afford 24b (0.38 g, 77%). $^1$H NMR (300 MHz, d-chloroform) δ 5.10 (t, 1H), 3.65 (t, 2H), 2.23-1.93 (m, 6H), 1.70-1.45 (m, 4H), 1.40-1.10 (m, 20H), 0.88 (t, 6H).

5-decylpentadec-4-en-1-ol (23 and 24 where $R^{6a}$ and $R^{6b}$ are each $C_{10}$ alkyl)

Scheme 32

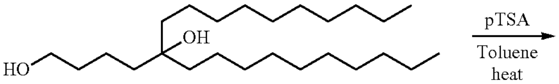

23c

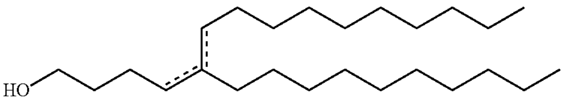

24c

Reaction was run and purified as the previous example using 2 g of diol 23c to give 1.38 g (68%) of the product 24c. $^1$H NMR (300 MHz, d-chloroform) δ 5.10 (t, 1H), 3.65 (t, 2H), 2.07-1.92 (m, 6H), 1.61-1.40 (m, 6H), 1.38-1.13 (m, 26H), 0.86 (t, 6H).

5-dodecylheptadec-4-en-1-ol (23 and 24 where $R^{6a}$ and $R^{6b}$ are each $C_{12}$ alkyl)

Scheme 33

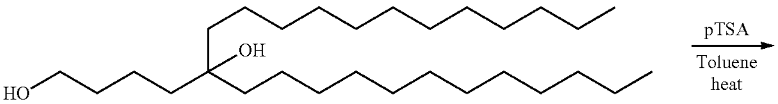

23d

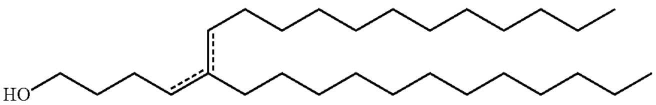

24d

Reaction was run as usual but keeping the temperature at 80° C. for 1 hr instead of 100° C. 1.1 g of diol 23d gave 0.89 g (79%) of 24d. $^{1}$H NMR (300 MHz, d-chloroform) δ δ 5.10 (t, 1H), 3.64 (t, 2H), 2.00-1.94 (m, 7H), 1.70-1.45 (m, 4H), 1.40-1.10 (m, 36H), 0.87 (t, 6H).

Synthesis of 5-octyltridecan-1-ol (13f), 5-decylpentadec-4-en-1-ol (13g), and 5-dodecylheptadec-4-en-1-ol (13h)

5-octyltridecan-1-ol (13b where $R^{6a}$ and $R^{6b}$ are each $C_8$ alkyl)

Scheme 34

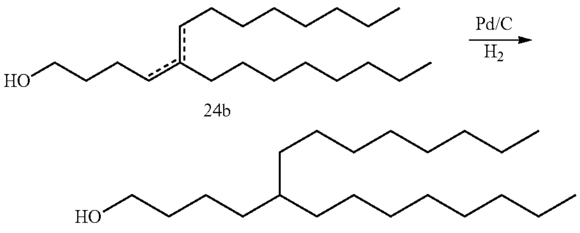

24b

13f

To a solution of compound 24b (1.1 g) in ethyl acetate (20 ml) 200 mg of Pd 10% on activated carbon, Pearlman (50-70% wet) was added and after degassing the mixture a hydrogen balloon was left over the mixture overnight. The mixture was filtered over celite, and the crude was purified using 0-10% EtOAc in hexane as eluent, to afford 13f (0.74 g, 67%). $^{1}$H NMR (300 MHz, d-chloroform) δ 3.67-3.62 (m, 2H), 1.57-1.50 (m, 2H), 1.33-1.10 (m, 31H), 0.87 (t, 6H).

5-decylpentadec-4-en-1-ol (13b where $R^{6a}$ and $R^{6b}$ are each $C_{10}$ alkyl)

Scheme 35

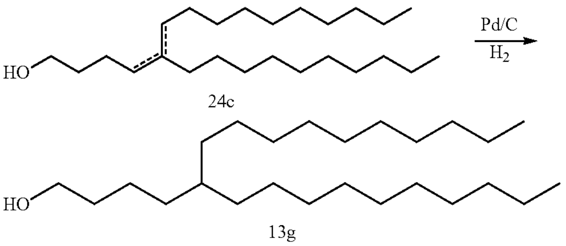

24c

13g

Reaction was run and purified as usual with 1.38 g of 24c treated with Pd/C under hydrogen to give 0.93 g (67%) of 5-decylpentadecan-1-ol 13g. $^{1}$H NMR (300 MHz, d-chloroform) δ 3.66-3.61 (m, 2H), 1.60-1.44 (m, 6H), 1.30-1.10 (m, 44H), 0.87 (t, 6H).

5-dodecylheptadec-4-en-1-ol (13b where $R^{6a}$ and $R^{6b}$ are each $C_{12}$ alkyl)

Scheme 36

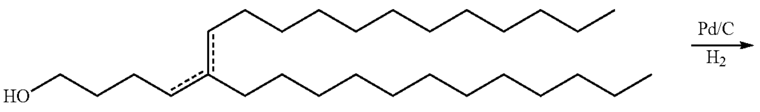

24d

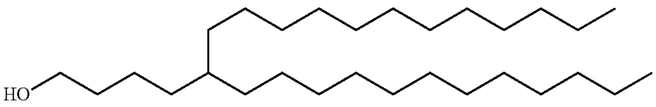

13h

Reaction was run for four hours and purified as usual with 0.89 g of 24d treated with Pd/C under hydrogen to give 0.66 g (74%) of 5-dodecylheptadecan-1-ol 13h. $^{1}$H NMR (300 MHz, d-chloroform) δ 3.66-3.61 (m, 2H), 1.58-1.51 (m, 2H), 1.30-1.10 (m, 44H), 0.88 (t, 6H).

Step 1: Synthesis of 5-octyltridecyl 5-(methoxy(methyl)amino)-5-oxopentanoate (15f), 5-decylpentadecyl 5-(methoxy(methyl)amino)-5-oxopentanoate (15g), 5-dodecylheptadecyl 5-(methoxy(methyl)amino)-5-oxopentanoate (15h)

5-octyltridecyl 5-(methoxy(methyl)amino)-5-oxopentanoate (15c where $R^{6a}$ and $R^{6b}$ are each $C_8$ alkyl)

Scheme 37

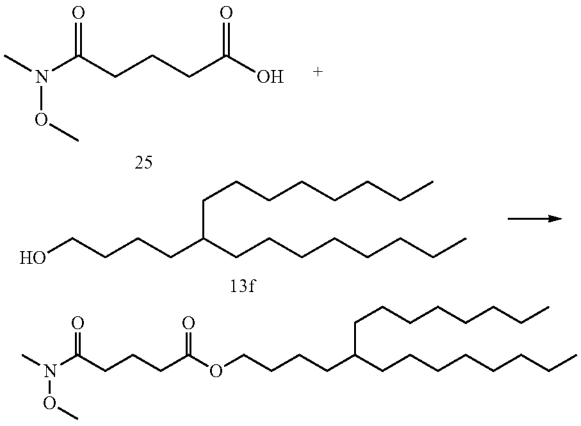

25

13f

15f

Alcohol 13f (0.97 g, 3.1 mmol) and amide 25 (0.65 g, 3.7 mmol) were dissolved in 8 ml of anhydrous DCM followed by EDCI (0.77 g, 4 mmol) and DMAP (0.57 g, 4.7 mmol). The reaction was stirred overnight under nitrogen and worked up adding 20 ml of $NH_4Cl$ aq solution and extracted with dichloromethane (50 ml) and ethyl acetate (50 ml). The organic layer was dried over $MgSO_4$. Solvent was evaporated under vacuo and purified by column chromatography using 0-25% EtOAc in hexane as eluent to afford 15f (0.53 g, 37%). $^{1}$H NMR (300 MHz, d-chloroform) δ 4.06 (t, 2H), 3.67 (s, 3H), 3.17 (s, 3H), 2.47 (t, 2H), 2.39 (t, 2H), 1.99-1.92 (m, 2H) 1.56-1.62 (m, 2H), 1.30-1.20 (m, 34H), 0.88 (t, 6H). MS found 470.4 $[M+H]^+$, calc. 469.41 for $[C_{28}H_{55}NO_4]$.

5-decylpentadecyl 5-(methoxy(methyl)amino)-5-oxopentanoate (15c where $R^{6a}$ and $R^{6b}$ are each $C_{10}$ alkyl)

Scheme 38

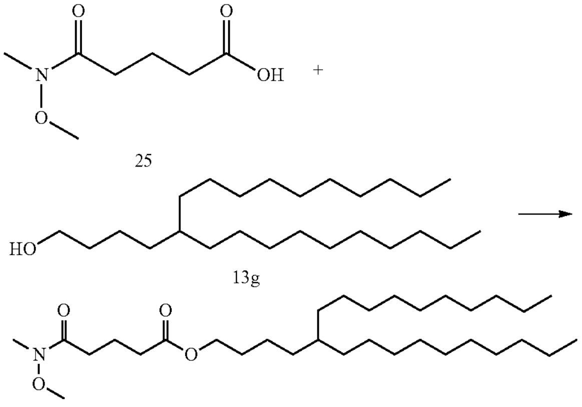

25

13g

15g

Reaction of 0.92 g of alcohol 13g and purification were done as in the previous example to afford 1.1 g (79%) of 5-decylpentadecyl 5-(methoxy(methyl)amino)-5-oxopentanoate 15i. $^{1}$H NMR (300 MHz, d-chloroform) δ 4.06 (t, 2H), 3.67 (s, 3H), 3.17 (s, 3H), 2.47 (t, 2H), 2.39 (t, 2H), 2.00-1.93 (m, 2H), 1.59-1.55 (m, 5H), 1.30-1.20 (m, 44H), 0.87 (t, 6H). MS found 526.4 $[M+H]^+$, calc. 525.5 for $[C_{32}H_{63}NO_4]$.

5-dodecylheptadecyl 5-(methoxy(methyl)amino)-5-oxopentanoate (15c where $R^{6a}$ and $R^{6b}$ are each $C_{12}$ alkyl)

Scheme 39

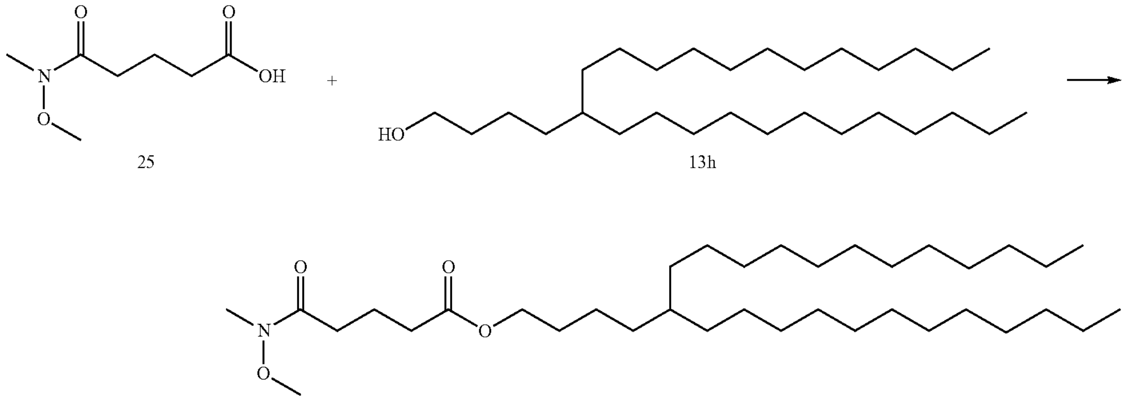

25

13h

15h

Reaction of 0.64 g of alcohol 13h and purification were done as in the previous example to afford 0.45 g (51%) of 5-dodecylheptadecyl 5-(methoxy(methyl)amino)-5-oxopentanoate 15h. $^1$H NMR (300 MHz, d-chloroform) δ 4.06 (t, 2H), 3.67 (s, 3H), 3.14 (s, 3H), 2.49 (t, 2H), 2.36 (t, 2H), 2.00-1.88 (m, 3H), 1.65-1.51 (m, 4H), 1.36-1.20 (m, 52H), 0.87 (t, 6H). MS found 582.5 $[M+H]^+$, calc. 581.5 for $[C_{36}H_{71}NO_4]$.

Step 2: Synthesis of 5-octyltridecyl 5-oxododecanoate (16f), 5-decylpentadecyl 5-oxododecanoate (16g), and 5-dodecylheptadecyl 5-oxododecanoate (16h)

5-octyltridecyl 5-oxododecanoate (16c where $R^{6a}$ and $R^{6b}$ are each $C_8$ alkyl)

Scheme 40

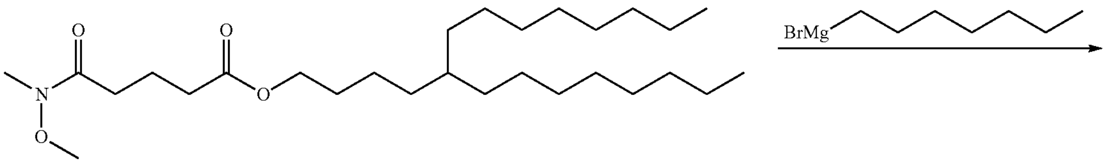

15f

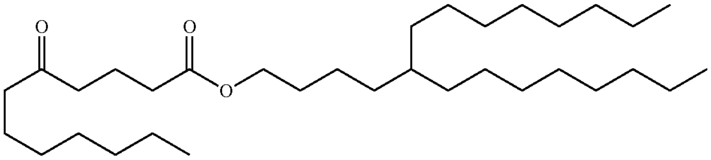

16f

To an ice-cold solution of 15f (0.3 g, 64 mmol) in 1 ml of anhydrous THF under nitrogen, heptyl magnesium bromide 1 M in ether (83 mmol) was added dropwise. The reaction was allowed to stir overnight and was quenched using $NH_4Cl_{aq}$ (1 ml) after cooling the reaction mixture to 0° C. The crude was extracted using hexanes (2×25 ml). The organic layer was dried over $MgSO_4$. Solvent was evaporated under vacuo. and purified by column chromatography using 0-10% EtOAc in hexane as eluent to afford 16f (0.13 g, 40%). $^1$H NMR (300 MHz, d-chloroform) δ 4.05 (t, 2H), 2.46 (t, 2H), 2.40-2.20 (m, 4H), 1.82-1.99 (m, 2H), 1.59-1.30 (m, 5H), 1.26-1.15 (m, 42), 0.87 (t, 9H). MS found 509.4 $[M+H]^+$ calc. 508.49 for $[C_{33}H_{64}O_3]$.

5-decylpentadecyl 5-oxododecanoate (16c where $R^{6a}$ and $R^{6b}$ are each $C_{10}$ alkyl)

Scheme 41

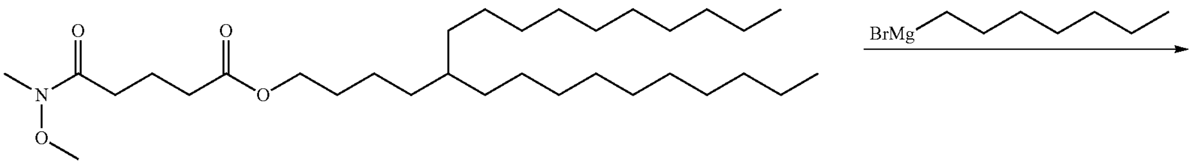

15g

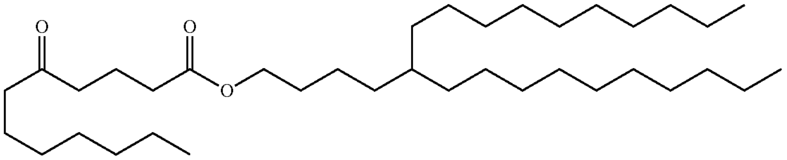

16g

Grignard addition of heptyl magnesium bromide to 1.1 g of 15g gave 0.33 g (28%) of 5-decylpentadecyl 5-oxododecanoate 16g. $^{1}$H NMR (300 MHz, d-chloroform) δ 4.05 (t, 2H), 2.46 (t, 2H), 2.41-2.29 (m, 4H), 1.90-1.84 (m, 2H), 1.57-1.40 (m, 10H), 1.30-1.10 (m, 46), 0.88 (t, 9H). MS found 565.5 $[M+H]^+$ calc. 564.5 for $[C_{37}H_{72}O_3]$.

5-dodecylheptadecyl 5-oxododecanoate (16c where $R^{6a}$ and $R^{6b}$ are each $C_{12}$ alkyl)

Scheme 42

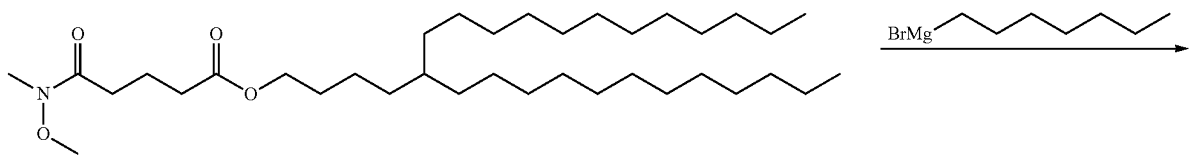

15h

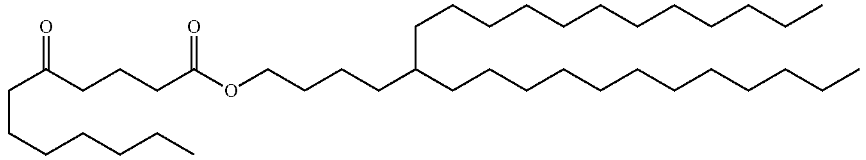

16h

Grignard addition of heptyl magnesium bromide to 0.72 g of 15h gave 0.2 g (26%) of 5-dodecylheptadecyl 5-oxododecanoate 16h. $^{1}$H NMR (300 MHz, d-chloroform) δ 4.05 (t, 2H), 2.46 (t, 2H), 2.41-2.28 (m, 4H), 1.94-1.83 (m, 2H), 1.61-1.50 (m, 7H), 1.35-1.10 (m, 56), 0.87 (t, 9H). MS found 621.6 $[M+H]^+$ calc. 620.6 for $[C_{41}H_{80}O_3]$.

Step 3: Synthesis of 5-octyltridecyl 5-hydroxydodecanoate (17f), 5-decylpentadecyl 5-hydroxydodecanoate (17g), and 5-dodecylheptadecyl 5-hydroxydodecanoate (17h)

5-octyltridecyl 5-hydroxydodecanoate (17c where $R^{6a}$ and $R^{6b}$ are each $C_8$ alkyl)

Scheme 43

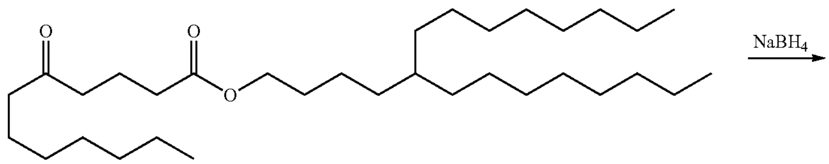

16f

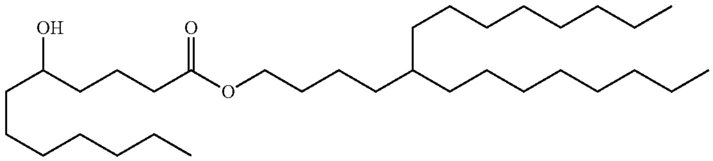

17f

To an ice-cold solution of 16f (0.1 g, 19 mmol) dissolved in THF/MeOH (1 ml/1 ml) $NaBH_4$ was added. The reduction reaction was followed by TLC. After 1 hr the starting material disappeared completely, and the reaction was quenched with $NH_4Cl_{aq}$ (0.5 ml). The crude was evaporated down to dryness then re-dissolved in DCM, washed once with water and the organic layer was dried over $MgSO_4$. The crude 17f (0.1 g) was used in the next step (Step 4) without further purification. $^1$H NMR (300 MHz, d-chloroform) δ 4.06 (t, 2H), 3.60-3.50 (br s, 1H), 2.33 (t, 2H), 1.73-1.30 (m, 10H), 1.26-1.20 (m, 34H), 0.88 (t, 9H).

5-decylpentadecyl 5-hydroxydodecanoate (17c where $R^{6a}$ and $R^{6b}$ are each $C_{10}$ alkyl)

Scheme 44

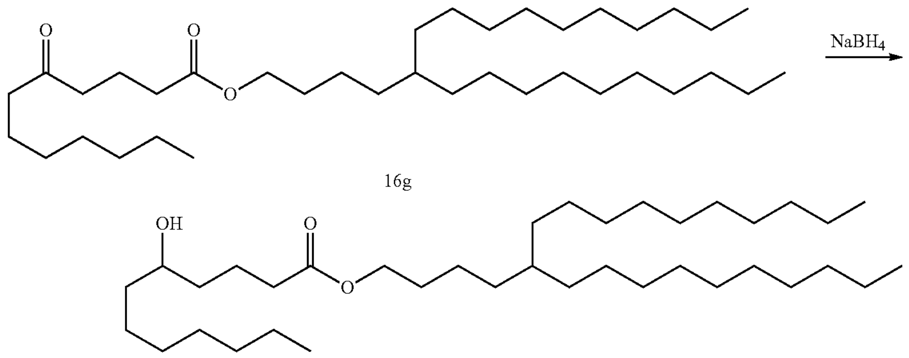

16g

17g

Reduction was run as described above for for synthesis of compound 17g, with the exception that 5-decylpentadecyl 5-oxododecanoate 16g was used as a starting material. Crude 17g was used without purification in next reaction in Step 4. $^1$H NMR (300 MHz, d-chloroform) δ 4.06 (t, 2H), 3.60-3.50 (br s, 1H), 2.33 (t, 2H), 1.62-1.5 (m, 4H), 1.45-1.40 (m, 3H), 1.30-1.20 (m, 45H), 0.88 (t, 9H).

5-dodecylpentadecyl 5-hydroxydodecanoate (17c where $R^{6a}$ and $R^{6b}$ are each $C_{12}$ alkyl)

Scheme 45

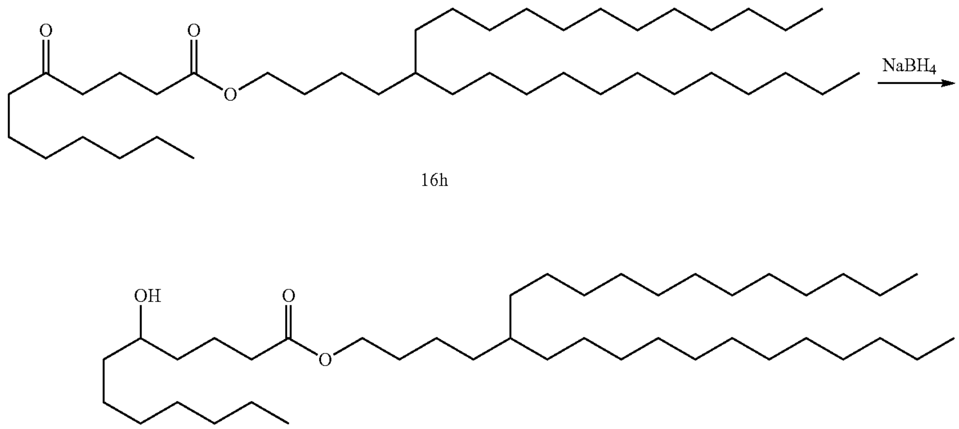

16h

17h

Reduction was run as described above for for synthesis of compound 17f, with the exception that 5-dodecylpentadecyl 5-oxododecanoate 16h was used as a starting material. Crude 17h was used without purification in next reaction in Step 4. $^{1}$H NMR (300 MHz, d-chloroform) δ 4.06 (t, 2H), 3.60-3.50 (br s, 1H), 2.33 (t, 2H), 1.90-1.40 (m, 19H), 1.30-1.20 (m, 50H), 0.88 (t, 9H).

Step 4: Synthesis of 5-octyltridecyl 5-((4-(dimethylamino)butanoyl)oxy)dodecanoate (Lipid 12), 5-decylpentadecyl 5-((4-(dimethylamino)butanoyl)oxy)dodecanoate (Lipid 3), and 5-dodecylheptadecyl 5-((4-(dimethylamino)butanoyl)oxy)dodecanoate (Lipid 4)

5-octyltridecyl 5-((4-(dimethylamino)butanoyl)oxy)dodecanoate (26 where $R^{6a}$ and $R^{6b}$ are each $C_8$ alkyl)

Scheme 46

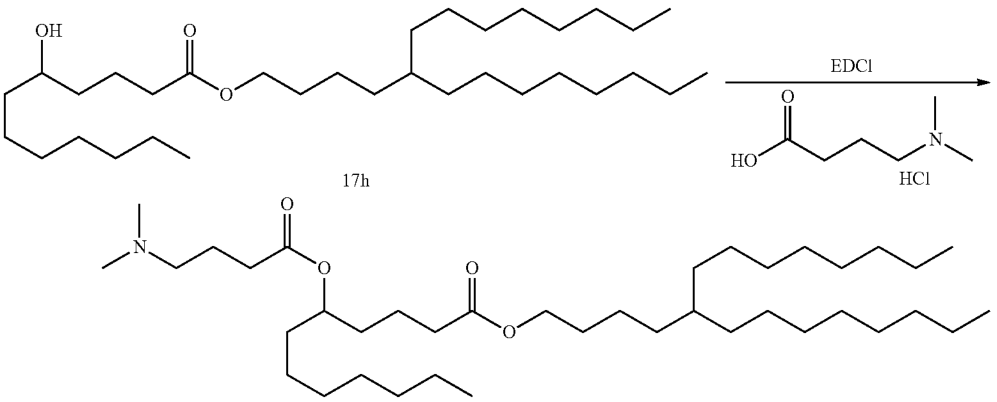

17h

Lipid 12

To a solution of 17f (0.1 g, 0.2 mmol) and 4-dimethylamino butyric acid HCl in DCM (1.5 ml) was added EDCI (83 mg, 0.3 mmol) DMAP (53 mg, 0.4 mmol) and finally triethyl amine (33 mg, 3 mmol). Reaction was allowed to stir overnight and quenched with saturated $NH_4Cl$ solution (2 ml) and extracted with DCM and EtOAc. The organic layer was dried over anhydrous $MgSO_4$, the solvent was evaporated under vacuo and purified by column chromatography using 0-5% MeOH in DCM as eluent to afford Lipid 12 (75 mg, 61%). $^{1}$H NMR (300 MHz, d-chloroform) δ 4.92-4.86 (m, 1H), 4.05 (t, 2H), 2.35-2.25 (m, 6H), 2.21 (s, 6H), 1.84-1.72 (m, 2H), 1.66-1.50 (m, 14H), 1.35-1.10 (m, 42H), 0.87 (t, 9H). MS found 624.5 $[M+H]^+$ calc. 623.59 for $[C_{39}H_{77}NO_4]$.

5-decylpentadecyl 5-((4-(dimethylamino)butanoyl)oxy)dodecanoate (26 where $R^{6a}$ and $R^{6b}$ are each $C_{10}$ alkyl)

Scheme 47

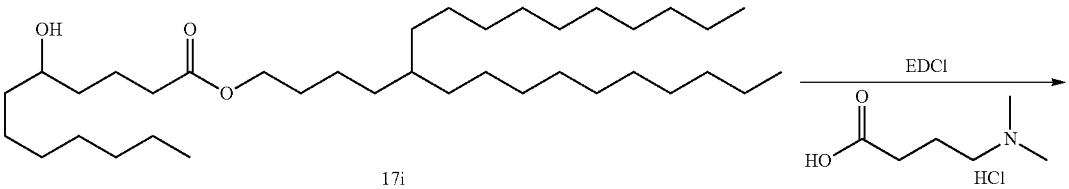

17i

-continued

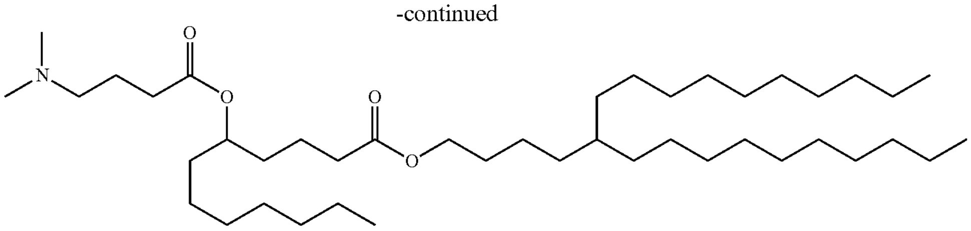

Lipid 3

Reaction of 0.3 g of compound 17g was run using the same procedure as in the previous description for Lipid 12 to afford 0.26 g (72%) of Lipid 3. $^{1}H$ NMR (300 MHz, d-chloroform) δ 4.90-4.84 (m, 1H), 4.05 (t, 2H), 2.33-2.22 (m, 6H), 2.21 (s, 6H), 1.82-1.70 (m, 2H), 1.66-1.45 (m, 9H), 1.35-1.10 (m, 52H), 0.87 (t, 9H). MS found 680.6 $[M+H]^+$ calc. 679.7 for $[C_{43}H_{85}NO_4]$.

5-dodecylheptadecyl 5-((4-(dimethylamino)butanoyl)oxy)dodecanoate (26 where $R^{6a}$ and $R^{6b}$ are each $C_{12}$ alkyl)

Scheme 48

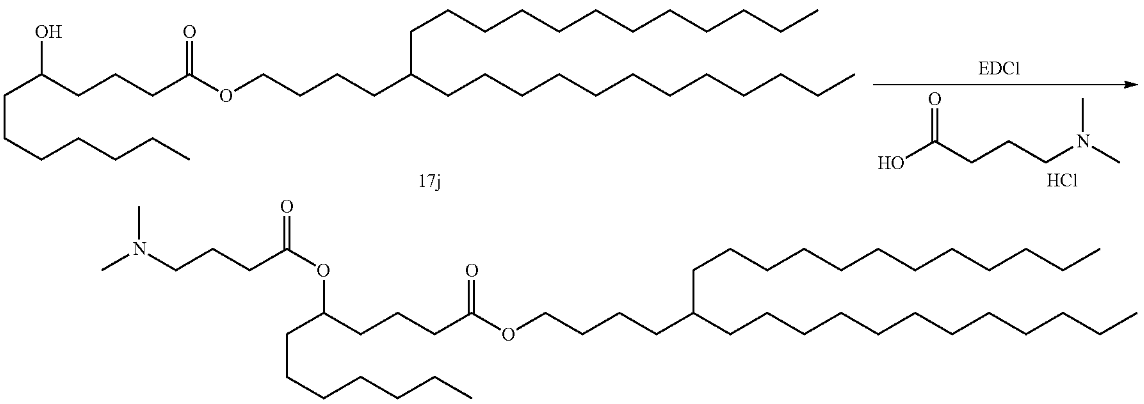

17j

Lipid 4

Reaction of 0.2 g of compound 17h was run using the same procedure as in the previous description for Lipid 12 to afford 0.15 g (63%) of Lipid 4 (300 MHz, d-chloroform) δ 4.90-4.84 (m, 1H), 4.05 (t, 2H), 2.34-2.26 (m, 6H), 2.25 (s, 6H), 1.83-1.70 (m, 2H), 1.67-1.40 (m, 8H), 1.35-1.10 (m, 61H), 0.87 (t, 9H). MS found 736.7 $[M+H]^+$ calc. 735.7 for $[C_{47}H_{93}NO_4]$.

Example 12: Synthesis of Lipid 13, Lipid 5, and Lipid 6

Referring to Scheme 7 and Alternative Synthesis (C) in Example 2, this example describes synthesis of Lipid 13, Lipid 5, and Lipid 6.

Synthesis of 6-oxotridecanoic acid (29)

Please refer to the synthesis procedure of compound 29 as described in Alternative Synthesis (C) in Example 2.

Synthesis of 4-octyldodecane-1,4-diol, 4-decyltetradecane-1,4-diol, and 4-dodecylhexadecane-1,4-diol 4-octyldodecane-1,4-diol (23a where $R^{6a}$ and $R^{6b}$ are each $C_8$ alkyl)

Octyl magnesium bromide (29 mL, 58 mmol) was measured to an oven dried round base flask under $N_2$ and cooled to 0° C. Then 7-butyrolactone (1.8 mL, 23.2 mmol) solution in $Et_2O$ (5 mL) was added dropwise at 0° C. The resulting mixture was stirred at room temperature for 16 h under $N_2$. The reaction was quenched with 3 M HCl solution and extracted with ether. The organic layer was washed with $H_2O$ and dried over anhydrous $Na_2SO_4$. Solvent was evaporated under vacuo and purified by column chromatography using 0-50% EtOAc in hexane as eluent to afford 4-octyldodecane-1,4-diol. $^{1}H$ NMR (300 MHz, d-chloroform) δ 3.65 (t, J=5.7 Hz, 2H), 1.60-1.44 (m, 7H), 1.25 (s, 26H), 0.87 (t, J=6.5 Hz, 6H).

4-decyltetradecane-1,4-diol (23a where $R^{6a}$ and $R^{6b}$ are each $C_{10}$ alkyl)

Decyl magnesium bromide (70 mL, 70 mmol) was measured to an oven dried rb flask under $N_2$ and cooled to 0° C. Then 7-butyrolactone (4.5 mL, 28 mmol) solution in $Et_2O$ (6.3 mL) was added dropwise at 0° C. The resulting mixture was stirred at room temperature for 16 h under $N_2$. The reaction was quenched with 1 M HCl solution and extracted with ether. The organic layer was washed with $H_2O$ and dried over anhydrous $Na_2SO_4$. Solvent was evaporated under vacuo and purified by column chromatography using 0-50% EtOAc in hexane as eluent to afford 4-decyltetradecane-1,4-diol (7.1 g, 71%). $^1H$ NMR (300 MHz, d-chloroform) δ 3.64 (t, J=5.5 Hz, 2H), 1.60-1.43 (m, 7H), 1.26 (s, 33H), 0.87 (t, J=6.5 Hz, 6H).

4-dodecylhexadecane-1,4-diol (23a where $R^{6a}$ and $R^{6b}$ are each $C_{12}$ alkyl)

Dodecyl magnesium bromide (100 mL, 70 mmol) was measured to an oven dried rb flask under $N_2$ and cooled to 0° C. Then 7-butyrolactone (1.8 g, 28 mmol) solution in $Et_2O$ (5 mL) was added dropwise at 0° C. The resulting mixture was stirred at room temperature for 16 h under $N_2$. The reaction was quenched with 1 M HCl solution and extracted with ether. The organic layer was washed with $H_2O$ and dried over anhydrous $Na_2SO_4$. Solvent was evaporated under vacuo and purified by column chromatography using 0-50% EtOAc in hexane as eluent to afford 4-dodecylhexadecane-1,4-diol (7.24 g, 62%). $^1H$ NMR (300 MHz, d-chloroform) δ 3.66 (t, J=4.8 Hz, 2H), 1.68-1.36 (m, 7H), 1.25 (s, 40H), 0.87 (t, J=6.6 Hz, 6H).

Synthesis of 4-octyldodec-3-en-1-ol, 4-decyltetradec-3-en-1-ol, and 4-dodecylhexane adec-3-en-1-ol 4-octyldodec-3-en-1-ol (24a where $R^{6a}$ and $R^{6b}$ are each $C_8$ alkyl)

Compound 23b (2.34 g, 7.4 mmol) and PTSA (para-toluene sulfonic acid) (0.28 g, 1.48 mmol) was dissolved in toluene (20 mL) and microwaved at 60° C. for 2 h. Then solvent was evaporated under vacuo and purified by column chromatography using 0-20% EtOAc in Hexane as eluent to afford 4-octyldodec-3-en-1-ol (0.41 g, 22%). $^1H$ NMR (300 MHz, d-chloroform) δ 5.14 (t, J=7.1 Hz, 1H), 3.64 (q, J=6.3 Hz, 2H), 2.10-1.89 (m, 6H), 1.67-1.57 (m, 3H), 1.28 (d, J=8.8 Hz, 24H), 0.88 (t, J=6.7 Hz, 6H).

4-decyltetradec-3-en-1-ol (24a where $R^{6a}$ and $R^{6b}$ are each $C_{10}$ alkyl)

Compound 23c (3.0 g, 8.1 mmol) and PTSA (para-toluene sulfonic acid) (0.31 g, 1.6 mmol) was dissolved in toluene (25 mL) and microwaved at 65° C. for 1 h. Then solvent was evaporated under vacuo and purified by column chromatography using 0-20% EtOAc in Hexane as eluent to afford 4-decyltetradec-3-en-1-ol (1.40 g, 49%). $^1H$ NMR (300 MHz, d-chloroform) δ 5.14 (t, J=7.1 Hz, 1H), 3.64 (q, J=6.3 Hz, 2H), 2.07-1.97 (m, 6H), 1.76-1.58 (m, 3H), 1.26 (s, 32H), 0.87 (t, J=6.6 Hz, 6H).

4-dodecylhexane adec-3-en-1-ol (24a where $R^{6a}$ and $R^{6b}$ are each $C_{12}$ alkyl)

Compound 23d (4.0 g, 9.4 mmol) and PTSA (para-toluenesulfonic acid) (0.36 g, 1.8 mmol) was dissolved in toluene (30 mL) and microwaved at 60° C. for 1 h. Then solvent was evaporated under vacuo and purified by column chromatography using 0-20% EtOAc in hexane as eluent to afford 4-dodecylhexane adec-3-en-1-ol (1.45 g, 38%). $^1H$ NMR (300 MHz, d-chloroform) δ 5.12 (dd, J=17.5, 7.5 Hz, 1H), 3.62 (p, J=6.6 Hz, 2H), 2.10-1.96 (m, 6H) 2.02, 1.74-1.51 (m, 3H), 1.25 (s, 40H), 0.88 (t, J=6.6 Hz, 6H).

Synthesis of 4-octyldodecan-1-ol, 4-decyltetradecan-1-ol, and 4-dodecylhexane adecan-1-ol 4-octyldodecan-1-ol (13c where $R^{6a}$ and $R^{6b}$ are each $C_8$ alkyl)

Compound 24b (0.24 g, 0.8 mmol) was dissolved in 5 mL of EtOAc and degassed and 0.1 g of 5% Pd/C was added and degassed again. Reaction was kept under $H_2$ for 4 h. Then reaction mixture was filtered through celite. Solvent was evaporated under vacuo and purified by column chromatography using 0-20% EtOAc in Hexane as eluent to afford 4-octyldodecan-1-ol (0.14 g, 58%). $^1H$ NMR (300 MHz, d-chloroform) δ 3.62 (dd, J=12.1, 6.6 Hz, 2H), 1.60-1.45 (m, 3H), 1.26 (t, J=9.8 Hz, 33H), 0.88 (t, J=6.7 Hz, 6H).

4-decyltetradecan-1-ol (13c where $R^{6a}$ and $R^{6b}$ are each $C_{10}$ alkyl)

Compound 24c (1.4 g, 3.98 mmol) was dissolved in 30 mL of EtOAc and degassed and 0.75 g of 5% Pd/C was added and degassed again. Reaction was kept under $H_2$ for 4 h. Then reaction mixture was filtered through celite. Solvent was evaporated under vacuo and purified by column chromatography using 0-20% EtOAc in hexane as eluent to afford 4-decyltetradecan-1-ol (0.42 g, 31%). $^1H$ NMR (300 MHz, d-chloroform) δ 3.62 (dd, J=12.1, 6.6 Hz, 2H), 1.56-1.51 (m, 3H), 1.26 (s, 41H), 0.88 (t, J=6.7 Hz, 6H).

4-dodecylhexane adecan-1-ol (13c where $R^{6a}$ and $R^{6b}$ are each $C_{12}$ alkyl)

Compound 24d (1.45 g, 3.55 mmol) was dissolved in 30 mL of EtOAc and degassed and 0.1 g of 5% Pd/C was added and degassed again. Reaction was kept under $H_2$ for 1.5 h. Then reaction mixture was filtered through celite. Solvent was evaporated under vacuo and purified by column chromatography using 0-10% EtOAc in hexane as eluent to afford 4-dodecylhexane adecan-1-ol (0.82 g, 56%). $^1H$ NMR (300 MHz, d-chloroform) δ 3.62 (dd, J=12.1 Hz, 2H), 1.56-1.51 (m, 3H), 1.26 (s, 49H), 0.88 (t, J=6.6 Hz, 6H).

Step 1: Synthesis of 4-octyldodecyl 6-oxotridecanoate, 4-decyltetradecyl 6-oxotridecanoate, and 4-dodecylhexane adecyl 6-oxotridecanoate 4-octyldodecyl 6-oxotridecanoate (34 where $R^{6a}$ and $R^{6b}$ are each $C_8$ alkyl)

To a solution of compound 33 (0.13 g, 0.6 mmol) in DCM (6 mL) and, EDCI (0.14 g, 0.72 mmol), and DMAP (0.09 g, 0.72 mmol) were added and stirred for 15 min under $N_2$ atmosphere. Then 4-octyldodecan-1-ol (13c where $R^{6a}$ and $R^{6b}$ are each $C_8$ alkyl) (0.2 g, 0.7 mmol) was added to the reaction mixture and stirred overnight. Next day reaction was diluted with DCM. The organic layer was washed with $H_2O$ and brine and dried over anhydrous $Na_2SO_4$. Solvent was evaporated under vacuo. and purified by column chromatography using 0-30% EtOAc in hexane as eluent to afford 4-octyldodecyl 6-oxotridecanoate (0.11 g, 43%). $^1$H NMR (300 MHz, d-chloroform) δ 4.03 (t, J=6.8 Hz, 2H), 2.40-2.30 (m, 6H), 1.59 (dd, J=7.2, 3.6 Hz, 8H), 1.24 (s, 39H), 0.87 (t, J=6.6 Hz, 9H).

4-decyltetradecyl 6-oxotridecanoate (34 where $R^{6a}$ and $R^{6b}$ are each $C_{10}$ alkyl)

To a solution of compound 33 (0.22 g, 1 mmol) in DCM (11 mL) and EDCI (0.23 g, 1.2 mmol), and DMAP (0.15 g, 1.2 mmol) were added and stirred for 15 min under $N_2$ atmosphere. Then 4-decyltetradecan-1-ol (13c where $R^{6a}$ and $R^{6b}$ are each $C_{10}$ alkyl) (0.42 g, 1.2 mmol) was added to the reaction mixture and stirred overnight. Next day reaction was diluted with DCM. The organic layer was washed with $H_2O$ and brine and dried over anhydrous $Na_2SO_4$. Solvent was evaporated under vacuo and purified by column chromatography using 0-30% EtOAc in hexane as eluent to afford 4-decyltetradecyl 6-oxotridecanoate (0.25 g, 44%). $^1$H NMR (300 MHz, d-chloroform) δ 4.03 (t, J=6.8 Hz, 2H), 2.48-2.26 (m, 6H), 1.60-1.55 (m, 8H), 1.24 (s, 47H), 0.87 (t, J=6.6 Hz, 9H).

4-dodecylhexane adecyl 6-oxotridecanoate (34 where $R^{6a}$ and $R^{6b}$ are each $C_{12}$ alkyl)

To a solution of compound 33 (0.55 g, 2.4 mmol) in DCM (22 mL) and, EDCI (0.46 g, 2.4 mmol), and DMAP (0. g, 1.2 mmol) were added and stirred for 15 min under $N_2$ atmosphere. Then 4-dodecylhexane adecan-1-ol (13c where $R^{6a}$ and $R^{6b}$ are each $C_{12}$ alkyl) (0.82 g, 2 mmol) was added to the reaction mixture and stirred overnight. Next day reaction was diluted with DCM. The organic layer was washed with $H_2O$ and brine and dried over anhydrous $Na_2SO_4$. Solvent was evaporated under vacuo. and purified by column chromatography using 0-30% EtOAc in hexane as eluent to afford 4-dodecylhexane adecyl 6-oxotridecanoate (0.53 g, 43%). $^1$H NMR (300 MHz, d-chloroform) δ 4.03 (t, J=6.8 Hz, 2H), 2.41-2.30 (m, 6H), 1.67-1.47 (m, 9H), 1.24 (d, 55H), 0.87 (t, J=6.6 Hz, 9H).

Step 2: Synthesis of 4-octyldodecyl 6-hydroxytridecanoate, 4-decyltetradecyl 6-hydroxytridecanoate, and 4-dodecylhexane adecyl 6-hydroxytridecanoate 4-octyldodecyl 6-hydroxytridecanoate (35 where $R^{6a}$ and $R^{6b}$ are each $C_8$ alkyl)

To a solution of 4-octyldodecyl 6-oxotridecanoate (34 where $R^{6a}$ and $R^{6b}$ are each $C_8$ alkyl) (0.3 g, 0.6 mmol) in 4 mL of THF:MeOH (1:1) was added $NaBH_4$ (0.01 g, 0.26 mmol) at 0° C. and stirred for 1 h, under $N_2$ atmosphere. The reaction was quenched with saturated $NH_4Cl$ solution and extracted with EtOAc. The organic phase was washed with brine and dried over anhydrous $Na_2SO_4$. Solvent was evaporated under vacuo. and purified by column chromatography using 0-20% EtOAc in hexane as eluent to afford 4-octyldodecyl 6-hydroxytridecanoate (0.09 g, 70%). $^1$H NMR (300 MHz, d-chloroform) δ 4.03 (t, J=6.8 Hz, 2H), 3.60 (s, 1H), 2.31 (t, J=7.4 Hz, 2H), 1.66-1.34 (m, 44H), 1.24 (s, 40H), 0.88 (t, J=6.6 Hz, 9H).

4-decyltetradecyl 6-hydroxytridecanoate (35 where $R^{6a}$ and $R^{6b}$ are each $C_{10}$ alkyl)

To a solution of 4-decyltetradecyl 6-oxotridecanoate (34 where $R^{6a}$ and $R^{6b}$ are each $C_{10}$ alkyl)_(0.51 g, 0.82 mmol) in 16 mL of THF:MeOH (1:1) was added $NaBH_4$ (0.03 g, 0.82 mmol) at 0° C. and stirred for 1 h, under $N_2$ atmosphere. The reaction was quenched with saturated $NH_4Cl$ solution and extracted with EtOAc. The organic phase was washed with brine and dried over anhydrous $Na_2SO_4$. Solvent was evaporated under vacuo. and purified by column chromatography using 0-10% EtOAc in hexane as eluent to afford 4-decyltetradecyl 6-hydroxytridecanoate (0.48 g, 94%). $^1$H NMR (300 MHz, d-chloroform) δ 4.03 (t, J=6.8 Hz, 2H), 3.60 (s, 1H), 2.31 (t, J=7.4 Hz, 2H), 1.66-1.37 (m, 8H), 1.26 (s, 59H), 0.87 (t, J=6.6 Hz, 9H).

4-dodecylhexane adecyl 6-hydroxytridecanoate (35 where $R^{6a}$ and $R^{6b}$ are each $C_{12}$ alkyl)

To a solution of 4-dodecylhexane adecyl 6-oxotridecanoate (34 where $R^{6a}$ and $R^{6b}$ are each $C_{12}$ alkyl)_(0.51 g, 0.82 mmol) in 16 mL of THF:MeOH (1:1) was added $NaBH_4$ (0.03 g, 0.82 mmol) at 0° C. and stirred for 1 h, under $N_2$ atmosphere. The reaction was quenched with saturated $NH_4Cl$ solution and extracted with EtOAc. The organic phase was washed with brine and dried over anhydrous $Na_2SO_4$. Solvent was evaporated under vacuo and purified by column chromatography using 0-10% EtOAc in hexane as eluent to afford 4-dodecylhexane adecyl 6-hydroxytridecanoate (0.48 g, 94%). $^1$H NMR (300 MHz, d-chloroform) δ 4.03 (t, J=6.8 Hz, 2H), 3.60 (s, 1H), 2.31 (t, J=7.4 Hz, 2H), 1.66-1.37 (m, 8H), 1.26 (s, 59H), 0.87 (t, J=6.6 Hz, 9H).

Step 3: Synthesis of 4-octyldodecyl 6-((4-(dimethylamino)butanoyl)oxy)tridecanoate (Lipid 13), 4-decyltetradecyl 6-((4-(dimethylamino)butanoyl)oxy)tridecanoate (Lipid 5), and 4-dodecylhexane adecyl 6-((4-(dimethylamino)butanoyl)oxy)tridecanoate (Lipid 6)

4-octyldodecyl 6-((4-(dimethylamino)butanoyl)oxy)tridecanoate (36 where $R^{6a}$ and $R^{6b}$ are each $C_8$ alkyl)

To a solution of compound 4-octyldodecyl 6-hydroxytridecanoate (35 where $R^{6a}$ and $R^{6b}$ are each $C_8$ alkyl) (0.09 g, 0.18 mmol) and 4-(dimethylamino)butanoic acid (0.04 g, 0.3 mmol) in DCM (2 mL), 0.11 mL of DIPEA was added. Then EDCI (0.06 g, 0.27 mmol), and DMAP (0.0005 g, 0.054 mmol) were added, and the mixture was stirred overnight at room temperature under $N_2$ atmosphere. Next day reaction was diluted with DCM. The organic layer was washed with $NaHCO_3$ (aq) and dried over anhydrous $Na_2SO_4$. Solvent was evaporated under vacuo and purified by column chromatography using 0-5% MeOH in DCM as eluent to afford Lipid 13 (0.08 g, 72%). $^1$H NMR (300 MHz, d-chloroform) δ 4.86 (t, J=6.1 Hz, 1H), 4.03 (t, J=6.8 Hz, 2H), 2.31-2.25 (m, 5H), 2.21 (s, 6H), 1.78 (p, J=7.5 Hz, 2H), 1.68-1.42 (m, 8H), 1.24 (d, J=8.5 Hz, 39H), 0.87 (dd, J=6.8, 4.8 Hz, 9H). MS found 624.5 $[M+H]^+$, calcd 623.59 for $[C_{39}H_{77}NO_4]$.

4-decyltetradecyl 6-((4-(dimethylamino)butanoyl)oxy)tridecanoate (36 where $R^{6a}$ and $R^{6b}$ are each $C_{10}$ alkyl)

To a solution of compound 4-decyltetradecyl 6-hydroxytridecanoate (35 where $R^{6a}$ and $R^{6b}$ are each $C_{10}$ alkyl) (0.21 g, 0.37 mmol) and 4-(dimethylamino)butanoic acid (0.093 g, 0.56 mmol) in DCM (2 mL), 0.23 mL of DIPEA was added. Then EDCI (0.107 g, 0.56 mmol), and DMAP (0.02 g, 0.17 mmol) were added, and the mixture was stirred overnight at room temperature under $N_2$ atmosphere. Next day reaction was diluted with DCM. The organic layer was washed with $NaHCO_3$ (aq) and dried over anhydrous $Na_2SO_4$. Solvent was evaporated under vacuo. and purified by column chromatography using 0-5% MeOH in DCM as eluent to afford Lipid 5 (0.09 g, 43%). $^1H$ NMR (300 MHz, d-chloroform) δ 4.86 (t, J=6.3 Hz, 1H), 4.03 (t, J=6.8 Hz, 2H), 2.42-2.22 (m, 5H), 2.21 (s, 6H), 1.78 (p, J=7.5 Hz, 2H), 1.67-1.45 (m, 8H), 1.24 (s, 52H), 0.87 (t, J=6.5 Hz, 9H). MS found 680.6 $[M+H]^+$, calcd 679.65 for $[C_{43}H_{85}NO_4]$.

4-dodecylhexane adecyl 6-((4-(dimethylamino)butanoyl)oxy)tridecanoate (36 where $R^{6a}$ and $R^{6b}$ are each $C_{12}$ alkyl)

To a solution of compound 4-dodecylhexane adecyl 6-hydroxytridecanoate (35 where $R^{6a}$ and $R^{6b}$ are each $C_{12}$ alkyl) (0.48 g, 0.77 mmol) and 4-(dimethylamino)butanoic acid (0.20 g, 1.16 mmol) in DCM (8 mL), 0.5 mL of DIPEA was added. Then EDCI (0.22 g, 1.16 mmol), and DMAP (0.03 g, 0.23 mmol) were added, and the mixture was stirred overnight at room temperature under $N_2$ atmosphere. Next day reaction was diluted with DCM. The organic layer was washed with $NaHCO_3$ (aq) and dried over anhydrous $Na_2SO_4$. Solvent was evaporated under vacuo and purified by column chromatography using 0-5% MeOH in DCM as eluent to afford Lipid 6 (0.15 g, 26%). $^1H$ NMR (300 MHz, d-chloroform) δ 4.86 (t, J=6.2 Hz, 1H), 4.02 (t, J=6.8 Hz, 2H), 2.38-2.23 (m, 5H), 2.21 (s, 6H), 1.89-1.65 (m, 6H), 1.65-1.40 (m, 8H), 1.24 (d, J=8.6 Hz, 56H), 0.87 (t, J=6.5 Hz, 9H). MS found 736.7 $[M+H]^+$, calcd 735.71 for $[C_{47}H_{93}NO_4]$.

Example 13: Synthesis of Lipid 14, Lipid 7, and Lipid 8

Referring to Scheme 8 and Alternative Synthesis (D) in Example 2, this example describes synthesis of Lipid 14, Lipid 7, and Lipid 8.

Synthesis of 7-(methoxy(methyl)amino)-7-oxoheptanoic acid (25a)

Please refer to the synthesis procedure of compound 25a as described in Alternative Synthesis (D) in Example 2.

Synthesis of ethyl 3-octylundec-2-enoate, ethyl 3-decyltridec-2-enoate, and 3-dodecylpentadec-2-enoate Ethyl 3-octylundec-2-enoate (12b where $R^{6a}$ and $R^{6b}$ are each $C_8$ alkyl)

To an ice-cold solution of 9-heptadecanone (10 where $R^{6a}$ and $R^{6b}$ are each $C_8$ alkyl) (2.05 g, 19.7 mmol) in 190 mL of THF (anh) was added neat ethyl 2-(diethoxyphosphoryl) acetate (33.4 g, 149 mmol) dropwise. The reaction was stirred for 30 min followed up by portionwise addition of NaH (5.3 g, 133 mmol, 60% in oil). The reaction mixture was refluxed for 18 h, cooled to 0° C., quenched with 300 mL of water, and extracted with ether. The organic layer was washed several times with water, brine, dried over $Na_2SO_4$ and concentrated providing 7.5 g of crude material which was used as is for the next step. $^1H$ NMR (300 MHz, d-chloroform) δ: 5.60 (s, 1H), 4.14 (q, J=7.1 Hz, 2H), 2.60-2.54 (m, 2H), 2.12-2.08 (m, 2H), 1.50-1.20 (m, 27H), 0.95-0.82 (m, 6H)

Ethyl 3-decyltridec-2-enoate (12b where $R^{6a}$ and $R^{6b}$ are each $C_{10}$ alkyl)

Crude product was obtained starting with 5.05 g of 11-heneicasanone (10 where $R^{6a}$ and $R^{6b}$ are each $C_{10}$ alkyl) and following the procedure above for analog ethyl 3-octylundec-2-enoate. The crude material was purified by column chromatography (1% EtOAc/hexanes) providing 5.2 g of pure ethyl 3-decyltridec-2-enoate (84% yield). $^1H$ NMR (300 MHz, d-chloroform) δ: 5.60 (s, 1H), 4.12 (q, J=7.1 Hz, 2H), 2.60-2.54 (m, 2H), 2.13-2.09 (m, 2H), 1.51-1.20 (m, 35H), 0.90-0.80 (m, 6H).

3-dodecylpentadec-2-enoate (12b where $R^{6a}$ and $R^{6b}$ are each $C_{12}$ alkyl)

To an ice-cold solution of pentacosan-13-one (10 where $R^{6a}$ and $R^{6b}$ are each $C_{12}$ alkyl) (2.70 g, 7.36 mmol) in 74 mL of THF (anh) was added neat triethyl phosphonoacetate (10.23 mL, 51.5 mmol) dropwise. The reaction was stirred for 30 min followed up by portionwise addition of NaH (1.77 g, 44.1 mmol, 60% in oil). The reaction mixture was refluxed for 18 h, cooled to 0° C., quenched with 300 mL of water, and extracted with ether. The organic layer was washed several times with water, brine, dried over $Na_2SO_4$ and concentrated. The crude material was purified by column chromatography (hexanes-EtOAc) providing 2.96 g of compound 3-dodecylpentadec-2-enoate in 92% yield. $^1H$ NMR (300 MHz, d-chloroform) δ: 5.60 (s, 1H), 4.14 (q, J=7.1 Hz, 2H), 2.60-2.50 (m, 2H), 2.12-2.05 (m, 2H), 1.50-1.20 (m, 43H), 0.95-0.82 (m, 6H).

Synthesis of 3-octylundecan-1-ol, 3-decyltridecan-1-ol, and 3-dodecylpentadecan-1-ol 3-octylundecan-1-ol (13d where $R^{6a}$ and $R^{6b}$ are each $C_8$ alkyl) Crude ethyl 3-octylundec-2-enoate (12a where $R^{6a}$ and $R^{6b}$ are each $C_8$ alkyl) (1.2 g) was dissolved in 5 mL of THF, cooled to 0° C., and $LiAlH_4$ (7.5 mL, 2 M in THF) was added dropwise. The reaction mixture was left stirring overnight, allowed to warm up to room temperature, and then quenched at 0° C. by the addition of 8 mL of a $THF/H_2O$ mixture (1:1 by volume). The reaction mixture was extracted with EtOAc and filtered through celite. The organic phase was washed twice with water, brine, dried over $Na_2SO_4$, and concentrated. Purification by column chromatography ($CH_2Cl_2$-EtOAc) provided 0.57 g of 3-octylundec-2-en-1-ol. Yield for 2 steps is 64%. $^1H$ NMR (300 MHz, d-chloroform) δ: 5.3 (t, J=7.1 Hz, 1H), 4.14 (d, J=7.1 Hz, 2H), 2.01-2.15 (m, 4H), 1.60-1.10 (m, 25H), 1.82-1.95 (m, 6H).

3-octylundec-2-en-1-ol (0.57 g, 2.0 mmol) was dissolved in EtOAc and subjected to reduction with $H_2$ (1 atm) using 200 mg of wet Pd/C-catalyst. Clean conversion provided 0.55 g (97% yield) of compound 3-octylundecan-1-ol. $^1H$ NMR (300 MHz, d-chloroform) δ: 3.66 (t, J=6.9 Hz, 2H), 1.51 (m, 2H), 1.41 (br s, 1H), 1.10-1.29 (m, 29H), 1.81-1.90 (m, 6H).

3-decyltridecan-1-ol (13d where $R^{6a}$ and $R^{6b}$ are each $C_{10}$ alkyl)

Starting with 1.0 g of ethyl 3-decyltridec-2-enoate (12a where $R^{6a}$ and $R^{6b}$ are each $C_{10}$ alkyl) and following the procedure for analog of 3-octylundec-2-en-1-ol, 0.90 g of 3-decyltridec-2-en-1-ol was obtained in quantitative yield.

$^1$H NMR (300 MHz, d-chloroform) δ: 5.37 (t, J=7.1 Hz, 1H), 4.13 (d, J=7.1 Hz, 2H), 1.98-2.10 (m, 4H), 1.50-1.10 (m, 33H), 1.82-1.95 (m, 6H).

3-decyltridecan-1-ol was obtained according to the procedure above for analog 3-octylundecan-1-ol, starting with 0.9 g of 5a and providing 840 mg of pure 3-decyltridecan-1-ol in 93% yield. $^1$H NMR (300 MHz, d-chloroform) δ: 3.66 (t, J=6.9 Hz, 2H), 1.60-1.45 (m, 2H), 1.42 (br s, 1H), 1.10-1.29 (m, 37H), 1.81-1.90 (m, 6H).

3-dodecylpentadecan-1-ol (13d where $R^{6a}$ and $R^{6b}$ are each $C_{12}$ alkyl)

3-dodecylpentadec-2-enoate (12a where $R^{6a}$ and $R^{6b}$ are each 12) (2.96 g, 6.78 mmol) was dissolved in 150 mL of EtOAc and subjected to reduction with $H_2$ (1 atm) using 200 mg of wet 10% Pd/C-catalyst. Clean conversion provided 2.95 g (99% yield) of compound ethyl 3-dodecylpentadecanoate. $^1$H NMR (300 MHz, d-chloroform) δ: 4.12 (q, J=7.1 Hz, 2H), 2.20 (d, J=6.9, 2H), 1.90-1.80 (m, 1H), 135-1.20 (m, 47H), (1.81-1.90 (m, 6H).

Ethyl 3-dodecylpentadecanoate (2.94 g, 6.70 mmo) was dissolved in 10 mL of THF, cooled to 0° C., and $LiAlH_4$ (6.0 mL, 2 M in THF, 12.1 mmol) was added dropwise. The reaction mixture was left stirring overnight, allowed to warm up to room temperature, and then quenched at 0° C. by the addition of 20 mL of a THF/$H_2O$ mixture (1:1 by volume). The reaction mixture was extracted with EtOAc and filtered through celite. The organic phase was washed twice with water, brine, dried over $Na_2SO_4$, and concentrated. Purification by column chromatography ($CH_2Cl_2$-EtOAc) provided 2.6 g of 3-dodecylpentadecan-1-ol in 98% yield. $^1$H NMR (300 MHz, d-chloroform) δ: 3.66 (t, J=6.9 Hz, 2H), 1.60-1.45 (m, 2H), 1.42 (br s, 1H), 1.10-1.29 (m, 45H), 1.81-1.90 (m, 6H).

Step 1: Synthesis of 3-octylundecyl 7-(methoxy (methyl)amino)-7-oxoheptanoate, 3-decyltridecyl 7-(methoxy(methyl)amino)-7-oxoheptanoate, and 3-dodecylpentadecyl 7-(methoxy(methyl)amino)-7-oxoheptanoate 3-octylundecyl 7-(methoxy(methyl)amino)-7-oxoheptanoate (15d where $R^{6a}$ and $R^{6b}$ are each $C_8$ alkyl)

Compound 25a (324 mg, 1.6 mmol) and 3-octylundecan-1-ol (13d where $R^{6a}$ and $R^{6b}$ are each $C_8$ alkyl) (545 mg, 1.9 mmol) were dissolved in 4 mL of dichloromethane and then DMAP (290 mg, 2.4 mmol) and EDCI (380 mg, 2.0 mmol) were added to this solution at room temperature. After stirring overnight, the reaction was quenched with $NH_4Cl$ (saturated aqueous solution) and extracted with dichloromethane. Organic phase was washed with water, brine, dried over $Na_2SO_4$ and concentrated. Column chromatography purification (Hexane-EtOAc) provided 0.50 g (66% yield) of pure title compound. $^1$H NMR (300 MHz, d-chloroform) δ: 4.06 (t, J=7.1, 2H), 3.67 (s, 3H), 3.17 (s, 3H), 2.41 (t, J=7.4, 2H), 2.29 (t, J=7.4, 2H), 1.7-1.5 (m, 6H), 1.4-1.1 (m, 31H), 0.87 (t, J=6.8, 6H) 3-decyltridecyl 7-(methoxy (methyl)amino)-7-oxoheptanoate (15d where $R^{6a}$ and $R^{6b}$ are each $C_{10}$ alkyl) Starting with 0.40 g (1.97 mmol) of compound 25a and 0.84 g of 3-decyltridecan-1-ol (13d where $R^{6a}$ and $R^{6b}$ are each $C_{10}$ alkyl) and following the procedure above (for analog 3-octylundecyl 7-(methoxy (methyl)amino)-7-oxoheptanoate), 0.82 g of the title compound was obtained in 80% yield. $^1$H NMR (300 MHz, d-chloroform) δ: 4.06 (t, J=7.1, 2H), 3.67 (s, 3H), 3.17 (s, 3H), 2.41 (t, J=7.4, 2H), 2.29 (t, J=7.4, 2H), 1.7-1.5 (m, 6H), 1.4-1.1 (m, 39H), 0.87 (t, J=6.8, 6H).

3-dodecylpentadecyl 7-(methoxy(methyl)amino)-7-oxoheptanoate (15d where $R^{6a}$ and $R^{6b}$ are each $C_{12}$ alkyl)

Compound 25a (400 mg, 1.97 mmol) and 3-dodecylpentadecan-1-ol (13d where $R^{6a}$ and $R^{6b}$ are each $C_{12}$ alkyl) (980 mg, 1.46 mmol) were dissolved in 6 mL of dichloromethane and then DMAP (380 mg, 2.96 mmol) and EDCI (480 mg, 1.46 mmol) were added to this solution at room temperature. After stirring overnight, the reaction was quenched with $NH_4Cl$ (saturated aqueous solution) and extracted with dichloromethane. Organic phase was washed with water, brine, dried over $Na_2SO_4$ and concentrated. Column chromatography purification (Hexane-EtOAc) provided 1.0 g (92% yield) of pure title compound. $^1$H NMR (300 MHz, d-chloroform) δ, J (Hz): 4.06 (t, J=7.1, 2H), 3.67 (s, 3H), 3.17 (s, 3H), 2.41 (t, J=7.4, 2H), 2.29 (t, J=7.4, 2H), 1.7-1.5 (m, 6H), 1.4-1.1 (m, 47H), 0.87 (t, J=6.8, 6H).

Step 2: Synthesis of 3-octylundecyl 7-oxotetradecanoate, 3-decyltridecyl 7-oxotetradecanoate, and 3-dodecylpentadecyl 7-oxotetradecanoate 3-octylundecyl 7-oxotetradecanoate (16d where $R^{6a}$ and $R^{6b}$ are each $C_8$ alkyl)

3-octylundecyl 7-(methoxy(methyl)amino)-7-oxoheptanoate (15d where $R^{6a}$ and $R^{6b}$ are each $C_8$ alkyl) was co-evaporated several times with toluene and dried overnight over $P_2O_5$ prior to the reaction. Dry compound 3-octylundecyl 7-(methoxy(methyl)amino)-7-oxoheptanoate (0.50 g, 1.1 mmol) was dissolved in 4 mL of THF in a flame-dried rbf, cooled to 0° C., and heptyl magnesium bromide (1 M in ether) (1.3 mL, 1.3 mmol) was added dropwise. The reaction mixture was stirred at room temperature for 3.5 h, then cooled to 0° C., quenched with $NH_4Cl$ (sat) and extracted with hexanes several times. Organic phase was dried over $Na_2SO_4$, concentrated, and purified by column chromatography (0-10% EtOAc in hexanes) providing 225 mg (42% yield) of title compound. $^1$H NMR (300 MHz, d-chloroform) δ: 4.07 (t, J=7.1, 2H), 2.45-2.35 (m, 4H), 2.35-2.25 (m, 2H), 1.70-1.50 (m, 8H), 1.60-1.20 (m, 39H), 1.90-1.85 (m, 9H).

3-decyltridecyl 7-oxotetradecanoate (16d where $R^{6a}$ and $R^{6b}$ are each $C_{10}$ alkyl)

Starting with 0.82 g (1.56 mmol) of 3-decyltridecyl 7-(methoxy(methyl)amino)-7-oxoheptanoate (15d where $R^{6a}$ and $R^{6b}$ are each $C_{10}$ alkyl) and following the procedure above (for analog 3-octylundecyl 7-oxotetradecanoate), 0.43 g of the title compound was obtained in 49% yield. $^1$H NMR (300 MHz, d-chloroform) δ: 4.07 (t, J=7.1, 2H), 2.45-2.35 (m, 4H), 2.35-2.25 (m, 2H), 1.70-1.50 (m, 8H), 1.60-1.20 (m, 47H), 1.90-1.85 (m, 9H).

3-dodecylpentadecyl 7-oxotetradecanoate (16d where $R^{6a}$ and $R^{6b}$ are each $C_{12}$ alkyl)

3-dodecylpentadecyl 7-(methoxy(methyl)amino)-7-oxoheptanoate (15d where $R^{6a}$ and $R^{6b}$ are each $C_{12}$ alkyl) was co-evaporated several times with toluene and dried overnight over $P_2O_5$ prior to the reaction. Dry compound 3-dodecylpentadecyl 7-(methoxy(methyl)amino)-7-oxoheptanoate 1.0 g, 1.8 mmol) was dissolved in 7 mL of THF in a flame-dried rbf, cooled to 0° C., and heptyl magnesium bromide (1 M in ether) (2.7 mL, 2.7 mmol) was added dropwise. The reaction mixture was stirred at room temperature for 3.5 h, then cooled to 0° C., quenched with $NH_4Cl$ (sat) and extracted with hexanes several times. Organic phase was dried over $Na_2SO_4$, concentrated, and purified by column chromatography (0-10% EtOAc in hexanes) providing 560 mg (52% yield) of title compound. $^1H$ NMR (300 MHz, d-chloroform) δ: 4.07 (t, J=7.1, 2H), 2.45-2.35 (m, 4H), 2.35-2.25 (m, 2H), 1.70-1.50 (m, 8H), 1.60-1.20 (m, 55H), 1.90-1.85 (m, 9H).

Step 3: Synthesis of 3-octylundecyl 7-hydroxytetradecanoate, 3-decyltridecyl 7-hydroxytetradecanoate, and 3-dodecylpentadecyl 7-hydroxytetradecanoate 3-octylundecyl 7-hydroxytetradecanoate (17d where $R^{6a}$ and $R^{6b}$ are each $C_8$ alkyl)

To an ice-cold compound 3-octylundecyl 7-oxotetradecanoate (16d where $R^{6a}$ and $R^{6b}$ are each $C_8$ alkyl) (220 mg, 0.43 mmol) dissolved in THF:MeOH=1:1 (2 mL) was added $NaBH_4$ (24.5 mg, 0.65 mmol) in one portion. After 5 min the ice bath was removed, and the reaction mixture was stirred at room temperature overnight. After confirming full conversion by TLC, the reaction mixture was quenched with 2 ml of $NH_4Cl$ (sat) and concentrated to dryness. The residue was mixed with $CH_2Cl_2$, washed with water, dried over $Na_2SO_4$, concentrated, and purified by column chromatography (hexanes-EtOAc) providing 220 mg of title compound in quantitative yield. $^1H$ NMR (300 MHz, d-chloroform) δ: 4.10-4.04 (m, 2H), 3.60-3.50 (m, 1H), 2.35-2.25 (m, 2H), 170-1.15 (m, 52H), 0.8-0.9 (m, 9H).

3-decyltridecyl 7-hydroxytetradecanoate (17d where $R^{6a}$ and $R^{6b}$ are each $C_{10}$ alkyl)

Title compound was obtained according to the procedure above for analog 3-octylundecyl 7-hydroxytetradecanoate, starting with 310 mg of 3-decyltridecyl 7-oxotetradecanoate (16d where $R^{6a}$ and $R^{6b}$ are each $C_{10}$ alkyl) and providing 300 mg of pure title compound in quantitative yield. $^1H$ NMR (300 MHz, d-chloroform) δ: 4.10-4.04 (m, 2H), 3.60-3.50 (m, 1H), 2.35-2.25 (m, 2H), 170-1.15 (m, 60H), 0.8-0.9 (m, 9H).

3-dodecylpentadecyl 7-hydroxytetradecanoate (17d where $R^{6a}$ and $R^{6b}$ are each $C_{12}$ alkyl)

To an ice-cold 3-dodecylpentadecyl 7-oxotetradecanoate (16d where $R^{6a}$ and $R^{6b}$ are each $C_{12}$ alkyl) (250 mg, 0.40 mmol) dissolved in THF:MeOH=1:1 (2 mL) was added $NaBH_4$ (22.8 mg, 0.56 mmol) in one portion. After 5 min the ice bath was removed, and the reaction mixture was stirred at room temperature for 3 hrs. After confirming full conversion by TLC, the reaction mixture was quenched with 2 ml of $NH_4Cl$ (sat) and concentrated to dryness. The residue was mixed with $CH_2Cl_2$, washed with water, dried over $Na_2SO_4$, concentrated, and purified by column chromatography (hexanes-EtOAc) providing 250 mg of title compound in quantitative yield. $^1H$ NMR (300 MHz, d-chloroform) δ: 4.10-4.04 (m, 2H), 3.60-3.50 (m, 1H), 2.35-2.25 (m, 2H), 170-1.15 (m, 68H), 0.8-0.9 (m, 9H).

Step 4: Synthesis of 3-octylundecyl 7-((4-(dimethylamino)butanoyl)oxy)tetradecanoate (Lipid 14), 3-decyltridecyl-7-((4-(dimethylamino)butanoyl)oxy) tetradecanoate (Lipid 7), and 3-dodecylpentadecyl 7-((4-(dimethylamino)butanoyl)oxy)tetradecanoate (Lipid 8)

3-octylundecyl 7-((4-(dimethylamino)butanoyl)oxy) tetradecanoate (18d where $R^{6a}$ and $R^{6b}$ are each $C_8$ alkyl)

4-(dimethylamino)butanoic acid hydrochloride (99 mg, 0.60 mmol) was dissolved in a $CH_2Cl_2$/DMF (4 mL/0.5 mL) mixture followed up addition of TEA (0.1 mL, 0.65 mmol), compound 3-octylundecyl 7-hydroxytetradecanoate (17d where $R^{6a}$ and $R^{6b}$ are each $C_8$ alkyl) (220 mg, 0.43 mmol), EDCI (135 mg, 0.65 mmol) and DMAP (80 mg, 0.65 mmol). The reaction mixture was stirred overnight at room temperature, quenched with $NH_4Cl$ (sat), and extracted with $CH_2Cl_2$. The organic phase was dried over $Na_2SO_4$, concentrated, and purified by column chromatography (0-15% MeOH in $CH_2Cl_2$) providing 195 mg of Lipid 14 (73% yield). $^1H$ NMR (300 MHz, d-chloroform) δ: 4.90-4.80 (m, 1H), 4.10-4.02 (m, 2H), 2.35-2.20 (m, 6H), 2.20 (s, 6H), 1.83-1.70 (m, 2H), 1.70-1.45 (m, 8H), 1.35-1.15 (m, 43), 1.95-1.85 (m, 9H) MS found 624.5 $[M+H]^+$, calcd 623.5 for $[C_{39}H_{77}NO_4]$.

3-decyltridecyl-7-((4-(dimethylamino)butanoyl)oxy) tetradecanoate (18d where $R^{6a}$ and $R^{6b}$ are each $C_{10}$ alkyl)

Lipid 7 was obtained according to the procedure above for analog Lipid 14, starting with 430 mg of 3-decyltridecyl 7-hydroxytetradecanoate (17d where $R^{6a}$ and $R^{6b}$ are each $C_{10}$ alkyl) and providing 370 mg of pure Lipid 7 in 72% yield. $^1H$ NMR (300 MHz, d-chloroform) δ: 4.90-4.80 (m, 1H), 4.10-4.02 (m, 2H), 2.35-2.20 (m, 6H), 2.20 (s, 6H), 1.83-1.70 (m, 2H), 1.70-1.45 (m, 9H), 1.25-1.15 (m, 50), 1.95-1.85 (m, 9H). MS found 680.6 $[M+H]^+$, calcd 679.6 for $[C_{43}H_{85}NO_4]$.

3-dodecylpentadecyl 7-((4-(dimethylamino)butanoyl)oxy)tetradecanoate (38 where $R^{6a}$ and $R^{6b}$ are each $C_{12}$ alkyl)

4-(dimethylamino)butanoic acid hydrochloride (87.4 mg, 0.52 mmol) was dissolved in a $CH_2Cl_2$/DMF (3 mL/0.5 mL) mixture followed up addition of TEA (0.085 mL, 0.6 mmol), compound 3-dodecylpentadecyl 7-hydroxytetradecanoate (17d where $R^{6a}$ and $R^{6b}$ are each $C_{12}$ alkyl) (250 mg, 0.40 mmol), EDCI (115 mg, 0.60 mmol) and DMAP (74 mg, 0.60 mmol). The reaction mixture was stirred overnight at room temperature, quenched with $NH_4Cl$ (sat), and extracted with $CH_2Cl_2$. The organic phase was dried over $Na_2SO_4$, concentrated, and purified by column chromatography (0-15% MeOH in DCM)_providing 148 mg of Lipid 8 (51% yield). $^1H$ NMR (300 MHz, d-chloroform) δ:4.90-4.80 (m, 1H), 4.12-4.02 (m, 2H), 2.35-2.20 (m, 6H), 2.20 (s, 6H), 1.83-1.73 (m, 4H), 1.70-1.45 (m, 7H), 1.25-1.15 (m, 58H), 1.95-1.85 (m, 9H). MS found 736.6 $[M+H]^+$, calcd 735.6 for $[C_{47}H_{93}NO_4]$.

Example 14: Synthesis of Lipid 23, Lipid 24, and Lipid 25

Referring to Scheme 9 and Alternative Synthesis (E) in Example 2, this example describes synthesis of Lipid 15, Lipid 9, and Lipid 10.

Synthesis of 8-(methoxy(methyl)amino)-7-oxooctanoic acid (25b)

Please refer to the synthesis procedure of compound 25b as described in Alternative Synthesis (E) in Example 2.

Step 1: Synthesis of heptadecan-9-ol (1a) and pentacosan-13-ol (1c)

Henicosan-11-one 10b (compound 10 when $R^{6a}$ and $R^{6b}$ are each 10) was commercially available from at least TCI America, Inc. (Portland, OR., USA).

Pentacosan-13-ol (compound 1 when $R^{6a}$ and $R^{6b}$ are each $C_{12}$ alkyl)

Scheme 49

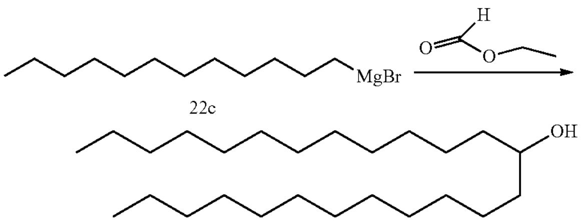

22c

1c

To an ice cold 0.5M/THF (40.5 mL, 0.020 mol) solution of 1-dodecylmagnesium bromide 22c in 10 mL of THF was added 0.69 g of ethylformate in 3 mL of THF. After stirring overnight at room temperature, the reaction was quenched with −60 mL $NH_4Cl$ (saturated aqueous solution) and extracted with either. Organic phase was washed with brine, dried over $Na_2SO_4$ and concentrated. The crude was purified by recrystallization from dichloromethane-hexanes providing 2.82 g (82% yield) of pure title compound. $^1H$ NMR (300 MHz, d-chloroform) δ: 3.58 (m, 1H), 1.50-1.12 (m, 45H), 0.90-0.80 (m, 6H).

Heptadecan-9-ol (compound 1 when $R^{6a}$ and $R^{6b}$ are each $C_6$ alkyl)

Scheme 51

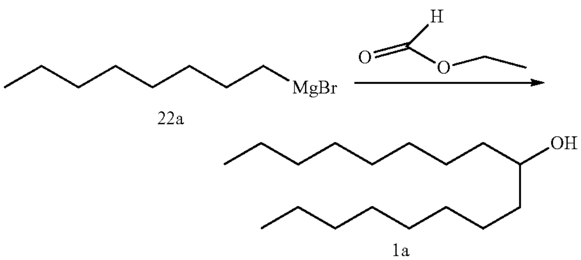

22a

1a

Alcohol 1a was prepared as in the previous description for pentacosan-13-ol (1c) using heptylmagnesium bromide 22a as starting material in 79% yield. $^1H$ NMR (300 MHz, d-chloroform) δ 3.57 (m, 1H), 2.37 (t, J=7.2, 1H), 1.50-1.12 (m, 28H), 0.90-0.80 (m, 6H).

Step 2: Synthesis of heptadecan-9-one (10a) and pentacosan-13-one (10c) Pentacosan-13-one (compound 10 when $R^{6a}$ and $R^{6b}$ are each $C_{12}$ alkyl)

Scheme 51

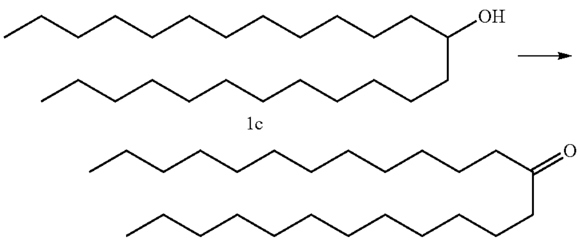

1c

10c

Compound 1c (0.82 g, 2.2 mmol) was mixed with 18 mL of dichloromethane, cooled to 0° C. and Dess-Martin periodinane (1.1 g, 2.5 mmol) was added to it in one portion. The reaction mixture was stirring at room temperature overnight, then cooled to 0° C. and quenched with 1:1 mixture of $NaHCO_3$ (sat) & $Na_2S_2O_3$ (15% aq) (25:25 mL) and stirred at room temperature for 20 min. Layers were separated, the organic layer was washed with water, brine, dried over $Na_2SO_4$ and concentrated providing 0.80 g of crude compound 10c which was used for the next step without purification. $^1H$ NMR (300 MHz, d-chloroform) δ: 2.40-2.30 (m, 4H), 1.61-1.50 (m, 5H), 1.30-1.15 (m, 38H), 0.90-0.80 (m, 6H).

Heptadecan-9-one (compound 10 when $R^{6a}$ and $R^{6b}$ are each $C_6$ alkyl)

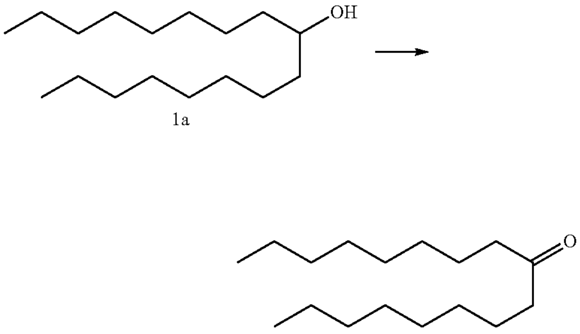

1a

10a

Compound 10a was prepared as in the previous description for pentacosan-13-one (10c) using heptadecane-9-ol (1a) as starting material. $^1H$ NMR (300 MHz, d-chloroform) δ 2.41-2.32 (m, 4H), 1.61-1.50 (m, 4H), 1.31-1.15 (m, 20H), 0.90-0.80 (m, 6H).

Step 3: Synthesis of 9-(methoxymethylene)heptadecane (31a), 11-(methoxymethylene)henicosane (31b), and 13-(methoxymethylene)pentacosane (31c)

Scheme 52

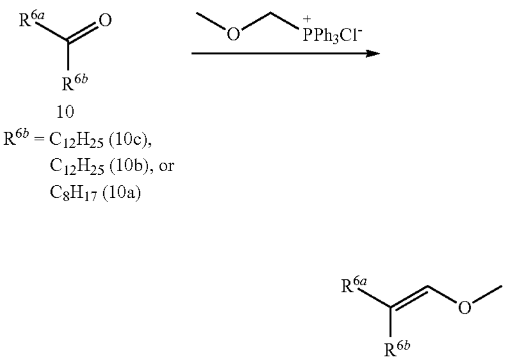

10

$R^{6a} = R^{6b} = C_{12}H_{25}$ (10c), $C_{12}H_{25}$ (10b), or $C_8H_{17}$ (10a)

31

$R^{6a} = R^{6b} = C_{12}H_{25}$ (31c), $C_{10}H_{21}$ (31b), or $C_8H_{17}$ (31a)

13-(methoxymethylene)pentacosane (compound 31 when $R^{6a}$ and $R^{6b}$ are each $C_{12}$ alkyl)

To a suspension containing of pentacosan-13-one (10c) (3.95 g, 10.80 mmol) and methoxymethyl)triphenyl phosphonium chloride (5.54 g, 16.20 mmol) in 130 mL of THF was added 1 M solution of potassium tert-butoxide (KOtBu) in THF (16.20 mL, 16.20 mmol) dropwise over 15 min. The reaction mixture was stirred overnight at room temperature, diluted with 450 mL of $Et_2O$ and washed with water, brine, dried over $Na_2SO_4$ and concentrated. The crude material was purified by column chromatography (0-2% EtOAc in hexanes) providing 4.30 g of compound 31c in 80% yield. $^1H$ NMR (300 MHz, d-chloroform) δ: 5.73 (s, 1H), 3.51 (s, 3H), 1.99-2.05 (m, 2H), 1.80-1.86 (m, 2H), 1.20-1.36 (m, 40H), 0.84-0.90 (m, 6H).

11-(methoxymethylene)henicosane (compound 31 when $R^{6a}$ and $R^{6b}$ are each $C_{10}$ alkyl)

Starting with 5.02 g of 10b and following the procedure for analog 31c, 4.29 g of 31b was obtained in 78% yield. $^1H$ NMR (300 MHz, d-chloroform) δ: 5.73 (s, 1H), 3.51 (s, 3H), 1.98-2.04 (m, 2H), 1.80-1.86 (m, 2H), 1.20-1.36 (m, 32H), 0.84-0.90 (m, 6H).

9-(methoxymethylene)heptadecane (compound 31 when $R^{6a}$ and $R^{6b}$ are each $C_8$ alkyl)

Starting with 2.57 g of 10a and following the procedure for analog 31c, 1.10 g of compound 31a was obtained in 40% yield. $^1H$ NMR (300 MHz, d-chloroform) δ: 5.73 (s, 1H), 3.51 (s, 3H), 1.99-2.04 (m, 2H), 1.80-1.86 (m, 2H), 1.22-1.36 (m, 24H), 0.84-0.90 (m, 6H).

Step 4: Synthesis of 2-octyldecanal (32a), 2-decyldodecanal (32b), and 2-dodecyltetradecanal (32c)

Scheme 53

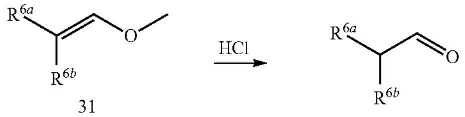

31

$R^{6a} = R^{6b} = C_{12}H_{25}$ (31c), $C_{10}H_{21}$ (31b), or $C_8H_{17}$ (31a)

32

$R^{6a} = R^{6b} = C_{12}H_{25}$ (32c), $C_{10}H_{21}$ (32b), or $C_8H_{17}$ (32a)

2-dodecyltetradecanal (compound 32 when $R^{6a}$ and $R^{6b}$ are each $C_{12}$ alkyl)

To an ice cold cloudy solution of 13-(methoxymethylene) pentacosane (31c) (3.4 g, 8.60 mmol) in dioxane/water (240 mL/125 mL) was added 4N HCl in dioxane (125 mL, 0.5 mol) dropwise, over 30 min. The reaction mixture was stirring at room temperature for 48 h. After confirming full conversion by TLC, the reaction mixture was diluted with ~0.5 L of ether, cooled to 0° C. and quenched by slow addition of $NaHCO_3$ (sat) & 10% $Na_2CO_3$. The layers were separated, and organic layer was washed with brine, dried over $Na_2SO_4$ and concentrated. The crude material was purified by column chromatography (0-5% EtOAc in hexanes) providing 3.28 g of compound 32c in quantitative yield. $^1H$ NMR (300 MHz, d-chloroform) δ: 9.51 (s, 1H), 2.19-2.26 (m, 1H), 1.55-1.65 (m, 2H), 1.38-1.48 (m, 2H), 1.18-1.32 (m, 40H), 0.82-0.90 (m, 6H).

2-decyldodecanal (compound 32 when $R^{6a}$ and $R^{6b}$ are each $C_{10}$ alkyl)

Starting with 4.29 g of 11-(methoxymethylene)henicosane (31b) and following the procedure for analog 32c, 3.95 g of compound 32b was obtained in 96% yield. $^1H$ NMR (300 MHz, d-chloroform) δ: 9.53 (s, 1H), 2.19-2.26 (m, 1H), 1.55-1.65 (m, 2H), 1.38-1.48 (m, 2H), 1.18-1.32 (m, 32H), 0.82-0.90 (m, 6H).

2-octyldecanal (compound 32 when $R^{6a}$ and $R^{6b}$ are each $C_8$ alkyl)

Starting with 1.10 g of 9-(methoxymethylene)heptadecane (31a) and following the procedure for analog 32c, 1.05 g of compound 32a was obtained in quantitative yield. $^1H$ NMR (300 MHz, d-chloroform) δ: 9.53 (s, 1H), 2.19-2.26 (m, 1H), 1.55-1.65 (m, 2H), 1.38-1.46 (m, 2H), 1.18-1.32 (m, 24H), 0.82-0.90 (m, 6H).

Step 5: Synthesis of 2-octyldecan-1-ol (13i), 2-decyldodecan-1-ol (13j), and 2-dodecyltetradecan-1-ol (13k)

Scheme 54

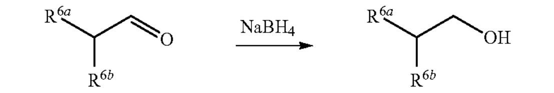

32

13e $R^{6a} = R^{6b} = C_{12}H_{25}$ (32c), $C_{10}H_{21}$ (32b), or $C_8H_{17}$ (32a)

$R^{6a} = R^{6b} = C_{12}H_{25}$ (13i), $C_{10}H_{21}$ (13j), or $C_8H_{17}$ (13k)

2-dodecyltetradecan-1-ol (compound 13e when $R^{6a}$ and $R^{6b}$ are each $C_{12}$ alkyl)

To an ice-cold compound 31c (3.27 g, 8.59 mmol) dissolved in THF:MeOH=1:1 (36 mL) was added $NaBH_4$ (550 mg, 14.60 mmol) in one portion. The reaction mixture was stirred overnight at room temperature, then quenched with 20 mL of $NH_4Cl$ (sat) at 0° C. and concentrated to dryness. The residue was mixed with $CH_2Cl_2$, washed with water, dried over $Na_2SO_4$, concentrated, and purified by column chromatography (hexanes-EtOAc) providing 3.12 g of compound 32c in quantitative yield. $^1H$ NMR (300 MHz, d-chloroform) δ: 3.53 (d, J=5.2 Hz, 2H), 1.42-1.45 (m, 1H), 1.20-1.35 (m, 45H), 0.82-0.90 (m, 6H).

2-decyldodecan-1-ol (compound 13e when $R^{6a}$ and $R^{6b}$ are each $C_{10}$ alkyl)

Starting with 4.17 g of 2-decyldodecanal (31b) and following the procedure for analog 13k, 4.10 g of compound 13j was obtained in quantitative yield. $^1H$ NMR (300 MHz, d-chloroform) δ: 3.53 (d, J=5.2 Hz, 2H), 1.55 (m, 1H), 1.20-1.35 (m, 37H), 0.82-0.90 (m, 6H).

2-octyldecan-1-ol (compound 13e when $R^{6a}$ and $R^{6b}$ are each $C_8$ alkyl)

Starting with 1.04 g of 2-octyldecanal (31a) and following the procedure for analog 13k, 1.02 g of compound 13i was obtained in quantitative yield. $^1H$ NMR (300 MHz, d-chloroform) δ: 3.53 (d, J=5.2 Hz, 2H), 1.55 (br s, 1H), 1.20-1.35 (m, 29H), 0.82-0.90 (m, 6H).

Step 6: Synthesis of 2-octyldecyl 8-(methoxy(methyl)amino)-8-oxooctanoate (15i), 2-decyldodecyl 8-(methoxy(methyl)amino)-8-oxooctanoate (15j), and 2-dodecyltetradecyl 8-(methoxy(methyl)amino)-8-oxooctanoate (15k)

Scheme 55

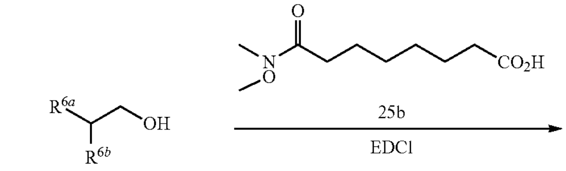

13e $R^{6a} = R^{6b} = C_{12}H_{25}$ (13i), $C_{10}H_{21}$ (13j), or $C_8H_{17}$ (13k)

-continued

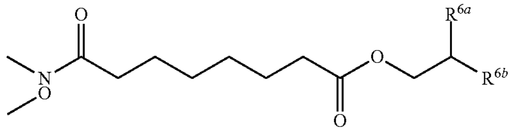

15e $R^{6a} = R^{6b} = C_{12}H_{25}$ (15i), $C_{10}H_{21}$ (15j), or $C_8H_{17}$ (15k)

2-dodecyltetradecyl 8-(methoxy(methyl)amino)-8-oxooctanoate (compound 15e when $R^{6a}$ and $R^{6b}$ are each $C_{12}$ alkyl)

Compound 25b (490 mg, 2.26 mmol) and 13k (1.0 g, 2.59 mmol) were dissolved in 7 mL of dichloromethane and then DMAP (430 mg, 3.50 mmol) and EDCI (530 mg, 2.82 mmol) were added to this solution at room temperature. After stirring overnight, the reaction was quenched with $NH_4Cl$ (saturated aqueous solution) and extracted with dichloromethane. Organic phase was washed with water, brine, dried over $Na_2SO_4$ and concentrated. Column chromatography purification (Hexane-EtOAc) provided 1.17 g (87% yield) of pure title compound 15k. $^1H$ NMR (300 MHz, d-chloroform) δ: 3.96 (d, J=6.0, 2H), 3.67 (s, 3H), 3.17 (3H), 2.35-2.45 (m, 2H), 2.20-2.30 (m, 2H), 1.60-1.70 (m, 4H), 1.20-1.40 (m, 49H), 0.80-0.90 (m, 6H)

2-decyldodecyl 8-(methoxy(methyl)amino)-8-oxooctanoate (compound 15e when $R^{6a}$ and $R^{6b}$ are each $C_{10}$ alkyl)

Starting with 0.55 g (2.53 mmol) of compound 25b and 1.03 g (3.04 mmol) of 2-decyldodecan-1-ol (13j) and following the procedure for analog 15k, 1.16 g of compound 15j was obtained in 87% yield. $^1H$ NMR (300 MHz, d-chloroform) δ: 3.96 (d, J=6.0, 2H), 3.67 (s, 3H), 3.17 (3H), 2.35-2.45 (m, 2H), 2.20-2.30 (m, 2H), 1.60-1.70 (m, 4H), 1.20-1.40 (m, 41H), 0.80-0.90 (m, 6H)

2-octyldecyl 8-(methoxy(methyl)amino)-8-oxooctanoate (compound 15e when $R^{6a}$ and $R^{6b}$ are each $C_8$ alkyl)

Starting with 0.63 g (2.85 mmol) of compound 25b and 1.01 g (3.70 mmol) of 2-octyldecan-1-ol (13i) and following the procedure for analog 15k, 1.22 g of compound 15i was obtained in 90% yield. $^1H$ NMR (300 MHz, d-chloroform) δ: 3.95 (d, J=6, 2H), 3.67 (s, 3H), 3.17 (3H), 2.35-2.45 (m, 2H), 2.20-2.30 (m, 2H), 1.55-1.65 (m, 4H), 1.20-1.40 (m, 33H), 0.80-0.90 (m, 6H).

Step 7: Synthesis of 2-octyldecyl 8-oxopentadecanoate (16i), 2-decyldodecyl 8-oxopentadecanoate (16j), and 2-dodecyltetradecyl 8-oxopentadecanoate (16k)

Scheme 56

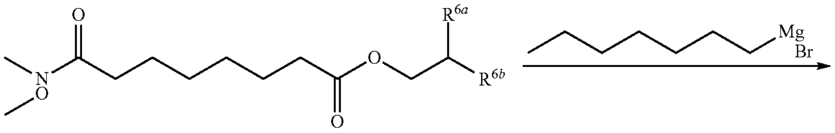

15e $R^{6a} = R^{6b} = C_{12}H_{25}$ (15i), $C_{10}H_{21}$ (15j), or $C_8H_{17}$ (15k)

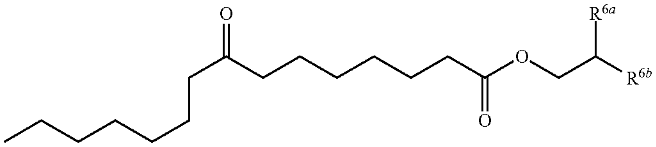

16e $R^{6a} = R^{6b} = C_{12}H_{25}$ (16i), $C_{10}H_{21}$ (16j), or $C_8H_{17}$ (16k)

2-dodecyltetradecyl 8-oxopentadecanoate (compound 16e when $R^{6a}$ and $R^{6b}$ are each $C_{12}$ alkyl)

Compound 15k was co-evaporated several times with toluene and dried overnight over $P_2O_5$ prior to the reaction. Dry compound 15k 1.17 g, 1.96 mmol) was dissolved in 7 mL of THF in a flame-dried round base flask, cooled to 0° C., and heptyl magnesium bromide (1M in ether) (2.95 mL, 2.95 mmol) was added dropwise. The reaction mixture was stirred at room temperature for 3.5 h, then cooled to 0° C., quenched with $NH_4Cl$ (sat) and extracted with hexanes several times. Organic phase was dried over $Na_2SO_4$, concentrated, and purified by column chromatography (0-10% EtOAc in hexanes) providing 660 mg (54% yield) of title compound 16k. $^1H$ NMR (300 MHz, d-chloroform) δ: 3.96 (d, J=6.0, 2H), 2.35-2.45 (m, 2H), 2.20-2.30 (m, 2H), 1.55-1.70 (m, 7H), 1.20-1.40 (m, 56H), 0.80-0.90 (m, 6H).

2-decyldodecyl 8-oxopentadecanoate (compound 16e when $R^{6a}$ and $R^{6b}$ are each $C_{10}$ alkyl)

Starting with 1.16 g of compound 15j and following the procedure for analog 16k, 0.67 g of compound 16j was obtained in 54% yield. $^1H$ NMR (300 MHz, d-chloroform) δ:3.96 (d, J=6.0, 2H), 2.35-2.45 (m, 2H), 2.20-2.30 (m, 2H), 1.55-1.70 (m, 7H), 1.20-1.40 (m, 48H), 0.80-0.90 (m, 6H).

2-octyldecyl 8-oxopentadecanoate (compound 16e when $R^{6a}$ and $R^{6b}$ are each $C_8$ alkyl)

Starting with 1.22 g of compound 15i and following the procedure for analog 16k, 0.73 g of compound 16i was obtained in 55% yield. $^1H$ NMR (300 MHz, d-chloroform) δ: 3.96 (d, J=6.0, 2H), 2.45-2.45 (m, 4H), 2.20-2.30 (m, 2H), 1.60-1.70 (m, 7H), 1.20-1.40 (m, 40H), 0.80-0.90 (m, 9H)

Step 8: Synthesis of 2-octyldecyl 8-hydroxypentadecanoate (17i), 2-decyldodecyl 8-hydroxypentadecanoate (17j), and 2-dodecyltetradecyl 8-hydroxypentadecanoate (17k)

Scheme 57

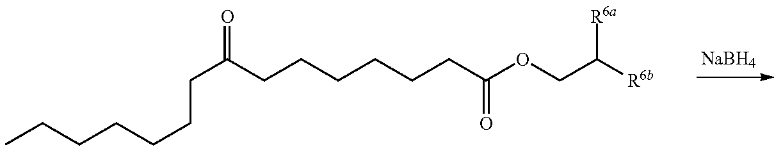

16e $R^{6a} = R^{6b} = C_{12}H_{25}$ (16i), $C_{10}H_{21}$ (16j), or $C_8H_{17}$ (16k)

-continued

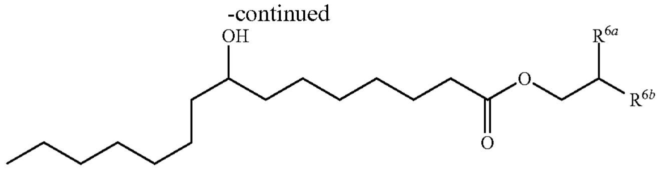

17e
$R^{6a} = R^{6b} = C_{12}H_{25}$ (17i),
$C_{10}H_{21}$ (17j), or
$C_8H_{17}$ (17k)

2-dodecyltetradecyl 8-hydroxypentadecanoate (compound 16e when $R^{6a}$ and $R^{6b}$ are each $C_{12}$ alkyl)

To an ice-cold compound 16k (366 mg, 0.59 mmol) dissolved in THF:MeOH=1:1 (3 mL) was added $NaBH_4$ (32.3 mg, 0.86 mmol) in one portion. The reaction mixture was stirred at room temperature for about 2 h until full conversion was confirmed by TLC, and then quenched with 2 ml of $NH_4Cl$ (sat) and concentrated to dryness. The residue was mixed with $CH_2Cl_2$, washed with water, dried over $Na_2SO_4$, concentrated, and purified by column chromatography (hexanes-EtOAc) providing 356 mg of compound 17k in 96% yield. $^1H$ NMR (300 MHz, d-chloroform) δ: 3.95 (d, J=5.8, 2H), 3.58 (br s, 1H), 2.25-2.35 (m, 2H), 1.55-1.65 (3H), 1.15-1.45 (m, 65H), 0.8-0.9 (m, 9H).

2-decyldodecyl 8-hydroxypentadecanoate (compound 16e when $R^{6a}$ and $R^{6b}$ are each $C_{10}$ alkyl)

Compound 17j was obtained according to the procedure above for analog 17k, starting with 310 mg of 16j and providing 290 mg of pure 17j in 93% yield. $^1H$ NMR (300 MHz, d-chloroform) δ: 3.95 (d, J=5.8, 2H), 3.57 (br s, 1H), 2.25-2.35 (m, 2H), 1.55-1.65 (3H), 1.15-1.45 (m, 57H), 0.8-0.9 (m, 9H). 2-octyldecyl 8-hydroxypentadecanoate (compound 16e when $R^{6a}$ and $R^{6b}$ are each $C_8$ alkyl)

Compound 17i was obtained according to the procedure above for analog 17k, starting with 300 mg of 16j and providing 300 mg of 17i in quantitative yield. $^1H$ NMR (300 MHz, d-chloroform) δ: 3.95 (d, J=5.8, 2H), 3.57 (br s, 1H), 2.25-2.35 (m, 2H), 1.55-1.65 (3H), 1.15-1.45 (m, 49H), 0.8-0.9 (m, 9H).

Step 9: Synthesis of 2-octyldecyl 8-((4-(dimethylamino)butanoyl)oxy)pentadecanoate (Lipid 15), 2-decyldodecyl 8-((4-(dimethylamino)butanoyl)oxy)pentadecanoate (Lipid 9), and 2-dodecyltetradecyl 8-((4-(dimethylamino)butanoyl)oxy)pentadecanoate (Lipid 10)

Scheme 58

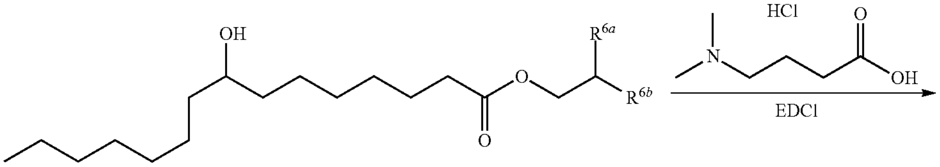

17e
$R^{6a} = R^{6b} = C_{12}H_{25}$ (17i),
$C_{10}H_{21}$ (17j), or
$C_8H_{17}$ (17k)

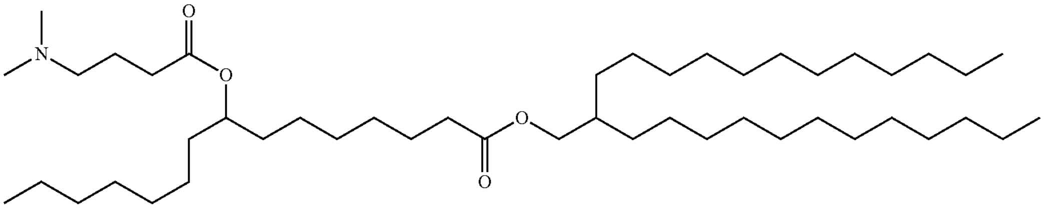

Lipid 10

-continued

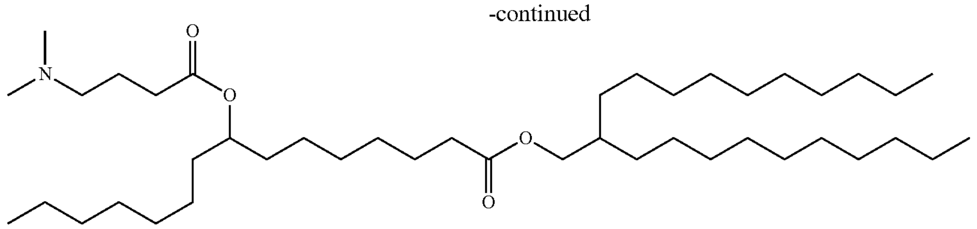

Lipid 9

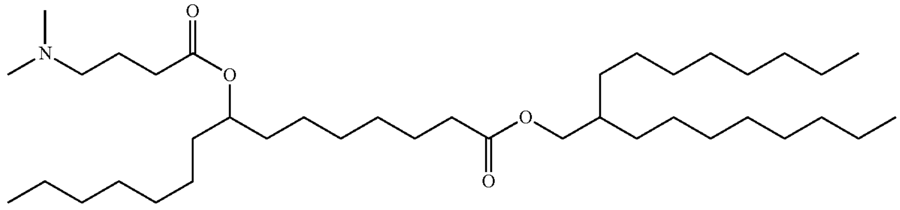

Lipid 15

2-dodecyltetradecyl 8-((4-(dimethylamino)butanoyl) oxy)pentadecanoate (Lipid 25) (compound 18e when $R^{6a}$ and $R^{6b}$ are each $C_{12}$ alkyl)

4-(dimethylamino)butanoic acid hydrochloride (128 mg, 0.76 mmol) was dissolved in a $CH_2Cl_2$/DMF (6 mL/0.5 mL) mixture followed up addition of TEA (0.2 mL, 1.43 mmol), compound 17k (356 mg, 0.57 mmol), EDCI (170 mg, 0.89 mmol) and DMAP (109 mg, 0.89 mmol). The reaction mixture was stirred overnight at room temperature, quenched with $NH_4Cl$ (sat), and extracted with $CH_2Cl_2$. The organic phase was dried over $Na_2SO_4$, concentrated, and purified by column chromatography (0-15% MeOH in DCM) providing 283 mg of Lipid 25 (68% yield). $^1H$ NMR (300 MHz, d-chloroform) δ ppm: 4.90-4.80 (m, 1H), 3.95 (d, J=5.7, 2H), 2.22-2.35 (m, 6H), 2.21 (s, 6H), 1.73-1.84 (m, 2H), 1.58-1.65 (m, 4H), 1.40-1.50 (m, 3H), 1.20-1.35 (m, 60H), 0.82-0.90 (m, 9H). MS found 736.6 $[M+H]^+$, calcd 735.6 for $[C_{47}H_{93}NO_4]$.

2-decyldodecyl 8-((4-(dimethylamino)butanoyl)oxy) pentadecanoate (Lipid 24) (compound 18e when $R^{6a}$ and $R^{6b}$ are each $C_{10}$ alkyl)

Lipid 24 was obtained according to the procedure above for analog Lipid 25, starting with 297 mg of 17j and providing 270 mg of pure Lipid 24 in 78% yield. $^1H$ NMR (300 MHz, d-chloroform) δ ppm: 4.90-4.80 (m, 1H), 3.95 (d, J=5.7, 2H), 2.22-2.35 (m, 6H), 2.21 (s, 6H), 1.40-1.80 (m, 9H), 1.15-1.30 (m, 52H), 0.82-0.90 (m, 9H). MS found 680.5 $[M+H]^+$, calcd 679.6 for $[C_{43}H_{85}NO_4]$.

2-octyldecyl 8-((4-(dimethylamino)butanoyl)oxy) pentadecanoate (Lipid 23) (compound 18e when $R^{6a}$ and $R^{6b}$ are each $C_{10}$ alkyl)

Lipid 23 was obtained according to the procedure above for analog Lipid 25, starting with 300 mg of 17i and providing 240 mg of Lipid 23 in 68% yield. $^1H$ NMR (300 MHz, d-chloroform) δ ppm: 4.90-4.80 (m, 1H), 3.95 (d, J=5.7, 2H), 2.22-2.35 (m, 6H), 2.21 (s, 6H), 1.70-1.82 (m, 2H), 1.40-1.60 (m, 7H), 1.15-1.30 (m, 44H), 0.82-0.90 (m, 9H). MS found 624.5 $[M+H]^+$, calcd 623.5 for $[C_{39}H_{77}NO_4]$.

Example 15: Synthesis of Cationic Lipids Comprising Quaternary Amine or Quaternary Ammonium Cation Each of Lipids 1-25 as described above and a lipid of Formula I may be converted into its corresponding lipid comprising a quaternary amine or a quaternary ammonium cation by treatment with chloromethane ($CH_3Cl$) in acetonitrile ($CH_3CN$) and chloroform ($CHCl_3$).

Example 16: Preparation of Lipid Nanoparticles

Lipid nanoparticles (LNP) were prepared at a total lipid to ceDNA weight ratio of approximately 10:1 to 30:1. Briefly, a cationic lipid of the present disclosure, a non-cationic lipid (e.g., distearoylphosphatidylcholine (DSPC)), a component to provide membrane integrity (such as a sterol, e.g., cholesterol) and a conjugated lipid molecule (such as a PEGylated lipid conjugate) e.g., 1-(monomethoxy-polyethyleneglycol)-2,3-dimyristoylglycerol, with an average PEG molecular weight of 2000 ("PEG-DMG")), were solubilized in alcohol (e.g., ethanol) at a mol ratio of, for example, 47.5:10.0:40.7:1.8, 47.5:10.0:39.5:3.0, or 47.5:10.0:40.2:2.3. The ceDNA was diluted to a desired concentration in buffer solution. For example, the ceDNA were diluted to a concentration of 0.1 mg/ml to 0.25 mg/ml in a buffer solution comprising sodium acetate, sodium acetate and magnesium chloride, citrate, malic acid, or malic acid and sodium chloride. In one example, the ceDNA was diluted to 0.2 mg/mL in 10 to 50 mM citrate buffer, pH 4. The alcoholic lipid solution was mixed with ceDNA aqueous solution using, for example, syringe pumps or an impinging jet mixer, at a ratio of about 1:5 to 1:3 (vol/vol) with total flow rates above 10 ml/min. In one example, the alcoholic lipid solution was mixed with ceDNA aqueous at a ratio of about 1:3 (vol/vol) with a flow rate of 12 ml/min. The alcohol was removed, and the buffer was replaced with PBS by dialysis. Alternatively, the buffers were replaced with PBS using centrifugal tubes. Alcohol removal and simultaneous buffer exchange were accomplished by, for example, dialysis or tangential flow filtration. The obtained lipid nanoparticles are filtered through a 0.2 m pore sterile filter. Additional or alternative method of preparing LNPs are described in detail, e.g., in International Patent Application Publication Nos. WO2021/046265 and WO2022/236479, the entire contents of each of which are hereby incorporated herein by reference.

In one study, lipid nanoparticles comprising exemplary ceDNAs were prepared using a lipid solution comprising Reference Lipid A, DSPC, Cholesterol and DMG-PEG2000 (mol ratio 47.5:10.0:40.7:1.8) as control. In some studies, a tissue-specific target ligand like N-Acetylgalactosamine (GalNAc) was included in the formulations comprising Reference Lipid A and cationic lipids of the present disclosure. A GalNAc ligand such as tri-antennary GalNAc (GalNAc3) or tetra-antennary GalNAc (GalNAc4) can be synthesized as known in the art (see, e.g., WO2017/084987 and WO2013/166121) and chemically conjugated to lipid or PEG as well-known in the art (see, Resen et al., J. Biol. Chem. (2001) "Determination of the Upper Size Limit for Uptake and Processing of Ligands by the Asialoglycoprotein Receptor on Hepatocytes in Vitro and in Vivo" 276:375577-37584). Aqueous solutions of ceDNA in buffered solutions were prepared. The lipid solution and the ceDNA solution were mixed using an in-house procedure on a NanoAssembler at a total flow rate of 12 mL/min at a lipid to ceDNA ratio of 1:3 (v/v).

TABLE 1

Test Material Administration in Study A

| Group No. | Animals per Group | LNP Treatment | Dose Level (mg/kg) | Dose Volume (mL/kg) | Treatment Regimen | Endpoints |
|---|---|---|---|---|---|---|
| 1 | 5 | PBS | 0.25 | 5 | Once on | Day 4 for |
| 2 | 5 | LNP 1 | | | Day 0, IV | IVIS; |
| 3 | 5 | LNP 2 | | | | Day 0 for |
| 4 | 5 | LNP 3 | | | | BW |

No. = Number; IV = intravenous; ROA = route of administration; LNP = lipid nanoparticle; IVIS = in vivo imaging session; BW = body weight

TABLE 2

Test Material Administration in Study B

| Group No. | Animals per Group | LNP Treatment | Dose Level (mg/kg) | Dose Volume (mL/kg) | Treatment Regimen | Endpoints |
|---|---|---|---|---|---|---|
| 5 | 5 | PBS | 0.5 | 5 | Once on | Day 4 for |
| 6 | 5 | LNP 4 | | | Day 0, IV | IVIS; |
| 7 | 5 | LNP 5 | | | | Day 0 for |
| | | | | | | BW |

No. = Number; IV = intravenous; ROA = route of administration; LNP = lipid nanoparticle; IVIS = in vivo imaging session; BW = body weight

TABLE 3

Test Material Administration in Study C

| Group No. | Animals per Group | LNP Treat-ment | Dose Level (mg/kg) | Dose Volume (mL/kg) | Treatment Regimen | Endpoints |
|---|---|---|---|---|---|---|
| 8 | 5 | PBS | 0.5 | 5 | Once on | Day 4 and |
| 9 | 5 | LNP 6 | | | Day 0, IV | Day 7 for |
| 10 | 5 | LNP 7 | | | | IVIS; Days |
| 11 | 5 | LNP 8 | | | | 0, 1, 2, 3, |
| 12 | 5 | LNP 9 | | | | 4, and 7 for |
| 13 | 5 | LNP 10 | | | | BW |
| 14 | 5 | LNP 11 | | | | |
| 15 | 5 | LNP 12 | | | | |
| 16 | 5 | LNP 13 | | | | |
| 17 | 5 | LNP 14 | | | | |
| 18 | 5 | LNP 15 | | | | |
| 19 | 5 | LNP 16 | | | | |
| 20 | 5 | LNP 17 | | | | |

No. = Number; IV = intravenous; ROA = route of administration; LNP = lipid nanoparticle; IVIS = in vivo imaging session; BW = body weight

TABLE 4

Description of LNP Compositions in Study A

| LNP | Components of LNP (mol ratio) |
|---|---|
| PBS | Not Applicable |
| LNP 1 | Reference Lipid A:DSPC:Chol:DMG-PEG2000 47.5:10.0:40.7:1.8 |
| LNP 2 | Lipid 20:DSPC:Chol:DMG-PEG2000 47.5:10.0:40.7:1.8 |
| LNP 3 | Lipid 20:DSPC:Chol:DMG-PEG2000 47.5:10.0:39.5:3.0 |

DSPC = distearoylphosphatidylcholine; Chol = Cholesterol; DMG-PEG2000 = 1-(monomethoxy-polyethyleneglycol)-2,3-dimyristoylglycerol ($PEG_{2000}$-DMG); and SS-OP = COATSOME ® SS-OP (NOF); GalNAc = N-Acetylgalactosamine; GalNAc4 = tetra-antennary GalNAc

TABLE 5

Description of LNP Compositions in Study B

| LNP | Components of LNP (mol ratio) |
|---|---|
| PBS | Not Applicable |
| LNP 4 | Reference Lipid A:DSPC:Chol:DMG-PEG2000:DSPE-PEG2000-GalNAc4 47.5:10.0:40.2:1.8:0.5 |
| LNP 5 | Lipid 20:DSPC:Chol:DMG-PEG2000:DSPE-PEG2000-GalNAc4 47.5:10.0:40.2:1.8:0.5 |

DSPC = distearoylphosphatidylcholine; Chol = Cholesterol; DMG-PEG2000 = 1-(monomethoxy-polyethyleneglycol)-2,3-dimyristoylglycerol ($PEG_{2000}$-DMG); and SS-OP = COATSOME ® SS-OP (NOF); GalNAc = N-Acetylgalactosamine; GalNAc4 = tetra-antennary GalNAc

TABLE 6

| Description of LNP Compositions in Study C | |
|---|---|
| LNP | Components of LNP (mol ratio) |
| PBS | Not Applicable |
| LNP 6 | Reference Lipid A:DSPC:Chol:DMG-PEG2000:DSPE-PEG2000-GalNAc4 47.5:10.0:39.5:2.5:0.5 |
| LNP 7 | Lipid 20:DSPC:Chol:DMG-PEG2000:DSPE-PEG2000-GalNAc4 47.5:10.0:39.5:2.5:0.5 |
| LNP 8 | Lipid 23:DSPC:Chol:DMG-PEG2000:DSPE-PEG2000-GalNAc4 47.5:10.0:39.5:2.5:0.5 |
| LNP 9 | Lipid 11:DSPC:Chol:DMG-PEG2000:DSPE-PEG2000-GalNAc4 47.5:10.0:39.5:2.5:0.5 |
| LNP 10 | Lipid 19:DSPC:Chol:DMG-PEG2000:DSPE-PEG2000-GalNAc4 47.5:10.0:39.5:2.5:0.5 |
| LNP 11 | Lipid 21:DSPC:Chol:DMG-PEG2000:DSPE-PEG2000-GalNAc4 47.5:10.0:39.5:2.5:0.5 |
| LNP 12 | Lipid 22:DSPC:Chol:DMG-PEG2000:DSPE-PEG2000-GalNAc4 47.5:10.0:39.5:2.5:0.5 |
| LNP 13 | Lipid 16:DSPC:Chol:DMG-PEG2000:DSPE-PEG2000-GalNAc4 47.5:10.0:39.5:2.5:0.5 |
| LNP 14 | Lipid 17:DSPC:Chol:DMG-PEG2000:DSPE-PEG2000-GalNAc4 47.5:10.0:39.5:2.5:0.5 |
| LNP 15 | Lipid 18:DSPC:Chol:DMG-PEG2000:DSPE-PEG2000-GalNAc4 47.5:10.0:39.5:2.5:0.5 |
| LNP 16 | Lipid 25:DSPC:Chol:DMG-PEG2000:DSPE-PEG2000-GalNAc4 47.5:10.0:39.5:2.5:0.5 |
| LNP 17 | Lipid 24:DSPC:Chol:DMG-PEG2000:DSPE-PEG2000-GalNAc4 47.5:10.0:39.5:2.5:0.5 |

DOPC = dioleoylphosphatidylcholine; Chol = Cholesterol; DSPE = distearoyl-phosphatidyl-ethanolamine; DMG-PEG2000 = 1-(monomethoxy-polyethyleneglycol)-2,3-dimyristoylglycerol ($PEG_{2000}$-DMG); and SS-OP = COATSOME ® SS-OP (NOF); GalNAc = N-Acetylgalactosamine;
GalNAc4 = tetra-antennary GalNAc

TABLE 7

| Description of LNP Compositions in Study D | |
|---|---|
| LNP | Components of LNP (mol ratio) |
| PBS | Not Applicable |
| LNP 6 | Reference Lipid A:DSPC:Chol:DMG-PEG2000:DSPE-PEG2000-GalNAc4 47.5:10.0:39.5:2.5:0.5 |
| LNP 9 | Lipid 11:DSPC:Chol:DMG-PEG2000:DSPE-PEG2000-GalNAc4 47.5:10.0:39.5:2.5:0.5 |
| LNP 18 | Lipid 1:DSPC:Chol:DMG-PEG2000:DSPE-PEG2000-GalNAc4 47.5:10.0:39.5:2.5:0.5 |
| LNP 19 | Lipid 2:DSPC:Chol:DMG-PEG2000:DSPE-PEG2000-GalNAc4 47.5:10.0:39.5:2.5:0.5 |
| LNP 20 | Lipid 12:DSPC:Chol:DMG-PEG2000:DSPE-PEG2000-GalNAc4 47.5:10.0:39.5:2.5:0.5 |
| LNP 21 | Lipid 3:DSPC:Chol:DMG-PEG2000:DSPE-PEG2000-GalNAc4 47.5:10.0:39.5:2.5:0.5 |
| LNP 22 | Lipid 4:DSPC:Chol:DMG-PEG2000:DSPE-PEG2000-GalNAc4 47.5:10.0:39.5:2.5:0.5 |
| LNP 23 | Lipid 13:DSPC:Chol:DMG-PEG2000:DSPE-PEG2000-GalNAc4 47.5:10.0:39.5:2.5:0.5 |
| LNP 24 | Lipid 5:DSPC:Chol:DMG-PEG2000:DSPE-PEG2000-GalNAc4 47.5:10.0:39.5:2.5:0.5 |
| LNP 25 | Lipid 6:DSPC:Chol:DMG-PEG2000:DSPE-PEG2000-GalNAc4 47.5:10.0:39.5:2.5:0.5 |
| LNP 26 | Lipid 14:DSPC:Chol:DMG-PEG2000:DSPE-PEG2000-GalNAc4 47.5:10.0:39.5:2.5:0.5 |
| LNP 27 | Lipid 7:DSPC:Chol:DMG-PEG2000:DSPE-PEG2000-GalNAc4 47.5:10.0:39.5:2.5:0.5 |
| LNP 28 | Lipid 8:DSPC:Chol:DMG-PEG2000:DSPE-PEG2000-GalNAc4 47.5:10.0:39.5:2.5:0.5 |
| LNP 29 | Lipid 15:DSPC:Chol:DMG-PEG2000:DSPE-PEG2000-GalNAc4 47.5:10.0:39.5:2.5:0.5 |
| LNP 30 | Lipid 9:DSPC:Chol:DMG-PEG2000:DSPE-PEG2000-GalNAc4 47.5:10.0:39.5:2.5:0.5 |
| LNP 31 | Lipid 10:DSPC:Chol:DMG-PEG2000:DSPE-PEG2000-GalNAc4 47.5:10.0:39.5:2.5:0.5 |

Example 17: Pre-Clinical In Vivo Studies of Lipid Nanoparticles

Several pre-clinical studies were carried out to evaluate the in vivo expression and the tolerability of ceDNA-luciferase formulated with LNP in mice. These LNPs comprise either Reference Lipid A as a control or a lipid of the present disclosure. The study design and procedures involved in these pre-clinical studies are as described below.

Materials and Methods

TABLE 8

| Blood Collection | |
|---|---|
| Group Number | Sample Collection Times Whole Blood (Tail, saphenous or orbital) SERUM[a] |
| | Day 0 about 5-6 hours post Test Material dose (no less than 5.0 hours, no more than 6.5 hours) |
| Volume/Portion | about 150 μL whole blood |
| Processing/Storage | 1 aliquot frozen at nominally −70° C. |

[a]Whole blood was collected into serum separator tubes, with clot activator

Species (number, sex, age): CD-1 mice (N=65 and 5 spare, male, about 4 weeks of age at arrival).

Cage Side Observations: Cage side observations were performed daily.

Clinical Observations: Clinical observations were performed about 1, about 5 to about 6 and about 24 hours post the Day 0 Test Material dose. Additional observations were made per exception. Body weights for all animals, as applicable, were recorded on Days 0, 1, 2, 3, 4 & 7. Additional body weights were recorded as needed.

Dose Administration: Test articles (LNPs: ceDNA-Luc) were dosed at 5 mL/kg on Day 0 for Groups 1-38 by intravenous administration to lateral tail vein.

In-life Imaging: On Day 4, all animals in were dosed with luciferin at 150 mg/kg (60 mg/mL) via intraperitoneal (IP) injection at 2.5 mL/kg. ≤15 minutes post each luciferin administration; all animals had an IVIS imaging session according to in vivo imaging protocol described below.

Anesthesia Recovery: Animals were monitored continuously while under anesthesia, during recovery and until mobile.

Interim Blood Collection: All animals had interim blood collected on Day 0; 5-6 hours post-test (no less than 5.0 hours, no more than 6.5 hours).

After collection animals received 0.5-1.0 mL lactated Ringer's; subcutaneously. Whole blood for serum were collected by tail-vein nick, saphenous vein or orbital sinus puncture (under inhalant isoflurane). Whole blood was collected into a serum separator with clot activator tube and processed into one (1) aliquot of serum.

In Vivo Imaging Protocol

- Luciferin stock powder was stored at nominally −20° C.
- Stored formulated luciferin in 1 mL aliquots at 2-8° C. protect from light.
- Formulated luciferin was stable for up to 3 weeks at 2-8° C., protected from light and stable for about 12 h at room temperature (RT).
- Dissolved luciferin in PBS to a target concentration of 60 mg/mL at a sufficient volume and adjusted to pH=7.4 with 5-M NaOH (about 0.5 l/mg luciferin) and HCl (about 0.5 L/mg luciferin) as needed.
- Prepared the appropriate amount according to protocol including at least a about 50% overage.

Injection and Imaging

- Shaved animal's hair coat (as needed).
- Per protocol, injected 150 mg/kg of luciferin in PBS at 60 mg/mL via IP.
- Imaging was performed immediately or up to 15 minutes post dose.
- Set isoflurane vaporizer to 1-3% (usually 2.5%) to anesthetize the animals during imaging sessions.
- Isoflurane anesthesia for imaging session:
  - Placed the animals into the isoflurane chamber and wait for the isoflurane to take effect, about 2-3 min.
  - Ensured that the anesthesia level on the side of the IVIS machine was positioned to the "on" position.
  - Placed animal(s) into the IVIS machine
- Performed desired Acquisition Protocol with settings for highest sensitivity.

Study A

Study A was the first pre-clinical study conducted with the objective of evaluating the ability of an exemplary lipid of the present disclosure, i.e., Lipid 20, to be formulated as LNP, and the in vivo expression and tolerability when the LNP-ceDNA-luciferase composition was administered to mice at the dosage of 0.25 mg/kg.

As a general rule, a polydispersity index (PDI) of 0.15 or lower is indicative of good homogeneity of the size of the LNPs formed and an encapsulation efficiency (EE) of 90% is indicative of satisfactory encapsulation rate. LNP 1 and LNP 2 that were both formulated with Lipid 20 but at varying DMG-PEG2000 amounts exhibited excellent PDI values that were lower than 0.15 and EE values that were greater than 90%.

FIG. 1A is a graph showing the total amount of luciferase expression as measured by fluorescence in mice on day 4 after administration of ceDNA encoding luciferase formulated in LNP1, LNP2 and LNP3. LNP1 is a lipid nanoparticle formulated with Reference Lipid A and used as a positive control, while LNP2 and LNP3 are lipid nanoparticles formulated with Lipid 20 as described in Table 4. PBS was used as a negative control. FIG. 1B is a graph showing the body weight changes at day 1 in the mice administered ceDNA encoding luciferase formulated in LNP1, LNP2, LNP3 and PBS as described above.

As shown in FIG. 1A, the group of mice treated with ceDNA-luciferase formulated with LNP 2 or LNP 3 (i.e., LNPs comprising Lipid 20) exhibited good luciferase expression at Day 4. LNPs comprising Lipid 1 were also well-tolerated in mice because, unlike the positive control LNP formulated with Reference Lipid A (i.e., LNP 1), the treatment did not cause statistically significant changes in body weight in the mice at Day 1 (see FIG. 1B).

Study B

The objective of Study B was to evaluate the in vivo expression and tolerability of ceDNA-luciferase formulated as an LNP composition comprising an exemplary lipid of the present disclosure, i.e., Lipid 20, and also GalNAc4 as the liver tissue-specific targeting ligand. The LNP-ceDNA-luciferase composition was administered to mice at the dosage of 0.5 mg/kg.

Figure 2A:
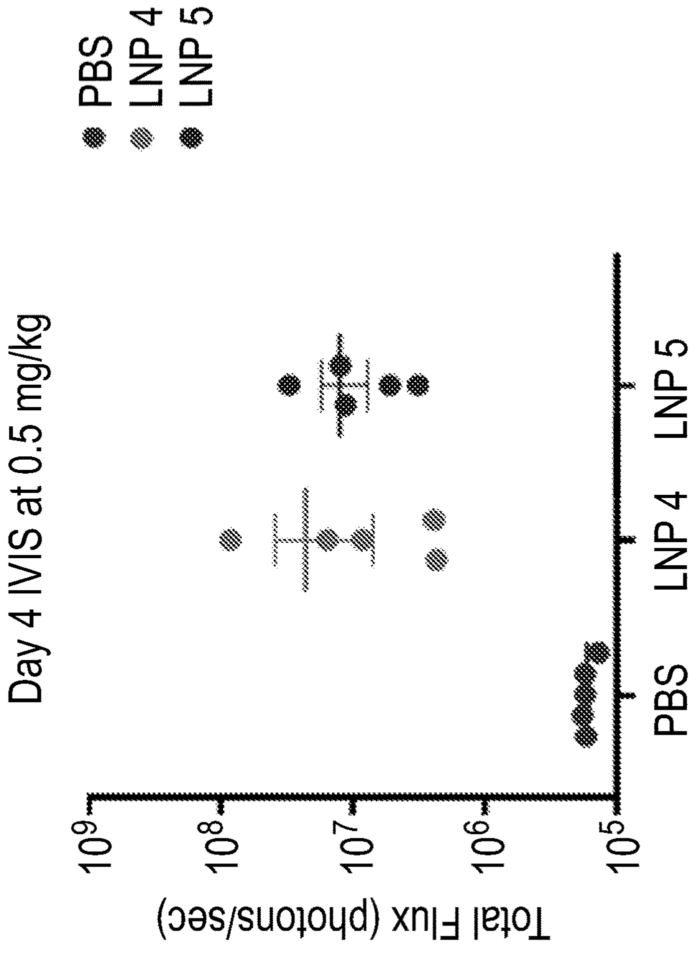
FIG. 2A is a graph showing the total amount of luciferase expression as measured by fluorescence in mice on day 4 after administration of ceDNA encoding luciferase formulated in LNP4 and LNP5. LNP4 is a lipid nanoparticle formulated with Reference Lipid A and GalNAc4 and used as a positive control, while LNP5 is a lipid nanoparticle formulated with Lipid 20 and GalNAc4 as described in Table 5. PBS was used as a negative control.
Figure 2B:
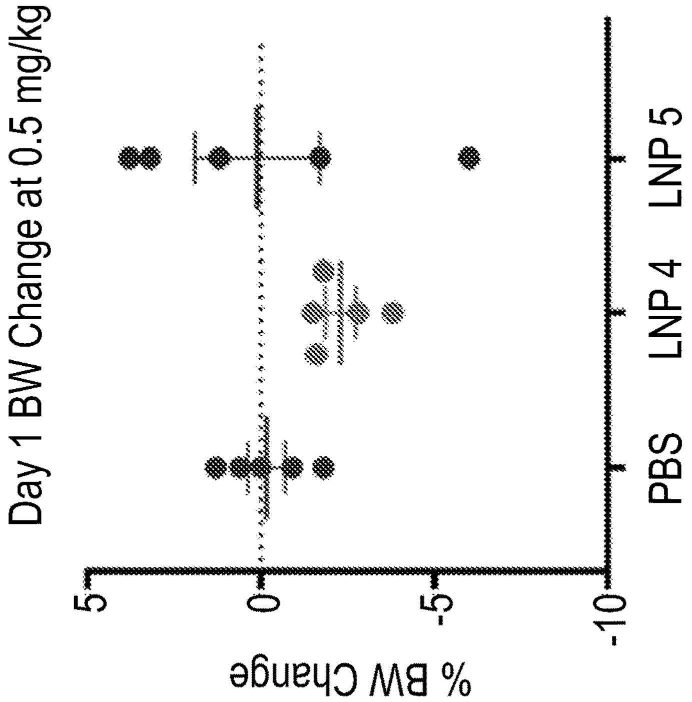
FIG. 2B is a graph showing the body weight changes at day 1 in the mice administered cdDNA encoding luciferase formulated in LNP4, LNP5 and PBS as described above.

FIG. 2A is a graph showing the total amount of luciferase expression as measured by fluorescence in mice on day 4 after administration of ceDNA encoding luciferase formulated in LNP4 and LNP5. LNP4 is a lipid nanoparticle formulated with Reference Lipid A and GalNAc4 and used as a positive control, while LNP5 is a lipid nanoparticle formulated with Lipid 20 and GalNAc4 as described in Table 5. PBS was used as a negative control. FIG. 2B is a graph showing the body weight changes at day 1 in the mice administered cdDNA encoding luciferase formulated in LNP4, LNP5 and PBS as described above.

The observations in Study B corroborated with those in Study A as described above. Specifically, as shown in FIG. 2A, good luciferase expression was observed at Day 4 in the group of mice treated with ceDNA-luciferase formulated with LNP 5 (i.e., LNP comprising Lipid 20). Furthermore, and unlike the positive control LNP formulated with Reference Lipid A (i.e., LNP 4), LNP comprising Lipid 20 was well-tolerated in mice even at an increased dosage of 0.5 mg/kg and did not cause statistically significant changes in body weight in the mice at Day 1 (see FIG. 2B).

Study C

The objective of Study C was to evaluate the in vivo expression and tolerability of ceDNA-luciferase formulated as LNP compositions comprising various exemplary lipids of the present disclosure and also GalNAc4 as the liver tissue-specific targeting ligand. The LNP-ceDNA-luciferase compositions were each administered to mice at the dosage of 0.5 mg/kg. All of the LNPs formulated for Study C that incorporate a cationic lipid of the present disclosure exhibited a polydispersity index (PDI) of ≤0.15 and an encapsulation efficiency (EE) of ≥90%.

Figures 3A, 3B, 3C:
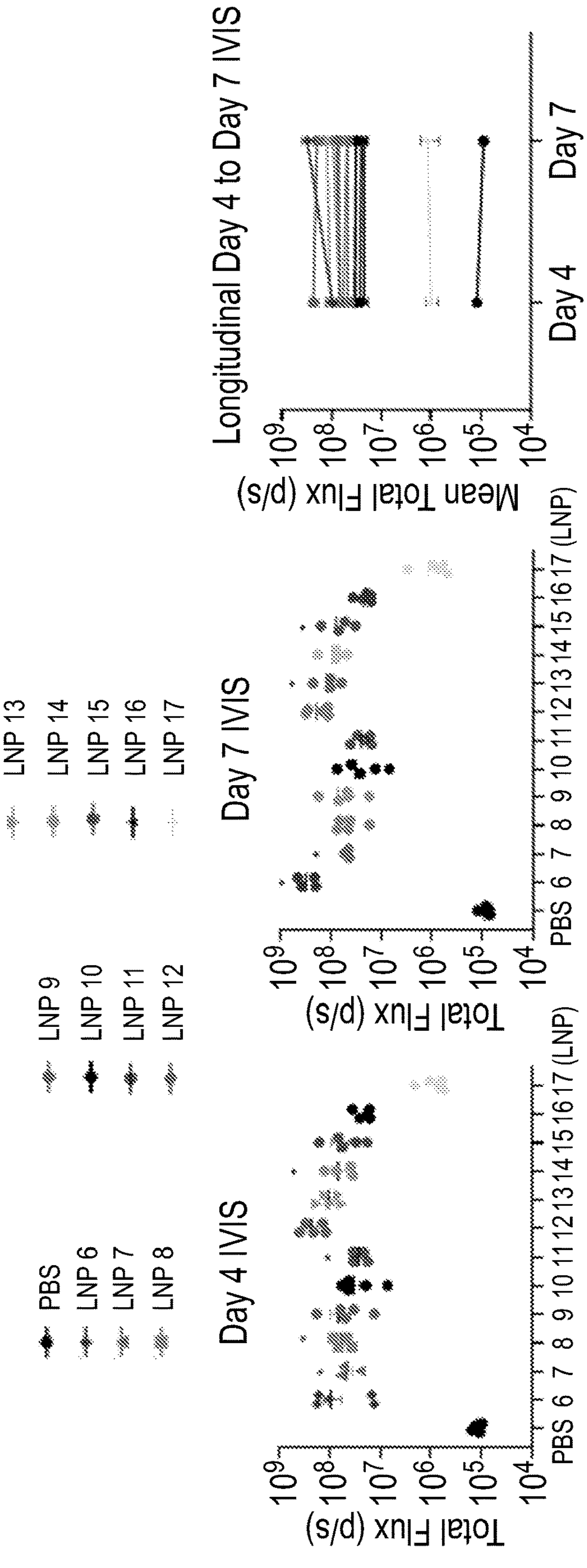
FIG. 3A is a graph showing the total amount of luciferase expression as measured by fluorescence in mice on day 4 after administration of ceDNA encoding luciferase formulated in LNPs comprising lipids of the invention described in Table 6, with PBS used as a negative control.
FIG. 3B is a graph showing the total amount of luciferase expression as measured by fluorescence in mice on day 7 after administration of ceDNA encoding luciferase formulated in LNPs comprising lipids of the invention described in Table 6, with PBS used as a negative control.
FIG. 3C is a graph showing the total amount of luciferase expression as measured by fluorescence in mice on day 4 and day 7 after administration of the ceDNA encoding luciferase formulated in LNPs described in Table 6.
Figure 3D:
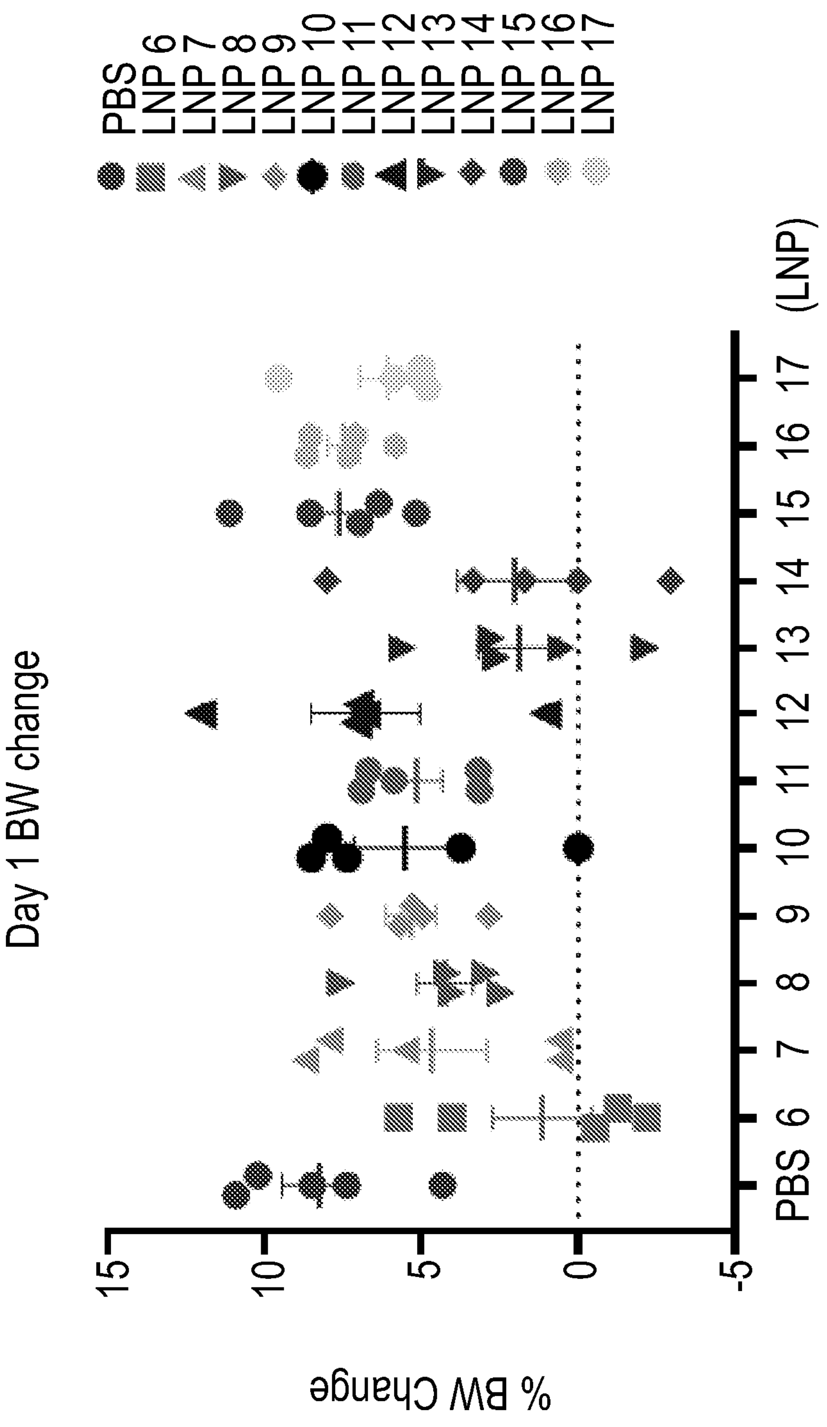
FIG. 3D is a graph showing the body weight changes at day 1 in the mice after administration of ceDNA encoding luciferase formulated in LNPs comprising lipids of the invention described in Table 6.

FIG. 3A is a graph showing the total amount of luciferase expression as measured by fluorescence in mice on day 4 after administration of ceDNA encoding luciferase formulated in LNPs comprising lipids of the invention described in Table 6, with PBS used as a negative control. FIG. 3B is a graph showing the total amount of luciferase expression as measured by fluorescence in mice on day 7 after administration of ceDNA encoding luciferase formulated in LNPs comprising lipids of the invention described in Table 6, with PBS used as a negative control. FIG. 3C is a graph showing the total amount of luciferase expression as measured by fluorescence in mice on day 4 and day 7 after administration of the ceDNA encoding luciferase formulated in LNPs described in Table 6. FIG. 3D is a graph showing the body weight changes at day 1 in the mice after administration of ceDNA encoding luciferase formulated in LNPs comprising lipids of the invention described in Table 6.

As shown FIG. 3A and FIG. 3B, on Day 4 and Day 7, the group of mice treated with ceDNA-luciferase constructs that were formulated with the lipids of the invention in the LNP exhibited equivalent (e.g., LNP 7 comprising Lipid 20, LNP 8 comprising Lipid 23, LNP 9 comprising Lipid 11, LNP 10 comprising Lipid 19, LNP 11 comprising Lipid 21) or higher (e.g., LNP 12 comprising Lipid 22, LNP 13 comprising Lipid 16, LNP 14 comprising Lipid 17, LNP 15 comprising Lipid 18, LNP 16 comprising Lipid 25) expression as compared to that of the group treated with the positive control ceDNA-luciferase formulated with Reference Lipid A (i.e., LNP 6). FIG. 3C demonstrates that high expression levels of the luciferase of the constructs formulated with the lipids of the invention in the LNP were stable and could be sustained from Day 4 to Day 7. FIG. 3D indicates that LNPs formulated with a lipid of the invention (e.g., LNP 7 comprising Lipid 20, LNP 8 comprising Lipid 23, LNP 9 comprising Lipid 11, LNP 10 comprising Lipid 19, LNP 11 comprising Lipid 21, LNP 12 comprising Lipid 22, LNP 15 comprising Lipid 18, LNP 16 comprising Lipid 13, LNP 17 comprising Lipid 24) were generally well-tolerated and did not cause statistically significant changes in body weight in the mice at Day 1.

Study D

The objective of Study D was to evaluate the in vivo expression and tolerability of ceDNA-luciferase formulated as LNP compositions comprising various exemplary lipids of the present disclosure other than the ones included in Study C (with the exception of LNP 9 that was also featured in Study C), and also GalNAc4 as the liver tissue-specific targeting ligand. The LNP-ceDNA-luciferase compositions were each administered to mice at the dosage of 0.5 mg/kg. All of the LNPs formulated for Study D that incorporate a cationic lipid of the present disclosure exhibited a polydispersity index (PDI) of ≤0.15 and an encapsulation efficiency (EE) of ≥95%.

Figures 4A, 4B, 4C:
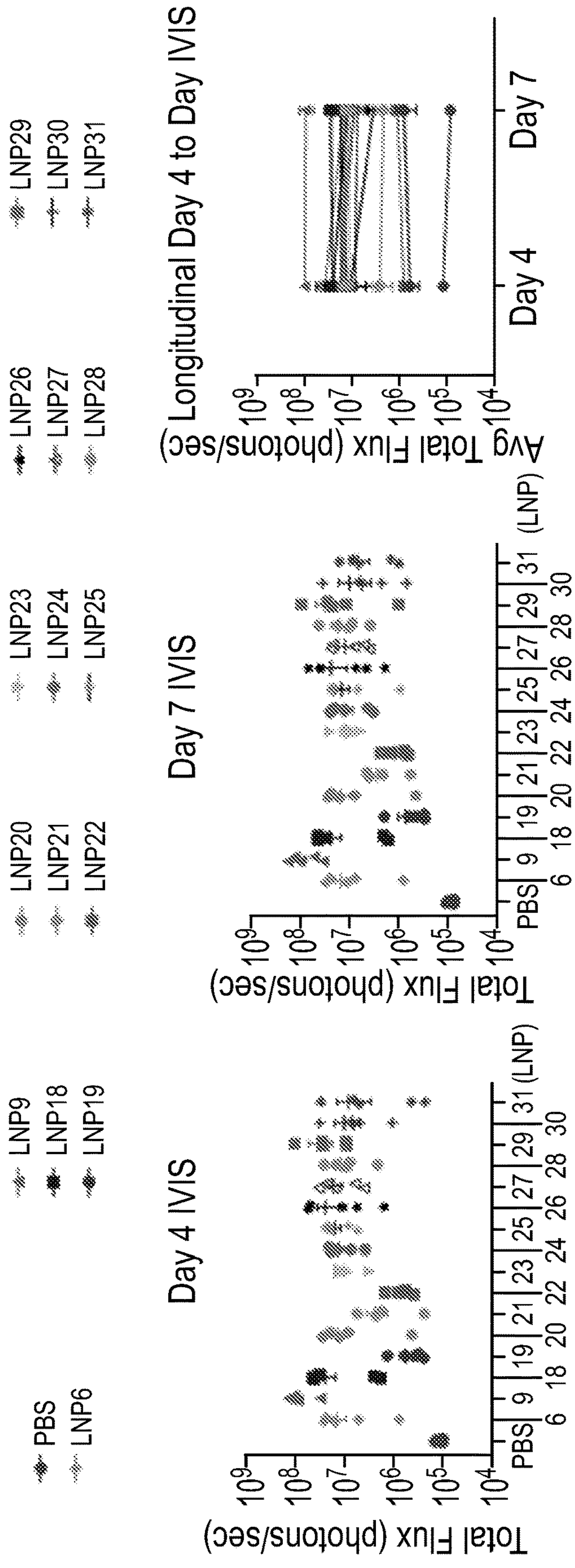
FIG. 4A is a graph showing the total amount of luciferase expression in mice as measured by fluorescence on day 4 after administration of ceDNA encoding luciferase formulated in LNPs comprising lipids of the invention described in Table 7, with PBS used as a negative control.
FIG. 4B is a graph showing the total amount of luciferase expression as measured by fluorescence in mice on day 7 after administration of ceDNA encoding luciferase formulated in LNPs comprising lipids of the invention described in Table 7, with PBS used as a negative control.
FIG. 4C is a graph showing the total amount of luciferase expression in mice on day 4 and day 7 after administration of the ceDNA encoding luciferase formulated in LNPs described in Table 7.
Figure 4D:
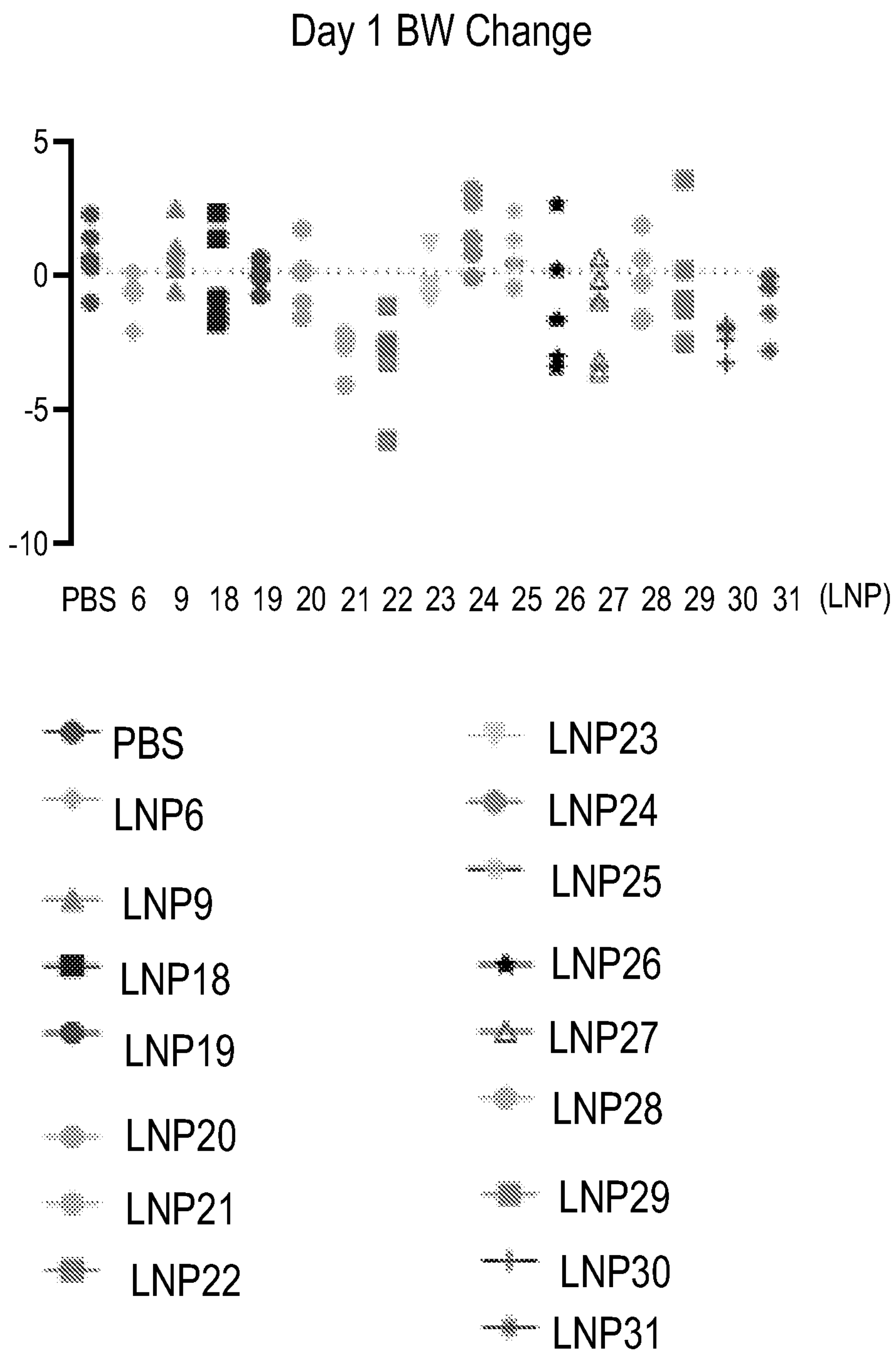
FIG. 4D is a graph showing the body weight changes at day 1 in the mice after administration of ceDNA encoding luciferase formulated in LNPs comprising lipids of the invention described in Table 7.

FIG. 4A is a graph showing the total amount of luciferase expression as measured by fluorescence in mice on day 4 after administration of ceDNA encoding luciferase formulated in LNPs comprising lipids of the invention described in Table 7, with PBS used as a negative control. FIG. 4B is a graph showing the total amount of luciferase expression as measured by fluorescence in mice on day 7 after administration of ceDNA encoding luciferase formulated in LNPs comprising lipids of the invention described in Table 7, with PBS used as a negative control. FIG. 4C is a graph showing the total amount of luciferase expression as measured by fluorescence in mice on day 4 and day 7 after administration of the ceDNA encoding luciferase formulated in LNPs described in Table 7. FIG. 4D is a graph showing the body weight changes at day 1 in the mice after administration of ceDNA encoding luciferase formulated in LNPs comprising lipids of the invention described in Table 7.

As shown FIG. 4A and FIG. 4B (outliers removed in both graphs), on Day 4 and Day 7, the group of mice treated with ceDNA-luciferase constructs that were formulated with the lipids of the invention in the LNP exhibited equivalent or higher expression as compared to that of the group treated with the positive control ceDNA-luciferase formulated with Reference Lipid A (i.e., LNP 6). FIG. 4C demonstrates that high expression levels of the luciferase of the constructs formulated with the lipids of the invention in the LNP were stable and could be sustained from Day 4 to Day 7. FIG. 4D indicates that LNPs formulated with a lipid of the invention (e.g., LNP 9 comprising Lipid 11, LNP 18 comprising Lipid 1, LNP 19 comprising Lipid 2, LNP 20 comprising Lipid 12, LNP 21 comprising Lipid 3, LNP 22 comprising Lipid 4, LNP 23 comprising Lipid 13, LNP 24 comprising Lipid 5, LNP 25 comprising Lipid 6, LNP 26 comprising Lipid 14, LNP 27 comprising Lipid 7, LNP 28 comprising Lipid 8, LNP 29 comprising Lipid 15, LNP 30 comprising Lipid 9, and LNP 31 comprising Lipid 10) were generally well-tolerated and did not cause statistically significant changes in body weight in the mice at Day 1.

Notably, LNP 9 comprising Lipid 11 that was also featured in Study C consistently showed in vivo ceDNA-luciferase expression that was higher than the in vivo ceDNA-luciferase expression of LNP 6 comprising Reference Lipid A, whether on Day 4 or Day 7 (FIG. 4A and FIG. 4B). FIG. 4C shows that apart from LNP 9, at least LNP 18 comprising Lipid 1 exhibited in vivo ceDNA-luciferase expression that was higher than the in vivo ceDNA-luciferase expression of LNP 6 comprising Reference Lipid A on Day 4, and such high level of expression was sustained through Day 7.

Thus, Studies A-D overall demonstrate that LNPs formulated with the cationic lipids of the present disclosure: (i) have sustained excellent and stable in vivo expression level of the transgene insert of the ceDNA; and (ii) are well-tolerated in vivo.

Example 18: Study E—Effects of Length of Aliphatic Chains in Hydrophobic Tails on LNP Encapsulation Efficiencies The encapsulation efficiency (EE) of a liposome or a lipid nanoparticle (LNP) is the ratio, proportion, fraction or percentage of therapeutic nucleic acid molecules or drug substance, such as ceDNA, that are completely encapsulated by a liposome or an LNP. The fraction of drug substance being encapsulated by an LNP was calculated by determining unencapsulated drug substance content by measuring the fluorescence upon the addition of PicoGreen dsDNA Assay Kit (Thermo Fisher Scientific®) to the LNP slurry ($C_{free}$) and comparing this value to the ceDNA content that was obtained upon lysis of the LNPs by 1% Triton X-100 ($C_{total}$), where % encapsulation=$(C_{total}-C_{free})/C_{total}\times100\%$.

The encapsulation efficiency of an LNP composition is believed to be an indicator of important properties of an LNP composition, such as but not limited to therapeutic window and purity. As briefly discussed above, all of the LNP compositions formulated using a lipid of the invention possessed an encapsulation efficiency (EE) of ≥90%. The objective of Study E was to evaluate, if any and however minor, statistically significant changes in the encapsulation efficiencies of the various LNP compositions incorporating a lipid of the present disclosure, when the length of specifically carbon atom content of the aliphatic chains in the hydrophobic tails, namely $R^4$ and/or $R^{6a}$ and $R^{6b}$ of Formula I, are varied. Moreover, for liver-targeting applications and without wishing to be bound by theory, the inventors believe that a lower average nanoparticle size potentially enables the LNP composition to more efficiently bypass the fenestrae of the endothelial cells that line liver sinusoids, thereby enabling the LNP composition to be more efficiently internalized by hepatocytes. It is further hypothesized that LNPs above a certain threshold size are prone to preferential uptake by cells of the reticuloendothelial system, which can provoke dose-limiting immune responses.

Table 9 below compares the average LNP diameter (nm) and the corresponding encapsulation efficiencies of LNP 6 (Reference Lipid A, control), LNP 7 (Lipid 20, $R^4$ of Formula I=$C_9$ alkyl; $R^{6a}$ and $R^{6b}$ are both $C_8$ alkyl), LNP 9 (Lipid 11, $R^4$ of Formula I=$C_7$ alkyl; $R^{6a}$ and $R^{6b}$ are both $C_8$ alkyl), LNP 10 (Lipid 19, $R^4$ of Formula I=$C_8$ alkyl; $R^{6a}$ and $R^{6b}$ are both $C_8$ alkyl), LNP 11 (Lipid 21, $R^4$ of Formula I=$C_{10}$ alkyl; $R^{6a}$ and $R^{6b}$ are both $C_8$ alkyl), and LNP 12 (Lipid 22, $R^4$ of Formula I=$C_{11}$ alkyl; $R^{6a}$ and $R^{6b}$ are both $C_8$ alkyl).

TABLE 8

LNP Average particle diameters and encapsulation efficiencies with varying $R^4$

| LNP | Lipid | Formula I No. of carbon atoms in $R^4$ | Formula I No. of carbon atoms in $R^{6a}$ and $R^{6b}$ | Average particle diameter (nm) | Encapsulation effiency (%) |
|---|---|---|---|---|---|
| 6 | Reference Lipid A | N/A | N/A | ≥65.0 | ≤92.0 |
| 7 | Lipid 20 | 9 | Both are 8 | ≤65.0 | ≤91.0 |
| 9 | Lipid 11 | 7 | | ≤65.0 | ≥93.0 |
| 10 | Lipid 19 | 8 | | ≤65.0 | ≤93.0 |
| 11 | Lipid 21 | 10 | | ≥65.0 | ≤93.0 |
| 12 | Lipid 22 | 11 | | ≥70.0 | ≤93.0 |

As shown in Table 8, control LNP 6 comprising Reference Lipid A has an an average diameter of ≥65.0 nm and an encapsulation efficiency of 92.0%. Among the other five LNPs that each incorporate a cationic lipid of Formula I where the only variable was the length of the unbifurcated hydrophobic tail, i.e., $R^4$, it was observed that when $R^4$ contains 9 carbon atoms or less (i.e., 7, 8 or 9 carbon atoms), the average particle diameter was no greater than 65.0 nm, but only LNP 7 comprising Lipid 11 had an improved encapsulation efficiency of at least 93.0% or higher.

Table 9 below compares the average LNP diameter (nm) and the corresponding encapsulation efficiencies of LNP 6 (Reference Lipid A, control), LNP 7 (Lipid 20, $R^4$ of Formula I=$C_9$ alkyl; $R^{6a}$ and $R^{6b}$ are both $C_8$ alkyl), LNP 13 (Lipid 16, $R^4$ of Formula I=$C_9$ alkyl; $R^{6a}$ and $R^{6b}$ are both $C_{10}$ alkyl), and LNP 14 (Lipid 17, $R^4$ of Formula I=$C_9$ alkyl; $R^{6a}$ and $R^{6b}$ are both $C_{10}$ alkyl).

TABLE 9

LNP Average particle diameters and encapsulation efficiencies with varying $R^{6a}$ and $R^{6b}$

| LNP | Lipid | Formula I No. of carbon atoms in $R^4$ | Formula I No. of carbon atoms in $R^{6a}$ and $R^{6b}$ | Average particle diameter (nm) | Encapsulation effiency (%) |
|---|---|---|---|---|---|
| 6* | Reference Lipid A | N/A | N/A | ≥65.0 | ≤92.0 |
| 7* | Lipid 20 | 9 | 8 | ≤65.0 | ≤91.0 |
| 13 | Lipid 16 | | 10 | ≥70.0 | ≥94.0 |
| 14 | Lipid 17 | | 12 | ≥75.0 | ≥92.0 |

*LNP 6 and LNP 7 in Table 10 and LNP 6 and LNP 7 in Table 9 were formulated at the same time with the same batch of reagents and the average particle diameters and encapsulation efficiencies were measured once.

As shown in Table 9, control LNP 6 comprising Reference Lipid A has an an average diameter of ≥65.0 nm and an encapsulation efficiency of 92.0%. Among the other five LNPs that each incorporate a cationic lipid of Formula I where the only variable was the length of the terminal branched aliphatic hydrocarbon chains in the bifurcated hydrophobic tail, i.e., $R^{6a}$ and $R^{6b}$, it was observed that when the average particle diameter increased as the number of carbon atoms in $R^{6a}$ and $R^{6b}$ increased from 8 to 12, but only LNP 13 comprising Lipid 16 ($R^{6a}$ and $R^{6b}$ are both $C_{10}$ alkyl) and LNP 14 comprising Lipid 17 ($R^{6a}$ and $R^{6b}$ are both $C_{12}$ alkyl) each had encapsulation efficiencies that were higher than the encapsulation efficiency of LNP 7 comprising Lipid 20 ($R^{6a}$ and $R^{6b}$ are both $C_8$ alkyl).

REFERENCES AND EQUIVALENTS

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting. It should be understood that this invention is not limited in any manner to the particular methodology, protocols, and reagents, etc., described herein and as such can vary. The terminology used herein is for the purpose of describing particular embodiments only and is not intended to limit the scope of the present invention, which is defined solely by the claims.

What is claimed is:

1. A lipid represented by Formula I:

I

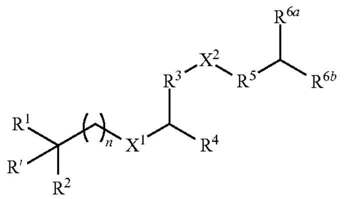

or a pharmaceutically acceptable salt thereof, wherein:

R' is absent, hydrogen, or $C_1$-$C_6$ alkyl; provided that when R' is hydrogen or $C_1$-$C_6$ alkyl, the nitrogen atom to which R', $R^1$, and $R^2$ are all attached is positively charged;

$R^1$ and $R^2$ are each independently hydrogen, $C_1$-$C_6$ alkyl, or $C_2$-$C_6$ alkenyl;

$R^3$ is selected from the group consisting of $C_{12}$ alkylene, $C_{11}$ alkylene, $C_{10}$ alkylene, $C_9$ alkylene, $C_8$ alkylene, $C_6$ alkylene, $C_5$ alkylene, $C_4$ alkylene, $C_3$ alkylene, $C_2$ alkylene, $C_1$ alkylene, $C_{12}$ alkenylene, $C_{11}$ alkenylene, $C_{10}$ alkenylene, $C_9$ alkenylene, $C_8$ alkenylene, $C_7$ alkenylene, $C_6$ alkenylene, $C_8$ alkenylene, $C_4$ alkenylene, $C_3$ alkenylene, and $C_2$ alkenylene;

$R^4$ is $C_1$-$C_{16}$ unbranched alkyl, $C_2$-$C_{16}$ unbranched alkenyl, or

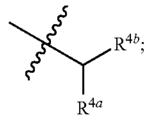

wherein:

$R^{4a}$ and $R^{4b}$ are each independently $C_1$-$C_{16}$ unbranched alkyl or $C_2$-$C_{16}$ unbranched alkenyl;

$R^5$ is absent, $C_1$-$C_8$alkylene, or $C_2$-$C_8$ alkenylene;

$R^{6a}$ and $R^{6b}$ are each independently $C_7$-$C_{16}$ alkyl or $C_7$-$C_{16}$ alkenyl; provided that the total number of carbon atoms in $R^{6a}$ and $R^{6b}$ as combined is greater than 15;

$X^1$ and $X^2$ are each independently-OC(═O)—, —SC(═O)—, —OC(═S)—, —C(═O)O—, —C(═O)S—, —S—S—, —C($R^a$)=N—, —N═C($R^a$)—, —C($R^a$)=NO—, —O—N═C($R^a$)—, —C(═O)N$R^a$—, —N$R^a$C(═O)—, —N$R^a$C(═O)N$R^a$—, —OC(═O)O—, —OSi($R^a$)$_2$O—, —C(═O)(C$R^a_2$)C(═O)O—, or OC(═O)(C$R^a_2$)C(═O)—; wherein:

$R^a$, for each occurrence, is independently hydrogen or $C_1$-$C_6$ alkyl; and n is an integer selected from 1, 2, 3, 4, 5, and 6.

2. The lipid according to claim 1, or a pharmaceutically acceptable salt thereof, wherein $X^1$ and $X^2$ are the same.

3. The lipid according to claim 1, or a pharmaceutically acceptable salt thereof, wherein $X^1$ and $X^2$ are each independently —OC(═O)—, —SC(═O)—, —OC(═S)—, —C(═O)O—, —C(═O)S—, or —S—S—.

4. The lipid according to claim 1, wherein the lipid is represented by Formula II:

II

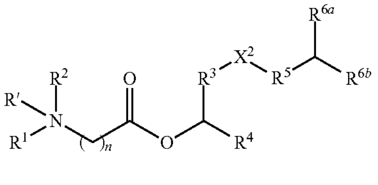

or a pharmaceutically acceptable salt thereof, wherein n is an integer selected from 1, 2, 3, and 4.

5. The lipid according to claim 1, wherein the lipid is represented by Formula III:

III

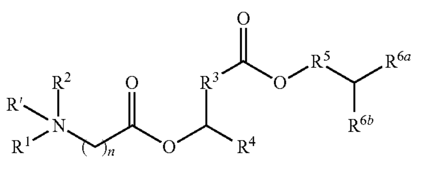

or a pharmaceutically acceptable salt thereof, wherein n is an integer selected from 1, 2, and 3.

6. The lipid according to claim 1, wherein the lipid is represented by Formula IV:

IV

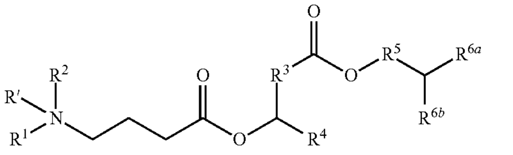

or a pharmaceutically acceptable salt thereof.

7. The lipid according to claim 1, or a pharmaceutically acceptable salt thereof, wherein $R^1$ and $R^2$ are each independently hydrogen, $C_1$-$C_3$ alkyl, or $C_2$-$C_3$ alkenyl.

8. The lipid according to claim 1, or a pharmaceutically acceptable salt thereof, wherein $R^1$ and $R^2$ are each independently hydrogen, $C_1$-$C_2$ alkyl.

9. The lipid according to claim 1, wherein the lipid is represented by Formula V:

V

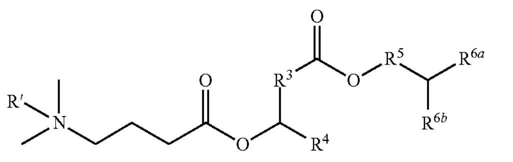

or a pharmaceutically acceptable salt thereof.

10. The lipid according to claim 1, or a pharmaceutically acceptable salt thereof, wherein $R^3$ is selected from the group consisting of $C_6$ alkylene, $C_5$ alkylene, $C_4$ alkylene and $C_3$ alkylene.

11. The lipid according to claim 1, or a pharmaceutically acceptable salt thereof, wherein $R^5$ is absent, $C_1$-$C_4$ alkylene, or $C_2$-$C_4$ alkenylene.

12. The lipid according to claim 1, or a pharmaceutically acceptable salt thereof, wherein $R^5$ is absent.

13. The lipid according to claim 1, or a pharmaceutically acceptable salt thereof, wherein $R^5$ is selected from the group consisting of $C_1$ alkylene, $C_2$ alkylene, $C_3$ alkylene, and $C_4$ alkylene.

14. The lipid according to claim 1, or a pharmaceutically acceptable salt thereof, wherein $R^4$ is $C_1$-$C_{14}$ unbranched alkyl, $C_2$-$C_{14}$ unbranched alkenyl, or

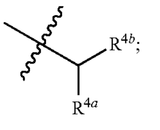

wherein $R^{4a}$ and $R^{4b}$ are each independently $C_1$-$C_{12}$ unbranched alkyl or $C_2$-$C_{12}$ unbranched alkenyl.

15. The lipid according to claim 1, or a pharmaceutically acceptable salt thereof, wherein $R^4$ is $C_2$-$C_{12}$ unbranched alkyl or $C_2$-$C_{12}$ unbranched alkenyl.

16. The lipid according to claim 1, or a pharmaceutically acceptable salt thereof, wherein $R^4$ is $C_5$-$C_{12}$ unbranched alkyl.

17. The lipid according to claim 1, or a pharmaceutically acceptable salt thereof, wherein $R^4$ is selected from the group consisting of $C_6$ unbranched alkyl, $C_7$ unbranched alkyl, $C_8$ unbranched alkyl and $C_9$ unbranched alkyl.

18. The lipid according to claim 1, or a pharmaceutically acceptable salt thereof, wherein $R^4$ is $C_{10}$-$C_{12}$ unbranched alkyl.

19. The lipid according to claim 1, or a pharmaceutically acceptable salt thereof, wherein $R^4$ is $C_2$-$C_7$ unbranched alkyl or $C_2$-$C_7$ unbranched alkenyl.

20. The lipid according to claim 1, or a pharmaceutically acceptable salt thereof, wherein $R^4$ is

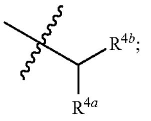

wherein $R^{4a}$ and $R^{4b}$ are each independently $C_5$-$C_9$ unbranched alkyl.

21. The lipid according to claim 1, or a pharmaceutically acceptable salt thereof, wherein $R^{6a}$ and $R^{6b}$ are each independently $C_7$-$C_{14}$ alkyl or $C_7$-$C_{14}$ alkenyl.

22. The lipid according to claim 1, or a pharmaceutically acceptable salt thereof, wherein $R^{6a}$ and $R^{6b}$ are each independently $C_7$ alkyl, $C_8$ alkyl, $C_9$ alkyl, $C_{10}$ alkyl, $C_{11}$ alkyl, $C_{12}$ alkyl, $C_8$ alkenyl, $C_{10}$ alkenyl, $C_{11}$ alkenyl, or $C_{12}$ alkenyl.

23. The lipid according to claim 1, or a pharmaceutically acceptable salt thereof, wherein $R^{6a}$ and $R^{6b}$ are each independently $C_7$ alkyl, $C_8$ alkyl, $C_9$ alkyl, $C_{10}$ alkyl, $C_{11}$ alkyl, or $C_{12}$ alkyl.

24. The lipid according to claim 1, or a pharmaceutically acceptable salt thereof, wherein $R^{6a}$ and $R^{6b}$ are each independently $C_9$ alkyl, $C_{10}$ alkyl, $C_{11}$ alkyl, $C_{12}$ alkyl, $C_{13}$ alkyl, $C_{14}$ alkyl, $C_{15}$ alkyl, $C_{16}$ alkyl, $C_9$ alkenyl, $C_{10}$ alkenyl, $C_{11}$ alkenyl, $C_{12}$ alkenyl, $C_{13}$ alkenyl, $C_{14}$ alkenyl, $C_{15}$ alkenyl, or $C_{16}$ alkenyl.

25. The lipid according to claim 24, or a pharmaceutically acceptable salt thereof, wherein $R^{6a}$ and $R^{6b}$ are each independently $C_9$ alkyl, $C_{10}$ alkyl, $C_{11}$ alkyl, $C_{12}$ alkyl, $C_{13}$ alkyl, $C_{14}$ alkyl, $C_{15}$ alkyl, and $C_{16}$ alkyl.

26. The lipid according to claim 1, or a pharmaceutically acceptable salt thereof, wherein $R^{6a}$ and $R^{6b}$ contain the same number of carbon atoms.

27. The lipid according to claim 1, or a pharmaceutically acceptable salt thereof, wherein $R^{6a}$ and $R^{6b}$ are the same.

28. The lipid according to claim 1, or a pharmaceutically acceptable salt thereof, wherein $R^{6a}$ and $R^{6b}$ are both $C_7$ alkyl, $C_8$ alkyl, $C_9$ alkyl, $C_{10}$ alkyl, $C_{11}$ alkyl or $C_{12}$ alkyl.

29. The lipid according to claim 1, or a pharmaceutically acceptable salt thereof, wherein $R^{6a}$ and $R^{6b}$ each contains a different number of carbon atoms.

30. The lipid according to claim 1, or a pharmaceutically acceptable salt thereof, wherein $R^{6a}$ is $C_9$ alkyl and $R^{6b}$ is $C_8$ alkyl; or $R^{6a}$ is $C_8$ alkyl and $R^{6b}$ is $C_9$ alkyl; or $R^{6a}$ is $C_9$ alkyl and $R^{6b}$ is $C_{10}$ alkyl; or $R^{6a}$ is $C_{10}$ alkyl and $R^{6b}$ is $C_9$ alkyl.

31. The lipid according to claim 1, or a pharmaceutically acceptable salt thereof, wherein R' is absent.

32. The lipid according to claim 1, wherein the lipid is selected from:

(Lipid 3)

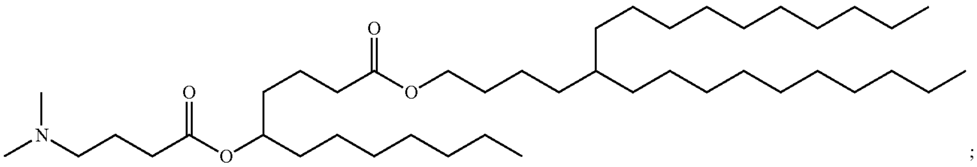

;

5-decylpentadecyl 5-((4-(dimethylamino)butanoyl)oxy)dodecanoate (Lipid 4)

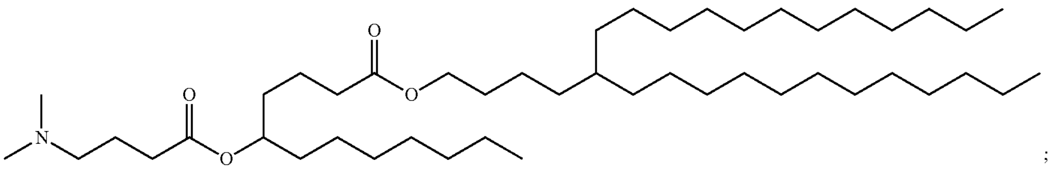

;

5-dodecylheptadecyl 5-((4-(dimethylamino)butanoyl)oxy)dodecanoate (Lipid 5)

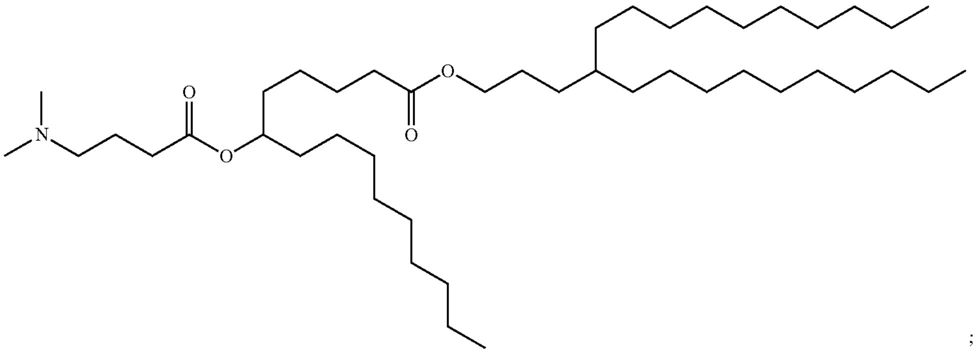

;

4-decyltetradecyl 6-((4-(dimethylamino)butanoyl)oxy)tridecanoate (Lipid 4)

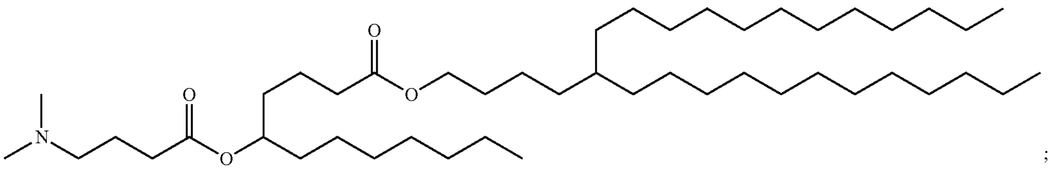

;

5-dodecylheptadecyl 5-((4-(dimethylamino)butanoyl)oxy)dodecanoate (Lipid 5)

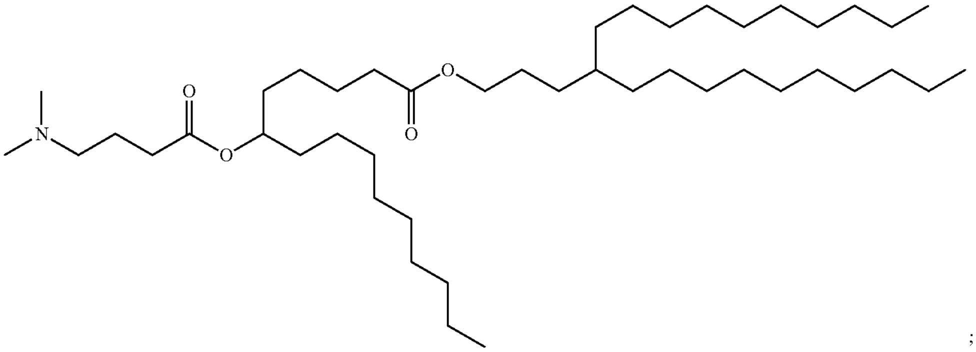

;

4-decyltetradecyl 6-((4-(dimethylamino)butanoyl)oxy)tridecanoate

-continued
(Lipid 6)
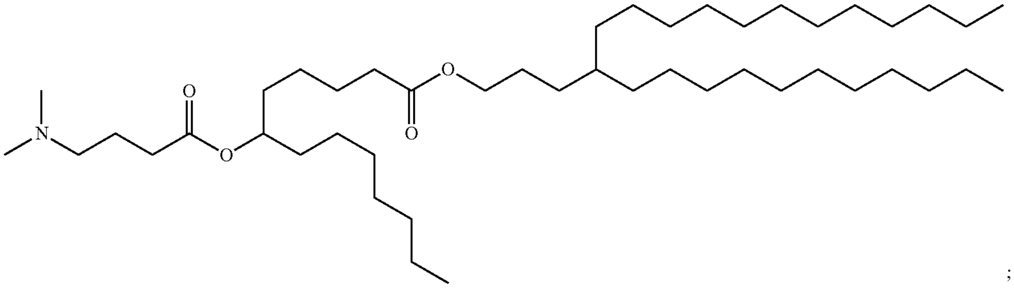
;
4-dodecylhexadecyl 6-((4-(dimethylamino)butanoyl)oxy)tridecanoate
(Lipid 7)
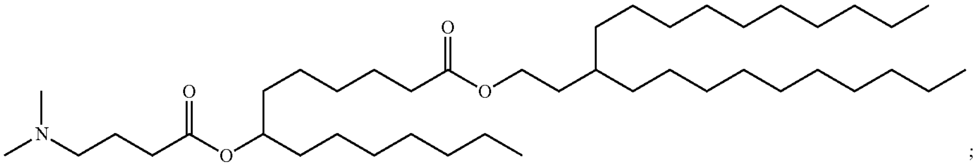
;
3-decyltridecyl 7-((4-(dimethylamino)butanoyl)oxy)tetradecanoate
(Lipid 8)
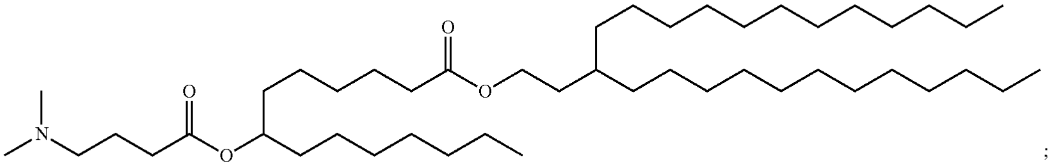
;
3-dodecylpentadecyl 7-((4-(dimethylamino)butanoyl)oxy)tetradecanoate
(Lipid 9)
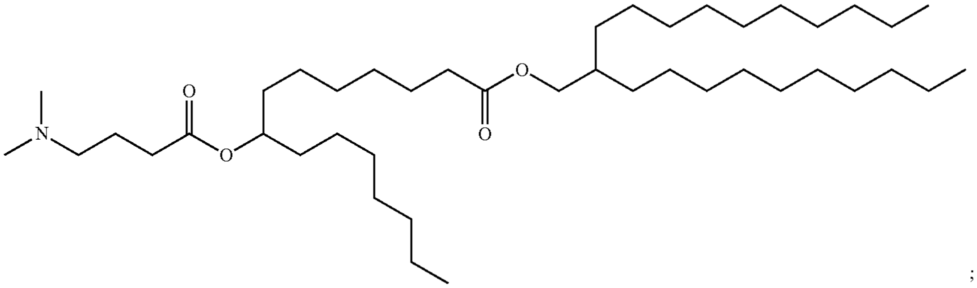
;
2-decyldodecyl 8-((4-(dimethylamino)butanoyl)oxy)pentadecanoate
(Lipid 10)
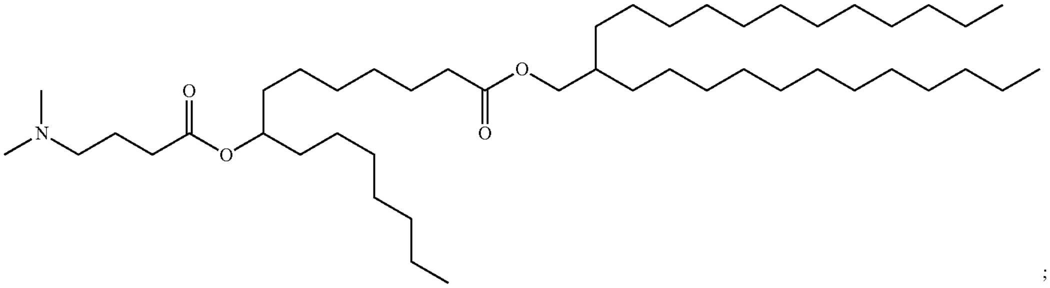
;
2-dodecyltetradecyl 8-((4-(dimethylamino)butanoyl)oxy)pentadecanoate -continued (Lipid 12)

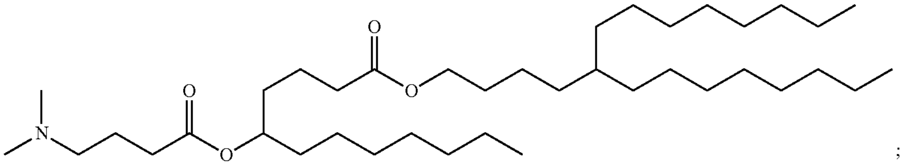

;

5-octyltridecyl 5-((4-(dimethylamino)butanoyl)oxy)dodecanoate (Lipid 13)

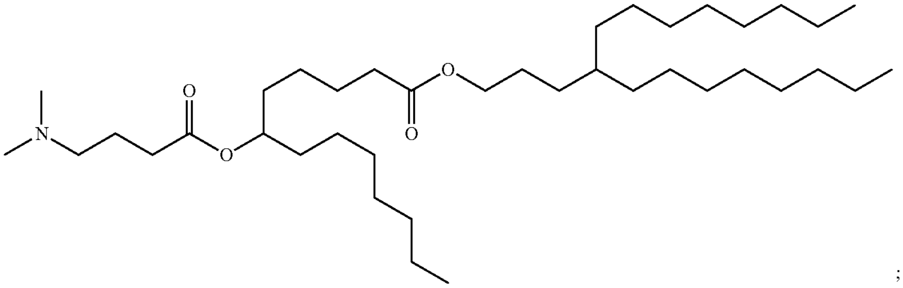

;

4-octyldodecyl 6-((4-(dimethylamino)butanoyl)oxy)tridecanoate (Lipid 14)

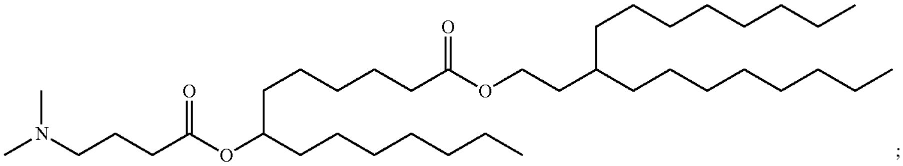

;

3-octylundecyl 7-((4-(dimethylamino)butanoyl)oxy)tetradecanoate (Lipid 15)

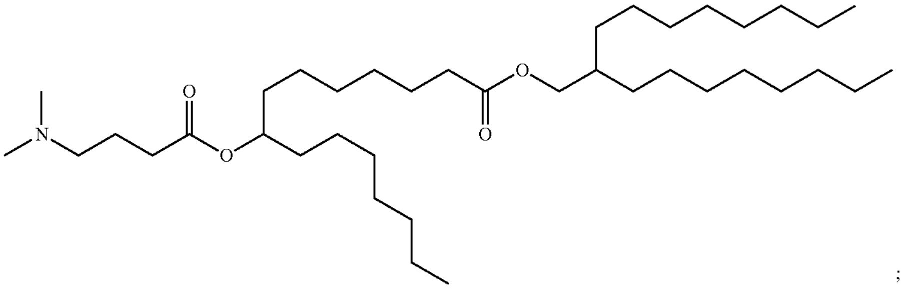

;

2-octyldecyl 8-((4-(dimethylamino)butanoyl)oxy)pentadecanoate (Lipid 18)

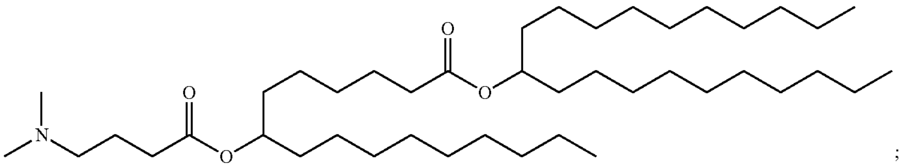

; and henicosan-11-yl 7-((4-(dimethylamino)butanoyl)oxy)hexadecanoate (Lipid 23)

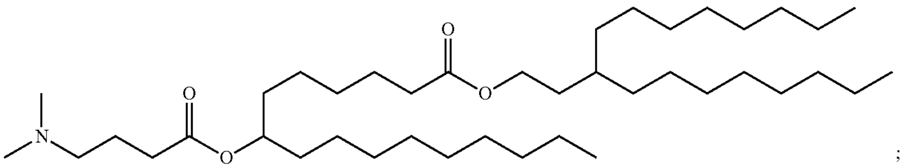

;

3-octylundecyl 7-((4-(dimethylamino)butanoyl)oxy)hexadecanoate or a pharmaceutically acceptable salt thereof.

33. A lipid nanoparticle (LNP) comprising the lipid according to claim 1, or a pharmaceutically acceptable salt thereof; and a therapeutic nucleic acid.

34. The lipid nanoparticle according to claim 33, wherein the therapeutic nucleic acid is encapsulated in the lipid.

35. The lipid nanoparticle according to claim 33, wherein the therapeutic nucleic acid is selected from the group consisting of a minigene, a plasmid, a minicircle, a small interfering RNA (siRNA), a microRNA (miRNA), an antisense oligonucleotide (ASO), a ribozyme, a ceDNA, a ministring, a Doggybone™, a protelomere closed ended DNA, a dumbbell linear DNA, a dicer-substrate dsRNA, a small hairpin RNA (shRNA), an asymmetrical interfering RNA (aiRNA), an mRNA, a tRNA, an rRNA, a DNA viral vector, a viral RNA vector, a non-viral vector and any combination thereof.

36. The lipid nanoparticle according to claim 33, wherein the therapeutic nucleic acid is mRNA.

37. The lipid nanoparticle according to claim 33, further comprising a sterol.

38. The lipid nanoparticle according to claim 37, wherein the sterol is cholesterol or beta-sitosterol.

39. The lipid nanoparticle according to claim 33, further comprising a non-cationic lipid.

40. The lipid nanoparticle according to claim 39, wherein the non-cationic lipid is selected from the group consisting of distearoyl-sn-glycero phosphoethanolamine (DSPE), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoylphosphatidylethanolamine (POPE), dioleoylphosphatidylethanolamine 4-(N-maleimidomethyl)-cyclohexane-1-carboxylate (DOPE-mal), dipalmitoylphosphatidyl ethanolamine (DPPE), dimyristoylphosphoethanolamine (DMPE), distearoylphosphatidylethanolamine (DSPE), monomethylphosphatidylethanolamine, dimethylphosphatidylethanolamine, 18-1-trans PE, 1-stearoyl-2-oleoylphosphatidyethanolamine (SOPE), hydrogenated soy phosphatidylcholine (HSPC), egg phosphatidylcholine (EPC), dioleoylphosphatidylserine (DOPS), sphingomyelin (SM), dimyristoylphosphatidylcholine (DMPC), dimyristoylphosphatidylglycerol (DMPG), distearoylphosphatidylglycerol (DSPG), dierucoylphosphatidylcholine (DEPC), palmitoyloleyolphosphatidylglycerol (POPG), dielaidoyl phosphatidylethanolamine (DEPE), 1,2-dilauroyl-sn-glycero-3-phosphoethanolamine (DLPE); 1,2-diphytanoyl-sn-glycero-3-phosphoethanolamine (DPHyPE); lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, lysophosphatidylcholine, dilinoleoylphosphatidylcholine, and mixtures thereof.

41. The lipid nanoparticle according to claim 39, wherein the non-cationic lipid is selected from the group consisting of dioleoylphosphatidylcholine (DOPC), distearoylphosphatidylcholine (DSPC), and dioleoyl phosphatidylethanolamine (DOPE).

42. The lipid nanoparticle according to claim 33, further comprising at least one PEGylated lipid.

43. The lipid nanoparticle according to claim 42, wherein the at least one PEGylated lipid is selected from the group consisting of PEG-dilauryloxypropyl; PEG-dimyristyloxypropyl; PEG-dipalmityloxypropyl, PEG-distearyloxypropyl; 1-(monomethoxy-polyethyleneglycol)-2,3-dimyristoylglycerol (DMG-PEG); PEG-dilaurylglycerol; PEG-dipalmitoylglycerol; PEG-disterylglycerol; PEG-dilaurylglycamide; PEG-dimyristylglycamide; PEG-dipalmitoylglycamide; PEG-disterylglycamide; (1-[8'-(Cholest-5-en-3 [beta]-oxy) carboxamido-3',6'-dioxaoctanyl] carbamoyl-[omega]-methyl-poly (ethylene glycol) (PEG-cholesterol); 3,4-ditetradecoxylbenzyl-[omega]-methyl-poly(ethylene glycol) ether (PEG-DMB), and 1,2-dimyristoyl-sn-glycero-3-phosphoethanolamine-N-[methoxy (polyethylene glycol) (DSPE-PEG).

44. The lipid nanoparticle according to claim 33, further comprising a tissue-specific targeting ligand.

45. The lipid nanoparticle according to claim 44, wherein the tissue-specific targeting ligand is an antibody, N-acetylgalactosamine (GalNAc) or a GalNAc derivative.

46. A pharmaceutical composition comprising the lipid according to claim 1 and a pharmaceutically acceptable excipient.

47. A method of treating a disease or disorder in a subject in need thereof, comprising administering to the subject an effective amount of the lipid nanoparticle according to claim 33.

48. The method according to claim 47, wherein the subject is a human.

49. The method according to claim 47, wherein the disease or disorder is selected from the group consisting of, melanoma, hemophilia A (clotting factor VIII (FVIII) deficiency), hemophilia B (clotting factor IX (FIX) deficiency), cystic fibrosis (CFTR defect), familial hypercholesterolemia (LDL receptor defect), hepatoblastoma, Wilson disease, phenylketonuria (PKU), congenital hepatic porphyria, an inherited disorder of hepatic metabolism, Lesch-Nyhan syndrome, sickle cell anemia, thalassaemia, xeroderma pigmentosum, Fanconi anemia, retinitis pigmentosa, ataxia telangiectasia, Bloom syndrome, retinoblastoma, a mucopolysaccharide storage disease, Niemann-Pick Disease Type A/B, Niemann-Pick Disease Type C1, Niemann-Pick Disease Type C2, Fabry disease, Schindler disease, GM2-gangliosidosis Type II (Sandhoff Disease), Tay-Sachs disease, Metachromatic Leukodystrophy, Krabbe disease, Mucolipidosis Type I, Mucolipidosis Type II/III, Mucolipidosis Type IV, Sialidosis Type I, Sialidosis Type II, Glycogen Storage disease Type I, Glycogen Storage disease Type II (Pompe disease), Gaucher disease Type I, Gaucher disease Type II, Gaucher disease Type III, cystinosis, Batten disease, Aspartylglucosaminuria, Salla disease, Danon disease (LAMP-2 deficiency), Lysosomal Acid Lipase (LAL) deficiency, neuronal ceroid lipofuscinoses (CLN1-8, INCL, and LINCL), sphingolipidoses, galactosialidosis, amyotrophic lateral sclerosis (ALS), Parkinson's disease, Alzheimer's disease, Huntington's disease, spinocerebellar ataxia, spinal muscular atrophy, Friedreich's ataxia, Duchenne muscular dystrophy (DMD), Becker muscular dystrophies (BMD), dystrophic epidermolysis bullosa (DEB), ectonucleotide pyrophosphatase 1 deficiency, generalized arterial calcification of infancy (GACI), Leber Congenital Amaurosis, Stargardt macular dystrophy (ABCA4 deficiency), ornithine transcarbamylase (OTC) deficiency, Usher syndrome, age-related macular degeneration (AMD), alpha-1 antitrypsin deficiency, progressive familial intrahepatic cholestasis (PFIC) type I (ATP8B1 deficiency), progressive familial intrahepatic cholestasis (PFIC) type II (ABCB11), progressive familial intrahepatic cholestasis (PFIC) type III (ABCB4), progressive familial intrahepatic cholestasis (PFIC) type IV (TJP2), and Cathepsin A deficiency.

50. The method of claim 49, wherein the mucopolysaccharide storage disease is selected from the group consisting of Hurler syndrome (MPS I), Scheie syndrome (MPS I S), Hurler-Scheie syndrome (MPS I H—S), Hunter syndrome (MPS II), Sanfilippo syndrome Type A (MPS IIIA), Sanfilippo syndrome Type B (MPS IIIB), Sanfilippo syndrome Type C (MPS IIIC), Sanfilippo syndrome Type D (MPS IIID), Morquio syndrome Type A (MPS IVA), Morquio syndrome Type B (MPS IVB), Maroteaux-Lamy syndrome (MPS VI), Sly syndrome (MPS VII) and hyaluronidase deficiency (MPS IX).

51. The method of claim 47, wherein the disease or disorder is a genetic disorder.

* * * * *